(12) United States Patent
Corbel et al.

(10) Patent No.: US 11,339,209 B2
(45) Date of Patent: May 24, 2022

(54) COMPOSITIONS, METHODS, AND THERAPEUTIC USES RELATED TO FUSOGENIC PROTEIN MINION

(71) Applicant: NOVARTIS AG, Basel (CH)

(72) Inventors: Stephane Corbel, San Diego, CA (US); Srihari Cidambi Sampath, San Diego, CA (US); Srinath Cidambi Sampath, San Diego, CA (US); Christian Schmedt, San Diego, CA (US); Qiao Zhang, San Diego, CA (US)

(73) Assignee: NOVARTIS AG, Basel (CH)

(*) Notice: Subject to any disclaimer, the term of this patent is extended or adjusted under 35 U.S.C. 154(b) by 279 days.

(21) Appl. No.: 16/349,553

(22) PCT Filed: Nov. 10, 2017

(86) PCT No.: PCT/IB2017/057060
§ 371 (c)(1),
(2) Date: May 13, 2019

(87) PCT Pub. No.: WO2018/087720
PCT Pub. Date: May 17, 2018

(65) Prior Publication Data
US 2019/0263899 A1    Aug. 29, 2019

Related U.S. Application Data

(60) Provisional application No. 62/421,514, filed on Nov. 14, 2016.

(51) Int. Cl.
A61P 35/00    (2006.01)
A61K 39/00    (2006.01)
(Continued)

(52) U.S. Cl.
CPC ............. *C07K 16/18* (2013.01); *A61K 9/127* (2013.01); *A61K 39/001102* (2018.08);
(Continued)

(58) Field of Classification Search
CPC .... C07K 16/18; C07K 14/47; C07K 2319/20; C07K 2319/40; C07K 2319/60;
(Continued)

(56) References Cited

U.S. PATENT DOCUMENTS 7,745,391 B2 * 6/2010 Mintz ............... A61P 31/00
514/19.3

FOREIGN PATENT DOCUMENTS

WO    WO-9531183 A1 * 11/1995 ........... C12N 9/0008
WO    2007/128984 A2    11/2007
(Continued)

OTHER PUBLICATIONS

GeneBank Accession # AL139392 Genome Reference Consortium; Submitted Jan. 22, 2013) Wellcome Trust Sanger Institute, Hinxton, Cambridgeshire, CB10 1SA, UK. and alignment with SEQ ID No. 2 (Jun. 8, 2021) (Year: 2013).*
(Continued)

*Primary Examiner* — Kevin K Hill
*Assistant Examiner* — Anjeanette Roberts
(74) *Attorney, Agent, or Firm* — Erin M. Foley

(57) ABSTRACT

The invention provides novel compositions, methods, and therapeutic uses related to fusogenic protein MINION (microprotein inducer of fusion).

14 Claims, 49 Drawing Sheets

Specification includes a Sequence Listing.

(51) Int. Cl.
| | |
|---|---|
| *A61K 9/127* | (2006.01) |
| *C07K 14/47* | (2006.01) |
| *C12N 5/077* | (2010.01) |
| *C12N 15/02* | (2006.01) |
| *C12N 15/86* | (2006.01) |
| *A61K 38/00* | (2006.01) |
| *C07K 16/18* | (2006.01) |
| *A61P 21/00* | (2006.01) |
| *C12N 5/14* | (2006.01) |
| *C12N 15/113* | (2010.01) |
| *C12N 15/65* | (2006.01) |

(52) U.S. Cl.
CPC .............. *A61P 21/00* (2018.01); *A61P 35/00* (2018.01); *C07K 14/47* (2013.01); *C12N 5/0658* (2013.01); *C12N 5/14* (2013.01); *C12N 15/02* (2013.01); *C12N 15/113* (2013.01); *C12N 15/65* (2013.01); *C12N 15/86* (2013.01); *A61K 38/00* (2013.01); *A61K 2039/892* (2018.08); *C07K 2319/20* (2013.01); *C07K 2319/40* (2013.01); *C07K 2319/60* (2013.01); *C07K 2319/61* (2013.01); *C12N 2740/10043* (2013.01); *Y02A 50/30* (2018.01)

(58) Field of Classification Search
CPC ...... C07K 2319/61; A61P 21/00; A61P 35/00; A61K 39/001102; A61K 9/127; A61K 2039/892; A61K 38/00; C12N 5/0658; C12N 5/14; C12N 15/02; C12N 15/113; C12N 15/65; C12N 15/86; C12N 2740/10043; Y02A 50/30
See application file for complete search history.

(56) References Cited

FOREIGN PATENT DOCUMENTS

| | | | | |
|---|---|---|---|---|
| WO | WO-2007128984 A2 | * | 11/2007 | ............... A61P 35/00 |
| WO | WO-2013110817 A1 | * | 8/2013 | ............... C12Q 1/6886 |
| WO | 2014/210448 A1 | | 12/2014 | |
| WO | WO-2014210448 A1 | * | 12/2014 | ............... C12N 5/16 |

OTHER PUBLICATIONS

Chen YM, Du ZW, Yao Z. Molecular cloning and functional analysis of ESGP, an embryonic stem cell and germ cell specific protein. Acta biochimica et biophysica Sinica. Dec. 1, 2005;37(12):789-96. Cited in IDS in IFW (Year: 2005).*
Rollins BJ, Stier P, Ernst T, Wong GG. The human homolog of the JE gene encodes a monocyte secretory protein. Molecular and Cellular Biology. Nov. 1989;9(11):4687. (Year: 1989).*
Vannucci L, Lai M, Chiuppesi F, Ceccherini-Nelli L, Pistello M. Viral vectors: a look back and ahead on gene transfer technology. New Microbiol. Jan. 1, 2013;36(1):1-22. (Year: 2013).*
Bernard M, Sanseau P, Henry C, Couturier A, Prigent C. Cloning of STK13, a Third Human Protein Kinase Related to *Drosophila* Aurora and Budding Yeast Ipl1 That Maps on Chromosome 19q13. 3-ter. Genomics. Nov. 1, 1998;53(3):406-9. (Year: 1998).*
Frengen E, Catanese J, Zhao B, et al. Large human and mouse PAC libraries for physical mapping and genome sequencing, and more versatile cloning vectors. Dec. 4, 1995; U.S. DOE Workshop on BACs; Abstract only, p. 32. Retrieved from https://web.ornl.gov/sci/techresources/meetings/bacpac.pdf (Year: 1995).*
Database UniProt, Nov. 2, 2016, XP-55441004, PubMed: 28569745, 2 pages.
Database Biosis, Clarivate Analytics, 2017, XP-002777333, 2 pages.
Millay, Douglas P. et al., "Myomaker is a membrane activator of myoblast fusion and muscle formation", Nature, Jul. 18, 2013, vol. 449, pp. 301-305, doi:10.1038/nature12343.
Zhang, Qiao et al., "The microprotein Minion controls cell fusion and muscle formation", Nature Communications, Jun. 1, 2017, vol. 8, pp. 1-15, DOI: 10.1038/ncomms15664.
Quinn, Malgorzata E. et al., "Myomerger induces fusion of non-fusogenic cells and is required for skeletal muscle development". Nature Communications, Jun. 1, 2017, vol. 8, pp. 1-9, DOI: 10.1038/ncomms15665.
Bi, Pengpeng et al., "Control of muscle formation by the fusogenic mircopeptide myomixer", Science, Apr. 21, 2017, vol. 356, No. 6335, pp. 323-327, ISSN: 0036-8075.

* cited by examiner

FIG. 1F

```
M.musculus    MPVPLPMVIRSLLSRLLLPVARLARQHLLPLLRRLARRLSSQDVREALLSCLFVLSQQPPD----SGEASRVDSQRKERLGPQK
R.norvegicus  MPVPLPMLRSLLSRLLLPVARLARQHLLPLLRRLARRLSQDVREALLSCLFVLSQQPPD----SGETSRVDSQRKERLGPRK
H.sapiens     MPTPLPLLLRLLSCLLLPAARLARQYLLPLLRRLARRLSQDVREALLGCLFILSQRHSPD----AGEASRVDRLERRERLGPQK
M.mulatta     MPAPLPLLLRLLSRLLLPVARLARQYLLPLLRRLARRLSQDVREALLGCLFILSQRHSPD----AGEASRVDRLERRERLGPQK
F.catus       MPAPLPLLLRLMSRLLLPATRLARRHLLPLLRRLARRLSQDVREALLGCLFILSQGRPPD----AEVSRVAGQERRERLAPPK
S.scrofa      MPAPLPLLLRTLIAPLLLPAARLARPHLLPLLRRLARRLSQDVREALLGCLVFLSQHPPDDAAAAGEASRVARLERFERIVSQK
              **.**:*::**  *:: ****.:****::*************,***.*****.**:*:***  :,**    : *.***   :*:**:  *

Secondary Struc:    βββββββββββββββββββ βββββββββββββββββββββ  ααααααααααβββββββ                                ββββββββ
```

| Somite stage | 4 | 5 | 6 | 7 | 8 | 9 | 10 | 11 | 12 | 13 | 14 | 15 | 16 | 17 |
|---|---|---|---|---|---|---|---|---|---|---|---|---|---|---|
| MyoD1 | 0.1 | 0.1 | 0.1 |  | 0.1 |  |  |  | 0.1 |  |  |  |  |  |
| Minion |  |  |  |  |  |  |  |  |  |  |  | 0.1 |  |  |

| Somite stage | 18 | 19 | 20 | 21 | 22 | 23 | 24 | 25 | 26 | 27 | 28 | 34 | 35 | 36 |
|---|---|---|---|---|---|---|---|---|---|---|---|---|---|---|
| MyoD1 |  |  |  |  |  |  | 0.1 | 0.1 | 0.1 | 0.1 | 0.2 | 1 | 1 | 2 |
| Minion | 0.2 |  | 0.1 | 0.1 | 0.1 | 0.1 | 0.1 | 0.1 | 0.4 | 0.2 | 0.2 | 0.5 | 0.3 | 0.7 |

FIG. 4A

| Het x Het | +/+ | Δ/+ | Δ/Δ | Total number |
|---|---|---|---|---|
| E18.5-E19.5 embryos | 19 (23%) | 47 (57%) | 17 (20%) | 83 |
| Adult mice | 51 (31%) | 111 (69%) | 0 | 162 |

*minion* genomic locus shRNA constructs:  C1 C2    U1 U2

Minion-FL (84AA)    MPVPLLPMVLRSLLSRLLLPVARLARQHLLPLIRRLARPLSSQWRSALLSCLLFVLSQQQPPDSGEASRVDHSQRKERLGPQK
Minion-155KO (74AA) MPVPLLPMVLRSLLSRLL...

FIG. 25E

| Het x Het | +/+ | Δ/+ | Δ/Δ | Total number |
|---|---|---|---|---|
| E16.5-E18.5 embryos | 5 | 12 | 9 | 26 |
| Adult mice | 18 | 26 | 0 | 44 |

COMPOSITIONS, METHODS, AND THERAPEUTIC USES RELATED TO FUSOGENIC PROTEIN MINION

CROSS-REFERENCE TO RELATED APPLICATIONS

This application claims the benefit of U.S. Provisional Application No. 62/421,514 filed Nov. 14, 2016, the content of which is hereby incorporated by reference in its entirety.

TECHNICAL FIELD

The present invention provides compositions, methods, and therapeutic uses related to fusogenic protein MINION (microprotein inducer of fusion).

SEQUENCE LISTING

The instant application contains a Sequence Listing which has been submitted electronically in ASCII format and is hereby incorporated by reference in its entirety. Said ASCII copy, created on Nov. 8, 2017, is named PAT057279-WO-PCT_SL_2017_11_08.txt and is 73,445 bytes in size.

BACKGROUND

Mouse MINION (microprotein inducer of fusion) protein was also known as embryonic stem cell and germ cell specific protein (ESGP), and was initially identified as a downstream gene regulated by the transcription factor Oct-4, which plays an important role in stem cell pluripotency maintenance (Chen Y et al., Acta Biochimica et Biophysica Sinica 2005, 37(12): 789-796). Mouse MINION was detected in fertilized oocyte, from 3.5 day postcoital (dpc) blastocyst to 17.5 dpc embryo, and in testis and ovary tissues in adult mice, but is dispensible for mouse embryonic stem cell self-renewal and differentiation. (Chen Y et al., 2005). Thus, the function of mouse MINION protein is unknown.

SUMMARY OF THE INVENTION

The present invention is based, at least in part, on the findings that microprotein MINION is required for fusion of muscle progenitor cells and skeletal muscle development, and that heterologous co-expression of MINION and Myomaker is sufficient to induce rapid and homogeneous cellular fusion even in non-muscle cells. The human ortholog of mouse MINION has not been reported before. As described herein, the present inventors identified the amino acid and cDNA sequences of human ortholog of MINION and found human MINION protein also has fusogenic activity, suggesting an evolutionarily conserved role for MINION protein in cell fusion. Accordingly, provided herein are compositions, methods, and therapeutic uses related to fusogenic protein MINION.

In one aspect, provided herein are expression vectors comprising a nucleic acid encoding a MINION polypeptide. In some embodiments, provided herein are expression vectors comprising a nucleic acid encoding a polypeptide comprising an amino acid sequence selected from any of SEQ ID NO: 1, 3, 9, 11, 13, 15, or a variant thereof. In some embodiments, the expression vector comprises a nucleic acid that encodes a polypeptide comprising SEQ ID NO: 1 with 1-4 mutations. In some embodiments, the expression vector comprises a nucleic acid that encodes a polypeptide comprising SEQ ID NO: 3 with 1-4 mutations. In some embodiments, the expression vector comprises a nucleic acid that encodes a polypeptide consisting of SEQ ID NO: 1. In some embodiments, the expression vector comprises a nucleic acid that encodes a polypeptide consisting of SEQ ID NO: 3. In some embodiments, the expression vector comprises a nucleic acid comprising SEQ ID NO: 2 or SEQ ID NO: 4. In some embodiments, the expression vector comprises a nucleic acid consisting of SEQ ID NO: 2 or SEQ ID NO: 4.

In some embodiments, the expression vector comprises a nucleic acid that encodes a polypeptide comprising SEQ ID NO: 1 or SEQ ID NO: 3 or a variant thereof, fused to a tag. The tag can be selected from a HA-tag (YPYDVPDYA, SEQ ID NO: 32), a Myc-tag (EQKLISEEDL, SEQ ID NO: 33), a FLAG-tag (DYKDDDDK, SEQ ID NO: 34), a His-tag (HHHHHH, SEQ ID NO: 35), an E-tag (GAPVPYPDPLEPR, SEQ ID NO: 36), a V5-tag (GKPIPNPLLGLDST, SEQ ID NO: 37), a VSV tag (YTDIEMNRLGK, SEQ ID NO: 38), a polyglutamate tag (EEEEEE, SEQ ID NO: 39), an AviTag (GLNDIFEAQKIEWHE, SEQ ID NO: 40), a SBP tag (MDEKTTGWRGGHVVEGLAGELEQLRAR-LEHHPQGQREP, SEQ ID NO: 41), a Strep-tag (WSHPQFEK, SEQ ID NO: 42), an Xpress tag (DLYDDDDK, SEQ ID NO: 43), an S-tag (KETAAAKFERQHMDS, SEQ ID NO: 44), a Softag 1 (SLAELLNAGLGGS, SEQ ID NO: 45), a Softag 3 (TQDPSRVG, SEQ ID NO: 46), a Calmodulin-tag (KRRWKKNFIAVSAANRFKKISSSGAL, SEQ ID NO: 47), a TC tag (CCPGCC, SEQ ID NO: 48), an Isopeptag (TDKDMTITFTNKKDAE, SEQ ID NO: 49), a SpyTag (AHIVMVDAYKPTK, SEQ ID NO: 50), a SnoopTag (KLGDIEFIKVNK, SEQ ID NO: 51), a Glutathione-S-Transferase (GST)-tag, a fluorescent protein-tag (e.g., a GFP tag), a Maltose binding protein (MBP)-tag, a Halo-tag, or a thioredoxin-tag.

In some embodiments, the expression vectors further comprise a promoter, e.g., a constitutive promoter, an inducible promoter, or a tissue-specific promoter, which regulates the expression of the MINION polypeptide.

In some embodiments, the expression vectors also comprise a polyadenylation signal. In some embodiments, the expression vectors also comprise a selectable marker.

Provided herein are also expression vectors for expressing both a MINION polypeptide or a variant thereof and a Myomaker polypeptide or a variant thereof. Thus, the expression vectors comprise a first nucleic acid encoding a MINION polypeptide or a variant thereof, and a second nucleic acid encoding a Myomaker polypeptide or a variant thereof.

In some embodiments, the second nucleic acid encodes a Myomaker polypeptide comprising an amino acid sequence selected from SEQ ID NO: 16, 18, 20, 22, 24, 26, 28, or 30, or a variant thereof. In some embodiments, the second nucleic acid encodes a Myomaker polypeptide consisting of an amino acid sequence selected from SEQ ID NO: 16, 18, 20, 22, 24, 26, 28, or 30, or a variant thereof. In some embodiments, the second nucleic acid encodes a Myomaker polypeptide comprising SEQ ID NO: 16. In some embodiments, the second nucleic acid encodes a Myomaker polypeptide consisting of SEQ ID NO: 16. In some embodiments, the second nucleic acid comprises SEQ ID NO: 17. In some embodiments, the second nucleic acid consists of SEQ ID NO: 17.

In some embodiments, the expression vector further comprises an internal ribosome entry site or a 2A sequence upstream of the second nucleic acid. For example, the expression vector can include a 2A sequence encoding a 2A oligopeptide selected from any one of SEQ ID NOs: 52-66. In some embodiments, the expression vector further comprises a second promoter (e.g., a constitutive promoter, an inducible promoter, or a tissue-specific promoter) upstream of the second nucleic acid, which regulates the expression of the second nucleic acid.

The expression vector can be a plasmid, a cosmid, an RNA, or a viral vector. In some embodiments, the expression vector is a viral vector based on any of the following viruses: adenovirus, adeno-associated virus, Herpes Simplex Virus (HSV), parvovirus, retrovirus, lentivirus, vaccinia virus, Sinbis virus, influenza virus, reovirus, Newcastle disease virus (NDV), measles virus, vesicular stomatitis virus (VSV), poliovirus, poxvirus, Seneca Valley virus, coxsackievirus, enterovirus, myxoma virus, or maraba virus.

In another aspect, provided herein are cells comprising any of the expression vectors described herein. In some embodiments, such cells comprising an expression vector for expressing a MINION polypeptide (e.g., a human MINION polypeptide). In some embodiments, such cells comprising an expression vector for expressing both a MINION polypeptide (e.g., a human MINION polypeptide) and a Myomaker polypeptide (e.g., a human Myomaker polypeptide). In some embodiments, such cells comprising an expression vector for expressing a MINION polypeptide (e.g., a human MINION polypeptide) and a second expression vector for expressing a Myomaker polypeptide (e.g., a human Myomaker polypeptide). Such cells can be a host cell or a therapeutic cell. In some embodiments, such a cell is a human cell, e.g., a muscle cell, a fibroblast, a bone marrow cell, a blood cell, a hepatocyte, a stem cell, an epithelial cell, an endothelial cell, or a tumor cell. In some embodiments, such a cell expresses a detectable marker.

In another aspect, provided herein are antibodies or antigen-binding fragments thereof that specifically bind to a MINION protein, e.g., a MINION protein described herein. In some embodiments, provided herein are antibodies or antigen-binding fragments thereof that specifically bind to a MINION protein comprising an amino acid sequence selected from any of SEQ ID NO: 1, 3, 5, 7, 9, 11, 13, or 15. In some embodiments, provided herein are antibodies or antigen-binding fragments thereof that specifically bind to a MINION protein consisting of an amino acid sequence selected from any of SEQ ID NO: 1, 3, 5, 7, 9, 11, 13, or 15.

In some embodiments, provided herein are antibodies or antigen-binding fragments thereof that specifically bind to a human MINION protein, e.g., a protein comprising SEQ ID NO: 1 or 3, or a variant thereof. In some embodiments, provided herein are monoclonal antibodies or antigen-binding fragments thereof that specifically bind to a human MINION protein, e.g., a protein comprising SEQ ID NO: 1 or 3, or a variant thereof. In some embodiments, the monoclonal antibody or antigen-binding fragments thereof that specifically bind to a human MINION protein is a chimeric, human or humanized antibody.

In another aspect, provided herein are liposomes comprising a MINION polypeptide. In some embodiments, provided herein are liposomes comprising a polypeptide comprising an amino acid sequence selected from SEQ ID NO: 1, 3, 5, 7, 9, 11, 13, or 15, or a variant thereof. In some embodiments, provided herein are liposomes comprising a polypeptide consisting of an amino acid sequence selected from SEQ ID NO: 1, 3, 5, 7, 9, 11, 13, or 15, or a variant thereof. In some embodiments, provided herein are liposomes comprising a polypeptide consisting of SEQ ID NO: 1 or a variant thereof. In some embodiments, provided herein are liposomes comprising a polypeptide consisting of SEQ ID NO: 3 or a variant thereof.

In some embodiments, the liposomes described herein also include a Myomaker polypeptide. In some embodiments, the liposomes described herein include a Myomaker polypeptide comprising an amino acid sequence selected from SEQ ID NO: 16, 18, 20, 22, 24, 26, 28, or 30, or a variant thereof. In some embodiments, the liposomes described herein include a Myomaker polypeptide consisting of an amino acid sequence selected from SEQ ID NO: 16, 18, 20, 22, 24, 26, 28, or 30, or a variant thereof. In some embodiments, the liposomes described herein include a Myomaker polypeptide consisting of SEQ ID NO: 16 or a variant thereof.

In some embodiments, the liposomes described herein further include a therapeutic agent, wherein the therapeutic agent is encapsulated in the liposome. The therapeutic agent can be selected from a nucleic acid, a protein, a low molecular weight compound, or a peptide nucleic acid.

In another aspect, provided herein are methods of delivering a therapeutic agent to a cell using any of the liposomes described herein. In some embodiments, such methods include contacting a cell with a liposome comprising a MINION polypeptide and a therapeutic agent, wherein the liposome fuses with the cell and thereby delivers the therapeutic agent to the cell. The method can be performed in vitro or in vivo. In some embodiments, the cell is a human cell. In some embodiments, the cell is a tumor cell or a dysfunctional cell.

In another aspect, provided herein are methods of fusing a first cell to a second cell. Such method can comprise the following steps: (a) providing a first cell expressing a MINION polypeptide and a Myomaker polypeptide; and (b) contacting the first cell with a second cell expressing a Myomaker polypeptide, wherein the first cell fuses with the second cell. The step (b) of the method can be performed in vitro or in vivo.

Also provided are methods of fusing a first cell to a second cell, which comprise: (a) providing a first cell expressing a MINION polypeptide, and a receptor that mediates homotypic interaction; and (b) contacting the first cell with a second cell expressing the same receptor expressed by the first cell, wherein the first cell fuses with the second cell. The step (b) of the method can be performed in vitro or in vivo. The receptor that mediates homotypic interaction can be selected from a cadherin, a selectin, a claudin, an occludin, a junctional adhesion molecule, or a tricellulin. In some embodiments, the receptor that mediates homotypic interaction is a cadherin selected from N-Cadherin, P-Cadherin, E-Cadherin, or M-Cadherin.

In some embodiments, the first and the second cells are human cells. In some embodiments, the first and the second cells are selected from a muscle cell, a fibroblast, a bone marrow cell, a blood cell, a hepatocyte, a stem cell, an epithelial cell, an endothelial cell, a dendritic cell, or a tumor cell. In some embodiments, the first cell is selected from muscle cell, a fibroblast, a bone marrow cell, a blood cell, a hepatocyte, a stem cell, an epithelial cell, an endothelial cell, or a dendritic cell, and the second cell is a tumor cell or a dysfunctional cell. In some embodiments, the first cell expresses a detectable marker.

In some embodiments, the first cell further comprises a gene of interest, and the fusion of the cells delivers the gene of interest to the second cell. In some embodiments, the gene of interest corrects a pathologic phenotype of the second cell. In some embodiments, the second cell further comprises a gene of interest, and the fusion of the cell delivers the gene of interest to the first cell. In some embodiments, the gene of interest corrects a pathologic phenotype of the first cell.

In some embodiments, the gene of interest is a gene of the mitochondrial DNA and the pathologic phenotype is selected from mitochondrial DNA depletion; mitochondrial myopathy; Myoclonic Epilepsy with Ragged Red Fibers (MERRF); mitochondrial myopathy, encephalomyopathy, lactic acidosis, stroke-like symptoms (MELAS); Kearns-Sayre syndrome (KSS); Leigh syndrome (subacute necrotizing encephalomyopathy) and maternally inherited Leigh syndrome (MILS); Mitochondrial neurogastrointestinal encephalomyopathy (MNGIE); Myoclonus epilepsy with ragged red fibers (MERRF); Neuropathy, ataxia and retinitis pigmentosa (NARP); or Pearson syndrome.

In a further aspect, provided herein are methods of treating a cancer in a subject by administering to the subject an effective amount of an oncolytic virus comprising a nucleic acid encoding a MINION polypeptide. Alternatively, provided herein is an oncolytic virus, comprising a nucleic acid encoding a MINION polypeptide for use in treating cancer. The cancer can be a head and neck cancer, skin cancer, breast cancer, prostate cancer, ovarian cancer, cervical cancer, lung cancer, liver cancer, renal cancer, pancreatic cancer, colorectal cancer, brain cancer, neuroblastoma, glioma, sarcoma, lymphoma, or leukemia. In some embodiments, the cancer is a sarcoma selected from angiosarcoma, dermatofibrosarcoma, epithelioid sarcoma, Ewing's sarcoma, fibrosarcoma, gastrointestinal stromal tumors (GISTs), Kaposi sarcoma, Leiomyosarcoma, liposarcoma, malignant fibrous histiocytoma, neurofibrosarcoma, rhabdomyosarcoma, undifferentiated pleomorphic sarcoma, or synovial sarcoma. The oncolytic virus can be administered to the subject intratumorally, transdermally, transmucosally, orally, intranasally, subcutaneously, intra-arterially, intravenously, intramuscularly, intrathecally, or intraperitoneally, or via pulmonary administration.

In some embodiments, such methods comprise administering to the subject an effective amount of an oncolytic virus comprising a nucleic acid encoding a MINION polypeptide, and a nucleic acid encoding a Myomaker polypeptide. In some embodiments, such methods comprise administering to the subject an effective amount of an oncolytic virus comprising a nucleic acid encoding a MINION polypeptide, and a nucleic acid encoding a receptor that mediates homotypic interaction. The receptor that mediates homotypic interaction can be selected from a cadherin, a selectin, a claudin, an occludin, a junctional adhesion molecule, or a tricellulin. In some embodiments, the receptor that mediates homotypic interaction is a cadherin selected from N-Cadherin, P-Cadherin, E-Cadherin, or M-Cadherin.

The oncolytic virus can be selected from any of the following viruses: oncolytic adenovirus, oncolytic adeno-associated virus, oncolytic Herpes Simplex Virus (HSV), oncolytic parvovirus, oncolytic retrovirus, oncolytic lentivirus, oncolytic vaccinia virus, oncolytic Sinbis virus, oncolytic influenza virus, oncolytic reovirus, oncolytic Newcastle disease virus (NDV), oncolytic measles virus, oncolytic vesicular stomatitis virus (VSV), oncolytic poliovirus, oncolytic poxvirus, oncolytic Seneca Valley virus, oncolytic coxsackievirus, oncolytic enterovirus, oncolytic myxoma virus, or oncolytic maraba virus. In some embodiments, the oncolytic virus specifically targets cancer cells. In some embodiments, the oncolytic virus selectively replicates in cancer cells. In some embodiments, the oncolytic virus expresses a detectable marker.

In some embodiments, the MINION polypeptide described in any of the above methods can comprise an amino acid sequence selected from SEQ ID NO: 1, 3, 5, 7, 9, 11, 13, or 15, or a variant thereof. In some embodiments, the MINION polypeptide consists of an amino acid sequence selected from SEQ ID NO: 1, 3, 5, 7, 9, 11, 13, or 15, or a variant thereof. In some embodiments, the MINION polypeptide comprises SEQ ID NO: 1 or a variant thereof. In some embodiments, the MINION polypeptide comprises SEQ ID NO: 3 or a variant thereof. In some embodiments, the MINION polypeptide consists of SEQ ID NO: 1 or a variant thereof. In some embodiments, the MINION polypeptide consists of SEQ ID NO: 3 or a variant thereof.

In some embodiments, the Myomaker polypeptide described in any of the above methods comprises an amino acid sequence selected from SEQ ID NO: 16, 18, 20, 22, 24, 26, 28, or 30, or a variant thereof. In some embodiments, the Myomaker polypeptide consists of an amino acid sequence selected from SEQ ID NO: 16, 18, 20, 22, 24, 26, 28, or 30, or a variant thereof. In some embodiments, the Myomaker polypeptide comprises SEQ ID NO: 16 or a variant thereof. In some embodiments, the Myomaker polypeptide consists of SEQ ID NO: 16 or a variant thereof.

In another aspect, provided herein are methods of treating cancer in a subject, the method comprising administering to the subject an effective amount of a cancer vaccine comprising a nucleic acid encoding a MINION polypeptide, and a nucleic acid encoding a Myomaker polypeptide. Further provided herein are methods of treating cancer in a subject, the method comprising administering to the subject an effective amount of a cancer vaccine comprising a nucleic acid encoding a MINION polypeptide, and a nucleic acid encoding a receptor that mediates homotypic interaction.

In some embodiments, the MINION polypeptide comprises an amino acid sequence selected from SEQ ID NO: 1, 3, 5, 7, 9, 11, 13, or 15, or a variant thereof. In some embodiments, the MINION polypeptide consists of an amino acid sequence selected from SEQ ID NO: 1, 3, 5, 7, 9, 11, 13, or 15, or a variant thereof. In some embodiments, the MINION polypeptide comprises SEQ ID NO: 1 or a variant thereof. In some embodiments, the MINION polypeptide comprises SEQ ID NO: 3 or a variant thereof. In some embodiments, the MINION polypeptide consists of SEQ ID NO: 1 or a variant thereof. In some embodiments, the MINION polypeptide consists of SEQ ID NO: 3 or a variant thereof. In some embodiments, the Myomaker polypeptide comprises an amino acid sequence selected from SEQ ID NO: 16, 18, 20, 22, 24, 26, 28, or 30, or a variant thereof. In some embodiments, the Myomaker polypeptide consists of an amino acid sequence selected from SEQ ID NO: 16, 18, 20, 22, 24, 26, 28, or 30, or a variant thereof. In some embodiments, the Myomaker polypeptide comprises SEQ ID NO: 16 or a variant thereof. In some embodiments, the Myomaker polypeptide consists of SEQ ID NO: 16 or a variant thereof. In some embodiments, the receptor that mediates homotypic interaction is selected from a cadherin, a selectin, a claudin, an occludin, a junctional adhesion molecule, or a tricellulin. In some embodiments, the receptor that mediates homotypic interaction is a cadherin selected from N-Cadherin, P-Cadherin, E-Cadherin, or M-Cadherin.

In some embodiments, the cancer vaccine comprises a dendritic-tumor fusion cell derived from a dendritic cell and a tumor cell. In some embodiments, the cancer vaccine simulates activation of $CD4^+$ or $CD8^+$ T cells. In some embodiments, the cancer vaccine presents one or more tumor-associated antigens. In some embodiments, the cancer vaccine presents the one or more tumor-associated antigens through major histocompatibility complex (MHC) class I or II pathways. In some embodiments, the cancer vaccine expresses a detectable marker. In some embodiments, the dendritic cell is an autologous dendritic cell. In some embodiments, the dendritic cell is an allogeneic dendritic cell. In some embodiments, the tumor cell is an autologous tumor cell. In some embodiments, the tumor cell is an allogeneic tumor cell. In some embodiments, the dendritic cell is an activated dendritic cell. In some embodiments, the tumor cell is an immunogenic tumor cell. In some embodiments, the tumor cell is a cancer stem cell.

In some embodiments, the cancer vaccine is administered to the subject intratumorally, transdermally, transmucosally, orally, intranasally, subcutaneously, intra-arterially, intravenously, intramuscularly, intrathecally, or intraperitoneally, or via pulmonary administration. In some embodiments, the cancer is selected from head and neck cancer, skin cancer, breast cancer, prostate cancer, ovarian cancer, cervical cancer, lung cancer, liver cancer, renal cancer, pancreatic cancer, colorectal cancer, brain cancer, neuroblastoma, glioma, sarcoma, lymphoma, or leukemia. In some embodiments, the cancer is a sarcoma selected from angiosarcoma, dermatofibrosarcoma, epithelioid sarcoma, Ewing's sarcoma, fibrosarcoma, gastrointestinal stromal tumors (GISTs), Kaposi sarcoma, Leiomyosarcoma, liposarcoma, malignant fibrous histiocytoma, neurofibrosarcoma, rhabdomyosarcoma, undifferentiated pleomorphic sarcoma, or synovial sarcoma.

In another aspect, provided herein are methods of treating muscular dystrophy in a subject in need thereof, comprising administering a pharmaceutical composition comprising a cell disclosed herein. In some embodiments, the cell comprises a vector disclosed herein. In some embodiments, the cell comprises a vector disclosed herein, and a second vector comprising a second nucleic acid encoding a Myomaker polypeptide or a variant thereof. In some embodiments, the cell is a human cell. In some embodiments, the cell is selected from a muscle cell, a fibroblast, a bone marrow cell, a blood cell, a hepatocyte, a stem cell, an epithelial cell, an endothelial cell, or a tumor cell. In some embodiments, the muscular dystrophy is selected from the group consisting of Duchenne muscular dystrophy (DMD), Becker muscular dystrophy (BMD), Congenital muscular dystrophy (CMD), Distal muscular dystrophy, Emery-Dreifuss muscular dystrophy (EDMD), Facioscapulohumeral muscular dystrophy (FMD), Limb-Girdle muscular dystrophy (LGMD), Myotonic muscular dystrophy (MMD), Oculopharnyngeal muscular dystrophy (OMD), Miyoshi myopathy (MM), Limb-girdle muscular dystrophy type 2B (LGMD2B), and Distal Myopathy (DM).

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIGS. 1A-1F show that MINION is a skeletal muscle-specific microprotein highly expressed during muscle development and regeneration. FIG. 1A is a Venn diagram showing overlap of RNA-seq of microprotein expression in regenerating adult mouse tibialis anterior (TA) muscle and differentiating C2C12 myoblasts (MB). CTX, cardiotoxin; FC: fold change compared to uninjured muscle (bottom left) or undifferentiated myoblasts (bottom right). FIG. 1B is a line graph depicting fold change of reads per kilobase per million mapped reads (RPKM) for selected genes upregulated after CTX injury. Values are normalized to uninjured muscle. Mean±SD of fold change, n=3 per time point. FIG. 1C shows representative Western blot for detecting MINION expression in control uninjured (Ctl) and CTX-injured regenerating adult TA muscle. GAPDH (glyceraldehyde-3-phosphate dehydrogenase) served as loading controls. FIG. 1D shows representative Western blot for detecting MINION expression in embryonic muscle samples. Day 4 post-CTX in adult TA muscle was used as positive control while normal saline (NS) injection was used as negative control. E, embryonic day; P: post-natal. GAPDH served as loading controls. FIG. 1E shows representative Western blot for detecting expression of MINION, Myogenin, or myosin heavy chain (MHC) in C2C12 myoblasts under differentiating conditions (DM) for the indicated number of days. MHC, myosin heavy chain. Tubulin served as loading controls. FIG. 1F shows amino acid sequence alignment of mouse MINION protein (*M. musculus*, SEQ ID NO: 5) with putative orthologs from other mammalian species, e.g., rat MINION (*R. norvegicus*, SEQ ID NO: 9), human MINION (*H. sapiens*, SEQ ID NO: 1), monkey MINION (*M. mulatta*, SEQ ID NO: 15), cat MINION (*F. catus*, SEQ ID NO: 11), and pig MINION (*S. scrofa*, SEQ ID NO: 13).

FIG. 2A shows immunofluorescence staining of MINION on transverse sections prepared from uninjured (left) or regenerating (right, 3 to 4 days post CTX injection) TA muscle. DAPI was used to counterstain nuclei. Scale bars: 20 µm. FIG. 2B shows representative Western blot for detecting MINION expression in various adult skeletal muscle groups and of cardiac muscle using indicated antibodies. 6-8 weeks old C57BL/6J mice were used. Ctl: uninjured TA muscle; CTX: regenerating TA muscle at day 4 post CTX injection; TA: tibialis anterior; Gastr: gastrocnemius; Quad: quadriceps femoris; Diaphr: diaphragm. FIG. 2C shows representative Western blot for detecting MINION expression in various adult tissues using indicated antibodies. 6-8 weeks old C57BL/6J mice were used. FIG. 2D shows expression of mouse Minion during embryonic development as detected by RNA-seq (EMBL-EBI Expression Atlas; www.ebi.ac.uk) (Mohun et al. Deciphering the Mechanisms of Developmental Disorders (DMDD): a new programme for phenotyping embryonic lethal mice. *Disease models & mechanisms* 6, 562-566, 2013; Petryszak et al. Expression Atlas update—a database of gene and transcript expression from microarray- and sequencing-based functional genomics experiments. *Nucleic acids research* 42, D926-932, 2014). Numbers indicate RNA expression level (FPKM). FIG. 2E shows expression of mouse myod1 (left) and Minion (right) in non-somitic muscle as detected by in situ hybridization at E14.5 (Eurexpress; www.eurexpress.org) (Diez-Roux et al. A high-resolution anatomical atlas of the transcriptome in the mouse embryo. *PLoS biology* 9, e1000582, 2011). Arrows indicate overlapping expression in extraocular and facial muscle.

FIG. 3A is a bar graph showing RT-qPCR quantification of MINION mRNA levels in C2C12 myoblasts under growth (GM) or differentiation (DM) conditions. Mouse embryonic stem cells (ESC) served as a positive control. FIG. 3B shows representative Western blot for detecting MINION expression in differentiating C2C12 myoblasts (at day 1, 3, 5 in DM), and of embryonic stem cell (ESC) using the indicated antibodies. Tubulin served as a loading control. FIG. 3C shows representative Western blot for detecting MINION expression in C2C12 myoblasts under growth (GM) or differentiation conditions (DM; day 3), using the indicated antibodies. Pax7 is a transcription factor high in undifferentiated cells, while Desmin is an intermediate filament protein high in differentiated muscle cells. Tubulin served as a loading control. FIG. 3D shows representative Western blot analysis of concentrated cell culture supernatant (Sup) from day 3 differentiating C2C12 myoblasts expressing control vector or C-terminally 3×FLAG-1×HA-tagged Minion. Both tagged (*) and endogenous (**) Minion are detected in whole cell extract (WCE). TGFβ and cleaved N-Cadherin (++) are positive controls, whereas Gapdh and intact N-Cadherin (+) are non-secreted negative controls. n=3. FIG. 3E shows representative Western blot for detecting MINION subcellular location. Western blot analysis was performed using the indicated antibodies. Four fractions were examined: Cyto., cytosolic; Mem., membrane; Nuc., nuclear; Cytosk., cytoskeletal. The membrane fraction contains both plasma membrane as well as intracellular membranes, including ER, Golgi, mitochondria, endosome, lysosome, etc. GAPDH: cytosolic fraction marker; N-Cadherin: plasma membrane marker; Calnexin: ER membrane marker; Histone H2B: nuclear fraction marker; Vimentin: cytoskeletal fraction marker.

FIGS. 4A-4B show MINION promoter structure is consistent with regulation by the muscle regulatory factors MyoD and Myogenin. FIG. 4A shows sequence alignment of the genomic regions surrounding mouse gm7325/MINION gene (SEQ ID NO: 96) and its human ortholog RP1-302G2.5 (SEQ ID NO: 97). The MINION ORF is highlighted in black. Seven conserved E-box motifs (CANNTG (SEQ ID NO: 109) and CANNTT (SEQ ID NO: 110)) within the promoter and 5'UTR region are highlighted in grey. FIG. 4B shows ENCODE MyoD and Myogenin ChIP-seq data from C2C12 myoblasts under growth conditions (GM) and at three time points under differentiation conditions (DM) examined surround the MINION genomic locus. Black bars indicate the first four conserved E-box motifs within the promoter region in FIG. 4A.

FIG. 5A is a diagram showing the strategy for CRISPR/Cas9-mediated mutagenesis of the MINION locus using a dual sgRNA approach. Gray box, MINION ORF; white box, non-coding exons; sgRNA, single guide RNA; Fwd and Rev, forward and reverse genotyping primers. FIG. 5B shows representative genotyping PCR results of MINION wild type (+/+) and heterozygous (Δ/+) mice carrying the 135-bp deletion depicted in FIG. 5A. FIG. 5C shows representative sequence traces from wild type (WT) allele (SEQ ID NO: 98) and knockout (KO) allele (SEQ ID NO: 99) bearing the 135-bp deletion. Black line indicates 5' boundary of the deleted interval. FIG. 5D is a set of photographs of skinned MINION$^{+/+}$ and MINION$^{Δ/Δ}$ P0 mice. Arrows and asterisks indicate forelimb and intercostal musculature, respectively. Scale bars: 1 mm. FIG. 5E shows histological and immunofluorescence analysis of embryonic tongue skeletal muscle. Top row: hematoxylin and eosin (H&E) staining of sagittal tongue sections. Inset demonstrates the area and orientation of sections depicted. Bottom row: immunofluorescence staining for muscle marker MHC and counterstained with DAPI (4',6-diamidino-2-phenylindole). Scale bars: 100 µm. FIG. 5F is a set of immunofluorescence images of sagittal sections of diaphragm muscle stained for the muscle marker Desmin and counterstained with DAPI. Scale bars: 200 µm. FIG. 5G shows quantification (bar graph, left) and representative images (right) of lung flotation assay using E18.5 mouse embryos following 1 hour exposure to room air.

FIG. 6A is a diagram showing the strategy for generation of MINION-deficient animals by CRISPR/Cas9 mediated genome editing. A 135 bp in-frame deletion (marked in light gray) within the MINION ORF (dark gray) was induced using a double sgRNA approach. The genomic target sequences of the gRNAs are indicated with straight lines. Fwd: forward PCR genotyping primer; Rev: reverse PCR genotyping primer. FIG. 6A discloses SEQ ID NOS 100-101, respectively, in order of appearance. FIG. 6B shows protein sequence alignment of the 84AA full-length mouse MINION (SEQ ID NO: 102) and the predicted 39AA truncated form (MINION$^Δ$) (SEQ ID NO: 103). The truncated form is predicted to contain only the N-terminal 26AA and C-terminal 12AA of the original microprotein. FIG. 6C shows representative agarose gel image of typical genotyping PCR results of E18.5 embryos from MINION$^{Δ/+}$×MINION$^{Δ/+}$ crosses (Het×Het). +/+: wild type (MINION$^{+/+}$); Δ/+: heterozygote (MINION$^{Δ/+}$); Δ/Δ: MINION knockout homozygote (MINION$^{Δ/Δ}$). FIG. 6D is a table summarizing genotyping results of both late-stage embryos and adult mice from MINION$^{Δ/+}$×MINION$^{Δ/+}$ crosses.

FIG. 7A shows representative Western blot for detecting MINION expression in limbs and tongues from E16.5/E17.5 embryos and P0 mice with indicated genotypes. Adult TA muscle at 4 days post cardiotoxin injection (CTX 4 dpi) was used as a positive control. Embryos from the same litter were used for each comparison. The full-length MINION was not observed in the MINION$^{Δ/Δ}$ embryos, and the predicted 39AA truncated protein was not observed either using the same anti-MINION antibody. FIG. 7B shows representative Western blot for detecting MINION expression in forelimbs from MINION$^{+/+}$ and MINION$^{Δ/+}$ E18.5 embryos of the same litter using indicated antibodies.

FIG. 8A is a photo of MINION$^{Δ/+}$ and MINION$^{Δ/Δ}$ E16 embryos. The arrow indicates accretion of dorsal and nuchal subcutaneous edema. Scale bar: 1 mm. FIG. 8B is a set of photos of MINION$^{+/+}$ (left) and MINION$^{Δ/Δ}$ (right) E17.5, either unskinned (top) or skinned (bottom). Arrow indicates expected location of forelimb musculature. Scale bars: 1 mm. FIG. 8C is a set of photos of E18.5 embryos of the indicated genotypes following air breathing after delivery by cesarean section. The MINION$^{Δ/Δ}$ embryos were atonic and exhibited an abnormal spinal curvature and became cyanotic and dead soon after delivery. FIG. 8D is a bar graph showing quantification of E18.5 embryo weight after delivery by cesarean section. Double asterisk: p<0.001; ns=not significant.

FIG. 9A is a set of histological images of hematoxylin and eosin (H&E) stained forelimb transverse sections of E14.5 embryos with indicated genotypes. No significant difference was observed between genotypes with respect to muscle group number, position or size. Scale bars: 100 µm. FIG. 9B is a set of histological images of H&E-stained E16.5 forelimb transverse sections of indicated genotypes. Inset demonstrates magnification of the region marked with dotted lines. Scale bars in main panels: 100 µm; scale bars in the inset: 10 µm. FIG. 9C is a set of histological images of H&E-stained forelimb transverse sections from E19.5 embryos with indicated genotypes. Inset demonstrates magnification of the region marked with dotted lines. Scale bars in main panels: 100 µm; scale bars in the inset: 10 µm. FIG. 9D is a set of Desmin immunofluorescence images of forelimb transverse sections from E19.5 embryos with indicated genotypes. Inset demonstrates magnification of the region marked with dotted lines. Desmin marks all differentiating myoblasts and myotubes and muscle fibers in the embryos. Nuclei were labeled by DAPI. Scale bars in main panels: 100 µm; scale bars in the inset: 10 µm.

FIG. 10A is a set of histological images of H&E-stained E19.5 forelimb longitudinal sections of indicated genotypes. Scale bars: 100 µm. FIG. 10B is a set of immunofluorescence images showing MHC expression in forelimb longitudinal sections for E19.5 embryos with indicated genotypes. Nuclei were stained with DAPI. Scale bars: 100 µm. FIG. 10C is a set of immunofluorescence images showing Desmin expression in intercostal muscle sagittal sections from E19.5 embryos with indicated genotypes. Nuclei were counterstained with DAPI. Scale bars: 100 µm.

FIG. 11A is a set of Desmin immunofluorescence images of tongue sections of E16.5 tongue transverse sections with indicated genotypes. Black box in histological image at left demonstrates the area shown at right in fluorescence images. Nuclei were counterstained with DAPI. Scale bars: 200 µm. FIG. 11B is a set of Desmin immunofluorescence images of E19.5 tongue transverse sections with indicated genotypes. Black box in histological image at left demonstrates the area shown at right in fluorescence images. Nuclei were counterstained with DAPI. Scale bars: 200 µm. FIG. 11C is the magnified view of the white boxed areas shown in FIG. 11B. The E19.5 MINION$^{\Delta/\Delta}$ tongue exhibited a great reduction of long myotubes. Scale bars: 200 µm.

FIG. 12A is a set of Desmin immunofluorescence images of primary embryonic myoblasts isolated from E18.5 MINION$^{+/+}$, MINION$^{\Delta/+}$ and MINION$^{\Delta/\Delta}$ embryos, following 3 days in differentiation medium. White arrowheads: myotubes; white arrows: elongating myoblast. FIG. 12B is a bar graph showing fusion index of myoblasts in FIG. 12A, calculated as % nuclei in Desmin$^+$ myotubes (≥3 nuclei) of total nuclei in Desmin$^+$ cells. Asterisk: P<0.05. FIG. 12C shows representative Western blot for detecting MINION, Myogenin, and MHC expression in C2C12 myoblasts lentivirally infected with either control luciferase targeting shRNA (Ctrl) or serially with two shRNA targeting the MINION 3'UTR (MINION$^{KD}$) and cultured in growth medium (GM) or differentiation medium (DM) for the indicated number of days. Tubulin was used as a loading control. FIG. 12D is a set of MHC immunofluorescence images of control (Ctrl) and MINION$^{KD}$ myofibers following 5 days in differentiation medium. Nuclei were counterstained with DAPI. Scale bars: 100 µm. FIG. 12E is a bar graph showing differentiation index of FIG. 12D, calculated as % nuclei in MHC$^+$ cells of total nuclei. NS=not significant. FIG. 12F is a bar graph showing fusion index of FIG. 12D, calculated as the fraction of nuclei contained within MHC$^+$ myotubes which had two or more nuclei, as compared to the number of total nuclei within each 20× image taken by IXM imaging. Double asterisk: p<0.001. FIG. 12G is a bar graph showing quantification of nuclei per myotube for FIG. 12D. Myotubes were binned into subgroups by total nuclear number as indicated. FIG. 12H is a set of MHC immunofluorescence images of MINION$^{KD}$ cells expressing either control protein (NanoLuc) or human Minion ortholog, after 5 days in differentiation medium. Nuclei were counterstained with DAPI. Scale bars: 100 µm.

FIG. 14A is a schematic diagram showing the mouse MINION genomic locus with the target regions of four shRNA constructs underlined. Solid black bar indicated the MINION ORF, and white bar indicated untranslated regions (UTRs). C1 and C2: shRNA constructs targeting the coding sequence; U1 and U2: shRNA constructs targeting the 3'UTR. FIG. 14B shows representative Western blot for detecting MINION expression in C2C12 myoblasts transduced with the indicated lentiviral shRNA constructs. An shRNA construct targeting the firefly (*Photinus pyralis*) luciferase gene was used as a negative control (Ctrl). After lentiviral infection and GFP sorting, the cells were expanded and kept in differentiation medium for 5 days. The two shRNA constructs targeting the MINION 3'UTR (U1/U2) were found to reduce MINION expression most efficiently. FIG. 14C shows representative Western blot for detecting MyoD1 and Desmine expression in control (Ctrl) or MINION$^{KD}$ C2C12 cells cultured in either growth medium (GM), or in differentiation medium (DM) for indicated number of days with indicated antibodies.

FIGS. 15A-15D show knockdown of MINION in primary myoblasts blocks myoblast fusion and multinucleated myotube formation. FIG. 15A is a set of MHC immunofluorescence images of control (Ctrl) and MINION$^{KD}$ primary myoblast-derived myofibers, formed after 4 days in differentiation medium. Nuclei were counterstained with DAPI. Scale bar: 100 µm. FIG. 15B is a bar graph showing quantification of differentiation index for FIG. 15A, calculated as the percentage of nuclei within MHC$^+$ cells among total nuclei in each field. ns=not significant. FIG. 15C is a bar graph showing quantification of fusion index for FIG. 15A, calculated as the percentage of nuclei within MHC$^+$ myotubes containing ≥2 nuclei among total nuclei in each field. Double asterisk: p<0.001. FIG. 15D is a bar graph showing quantification of the percentage of myotube numbers for the experiment done in FIG. 15A. Myotubes were binned by nuclear number as indicated, and the percentage of myotubes within each subgroup was calculated.

FIGS. 16A-16B are representative Western blots for detecting MINION expression in MINION$^{KD}$ cells after retroviral expression of untagged or C-terminally tagged MINION and culture in differentiation medium for 5 days. Retroviral vectors carrying full-length mouse MINION CDS (the coding sequence), C-terminally 3×FLAG-1×HA-tagged mouse MINION CDS and C-terminally 3×FLAG-1×HA-tagged human MINION ortholog CDS were used for reconstitution. A C-terminally 1×FLAG-tagged Nanoluc retroviral vector was used as negative control. The anti-FLAG antibody recognizes three tagged proteins at the correct size (FIG. 16A), while the anti- MINION antibody not only recognizes the mouse MINION protein (tagged and untagged) but also weakly recognizes the human MINION ortholog (FIG. 16B). Note: the pCI-GAR gateway retroviral vectors carrying tagged human and mouse MINION CDS inherited an extra start codon at the 5' end of and in-frame with the genuine start codon, giving rise to an extra band of slightly larger size (asterisk). FIG. 16C is a set of MHC immunofluorescence images of MINION$^{KD}$ C2C12 cells with exogenous expression of tagged NanoLuc, untagged mouse MINION, tagged mouse MINION and tagged human MINION ortholog after 5 days in differentiation medium. Nuclei were counterstained with DAPI. Scale bars: 100 µm.

FIG. 17A is a schematic diagram showing four retroviral vectors containing either intact mouse/human MINION CDS, or those with 1 bp frameshift (FS) mutations within the start codons. These single base pair mutations are predicted to disrupt the expression of full-length mouse/human MINION proteins without significantly altering RNA sequence. FIG. 17B is a set of MHC immunofluorescence images of MINION$^{KD}$ C2C12 cells with exogenous expression of constructs indicated in FIG. 17A, and following 5 days in differentiation medium. Nuclei were counterstained with DAPI. Scale bars: 100 µm.

FIG. 19A is representative Western blot showing MINION is undetectable in placenta and periplacental tissue from MINION$^{\Delta/+}$ and MINION$^{\Delta/\Delta}$ embryos. TA muscles with normal saline injection (NS; day 4) and cardiotoxin injection (CTX; day 4) were used as negative and positive controls, respectively. FIG. 19B is representative Western blot showing MINION is undetectable in soluble RANKL ligand-induced cell-cell fusion and osteoclast formation in the macrophage line Raw264.7. C2C12 cells cultured either in growth medium (GM), or in differentiation medium for 5 days (DM) were used as positive and negative controls respectively.

FIGS. 21A-21G show coexpression of MINION and Myomaker is sufficient to induce cell fusion in a heterologous system. FIG. 21A shows representative Western blot for detecting Myomaker expression in wild-type C2C12 myoblasts in GM, or in control (Ctrl) or MINION$^{KD}$ C2C12 myoblasts cultured under differentiation conditions (DM) for 3 days. FIG. 21B is a set of MHC immunofluorescence images of control (Ctrl) and MINION$^{KD}$ C2C12 myoblasts expressing Luciferase (Ctrl), MINION, or myomaker, after 5 days in differentiation medium. Nuclei were counterstained with DAPI. Scale bars: 100 µm. FIG. 21C shows representative Western blot for detecting Myomaker and MINION expression in cell lines shown in FIG. 21B. FIG. 21D shows representative Western blots for detecting Myomaker and MINION expression in 10T1/2 fibroblasts expressing Luciferase (Ctrl), Myomaker or MINION. FIG. 21E is a bar graph showing quantification of GFP$^+$ syncytia (defined as containing 4 or more nuclei) in fibroblasts expressing different combinations of proteins as indicated. Syncytia formation was scored 24 hours after seeding. FIG. 21F is a set of fluorescence images from cell mixing experiments using differentially labeled 10T1/2 fibroblasts. Cells were serially infected with retroviruses encoding the indicated combinations of MINION, Myomaker, or control (label omitted for simplicity). CellTrace Violet and CellTracker Deep Red dyes were used for labeling. The arrowheads indicate syncytia containing both Deep Red$^+$ cells and Violet$^+$ nuclei. The arrows indicate syncytia derived from Deep Red$^+$ cells only. Scale bars: 50 µm. FIG. 21G is a bar graph showing quantification of fusion in FIG. 21F (bottom panels), measured as % Deep Red$^+$ syncytia ($\geq$4 nuclei) containing $\geq$1 Violet$^+$ nucleus.

FIGS. 25A-25E show generation of a second Minion knockout allele by CRISPR/Cas9 gene editing. FIG. 25A shows a strategy for CRISPR/Cas9 mutagenesis of the gm7325/Minion locus using a dual sgRNA approach with two different sgRNAs (gRNA3 (SEQ ID NO:104) and gRNA4 (SEQ ID NO:105)). Gray box, Minion ORF; white box, non-coding exons; gRNA, single guide RNA; light gray box, new coding region after the 155 bp deletion; Fwd-2 (SEQ ID NO:106) and Rev-2 (SEQ ID NO:107), forward and reverse genotyping primers to detect the 155 bp deletion. FIG. 25B is a representative agarose gel picture of typical genotyping PCR results using E16.5 to E18.5 embryos from Minion$^{\Delta/+}$×Minion$^{\Delta/+}$ crosses. +/+: wild type (Minion$^{+/+}$); Δ/+: heterozygote (Minion$^{\Delta/+}$); Δ/Δ: Minion knockout homozygote (Minion$^{\Delta/\Delta}$). n=5 (26 E16.5-E18.5 embryos total). FIG. 25C shows representative photographs of unskinned Minion$^{\Delta/+}$ and Minion$^{\Delta/\Delta}$ E18.5 embryos. n=3. Scale bars: 1 mm. FIG. 25D shows a protein sequence alignment of the 84 aa full-length mouse Minion (Minion-FL) (SEQ ID NO: 102) and the predicted 74 aa truncated form (Minion-155KO) (SEQ ID NO: 108). The truncated form is predicted to contain only the N-terminal 18 aa of the original protein (in bold). FIG. 25E shows a summary of genotyping results of both late-stage embryos (E16.5 to E18.5) and adult mice from Minion$^{\Delta/+}$×Minion$^{\Delta/+}$ crosses.

FIG. 26A shows representative immunofluorescence images of non-somitic facial musculature from sagittal sections of E18.5 embryos with the indicated genotypes. Desmin staining is shown. Black box in histological image at left demonstrates the area shown at right in fluorescence images. FIG. 26B shows representative immunofluorescence images of non-somitic jaw and facial musculature on transverse sections from E19.5 embryos with the indicated genotypes. MHC and DAPI staining are shown. Two litters of embryos were examined, and 1-2 embryos of each genotype and in the same litter were compared in each experimental repeat. Scale bars, 1 mm for H&E images and 500 μm for immunofluorescence images.

FIG. 27A shows representative immunofluorescence images of Ctrl and Minion$^{KD}$ C2C12 myoblasts and myotubes after 3.5 days in DM. Left: Minion, MHC and DAPI are shown; Middle: grayscale images for Minion only; Right: grayscale images for control IgG. Insets marked by white dotted lines are magnified in FIG. 27B. n=2. FIG. 27B shows enlarged images of the insets in FIG. 27A. White arrowheads indicate the fused multinuclear myotubes and yellow arrows indicate unfused differentiating elongating myoblasts, both of which express Minion protein. FIG. 27C shows representative immunofluorescence staining of longitudinal sections of regenerating adult (10 week old) TA muscle 3 days post CTX injection. Left: Minion, Laminin and DAPI; Middle: Minion only (grayscale); Right: DAPI (grayscale). White arrowheads indicate nascent myotubes and yellow arrows indicate unfused differentiating elongating myoblasts, both of which express Minion protein. n=3. Scale bars: (FIGS. 27A-27B) 100 μm and (FIG. 27C) 30 μm.

FIG. 28A shows representative immunofluorescence images of cell-mixing between 10T1/2 fibroblasts and wild-type C2C12 myoblasts (1:2 ratio) after 3 days in differentiation medium. Differentiating myoblasts and myotubes are marked by MHC. 10T1/2 fibroblasts were infected with retrovirus expressing GFP and proteins of interest (left, NanoLuc control; middle, mouse Myomaker; right, mouse Minion). DAPI marks nuclei. Fibroblasts expressing Myomaker fused with wild-type differentiating myoblasts and myotubes to become large thick myotubes (white arrowheads), while fibroblasts expressing Minion failed to do so. White arrows indicate MHC-positive myotubes that are not fused to fibroblasts. n=2 (eight technical replicates each). 0.7 mm×0.7 mm fields are shown. FIG. 28B shows representative immunofluorescence images of cell mixing between 10T1/2 fibroblasts expressing Myomaker and C2C12 myoblasts after 3 days in DM. 0.7 mm×0.7 mm fields at ×20 magnification are shown. Control and Minion$^{KD}$ myoblasts were used. Differentiating myoblasts and myotubes are marked by MHC. 10T1/2 fibroblasts expressing Myomaker were labelled with CellTrace Violet dye before mixing. Fibroblasts expressing Myomaker fused with differentiating control myoblasts (white arrowheads), but failed to fuse to Minion$^{KD}$ myoblasts. n=2 (eight technical replicates each).

FIG. 29A shows that Minion-associated proteins were identified by affinity purification-MS analysis from day 3.5 differentiating C2C12 myoblasts expressing FLAG-tagged Minion (see Table 5), and were grouped into protein classes using Panther (Mi et al. PANTHER version 11: expanded annotation data from Gene Ontology and Reactome pathways, and data analysis tool enhancements. *Nucleic acids research* 45, D183-D189, 2017). The number of significantly enriched proteins in each class is indicated. n=3. FIG. 29B shows a representative Western blot confirmation of an example hit. Minion and Gapdh serve as positive and negative controls respectively.

FIG. 30A shows representative fluorescence images of 10T1/2 fibroblasts co-overexpressing Minion and Myomaker. F-actin (Alexa546-Phalloidin) and DAPI staining are shown. White arrowheads point to the boundaries of multinuclear cells. n=2 (six technical replicates each, five fields each). FIG. 30B shows representative fluorescence images of 10T1/2 fibroblasts co-overexpressing Minion and Myomaker and treated for 24 h with DMSO control or the actin polymerization inhibitors latrunculin B (0.1 μM) or cytochalasin D (0.3 μM) (Bothe & Baylies *Drosophila* myogenesis. *Curr. Biol.* 26, R786-R791, 2016). n=2 (six technical replicates each, five fields each). Scale bars, 100 μm (FIGS. 30A-30B). FIG. 30C shows a proposed model for Minion and Myomaker-induced cell-cell fusion. We suggest that Minion and Myomaker have separable roles in the fusion process; Myomaker mediates pre-fusion pore events such as cell-cell recognition and/or, membrane apposition, whereas Minion mediates later fusion pore formation, at least in part via induction of cytoskeletal rearrangements.

DETAILED DESCRIPTION

Figure 1A:
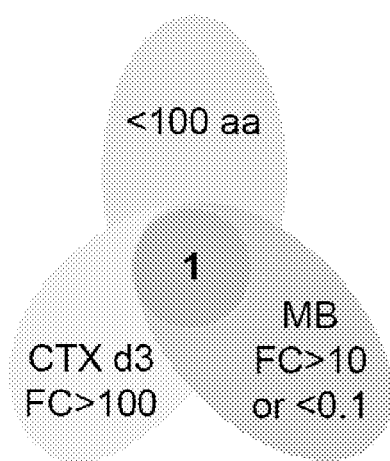

The present invention is based, at least in part, on the findings that microprotein MINION is required for fusion of muscle progenitor cells and skeletal muscle development, and that heterologous co-expression of MINION and Myomaker is sufficient to induce rapid and homogeneous cellular fusion even in non-muscle cells. The human ortholog of mouse MINION has not been reported before. As described herein, the present inventors identified the amino acid and cDNA sequences of human ortholog of MINION and found human MINION protein also has fusogenic activity, suggesting an evolutionarily conserved role for MINION protein in cell fusion. Accordingly, provided herein are compositions, methods, and therapeutic uses related to fusogenic protein MINION.

Definitions

The terms "human MINION protein" and "human MINION microprotein" are used interchangeably herein (also known as microprotein inducer of fusion, Gm7325, ESGP, embryonic stem cell and germ cell specific protein, or EG653016) and refer to a protein having the amino acid sequence of SEQ ID NO: 1 (isoform 1) or SEQ ID NO: 3 (isoform 2). A "human MINION polypeptide" refers to a naturally occurring human MINION microprotein (e.g., the protein of SEQ ID NO: 1 or SEQ ID NO: 3) or a variant thereof. The protein and cDNA sequences of human MINION isoform 1 or isoform 2 are provided in Table 1 below.

TABLE 1

MINION amino acid and nucleotide sequences

| SPECIES | ISOFORM | SEQ ID NO | SEQUENCE |
| --- | --- | --- | --- |
| *Homo sapiens* | MINION isoform 1 amino acid | 1 | MPTPLLPLLLRLLLSRLLLPAARLARQYLLPLLRRLARRLGSQ DMREALLGCLLFILSQRHSPDAGEASRVDRLERRERLGPQK |
| *Homo sapiens* | MINION isoform 1 cDNA | 2 | gagactgattctgagcagcagactgcccggcactgactcactg gccctgccATGCCCACGCCACTGCTCCCGCTGCTGCTTCGATT GCTGCTGTCCCGCCTGCTGCTGCCTGCTGCCCGCCTGGCCCGC CAATACCTCCTGCCCCTGCTGCGCCGATTGGCCCGCCGCCTGG GCTCCCAGGACATGCGAGAGGCTTTGCTGGGCTGTCTGCTGTT CATTCTCAGCCAGCGACACTCGCCAGACGCTGGGGAGGCCTCA AGAGTGGACCGCCTGGAGAGGAGGGAGAGGTTAGGCCCCCAAA AGTGAggccacaagtcctggcagcagctgtatccacaaaatgc tacttaggagtaggataaGActggcaccagcactgaccgaagc ctgcccagtggacagaagatatagtgagggagtgcatgagagg gatctgccacagacatgcctctccactcccaacagaaatgtct actggaagaatgcatgcatctagcacaaaactgattattgccc ctctgtcctccagcagacctcccaaagaccactcctaatcacc tctggcctcaggcgggaggggaactaacacccacccacccctg ccctccctgcaaatgggaacatcaaggacccagtgcttaactg agggacaagtgacaatttagcagagaggcaagatttgaatcca gactgtatccagactcaggacctaccttaaaataatatctgag agcCtatggaggcagacctgcctgcaaagcccagcactcagca agtgctcaataaatatttgatttgaattattc (ORF in uppercase) |
| *Homo sapiens* | MINION isoform 2 amino acid | 3 | MPTPLLPLLLRLLLSCLLLPAARLARQYLLPLLRRLARRLGSQ DMREALLGCLLFILSQRHSPDAGEASRVDRLERRERLGPQK |
| *Homo sapiens* | MINION isoform 2 cDNA | 4 | gagactgattctgagcagcagactgcccggcactgactcactg gccctgccATGCCCACGCCACTGCTCCCGCTGCTGCTTCGATT GCTGCTGTCCTGCCTGCTGCTGCCTGCTGCCCGCCTGGCCCGC CAATACCTCCTGCCCCTGCTGCGCCGATTGGCCCGCCGCCTGG GCTCCCAGGACATGCGAGAGGCTTTGCTGGGCTGTCTGCTGTT CATTCTCAGCCAGCGACACTCGCCAGACGCTGGGGAGGCCTCA AGAGTGGACCGCCTGGAGAGGAGGGAGAGGTTAGGCCCCCAAA AGTGAggccacaagtcctggcagcagctgtatccacaaaatgc tacttaggagtaggataatcctggcaccagcactgaccgaagc ctgcccagtggacagaagatatagtgagggagtgcatgagagg gatctgccacagacatgcctctccactcccaacagaaatgtct actggaagaatgccagcatctagcacaaaactgattattgccc ctctgtcctccagcagacctcccaaagaccactcctaatcacc tctggcctcaggcgggaggggaactaacacccacccacccctg ccctccctgcaaatgggaacatcaaggacccagtgcttaactg agggacaagtgacaatttagcagagaggcaagatttgaatcca gactgtatccagactcaggacctaccttaaaataatatctgag agcttatggaggcagacctgcctgcaaagcccagcactcagca agtgctcaataaatatttgatttgaattattc (GenBank Accession No. NM_001315494.1; ORF in uppercase) |
| *Mus musculus* | MINION isoform 1 amino acid | 5 | MPVPLLPMVLRSLLSRLLLPVARLARQHLLPLLRRLARRLSSQ DMREALLSCLLFVLSQQQPPDSGEASRVDHSQRKERLGPQK (GenBank Accession No. NP_001170939.1) |
| *Mus musculus* | MINION isoform 1 cDNA | 6 | gaaattgattctgagcagactgactggtgagagctgccactgg ccggttagaactggtgagcaggagggcaagaagttcaggcttc aggtgcaggtcctgccATGCCCGTTCCATTGCTCCCGATGGTG CTTCGATCGCTGCTGTCCCGCCTGCTGCTGCCTGTTGCCCGCC TGGCCCGGCAGCACCTCCTGCCCTTGCTGCGCCGGCTGGCCCG CCGACTGAGCTCCCAAGACATGAGAGAGGCTCTGCTGAGCTGT CTGCTCTTTGTCCTCAGCCAGCAACAGCCACCGGATTCTGGAG AGGCCTCCAGAGTGGACCACTCCCAGAGGAAGGAGAGATTGGG CCCCCAGAAGTGAggccacgggtcctggaaacagcaacgccca tcaaagtacttaggagccggttagtccaggcgtcggtccgcac gcacgggcatggacggcagactgcccagtgggcgaagacagtc cgggctgagtgcaagagggctctgacctgaacagacccactcc cctagctcctagcaggctacagattgtgagattgaccatcctc tctgcagctccctctgccttatctctggcctccagggtggacc tgcaaatgcgggtatcaaggtcagttaagagatgatgatcact |

TABLE 1-continued

MINION amino acid and nucleotide sequences

| SPECIES | ISOFORM | SEQ ID NO | SEQUENCE |
|---|---|---|---|
| | | | tagactcaagacaatttagctaagaggtggtatttaaatccaa<br>actgtcccgtctaccttaaaattataagccatgatcccgttaa<br>agaatgagtactacaaagatggtacgcagcaggtagtcaataa<br>acgaggacagtgtgagttattgg<br>(GenBank Accession No. NM_001177468.1; ORF in uppercase) |
| Mus musculus | MINION isoform 2 amino acid | 7 | MPEESCTVKLIQLKTGEYRGAGPAMPVPLLPMVLRSLLSRLLL<br>PVARLARQHLLPLLRRLARRLSSQDMREALLSCLLFVLSQQQP<br>PDSGEASRVDHSQRKERLGPQK<br>(GenBank Accession No. NP_001170941.1) |
| Mus musculus | MINION isoform 2 cDNA | 8 | agtccccaccaccaccagccctgggctccatcccatctgtgat<br>aacagtgagtgaactccttaaccagattcATGCCAGAAGAAAG<br>CTGCACTGTAAAACTAATCCAGTTGAAAACTGGGGAGTACAGA<br>GGTGCAGGTCCTGCCATGCCCGTTCCATTGCTCCCGATGGTGC<br>TTCGATCGCTGCTGTCCCGCCTGCTGCTGCCTGTTGCCCGCCT<br>GGCCCGGCAGCACCTCCTGCCCTTGCTGCGCCGGCTGGCCCGC<br>CGACTGAGCTCCCAAGACATGAGAGAGGCTCTGCTGAGCTGTC<br>TGCTCTTTGTCCTCAGCCAGCAACAGCCACCGGATTCTGGAGA<br>GGCCTCCAGAGTGGACCACTCCCAGAGGAAGGAGAGATTGGGC<br>CCCCAGAAGTGAggccacgggtcctggaaacagcaacgcccat<br>caaagtacttaggagccggttagtccaggcgtcggtccgcacg<br>cacgggcatggacggcagactgcccagtgggcgaagacagtcc<br>gggctgagtgcaagagggctctgacctgaacagacccactccc<br>ctagctcctagcaggctacagattgtgagattgaccatcctct<br>ctgcagctccctctgccttatctctggcctccagggtggacct<br>gcaaatgcgggtatcaaggtcagttaagagatgatgatcactt<br>agactcaagacaatttagctaagaggtggtatttaaatccaaa<br>ctgtcccgtctaccttaaaattataagccatgatcccgttaaa<br>gaatgagtactacaaagatggtacgcagcaggtagtcaataaa<br>cgaggacagtgtgttgttattgg<br>(GenBank Accession No. NM_001177470.1; ORF in uppercase) |
| Rattus norvegicus | MINION cDNA | 9 | MPVPLLPLMLRSLLSRLLLPVARLARQHLLPLLRRLARRLSSQ<br>DVREALLSCLLFVLSQQQPPDSGETSRVDHSQRKERLGPRK |
| Rattus norvegicus | MINION cDNA | 10 | ggtcctggtcctgccATGCCCGTTCCACTGCTCCCGTTGATGC<br>TTCGATCGCTGCTATACGCCTGCTGCTGCCTGTTGCCCGCCT<br>GGCCCGTCAGCACCTCCTGCCCTTGCTGCGCCGTCTGGCCCGC<br>CGACTGAGCTCCCAAGACGTGAGAGAGGCTTTGCTGAGCTGTC<br>TGCTGTTTGTCCTCAGCCAACAACAGCCACCGGATTCTGGAGA<br>GACCTCTAGAGTGGACCACTCCCAGAGGAAGGAGAGATTGGGT<br>CCCCGGAAGTGA<br>(ORF in uppercase) |
| Felis catus | MINION cDNA | 11 | MPAPLLPLLLRTLMSRLLLPATRLARRHLLPLLRRLARRLGSQ<br>DVREALLGCLLFILSQSRPPDAEEVSRVAGQERRERLAPPK |
| Felis catus | MINION cDNA | 12 | ATGCCCGCTCCACTGCTCCCACTGCTGCTTCGAACCCTGATGT<br>CCCGCTTGCTGCTGCCTGCCACCCGCCTGGCCCGCCGGCACCT<br>CCTGCCCCTCCTGCGCCGACTGGCCCGCCGCCTGGGCTCGCAG<br>GATGTTCGAGAAGCTTTGCTGGGCTGTCTGTTGTTCATCCTCA<br>GCCAGAGCCGCCCGCCCGACGCTGAGGAGGTCTCCAGAGTGGC<br>TGGCCAGGAGAGGAGGGAGAGGCTAGCTCCCCCAAAATGA<br>(ORF in uppercase) |
| Sus scrofa | MINION amino acid | 13 | MPAPLLPLLLRTLLARLLLPAARLARRHLLPLLRRLARRLGSQ<br>DMREALLGCLVFLLSQRHPPDDAAAAGEASRVARLERRERIVS<br>QK |
| Sus scrofa | MINION cDNA | 14 | ATGCCCGCTCCGCTGCTCCCGCTGCTGCTGCGAACGCTGCTGG<br>CCCGCCTGCTGCTGCCCGCTGCCCGCCTGGCCCGTCGGCACCT<br>CCTGCCTCTGCTGCGCCGGCTGGCCCGCCGCCTGGGCTCCCAG<br>GATATGCGAGAGGCTTTACTGGGCTGTCTGGTGTTCCTCCTCA<br>GCCAGAGACACCCGCCAGATGATGCCGCTGCTGCCGGGGAGGC<br>CTCCAGAGTGGCCCGCCTGGAGAGGAGGGAGAGGATAGTTTCT<br>CAAAAA<br>(ORF in uppercase) |
| Macaca mulatta | MINION amino acid | 15 | MPAPLFPLLLRLLLSRLLLPVARLARQYLLPLLRRLARRLGSQ<br>DMREALLGCLLFILSQRHSPDAGEASRVDRLERRERLGPQK |

A "mouse MINION polypeptide" refers to a naturally occurring mouse MINION protein or a variant thereof. Two naturally occurring mouse MINION protein isoforms (SEQ ID NO: 5 and SEQ ID NO: 7) have been reported. The amino acid and nucleotide sequences of mouse MINION isoforms are shown in Table 1. Table 1 also provides MINION sequences of other species, e.g., rat (*R. norvegicus*), monkey (*M. mulatta*), cat (*F. catus*), and pig (*S. scrofa*).

The term "a MINION polypeptide" is used to refer collectively to all naturally occurring isoforms of a MINION protein of any species, or a variant thereof. For example, a "MINION polypeptide" can be any MINION polypeptide listed in Table 1 or a variant thereof.

Myomaker (also known as Tmem8c or Tmem226) is a transmembrane protein specifically expressed in muscle cells. A "human Myomaker polypeptide" refers to a naturally occurring human Myomaker protein (e.g., the protein of SEQ ID NO: 16) or a variant thereof. Human Myomaker protein and mRNA sequences are provided in Table 2.

TABLE 2

Myomaker amino acid and nucleotide sequences

| SPECIES | ISOFORM | SEQ ID NO | SEQUENCE |
|---|---|---|---|
| *Homo sapiens* | Myomaker amino acid | 16 | MGTLVAKLLLPTLSSLAFLPTVSIAAKRRFHMEAMVYLFTLFFVALHHACNGPG LSVLCFMRHDILEYFSVYGTALSMWVSLMALADFDEPKRSTFVMFGVLTIAVRI YHDRWGYGVYSGPIGTAILIIAAKWLQKMKEKKGLYPDKSVYTQQIGPGLCFGA LALMLRFFFEDWDYTYVHSFYHCALAMSFVLLLPKVNKKAGSPGTPAKLDCSTL CCACV (GenBank Accession No. NP_001073952.1) |
| *Homo sapiens* | Myomaker cDNA | 17 | gccctgccca aagggagctg gccttccac ttcgtgctcc tgtgctgggg acctgggaca ccagcaccct ccccacccca gccagtgctt tcctcctggc ccatggggac gctggtggcc aagctgctcc tgcccaccct cagcagcctg gccttcctcc ccactgtcag catcgcggcc aagaggcggt tccacatgga ggccatggtc tacctcttca ccctgttctt cgtggcgctc caccatgcct gcaatggacc cggcttgtct gtgctgtgct tcatgcgtca cgacatcctg gagtatttca gtgtctacgg gacagccctg agcatgtggg tctcgctgat ggcactggcc gacttcgacg aacccaagag gtcaacattt gtgatgttcg gcgtcctgac cattgctgtg cggatctacc atgaccgatg gggctacggg gtgtactcgg gccccatcgg cacagccatc ctcatcatcg cggcaaagtg gctacagaag atgaaggaga agaagggcct gtacccagac aagagcgtct acacccagca gataggcccc ggcctctgct tcggggcgct ggccctgatg ctacgcttct tctttgagga ctgggactac acttatgtcc acagcttcta ccactgtgcc ctggctatgt cctttgttct gctgctgccc aaggtcaaca agaaggctgg atccccgggg accccggcca agctggactg ctccaccctg tgctgtgctt gtgtctgatg ctgcgcccag cccggctctg agccctgcc ctccccagct cacacttg (GenBank Accession No. NM_001080483.2) |
| *Mus musculus* | Myomaker isoform 1 amino acid | 18 | MGTVVAKLLLPTLSSLAFLPTVSIATKRRFYMEAMVYLFTMFFVAFSHACDGPG LSVLCFMRRDILEYFSIYGTALSMWVSLMALADFDEPQRSTFTMLGVLTIAVRT FHDRWGYGVYSGPIGTATLIIAVKWLKKMKEKKGLYPDKSIYTQQIGPGLCFGA LALMLRFFFEEWDYTYVHSFYHCALAMSFVLLLPKVNKKAGNAGAPAKLTFSTL CCTCV (GenBank Accession No. NP_079652.1) |
| *Mus musculus* | Myomaker isoform 1 cDNA | 19 | gagcacttaa gccctccttg tgggtgctgc cacagctgcg gtcagggctg ctggagaagc aaagaagtgg gctcttttc ttcctgccct ggagaccagg ggggccttta ccaccttctc cccagtcagt gccttcctcc tggtccatgg ggacagttgt agccaaactg ctcctgccta ccctcagcag cctggccttc ctcccgacag tgagcatcgc taccaagagg cgtttctaca tggaggccat ggtctacctc ttcaccatgt tctttgtggc gttctcccat gcctgtgatg ggcctggttt gtctgtgctg tgcttcatgc gccgtgacat tctggagtac ttcagcatct atggaacagc cctgagcatg tgggtctccc tgatggcact ggccgacttt gatgaacccc agagatcgac cttcacaatg cttggcgtcc ttaccatcgc tgtgcggact tttcatgacc gctggggtta cggggtatac tccggtccca taggcacggc caccctcatc attgctgtaa agtggctgaa gaagatgaaa gagaagaagg gcctgtaccc cgacaagagc atctacaccc agcagatagg ccccggcctg tgctttgggg ccctggccct gatgcttcga ttcttctttg aggaatggga ttacacctac gtccacagct tctaccactg tgccctggcc atgtcctttg tcctgctgct gcccaaggtc aacaagaagg ctgggaacgc aggggccccc gccaagctga ccttctccac cctctgctgc acttgtgtct gactatacc ccccacacac acacacacac caggcccctg ccttcctgcc tggcagtcct gctgtctctc ccaaggtact tcctatactt tgttatgcgg cctgtacatg agaaatggtc ttctctacac cccaagagac cagcaggcct gctgcattct gctgagtgct gcttagggac ccactggttc tgtgttcacc agttgcttca ctctgttcag gaaaaaaaag aactttatcc cccaaggcct cacaaccata ggtgtgcctg gcagagaacc ctagaccagt aaatacccag cagcatgcag ggttatctat ttcccaggtc ctgcctgtca gaatcgtctg ctttccctag gaaactggga ttgccctttt aaccccctgcc caggctctga aagctctcca cttaggaagc tggagccagc gaacctttgca tacccctgcc tgagtcccat cccttctgca ggttttcgat caagccattc acagtaaact cttgatcagc cactagtcat tagcttcgcc taacatacat tctagttcct ggaaaaaaaa aaaaaaaaaa aaaaaaaaaa aaaaaaaaaa a (GenBank Accession No. NM_025376.3) |

TABLE 2-continued

Myomaker amino acid and nucleotide sequences

| SPECIES | ISOFORM | SEQ ID NO | SEQUENCE |
|---|---|---|---|
| Mus musculus | Myomaker isoform 2 amino acid | 20 | MGKGFSHACDGPGLSVLCFMRRDILEYFSIYGTALSMWVSLMALADFDEPQRST FTMLGVLTIAVRTFHDRWGYGVYSGPIGTATLIIAVKWLKKMKEKKGLYPDKSI YTQQIGPGLCFGALALMLRFFFEEWDYTYVHSFYHCALAMSFVLLLPKVNKKAG NAGAPAKLTFSTLCCTCV (GenBank Accession No. NP_001153074.1) |
| Mus musculus | Myomaker isoform 2 cDNA | 21 | atcagcactt gcttgggggg aatctaaggg cttcctcttt tatggagaga cagggtcca ggataaaagg ctcctatgca aagactggca taggaatgtg tacactttca gtcagtcatg ggcaaaggtt tctcccatgc ctgtgatggg cctggtttgt ctgtgctgtg cttcatgcgc cgtgacattc tggagtactt cagcatctat ggaacagccc tgagcatgtg ggtctccctg atggcactgg ccgactttga tgaacccag agatcgacct tcacaatgct tggcgtcctt accatcgctg tgcggacttt tcatgaccgc tggggttacg gggtatactc cggtcccata ggcacggcca ccctcatcat tgctgtaaag tggctgaaga agatgaaaga agaagaaggc ctgtaccccg acaagagcat ctacacccag cagataggcc ccggcctgtg ctttggggcc ctggccctga tgcttcgatt cttcttttgag aatgggatt acacctacgt ccacagcttc taccactgtg ccctggccat gtcctttgtc ctgctgctgc ccaaggtcaa caagaaggct gggaacgcag ggccccgc caagctgacc ttctccaccc tctgctgcac ttgtgtctga ctataccccc cacacacac acacacacca ggcccctgcc ttcctgcctg gcagtcctgc tgtctctccc aaggtacttc ctatactttg ttatgcggcc tgtacatgag aaatggtctt ctctacaccc caagagacca gcaggcctgc tgcattctgc tgagtgctgc ttagggaccc actggttctg tgttcaccag ttgcttcact ctgttcagga aaaaaagaa ctttatcccc caaggcctca caaccatagg tgtgcctggc agagaaccct agaccagtaa atacccagca gcatgcaggg ttatctattt cccaggtcct gcctgtcaga atcgtctgct ttccctagga aactggatt gcccttttaa cccctgccca ggctctgaaa gctctccact taggaagctg gagccagcga accttgcata cccctgcctg agtcccatcc cttctgcagg ttttcgatca agccattcac agtaaactct tgatcagcca ctagtcatta gcttcgccta acatacattc tagttcctgg aaaaaaaaa aaaaaaaaa aaaaaaaaaa aaaaaaaaa (GenBank Accession No. NM_001159602.1) |
| Rattus norvegicus | Myomaker amino acid | 22 | MGLHLRSQLLPLRPGHVLRPAAAQGQQEGWERRGPRQADLLHSLLHLCLTVAPL LQAPAFLSGSPAVSPGILPTLSQWNVHEEWPPLHPERPAGLLQSAKCCLGTHEF CVHQLLHSIQEKKERELYPPRLHNHRCALQSPRPVSIGPKSQPSSVHNSSIRVI YFPGPACQDCLPFLGNWDCPFYPCPGPESSQFRELDPVSPVPVWTQAWCPCLSP IPSAVFRSSHSQ (GenBank Accession No. NP_001127989.1) |
| Rattus norvegicus | Myomaker cDNA | 23 | gcatcagctg ttggaccttc tccatgtgtc actgggcaca tgctgcctca gagcacttaa gccctcctcg tgggcgctgc cacagctgcg gcaagggttg ctgaagaaga gaagtgggct ctattttcc ctgccctgga gaccaaggag gccttcacta cctcctcccc tgccagtgcc ttcttcctgg cccatgggga cagttgtagc caaactgctc ctgcctaccc tcagcagcct ggccttcctc cccacagtga gcattgctac caagcggcgt ttttacatgg aggccatgat ctatctcttc accatgttct tgtggcgtt ctcccatgcc tgcgacgggc ctggcttgtc cgtgctatgc ttcatgcgcc gtgatattct ggagtacttc agcatctatg gacagccct gagcatgtgg gtctccctga tggcactggc cgactttgat gaaccccaga gatcaacctt cacgatgttt ggtgtcctta ccattgccgt gcggacttac catgaccact ggggctacgg ggtgtactct ggtcccatag gcaccgccac cctcatcatt gcagtaaagt ggctgaagaa gatgaaagag aagaagggtc tgtaccctga caagagcatc tacacccagc agataggtcc cggcctctgc tttggggcc tggccctgat gcttcgcttc ttctttgagg aatgggatta cacctacgtt cacagcttct accactgcgc cctggccatg tccttcgtcc tgctgctgcc caaggtcaac aagaaggctg gaacgcagg gaccccgcc aagctgacct ctccactctg ctgctgcact tgtgtctgac agtagcccc cccctgcctt cctgtctggc agccctgctg tctctcccgg gatacttcct acactttccc agtggaatgt ccatgaggaa tggcctcctc tgcaccccga gaccagca gggctgctgc agtcggcgaa gtgctgctta ggacccacg aattctgtgt tcaccagttg cttcactcta ttcaggaaaa aaagagaga gaactttatc ccccaaggct gcataaccat aggtgtgcct tgcagaccc taggccagtc agtattggcc ccaagtcaca acccagcagt gtacacaaca gcagcatacg ggttatctat ttcccaggcc ctgcctgcca ggattgtctg ccttttcctag gaaactggga ttgcccttc tacccctgcc caggccctga agctcccaga tttcgggagc tggacccagt gagcccagtt ccagtctgga cccaggcttg gtgccctgc ctgagtccca tccttcagc agtttttcgg tcgaccact cacagtaaac tcttgatcag tcactagt (GenBank Accession No. NM_001134517.1) |

TABLE 2-continued

Myomaker amino acid and nucleotide sequences

| SPECIES | ISOFORM | SEQ ID NO | SEQUENCE |
|---|---|---|---|
| *Felis catus* | Myomaker isoform 1 amino acid | 24 | MGTLVAKLLLPTLSSLAFLPTVSIAAKRRFHMEAMVYLFTMFFVAFHHACNGPG LSVLCFMRHDVLEYFSVYGTALSMWVSLMALADFDEPKRSTFVMFGVLTIAVRI YHDRWGYGVYSGPIGVAVLVIATKWLQLMKEKKGLYPDKSVYTQQIGPGLCFGA LALMLRFFFEDWDYTYVHSFYHCALAMSFVLLLPKVNKKAGSAGPPAKLNCPAL CCACV<br>(GenBank Accession No. XP_006939684.1) |
| *Felis catus* | Myomaker isoform 1 cDNA | 25 | tcggagcccc caccgaacgg agcaggcctc gtcccttccg tgttctctgc<br>cctggggacc cgggcggccc gcaccctccc ctcctcccca accggcgccc<br>tcctccctgg cccatgggga cgctcgtggc aaagctgctc ctcccacccc<br>tcagcagcct ggctttcctc cccacggtca gcatcgctgc caagcgccgc<br>ttccacatgg aggccatggt ctacctgttc accatgttct tcgtggcgtt<br>ccaccacgcc tgcaacgggc ccggcctgtc agtcctctgc ttcatgcgcc<br>acgacgtcct ggagtacttc agcgtctacg ggacagcgct gagcatgtgg<br>gtctcactga tggcgctggc cgacttcgac gaacccaaga ggtcgacctt<br>tgtgatgttt ggcgtcctga ccatcgcggt ccggatctac cacgaccgct<br>ggggctatgg cgtgtactcg ggccccattg gcgtggctgt ccttgtcatc<br>gccaccaagt ggctgcagct catgaaggag aagaagggtc tgtacccga<br>caagagcgtc tacacccagc agataggccc cggcctctgt ttcggggcgc<br>tggccctcat gttacgattc ttctttgagg attgggatta cacctacgtg<br>cacagttttct accactgcgc gctggccatg tcctttgtcc tcctgctgcc<br>caaggtcaac aagaaggccg gaagcgcggg ccccccgcc aagctgaact<br>gccccgccct ctgctgtgct tgcgtctgac cgcgcgccgc gcccgccccc<br>tgccccctgc cagcccctgc cctgccgcat ctcccgcctg cggagagacc<br>cccatggccc ccccccccgg ctctgagcac ccaggagaaa tgtctcccct<br>cagagggatt tggggagcat cctgccaagg ctgctggga gcccacttac<br>taggtttcta cggagcacaa accaccgtgc tggaaggaaa aggacttcct<br>gccccgctcc tgctccccca cagtcatggc cagtctgcgt ccgcaggacc<br>ccacagccaa catgggtccc ccaccccgt cccccttcc tcctcaccca<br>gccacaaagg gactctgccc atgcccccct cacaacaccc gtctcctcct<br>ggaccctggt tgtcaccgct tctgtcctgt gccctcgggc tctgagcaga<br>cccgtgtagg aagccaaggc cagtggggac cggctctgtc caggcctgct<br>ggccgtccct ccagccgggt ccctgaatca agccctgtca gttacggcag<br>cccacaggaa gctcctcagc ccttgacctt cccgtgtgcc agaggccgta<br>tgatcatcgc ttcatctaat tcgtgaaaca agtctgcatt aaaggatgat<br>cactcccttc tacagacaga agcccgagc caggcccg ccgccaccaa<br>gcccgccccc tcgctgtgca gccgcccacg ggctgggcgc gagcacctgt<br>gttggccctt cgagcggctc caccctgggc taacggccag cgtgggaagg<br>gggtctgggc ccagggacac ccgcgcgag gccagcgggc ccggagccgg<br>gcgcacgggg caggcttgcg gcagcgctga gggagggcgg ccggctcccg<br>cctacagccc gtctgtgctg ggccccgcga gggtgggggc cggcctccca<br>gacatcacct cacaaacctg agcctcccca gcagccccag cccaccccag<br>cttcccgaac gatgtgggca catctgtcag gcaggaagtt acctacacct<br>gtctggggcc cgttttgtgt ttccagacg tgcacccca cccccaccgc<br>acgggcggc cccttatttg tcctgaagtc acctcttgct ccctcaggg<br>ggccgggaga gagctgggga caaggctggc ccctcggcga ggcaccccg<br>gtctgtcggc ctccctgact gtccagaggt cccacgcgtg gggcccggac<br>gcccacagtc tcactctggc tcagcccctt cctgagccta cagactggat<br>gacagagcag cctctgggca gctcgcacgg gctcggagtc ctggccgggc<br>cccggggagc aggcctcagc ctcgctctgc ttcccagttg aggaagctga<br>gcccacagct tcggggtcgt cctcccagac ggacatgtcc ccgcatcccc<br>cgcccggcgc agggacgggc agaagccgct tccgttggct tctggtccgg<br>ttgaggggtg tgcacacaca ggtgcccgct cacaccgtga agagataggg<br>cccccctggaa acagcatcgt cctgtccggc ctgtctccca gctccgcgag<br>gggagacacc gggcaggaag gaaagcgaag gctgtggggg ccacgcgggg<br>ggcccgcggg catcactctg gaagcaggcc tctgccagtc gcctccctcc<br>ccgtcacctc cctccatcc cctccccgt gcccccccca cacacacacc<br>cgacgagcac atcccagctc ccagctccgc ggcagcagat ggaaagttgg<br>aggccgcggg atgctcctga gcaggagga ggtgaggggc cggccaagag<br>cgttaaggac catactaaca ggctactcac tgcggccacg ctgatttatg<br>aggccgtctg ggagcccagc caagtctgta agtcatggac aattaggagg<br>ctcgctccag ccctcagccc cgtccgcctc tggggtctta ggccccaccgc<br>gcccctcctc agcagggtca gcaccgtgga accccacgg tgcagatagg<br>gacacggagg gccgggaggc cggcggccgg ccccggtgac ttggacactg<br>ggtgctgagc ggtggctgtg ccagggtct gactcctaac cctagcggca<br>tcttcctctg cttccaaggc tcactttgac atcttgggg ctccagccaa<br>gggccgtgg ggggagtgcc cgggaggggg acagaaagag aagaggacac<br>ttggaacctc cagccctaca cctagagact aacaaggaag aaaagaagtc<br>tcatggcctt cagaccaaac acctctgagt cccagtgtcc tcgagcccgg<br>ggccttcgtg ccctacaatc cagcagtcat ggcatccggt gccaggaggg<br>acctccgagg ccccccccag accccctgg ggctctggac gggactcacc |

TABLE 2-continued

Myomaker amino acid and nucleotide sequences

| SPECIES | ISOFORM | SEQ ID NO | SEQUENCE |
|---|---|---|---|
| | | | tccagccaga tctgatgagg gaagcctggg tcccgactcc agcgtgcgcc tggaagccga gcccgagatg atggcagccc cagagcagcc tgtgcagtag aacttgcttt aatgatggag gcgaggcggg ggcgcccggg gggct (GenBank Accession No. XM_006939622.2) |
| *Felis catus* | Myomaker isoform 2 amino acid | 26 | MGTLVAKLLLPTLSSLAFLPTVSIAAKRRFHMEAMVYLFTMFFVAFHHACNGPG LSVLCFMRHDVLEYFSVYGTALSMWVSLMALADFDEPKRSTFVMFGVLTIAVRI YHDRWGYGVYSGPIGVAVLVIATKWDWDYTYVHSFYHCALAMSFVLLLPKVNKK AGSAGPPAKLNCPALCCACV (GenBank Accession No. XP_011287016.1) |
| *Felis catus* | Myomaker isoform 2 cDNA | 27 | tcggagcccc caccgaacgg agcaggcctc gtcccttccg tgttctctgc cctggggacc cgggcgggcc gcaccctccc ctcctcccca accggcgcc tcctccctgg cccatgggga cgctcgtggc aaagctgctc ctccccaccc tcagcagcct ggctttcctc cccacggtca gcatcgctgc caagcgccgc ttccacatgg aggccatggt ctacctgttc accatgttct tcgtggcgtt ccaccacgcc tgcaacgggc ccggcctgtc agtcctctgc ttcatgcgcc acgacgtcct ggagtacttc agcgtctacg gacagcgct gagcatgtgg gtctcactga tggcgctggc cgactcgac gaacccaaga ggtcgacctt tgtgatgttt ggcgtcctga ccatcgcggt ccggatctac cacgaccgct ggggctatgg cgtgtactcg ggccccattg gcgtggctgt cctcgtcatc gccaccaagt gggattggga ttacacctac gtgcacagtt tctaccactg cgcgctggcc atgtcctttg tcctcctgct gcccaaggtc aacaagaagg ccggaagcgc ggggccccc gccaagctga actgccccgc cctctgctgt gcttgcgtct gaccgcgcgc cgcgcccgcc ccctgccccc tgccagcccc tgccctgccg catctcccgc ctgcggagag accccatgg ccccccccc cggctctgag cacccaggag aaatgtctcc cctcagaggg atttggggag catcctgcca agggctgctg ggagcccact tactaggttt ctacggagca caaaccaccg tgctggaagg aaaaggactt cctgccccgc tcctgctccc ccacagtcat ggccagtctg cgtccgcagg accccacagc caacatgggt cccccaccc cgtcccctt tcctcctcac ccagccacaa agggactctg cccatgcccc cctcacaaca cccgtctcct cctggaccct ggttgtcacc gcttctgtcc tgtgccctcg ggctctgagc agacccgtgt aggaagccaa ggccagtggg gaccggctct gtccagcct gctggccgtc cctccagccg ggtccctgaa tcaagccctg tcagttacgg cagcccacag gaagctcctc agcccttgac cttcccgtgt gccagaggcc gtatgatcat cgcttcatct aattcgtgaa acaagtctgc attaaaggat gatcactccc ttctacagac agaagcccga ggcgcaggt ccatgggtg cccgaggcct cgagcaggcg agtgcagacc cgggccaggc ccgccgccac caagcccgcc cctcgctgt gcagccgccc acgggctggg cgcgagcacc tgtgttggcc cttcgagcgg ctccaccctg ggctaacggc cagcgtggga aggggtctg ggcccaggga cacccgcgcg gaggccagcg ggcccggagc cgggcgcacg ggcaggctt gcggcagcgc tgagggaggg cggccggctc ccgcctacag cccgtctgtg ctggggccccg cgaggtggg ggccggcctc ccagacatca cctcacaaac ctgagcctcc ccagcagccc cagcccaccc cagcttcccg aacgatgtgg gcacatctgt caggcaggaa gttacctaca cctgtctggg gcccgttttg tgtttccaga cggtgcaccc ccacccccac cgcacggggc ggcccttat ttgtcctgaa gtcacctctt gctccctca ggggggccggg agagagctgg ggacaaggct ggccccctcgg cgaggcaccc ccggtctgtc ggcctccctg actgtccaga ggtcccacgc gtggggcccg gacgcccaca gtctcactct ggctcagccc cttcctgagc ctacagactg gatgacagag cagcctctgg gcagctcgca cgggctcgga gtcctggccg ggccccgggg agcaggcctc agcctcgctc tgcttcccag ttgaggaagc tgagcccaca gcttcgggt cgtcctccca gacggacatg tccccgcatc ccccgcccgg cgcagggacg ggcagaagcc gcttccgttg gcttctggtc cggttgaggg gtgtgcacac acaggtgccc gctcacaccg tgaagagata gggcccctg gaaacagcat cgtcctgtcc ggcctgtctc ccagctccgc gaggggagac accgggcagg aaggaaagcg aaggctgtgg gggccacgcg ggggcccgc gggcatcact ctggaagcag gcctctgcca gtcgcctccc tccccgtcac ctccctccca tcccctcccc cgtgccccc cacacacac acccgacgag cacatcccag ctcccagctc cgcggcagca gatggaaagt tggaggccgc gggatgctcc tgagcaggga ggaggtgagg ggccggccaa gagcgttaag gaccatacta acaggctact cactgcggcc acgctgattt atgaggccgt ctgggagccc agccaagtct gtaagtcatg gacaattagg aggctcgctc cagccctcag ccccgtccgc ctctgggct ctaggccac cgcgcccctc ctcagcaggg tcagcaccgt ggagacccca cggtgcagat agggacacgg agggccggga ggccggcggc cggccccgt gacttggaca ctgggtgctg agcggtggct gtgcccaggg tctgactcct aaccctagcg gcatcttcct ctgcttccaa ggcccacttt gacatcttgg gggctccagc caagggccgg tggggggagt gcccgggagg gggacagaaa gagaagagga cacttggaac ctccagccct acacctagag actaacaagg aagaaaagaa gtctcatggc cttcagacca aacacctctg agtcccagtg tcctcgagcc cggggccttc gtgccctaca atccagcagt catggcatcc ggtgccagga gggaccttcg aggccccccc cagacccccc tgggctctg acgggactc acctccagcc agatctgatg |

TABLE 2-continued

Myomaker amino acid and nucleotide sequences

| SPECIES | ISOFORM | SEQ ID NO | SEQUENCE |
|---|---|---|---|
| | | | agggaagcct gggtcccgac tccagcgtgc gcctggaagc cgagcccgag atgatggcag ccccagagca gcctgtgcag tagaacttgc tttaatgatg gaggcgaggc gggggcgccc gggggggct<br>(GenBank Accession No. XM_011288714.1) |
| *Sus scrofa* | Myomaker amino acid | 28 | MGTVMAKLLLPTLSSLAFLPTVSIAAKRRFHMEAMVYLFTTFFVAFYHACHGPG LAMICFLRLDILEYFSVYGTALSMWVSLMALADFDEPKRSTFVMFGVLTIAVRI YHDRWGYGVYSGPIGTAALIIAAKWLQQMKDQRRLYPDKSVYTQQIGPGLCFGA LALMLRFFFEEWDYTYVHSFYHCALAMSFVLLLPKANKKAGSAGPPAKLDCSTL CCACI<br>(GenBank Accession No. XP_003353750.1) |
| *Sus scrofa* | Myomaker cDNA | 29 | gatgagacaa gacaagaaaa aagaaaagga agagctcctc ccaccgtacg ttttaaatcc gtgccttta tcgtgggcgg catcattcga tcacgatgaa aaacacaacg ggagaaatgc tgttcttta ctgacaacaa tcaagggatg aactcatgaa gccagcatga ttccgtcagt gcctgtaggg agagagggtc gcctgcgcag ctcacacgcc cggatcgtct cttggccaga ggatgatggg ggggggagc atcctgccag gctgctccct cgagacctgt ttagcaagag aaggaatgtc tccagggcca aggaaggccg agagccctag catccgcctt gccttgggga cactgataga ggtggtcctg gcttgtgtcc ttcaggttca aagctatgtg accgcagaga aaagacagtg agtttcgtgt gttcaggcac caaggaagcc tgcttggagc aggagcaggt gagcaagaag ggcatgggcg ctggtaggtt ggcttcttct ggtgaccgga acgggctcag ccttggcctc tctctcgccc ccaccccgg gccctgtgca cacgtgactc cagcagcagg gtctgctttc ctctcgtgtt ctgggctcct gagcgccctg gagaggggcg aggatggaga gtggctgaac atcggggtg cggatgggga ctccgctcca tcgaagctgt ggcctccaaa acaaggggg gactccttga atcaactgct ctgatccctc caaaacaaag gagagagaga gggtgaggca agggccgacc agcgggatca gctgttggct ctcctcccg ggcggtggac atgtgcgcgc ccctcccgc ctcgcagggt atttaaaccg cagctgccat cggagccccc gctggcagga gcgacccttc tccctgcctc ttccctgccc tggggacccg ggaggcccgc accctccctt cctccccggc ccatgggac cgtcatggcc aaaactgctgc tacccacgct gagcagcctg gccttcctcc ccacggtcag catcgctgcc aagcggcggt tccacatgga ggccatggtc tatctcttca ccacgttctt cgtggcgttc taccacgcct gccacgggcc gggcctggct atgatctgct ttctgcgcct tgacatcctg gagtatttca gcgtctacgg aaccgccctg agcatgtggg tctcgctgat ggcgctggct gacttcgacg agcccaagag gtcgactttc gtgatgtttg gcgtcctgac catcgccgtg cggatctacc acgaccgctg gggctacggc gtgtactcgg gccccatcgg cacggccgcc ctcatcatcg cggccaagtg gctgcagcag atgaaggacc aacggcgcct gtatccagac aagagcgtgt acacacagca gataggcccc ggcctctgct tcggggcgct ggcctcatg ctgcgctttt tcttcgagga gtgggattat acctacgtcc acagcttcta ccactgcgcc ctggccatgt ccttcgtcct gctgctgccc aaggccaaca gaaaggctgg aagcgcaggg ccacccgcca agctggactg ctccaccctc tgctgtgctt gtatctgacc gcgtggccca aagctcccag ccccccccc gccctgcctg gtccttccgg actcagaaa cgccccttct cagagcctgc gggctctctg gggtctgggg agcatcccgc caagtgcttt ttgagaaccc acttcttctg tgtcccccgg gtgccaagga gggtgctgga agaaacaaa catcctgatg gacaggtgtg tctgcagaag cccggagcca gacactgccc ccctccacg tccctcccc gcttccccgg acagcccat cccagccacc aaggggcccc gcctgccacc ctggtcccac acgctcccca cacccctgt ttcctgctct tgacccatgc cctcaggttc ggcgagccag ggccagcagg gccacttggt ccctgcccca ggcctggctg cccttggct gtccccccag ccaggtcgct aaatcaaacc atttccactc ac<br>(GenBank Accession No. XM_003353702.3) |
| *Macaca mulatta* | Myomaker amino acid | 30 | MGTLVAKLLLPTLSSLAFLPTVSIAAKRRFHMEAMVYLFTLFFVALHHACNGPG LSVLCFMRHDILEYFSVYGTALSMWVSLMALADFDEPKRSTFVMFGVLTIAVRI YHDRWGYGVYSGPIGTAILIIAAKWLQKMKEKKGLYPDKSVYTQQIGPGLCFGA LALMLRFFFEDWDYTYVHSFYHCALAMSFVLLLPKVNKKAGAPGAPAKLDCSTL CCACV<br>(GenBank Accession No. XP_014971917.1) |
| *Macaca mulatta* | Myomaker cDNA | 31 | tccgtctcaa aaaagaaaa gagaaatca gagacaagtg ctggtcacgt ggcgcgtcag ctgtcggccc tccccatgtg ttgcttgaca tgtgcatgta catccccgcc tccgtccagg gcatttaaac cctctgctgg gcgctcccg cagctgccat cagagccctg ctcaaaggga gctggccttc cccttcgtg ctcctgtgct ggggacccag ggcgccagca cccacccgc cccagccagt gcttccctcc aggcctatgg ggacgctggt ggccaagcta ctcctgccca ccctcagcag cctgsccttc ctcccccactg tcagcatcgc ggccaagagg cggttccaca tggaggccat ggtctacctc ttcaccctgt tcttcgtggc gctccaccat gcctgcaacg gacccggctt gtctgtgctg tgcttcatgc gacacgacat cctggaatac ttcagcgtct acggaacagc cctgagcatg tgggtctcgc tgatggcact ggccgacttc gatgagccca gaggtcaac atttgtgatg ttcggcgtcc tgaccattgc tgtgaggatc taccacgacc |

TABLE 2-continued

Myomaker amino acid and nucleotide sequences

| SPECIES | ISOFORM | SEQ ID NO | SEQUENCE |
|---|---|---|---|
| | | | gctggggcta cggggtgtac tcaggcccca tcggcacagc catcctcatc
attgcggcaa agtggctgca gaagatgaag gagaagaagg gcctgtaccc
agacaagagc gtctacaccc agcagatagg ccccggcctc tgcttcgggg
cgctggccct gatgctacgc ttcttcttcg aggactggga ctacacctat
gtccacagct tctaccactg tgccctggcc atgtcctttg ttctgctgct
gcccaaggtc aacaagaagg ctggagcccc ggggcccccg gccaagctgg
actgctccac cctgtgctgt gcttgtgtct gatgctgcgc ccagcccggc
tctgagcccc tgccctcccc agctcacgct tggccagagt cccagacagt
ttctcctcct gcagctcctg ctgtccttcc ctgccccaga gcatgcagga
gaaacatctc ttgcataccc taagaggccc ccggggtct gtgaagggcc
catcacactg cactaaatgc ttcttaagaa cccgcttatt ccgttgtgac
ggggtgcaca gcagcaggac caagctgaaa agataagaat gttctcctcc
caggccttgt cacgacccat tggcgtgtct ggtggagccc taggtctggc
gtctgcccac cccactgctg gccagcggcc caggagtccc agccgtgtgc
cagccatgac gggggggctc ccatgtcttc agttttctcc tgggaactgc
tatcaccatc tctgtcctgt gtcctcaggc tccgagcaac cccatttagg
aagctgaggc cagcggggcc agctggatcc ctggcccagg ccagtctggc
cccaccoctt ccgctgggtc cctgaatcaa gccgttttca taattataac
caataagaag tgcctcaatg tatcaacctc a
(GenBank Accession No. XM_015116431.1) |

A "mouse Myomaker polypeptide" refers to a naturally occurring mouse Myomaker protein (e.g., the protein of SEQ ID NO: 18 or 20) or a variant thereof. The amino acid and cDNA sequences of mouse Myomaker isoforms can be found in Table 2. Table 2 also includes Myomaker sequences of other species, e.g., rat (*R. norvegicus*), monkey (*M. mulatta*), cat (*F. catus*), and pig (*S. scrofa*).

The term "a Myomaker polypeptide" is used to refer collectively to all naturally occurring isoforms of a Myomaker protein of any species, or a variant thereof. For example, a "Myomaker polypeptide" can be any Myomaker polypeptide listed in Table 2 or a variant thereof.

As used in the specification and claims, the singular form "a", "an" and "the" include plural references unless the context clearly dictates otherwise. For example, the term "a cell" includes a plurality of cells, including mixtures thereof.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about." It also is to be understood, although not always explicitly stated, that the reagents described herein are merely examples and that equivalents of such are known in the art.

The term "cDNA" refers to complementary DNA, e.g., mRNA molecules present in a cell or organism made into cDNA with an enzyme such as reverse transcriptase. A "cDNA library" is a collection of all of the mRNA molecules present in a cell or organism, all turned into cDNA molecules with the enzyme reverse transcriptase, then inserted into "vectors" (other DNA molecules that can continue to replicate after addition of foreign DNA). Example vectors for libraries include bacteriophage (also known as "phage"), viruses that infect bacteria, for example, lambda phage. The library can then be probed for the specific cDNA (and thus mRNA) of interest.

The term "combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the present invention and a combination partner, are both administered to a patient simultaneously in the form of a single entity or dosage. The term "non-fixed combination" means that the active ingredients, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

An "effective amount" refers to an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A "therapeutically effective amount" of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but are not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The term "variant" refers to a polypeptide that has a substantially identical amino acid sequence to a reference polypeptide, or is encoded by a substantially identical nucleotide sequence, and is capable of having one or more activities of the reference polypeptide. For example, a variant can have about 85%, 90%, 91%, 92%, 93%, 94%, 95%, 96%, 97%, 98%, 99% or higher sequence identity to a reference polypeptide, while retain one or more activities of the reference polypeptide.

A "gene" refers to a polynucleotide containing at least one open reading frame (ORF) that is capable of encoding a particular polypeptide or protein after being transcribed and translated. A polynucleotide sequence can be used to identify larger fragments or full-length coding sequences of the gene with which they are associated. Methods of isolating larger fragment sequences are known to those of skill in the art.

The term "isolated" refers to altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof. A "microprotein" or "micropeptide" refers to a protein or polypeptide that is less than 100 amino acids long.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. Percentage of "sequence identity" can be determined by comparing two optimally aligned sequences over a comparison window, where the fragment of the amino acid sequence in the comparison window may comprise additions or deletions (e.g., gaps or overhangs) as compared to the reference sequence (which does not comprise additions or deletions) for optimal alignment of the two sequences. The percentage can be calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity. The output is the percent identity of the subject sequence with respect to the query sequence.

The term "subject" refers to an animal, human or non-human, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

The term "treat" or "treatment" refers to both therapeutic treatment and prophylactic or preventive measures, wherein the object is to prevent or slow down an undesired physiological change or disorder. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding that are statistically significant (e.g., P value<0.05 or 0.02). The terms "induce", "inhibit", "potentiate", "elevate", "increase", "decrease" or the like, e.g., which denote distinguishable qualitative or quantitative differences between two states, may refer to a difference, e.g., a statistically significant difference, between the two states.

MINION Polypeptides and Fragments or Variants Thereof

Mouse MINION (ESGP) protein was encoded by a single open reading frame (ORF) (Chen Y et al., Acta Biochimica et Biophysica Sinica 2005, 37(12): 789-796). The 84 amino acid protein described in Chen et al., has an amino acid sequence of SEQ ID NO: 5 (isoform 1). A longer isoform of mouse MINION (isoform 2) was also described, which has the amino acid sequence of SEQ ID NO: 7, and a distinct N-terminus compared to isoform 1. The function of mouse MINION isoforms was unknown.

The present inventors found that mouse MINION is a skeletal muscle-specific microprotein highly expressed during muscle development and regeneration (see Example 2), and is required for fusion of muscle progenitors and skeletal muscle development (see Examples 3 and 4). Moreover, forced heterologous expression of MINION, along with another protein Myomaker, is found to be sufficient to induce cell fusion even in non-muscle cells (e.g., fibroblasts) (see Example 5). This is surprising since it was reported that Myomaker alone cannot promote fibroblast-fibroblast fusion although it was capable of promoting fusion of fibroblasts to myoblasts (Millay et al., Nature. 2013; 499(7458):301-5).

The human ortholog of mouse MINION has not been reported before. As described herein, the present inventors found human ortholog of MINION has an amino acid sequence of SEQ ID NO: 1 or SEQ ID NO: 3, and a cDNA sequence of SEQ ID NO: 2 or SEQ ID NO: 4. The present inventors found that human MINION protein also has fusogenic activity, suggesting an evolutionarily conserved role for the MINION protein in cell fusion. MINION amino acid and nucleotide sequences of other species, e.g., rat (*R. norvegicus*), monkey (*M. mulatta*), cat (*F. catus*), and pig (*S. scrofa*) are also provided in Table 1.

A MINION polypeptide can be a variant of a naturally occurring MINION protein (e.g., any MINION protein listed in Table 1). For example, a human MINION polypeptide can be a variant of a naturally occurring human MINION protein (e.g., the protein of SEQ ID NO:1 or SEQ ID NO: 3, or another naturally occurring isoform thereof). A mouse MINION polypeptide can be a variant of a naturally occurring mouse MINION protein (e.g., a protein of SEQ ID NO: 5 or SEQ ID NO: 7, or another naturally occurring isoform thereof).

A MINION variant can differ from a naturally occurring MINION protein by, for example, a modification (e.g., substitution, deletion, or insertion) of one or more amino acid residues in the naturally occurring MINION protein, but retains the biological activities of MINION, e.g., fusogenic activity. The MINION variant can have one or more conservative or nonconservative amino acid substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some embodiments, the MINION variant includes one or more mutations (e.g., substitutions (e.g., conservative substitutions or substitutions), insertions, or deletions) of non-essential amino acids relative to a naturally occurring MINION protein. A "non-essential" amino acid residue is a residue that can be altered from the wild-type sequence of MINION protein without abolishing or more preferably, without substantially altering a biological activity, such as the fusogenic activity, whereas changing an "essential" amino acid residue results in a substantial loss of biological activity.

A MINION variant may have at least one, two, three, or four, and no more than 10, 9, 8, 7, 6, or 5 mutations (e.g., substitutions (e.g., conservative substitutions or substitutions of non-essential amino acids), insertions, or deletions) relative to a naturally occurring MINION protein. Whether or not a particular substitution will be tolerated, i.e., will not adversely affect biological properties, such as fusogenic activity, can be predicted, e.g., by evaluating whether the mutation is conservative or by an activity assay.

In some embodiments, a MINION variant can have about 85%, 90%, 91%, 92%, 93%, 94%, 95%, 96%, 97%, 98%, 99% or higher sequence identity to a naturally occurring MINION protein. For example, a human MINION variant can have about 85%, 90%, 91%, 92%, 93%, 94%, 95%, 96%, 97%, 98%, 99% or higher sequence identity to SEQ ID NO: 1 or SEQ ID NO: 3. A mouse MINION variant can have about 85%, 90%, 91%, 92%, 93%, 94%, 95%, 96%, 97%, 98%, 99% or higher sequence identity to SEQ ID NO: 5 or SEQ ID NO: 7.

Calculations of "homology" or "sequence identity" between two sequences (the terms are used interchangeably herein) can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

In some embodiments, the MINION variant can comprise at least one non-naturally encoded amino acid. A "non-naturally encoded amino acid" refers to an amino acid that is not one of the common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetyl-glucosaminyl-L-serine, N-acetylglucosaminyl-L-threonine, and O-phosphotyrosine.

A non-naturally encoded amino acid is typically any structure having any substituent side chain other than one used in the twenty natural amino acids. Because the non-naturally encoded amino acids typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Methods of making and introducing a non-naturally-occurring amino acid into a protein are known. See, e.g., U.S. Pat. Nos. 7,083,970, and 7,524,647. The general principles for the production of orthogonal translation systems that are suitable for making proteins that comprise one or more desired unnatural amino acid are known in the art, as are the general methods for producing orthogonal translation systems. For example, see International Publication Numbers WO2002/086075; WO2002/085923; WO2004/094593; WO2005/007870; WO2005/007624; WO2006/110182; and WO2007/103490, each of these applications is incorporated herein by reference in its entirety. For discussion of orthogonal translation systems that incorporate unnatural amino acids, and methods for their production and use, see also, Wang and Schultz, (2005) "Expanding the Genetic Code." Angewandte Chemie Int Ed 44: 34-66; Xie and Schultz, (2005) "An Expanding Genetic Code." Methods 36: 227-238; Xie and Schultz, (2005) "Adding Amino Acids to the Genetic Repertoire." Curr Opinion in Chemical Biology 9: 548-554; and Wang, et al., (2006) "Expanding the Genetic Code." Annu Rev Biophys Biomol Struct 35: 225-249; Deiters, et al, (2005) "In vivo incorporation of an alkyne into proteins in *Escherichia coli*." Bioorganic & Medicinal Chemistry Letters 15:1521-1524; Chin, et al., (2002) "Addition of p-Azido-L-phenylalanine to the Genetic Code of *Escherichia coli*." J Am Chem Soc 124: 9026-9027; and International Publication No. WO2006/034332, filed on Sep. 20, 2005, the contents of each of which are incorporated by reference in their entirety. Additional details are found in U.S. Pat. Nos. 7,045,337; 7,083,970; 7,238,510; 7,129,333; 7,262,040; 7,183,082; 7,199,222; and 7,217,809.

Another type of modification that can optionally be introduced into a MINION polypeptide (e.g., within the polypeptide chain or at either the N- or C-terminal), e.g., to extend in vivo half-life, is PEGylation or incorporation of long-chain polyethylene glycol polymers (PEG). Introduction of PEG or long chain polymers of PEG increases the effective molecular weight of the present polypeptides, for example, to prevent rapid filtration into the urine. In some embodiments, a Lysine residue in the MINION sequence is conjugated to PEG directly or through a linker. Such linker can be, for example, a Glu residue or an acyl residue containing a thiol functional group for linkage to the appropriately modified PEG chain. An alternative method for introducing a PEG chain is to first introduce a Cys residue at the C-terminus or at solvent exposed residues such as replacements for Arg or Lys residues. This Cys residue is then site-specifically attached to a PEG chain containing, for example, a maleimide function. Methods for incorporating PEG or long chain polymers of PEG are well known in the art (described, for example, in Veronese, F. M., et al., Drug Disc. Today 10: 1451-8 (2005); Greenwald, R. B., et al., Adv. Drug Deliv. Rev. 55: 217-50 (2003); Roberts, M. J., et al., Adv. Drug Deliv. Rev., 54: 459-76 (2002)), the contents of which is incorporated herein by reference. Other methods of polymer conjugations known in the art can also be used in the present invention, e.g., WO2008/098930; Lewis, et al., Bioconjug Chem., 19: 2144-55 (2008); Deiters, A, et al. (2004). Bio-org. Med. Chem. Lett. 14, 5743-5. In some embodiments, a phosphorylcholine-containing polymer conjugate with the MINION polypeptide can be used. In some embodiments, p-azidophenylalanine can be incorporated into the MINION polypeptides and then reacted with a PEG polymer having an acetylene moiety in the presence of a reducing agent and copper ions to facilitate an organic reaction known as "Huisgen [3+2]cycloaddition." A person of skill would readily recognize that other biocompatible polymer conjugates can be utilized.

In some embodiments, a variant of the MINION polypeptide can comprise MINION, fused to a heterologous peptide such as a tag or a fusion domain. Fusions may be constructed such that the heterologous peptide (e.g., a tag or a fusion domain) is fused at the amino terminus or at the carboxy terminus of MINION polypeptide. Examples of tags or fusion domains include, but are not limited to, a HA-tag (YPYDVPDYA, SEQ ID NO: 32), a Myc-tag (EQKLISEEDL, SEQ ID NO: 33), a FLAG-tag (DYKDDDDK, SEQ ID NO: 34), a His-tag (HHHHHH, SEQ ID NO: 35), an E-tag (GAPVPYPDPLEPR, SEQ ID NO: 36), a V5-tag (GKPIPNPLLGLDST, SEQ ID NO: 37), a VSV tag (YTDIEMNRLGK, SEQ ID NO: 38), a polyglutamate tag (EEEEEE, SEQ ID NO: 39), an AviTag (GLNDIFEAQKIEWHE, SEQ ID NO: 40), a SBP tag (MDEKTTGWRGGHVVEGLAGELEQLRAR-LEHHPQGQREP, SEQ ID NO: 41), a Strep-tag (WSHPQFEK, SEQ ID NO: 42), an Xpress tag (DLYDDDDK, SEQ ID NO: 43), an S-tag (KETAAAKFERQHMDS, SEQ ID NO: 44), a Softag 1 (SLAELLNAGLGGS, SEQ ID NO: 45), a Softag 3 (TQDPSRVG, SEQ ID NO: 46), a Calmodulin-tag (KRRWKKNFIAVSAANRFKKISSSGAL, SEQ ID NO: 47), a TC tag (CCPGCC, SEQ ID NO: 48), an Isopeptag (TDKDMTITFTNKKDAE, SEQ ID NO: 49), a SpyTag (AHIVMVDAYKPTK, SEQ ID NO: 50), a SnoopTag (KLGDIEFIKVNK, SEQ ID NO: 51), a Glutathione-S-Transferase (GST)-tag, a fluorescent protein-tag (e.g., a GFP tag), a Maltose binding protein (MBP)-tag, a Halo-tag, or a thioredoxin-tag.

A fusion domain or a tag may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QLAexpress™ system (Qiagen) useful with a His6 tag. As another example, a fusion domain may be selected so as to facilitate detection of the MINION proteins. Examples of such detection domains include the various fluorescent proteins (e.g., GFP), as well as "epitope tags," which are usually short peptide sequences for which a specific antibody is available. Well known epitope tags for which specific monoclonal antibodies are readily available include a HA-tag, a Myc-tag, a FLAG-tag. Other known tags include an E-tag, a V5-tag, a VSV tag, a polyglutamate tag, an AviTag, a SBP tag, a Strep-tag, an Xpress tag, an S-tag, a Softag 1, a Softag 3, a Calmodulin-tag, a TC tag, an Isopeptag, a SpyTag, a SnoopTag, as described above.

In some cases, the tags or fusion domains can have a protease cleavage site, which allows the relevant protease to partially digest the fusion proteins and thereby liberate the MINION polypeptide from the fusion protein. In certain embodiments, an MINION polypeptide can be fused with a domain that stabilizes the protein in vivo (e.g., a "stabilizer" domain). By "stabilizing" is meant anything that increases serum half life, regardless of whether this is because of decreased destruction, decreased clearance by the kidney, or other pharmacokinetic effect. Fusions with the Fc domain of an immunoglobulin are known to confer desirable pharmacokinetic properties on a wide range of proteins. Likewise, fusions to human serum albumin (HSA) can confer desirable properties. Other types of fusion domains that may be selected include multimerizing (e.g., dimerizing, tetramerizing) domains and functional domains (that confer an additional biological function, as desired).

Further provided herein are fragments of a MINION polypeptide which retain the biological function of a native MINION polypeptide, such as fusogenic activity, interaction with Myomaker, etc. For example, some embodiments of the present disclosure provide fragments of a MINION polypeptide that contain an "AxLyCxL" domain, which has been shown to be required for the fusogenic activity of MINION (Shi et al., Requirement of the fusogenic micropeptide myomixer for muscle formation in zebrafish. PNAS 114, 11950 (2017), the content of which is hereby incorporated by reference in its entirety). In some embodiments, the fragments of a MINION polypeptide comprise amino acids 48-54 of SEQ ID NO: 1. In some embodiments, the fragments of a MINION polypeptide comprise amino acids 48-54 of SEQ ID NO: 3. In some embodiments, the fragments of a MINION polypeptide comprise amino acids 48-54 of SEQ ID NO: 5. In some embodiments, the fragments of a MINION polypeptide comprise amino acids 72-78 of SEQ ID NO: 7. Some embodiments of the present disclosure provide fragments of a MINION polypeptide that contain the N-terminal hydrophobic region (amino acids 5-25 of human MINION), and positively charged Arg residues within the first α-helix following the N-terminal hydrophobic region the disruption of which resulted in a loss of fusogenic activity and perturbed interaction with Myomaker (Bi P, Ramirez-Martinez A, Li H, Cannavino J, McAnally J R, Shelton J M, Sanchez-Ortiz E, Bassel-Duby R, Olson E N: Control of muscle formation by the fusogenic micropeptide myomixer. Science 356, 323 (2017), the content of which is hereby incorporated by reference in its entirety). In some embodiments, the fragments of a MINION polypeptide comprise amino acids 5-46 of SEQ ID NO: 1. In some embodiments, the fragments of a MINION polypeptide comprise amino acids 5-46 of SEQ ID NO: 3. In some embodiments, the fragments of a MINION polypeptide comprise amino acids 5-46 of SEQ ID NO: 5. In some embodiments, the fragments of a MINION polypeptide comprise amino acids 29-70 of SEQ ID NO: 7. The fragment of a MINION polypeptide can have a variety of lengths. For example, the fragment of a MINION polypeptide can have a length that is, is about, is at least, is more than, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, 50 amino acids, or a range that is between any two of the above values.

In some embodiments, a MINION peptide, variant thereof or fragment thereof may comprise one or more post-translational modifications, e.g., lipidation, glycosylation, phosphorylation, etc. Examples are as follows. Phosphorylation sites in *Mus musculus* MINION as predicted using GPS (gps.biocuckoo.org) include: serine 12, serine 15, serine 41, serine 42, serine 51, serine 58, serine 65, serine 69, and serine 74. Palmitoylation is predicted in *Mus musculus* MINION using GPS-Lipid (gps.biocuckoo.org) on cysteine 52. O-glycosylation of *Mus musculus* MINION is predicted using NetOGlyc 4.0 (www.cbs.dtu.dk) on serine 69 and serine 74.

Myomaker Polypeptide and Variants

Myomaker (also known as Tmem8c or Tmem226) is a membrane protein expressed specifically in skeletal muscle during embryogenesis and adult muscle regeneration (Millay et al., Nature. 2013 Jul. 18; 499(7458):301-5).

Myomaker has been reported to be both necessary and sufficient to promote myoblast fusion in vivo and in vitro (Millay et al., 2013). Millay et al. also reported that Myomaker can promote fusion of fibroblasts to myoblasts but cannot promote fibroblast-fibroblast fusion. Methods of fusing a non-muscle cell to a muscle cell by expressing exogenous Myomaker protein in the non-muscle cell have been described in WO2014/210448.

A Myomaker polypeptide can be a variant of a naturally occurring Myomaker protein (e.g., any Myomaker protein listed in Table 2). For example, a human Myomaker polypeptide can be a variant of a naturally occurring human Myomaker protein (e.g., a protein of SEQ ID NO: 16, or a naturally occurring isoform thereof). A mouse Myomaker polypeptide can be a variant of a naturally occurring mouse Myomaker protein (e.g., a protein of SEQ ID NO: 18 or SEQ ID NO: 20, or another naturally occurring isoform thereof). Table 2 provides Myomaker amino acid and nucleotide sequences of human, mouse, rat, monkey, cat, and pig.

A Myomaker variant can differ from a naturally occurring Myomaker protein by, for example, a modification (e.g., substitution, deletion, or insertion) of one or more amino acid residues in the naturally occurring Myomaker protein, but retains the biological activities of Myomaker, e.g., fusogenic activity. The Myomaker variant can have one or more conservative or nonconservative amino acid substitution. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In some embodiments, the Myomaker variant includes one or more mutations (e.g., substitutions (e.g., conservative substitutions or substitutions), insertions, or deletions) of non-essential amino acids relative to a naturally occurring Myomaker protein. A "non-essential" amino acid residue is a residue that can be altered from the wild-type sequence of Myomaker protein without abolishing or more preferably, without substantially altering a biological activity, such as fusogenic activity, whereas changing an "essential" amino acid residue results in a substantial loss of biological activity.

A Myomaker variant may have at least one, two, three, or four, and no more than 10, 9, 8, 7, 6, or 5 mutations (e.g., substitutions (e.g., conservative substitutions or substitutions of non-essential amino acids), insertions, or deletions) relative to a naturally occurring Myomaker protein. Whether or not a particular substitution will be tolerated, i.e., will not adversely affect biological properties, such as fusogenic activity, can be predicted, e.g., by evaluating whether the mutation is conservative or by an activity assay.

In some embodiments, a Myomaker variant can have about 85%, 90%, 91%, 92%, 93%, 94%, 95%, 96%, 97%, 98%, 99% or higher sequence identity to a naturally occurring Myomaker protein. For example, a human Myomaker variant can have about 85%, 90%, 91%, 92%, 93%, 94%, 95%, 96%, 97%, 98%, 99% or higher sequence identity to SEQ ID NO: 16. A mouse Myomaker variant can have about 85%, 90%, 91%, 92%, 93%, 94%, 95%, 96%, 97%, 98%, 99% or higher sequence identity to SEQ ID NO: 18 or SEQ ID NO: 20.

Calculations of "homology" or "sequence identity" between two sequences (the terms are used interchangeably herein) can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

In addition, substantial identity exists when the nucleic acid segments hybridize under selective hybridization conditions (e.g., highly stringent hybridization conditions), to the complement of the strand. The nucleic acids may be present in whole cells, in a cell lysate, or in a partially purified or substantially pure form.

In some embodiments, the Myomaker variant can comprise at least one non-naturally encoded amino acid. In some embodiments, the Myomaker variant can be a PEGylated Myomaker with extended in vivo half-life. In some embodiments, a variant of the Myomaker polypeptide can comprise Myomaker, fused to a tag or a fusion domain. Exemplary non-naturally encoded amino acids, PEGylation methods, and fusion partners described above for MINION variants are also applicable to Myomaker variants.

Nucleic Acids Encoding MINION Polypeptide, Expression Vectors, and Cells

The invention also provides nucleic acids encoding a MINION polypeptide (e.g., a human MINION polypeptide), expression vectors for expression of a MINION polypeptide (e.g., a human MINION polypeptide), and cells containing such expression vectors. In other aspects, the invention provides a polynucleotide encoding a MINION polypeptide (e.g., a human MINION polypeptide), and expression vectors and host cells comprising such a polynucleotide.

Provided herein are expression vectors that can be employed to express a MINION polypeptide (e.g., a human MINION polypeptide). The term "expression vector" refers to a carrier nucleic acid molecule into which a desired coding sequence can be inserted for introduction into a cell where it can be expressed. Expression vector can be a plasmid, a cosmid, an RNA, a viral vector, or artificial chromosomes (see, e.g., Harrington et al., Nat Genet 15:345, 1997). For example, nonviral vectors useful for expression of a polypeptide in mammalian (e.g., human) cells include pThioHis A, B & C, pcDNA3. 1/His, pEBVHis A, B & C (Invitrogen, San Diego, Calif.), MPSV vectors, and numerous other vectors known in the art for expressing other proteins. Useful viral vectors include, but are not limited to, vectors based on any of the following viruses: adenovirus, adeno-associated virus, Herpes Simplex Virus (HSV), parvovirus, retrovirus, lentivirus, vaccinia virus, Sinbis virus, influenza virus, reovirus, Newcastle disease virus (NDV), measles virus, vesicular stomatitis virus (VSV), poliovirus, poxvirus, Seneca Valley virus, coxsackievirus, enterovirus, myxoma virus, or maraba virus. In some embodiments, the expression vector can be capable of autonomous replication or it can integrate into a host DNA.

In some embodiments, the expression vector can be a recombinant DNA molecule containing a MINION polypeptide-coding sequence (e.g., a human MINION polypeptide-coding sequence). The recombinant expression vector typically includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. Expression vectors can also include elements designed to optimize messenger RNA stability and translatability in host cells, and/or drug selection markers for establishing permanent, stable cell clones expressing a human MINION polypeptide. The design of the expression vector can depend on such factors as the choice of the host cell to be transformed, the level of expression of protein desired, and the like. General methods for generating such recombinant expression vectors can be found in Sambrook and Russell eds. (2001) Molecular Cloning: A Laboratory Manual, 3rd edition; the series Ausubel et al. eds. (2007 with updated through 2010) Current Protocols in Molecular Biology, among others known in the art.

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally-associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, can be employed as well.

The promoters employed can be constitutive, inducible, tissue-specific, and/or useful under the appropriate conditions to direct high level expression of the introduced DNA segment, such as is advantageous in the large-scale production of recombinant proteins and/or peptides. In some embodiments, a constitutive promoter is employed to provide constant expression of a MINION polypeptide (e.g., a human MINION polypeptide). In some embodiments, an inducible promoter is employed to prevent expression of a MINION polypeptide (e.g., a human MINION polypeptide) except under inducing conditions. Inducible promoters include, e.g., arabinose, lacZ, a metallothionein promoter, a glucocorticoid promoters or a heat shock promoter. In addition, other regulatory elements may also be incorporated to improve expression of a nucleic acid encoding a MINION polypeptide (e.g., a human MINION polypeptide), e.g., enhancers, ribosomal binding site, transcription termination sequences, and the like. In some embodiments, a tissue-specific promoter is employed to provide expression of a MINION polypeptide (e.g., a human MINION polypeptide) only in specific tissues. The identity of tissue-specific promoters or elements, as well as assays to characterize their activities, is well known to those of skill in the art. Examples of such regions include the human LIMK2 gene (Nomoto et al. 1999, Gene, 236(2):259-271), the somatostatin receptor 2 gene (Kraus et al., 1998, FEES Lett., 428(3): 165-170), murine epididymal retinoic acid-binding gene (Lareyre et al., 1999, J. Biol. Chem., 274(12):8282-8290), human CD4 (Zhao-Emonet et al., 1998, Biochirn. Biophys. Acta, 1442 (2-3): 109-119), mouse alpha2 (XI) collagen (Tsumaki, et al., 1998, J. Biol. Chem., 273(36):22861-22864), D1A dopamine receptor gene (Lee, et al., 1997, J. Auton. Nerv. Syst., 74(2-3):86-90), insulin-like growth factor II (Wu et al., 1997, Biochem. Biophys. Res. Commun., 233(1):221-226), human platelet endothelial cell adhesion molecule-1 (Almendro et al., 1996, J. Immunol., 157(12):5411-5421), muscle creatine kinase (MCK) promoter (Wang et al., Gene Ther. 2008 November; 15(22):1489-99).

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

Expression can employ any appropriate host cells known in the art, for example, mammalian host cells, bacterial host cells, yeast host cells, insect host cells, etc. Both prokaryotic and eukaryotic expression systems are widely available. In some embodiments, the expression system is a mammalian cell expression, such as a CHO cell expression system. In some embodiments, a nucleic acid may be codon-optimized to facilitate expression in a desired host cell. It will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (2001), incorporated herein by reference.

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see Chandler et al., 1997, Proc. Natl. Acad. Sci. USA, 94(8):3596-601).

The vectors or constructs of the present disclosure will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences. Terminators contemplated for use in the disclosure include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

In expression, particularly eukaryotic expression, one will typically include a polyadenylation signal to effect proper polyadenylation of the transcript. The nature of the polyadenylation signal is not believed to be crucial to the successful practice of the disclosure, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

To propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

In certain embodiments of the disclosure, cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

In some embodiments, provided herein are expression vectors comprising a nucleic acid encoding a MINION polypeptide or a variant thereof. In some embodiments, provided herein are expression vectors comprising a nucleic acid encoding a MINION polypeptide of Table 1 or a variant thereof. In some embodiments, provided herein are expression vectors comprising a nucleic acid encoding a MINION polypeptide comprising an amino acid sequence selected from any of SEQ ID NOs: 1, 3, 5, 7, 9, 11, 13, or 15, or a variant thereof. In some embodiments, provided herein are expression vectors comprising a nucleic acid encoding a MINION polypeptide consisting of an amino acid sequence selected from any of SEQ ID NOs: 1, 3, 5, 7, 9, 11, 13, or 15, or a variant thereof. In some embodiments, provided herein are expression vectors comprising a nucleic acid selected from any of SEQ ID NOs: 2, 4, 6, 8, 10, 12, or 14.

In some embodiments, provided herein are expression vectors comprising a nucleic acid encoding a polypeptide comprising SEQ ID NO: 1 or SEQ ID NO: 3 or a variant thereof. In some embodiments, the expression vector comprises a nucleic acid encoding a polypeptide comprising SEQ ID NO: 1 with 1-4 mutations. In some embodiments, the expression vector comprises a nucleic acid encoding a polypeptide consisting of SEQ ID NO: 1. In some embodiments, the expression vector comprises a nucleic acid encoding a polypeptide comprising SEQ ID NO: 3 with 1-4 mutations. In some embodiments, the expression vector comprises a nucleic acid encoding a polypeptide consisting of SEQ ID NO: 1. In some embodiments, the expression vector comprises a nucleic acid encoding a polypeptide consisting of SEQ ID NO: 3. In some embodiments, the expression vector comprises a nucleic acid comprising SEQ ID NO: 2. In some embodiments, the expression vector comprises a nucleic acid comprising SEQ ID NO: 4. In some embodiments, the expression vector comprises a nucleic acid consisting of SEQ ID NO: 2. In some embodiments, the expression vector comprises a nucleic acid consisting of SEQ ID NO: 4.

In some embodiments, the expression vector comprises a promoter, e.g., a constitutive promoter, an inducible promoter, or a tissue-specific promoter. In some embodiments, the expression vector comprises a polyadenylation signal. In some embodiments, the expression vector comprises a selectable marker.

In some embodiments, the expression vector comprises a nucleic acid encoding a polypeptide comprising SEQ ID NO: 1 or SEQ ID NO: 3, fused to a tag. The tag can be selected from a HA-tag (YPYDVPDYA, SEQ ID NO: 32), a Myc-tag (EQKLISEEDL, SEQ ID NO: 33), a FLAG-tag (DYKDDDDK, SEQ ID NO: 34), a His-tag (HHHHHH, SEQ ID NO: 35), an E-tag (GAPVPYPDPLEPR, SEQ ID NO: 36), a V5-tag (GKPIPNPLLGLDST, SEQ ID NO: 37), a VSV tag (YTDIEMNRLGK, SEQ ID NO: 38), a polyglutamate tag (EEEEEE, SEQ ID NO: 39), an AviTag (GLNDIFEAQKIEWHE, SEQ ID NO: 40), a SBP tag (MDEKTTGWRGGHVVEGLAGELEQLRAR-LEHHPQGQREP, SEQ ID NO: 41), a Strep-tag (WSHPQFEK, SEQ ID NO: 42), an Xpress tag (DLYDDDDK, SEQ ID NO: 43), an S-tag (KETAAAKFERQHMDS, SEQ ID NO: 44), a Softag 1 (SLAELLNAGLGGS, SEQ ID NO: 45), a Softag 3 (TQDPSRVG, SEQ ID NO: 46), a Calmodulin-tag (KRRWKKNFIAVSAANRFKKISSSGAL, SEQ ID NO: 47), a TC tag (CCPGCC, SEQ ID NO: 48), an Isopeptag (TDKDMTITFTNKKDAE, SEQ ID NO: 49), a SpyTag (AHIVMVDAYKPTK, SEQ ID NO: 50), a SnoopTag (KLGDIEFIKVNK, SEQ ID NO: 51), a Glutathione-S-Transferase (GST)-tag, a fluorescent protein-tag (e.g., a GFP tag), a Maltose binding protein (MBP)-tag, a Halo-tag, or a thioredoxin-tag.

In some embodiments, the expression vectors further comprise a second nucleic acid encoding a Myomaker polypeptide or a variant thereof. Thus, provided herein are expression vectors for expressing both a MINION polypeptide and a Myomaker polypeptide. In some embodiments, the expression vector comprises a second nucleic acid encoding a Myomaker polypeptide of Table 2 or a variant thereof. In some embodiments, the expression vector comprises a second nucleic acid encoding a polypeptide comprising an amino acid sequence selected from any of SEQ ID NOs: 16, 18, 20, 22, 24, 26, 28, or 30, or a variant thereof. In some embodiments, the expression vector comprises a second nucleic acid encoding a polypeptide consisting of an amino acid sequence selected from any of SEQ ID NOs: 16, 18, 20, 22, 24, 26, 28, or 30, or a variant thereof. In some embodiments, the expression vector comprises a second nucleic acid selected from any of SEQ ID NOs: 17, 19, 21, 23, 25, 27, 29, or 31, or a variant thereof.

In some embodiments, the expression vector comprises a second nucleic acid encoding a polypeptide comprising SEQ ID NO: 16. In some embodiments, the expression vector comprises a second nucleic acid encoding a polypeptide consisting of SEQ ID NO: 16. In some embodiments, the expression vector comprises a second nucleic acid comprising SEQ ID NO: 17. In some embodiments, the expression vector comprises a second nucleic acid consisting of SEQ ID NO: 17. In some embodiments, the expression vectors further comprise a second promoter upstream of the second nucleic acid. The second promoter can be a constitutive promoter, an inducible promoter, or a tissue-specific promoter.

In some embodiments, the expression vectors for expressing both a MINION polypeptide and a Myomaker polypeptide comprise an internal ribosome entry site (IRES) upstream of the Myomaker-coding sequence. IRES elements are able to bypass the ribosome scanning model of 5'-methylated Cap dependent translation and begin translation at internal sites (Pelletier and Sonenberg, 1988, Nature, 334: 320-325). IRES elements from two members of the picornavirus family (polio and encephalomyocarditis) have been described (Pelletier and Sonenberg, 1988), as well an IRES from a mammalian message (Macejak and Sarnow, 1991, Nature, 353:90-94, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

In some embodiments, the expression vectors for expressing both a MINION polypeptide and a Myomaker polypeptide comprise a 2A sequence upstream of the Myomaker-coding sequence. The 2A oligopeptide sequence was first characterized from the positive-stranded RNA picornavirus Foot-and-Mouth Disease Virus (FMDV); and FMDV 2A or F2A was shown to mediate a co-translational 'cleavage' between the upstream (capsid proteins) and downstream (RNA replication proteins) domains of the FMDV polyprotein (Ryan M D, EMBO J 1994; 134: 928-933; Ryan M D, J Gen Virol 1991; 72: 2727-2732; Donnelly MLL, J Gen Virol 1997; 78:13-21; Donnelly MLL, J Gen Virol 2001; 82:1013-1025). Active 2A sequences were characterized in the genomes of viruses from other genera of the picornaviruses, plus '2A-like' sequences found within the genomes of a range of different RNA viruses and non-LTR retrotransposons (Donnelly MLL, J Gen Virol 2001; 82:1027-1041; Heras S R, Cell Mol Life Sci 2006; 63:1449-1460; Luke G A, J Gen Virol 2008; 89:1036-1042; Odon V, Mol Biol Evol 2013; 30:1955-1965; Luke G A, Mob Gen Elements 2014; 3:e27525). These 2A or "2A-like" oligopeptide sequences were shown to mediate a translational 'recoding' event referred-to as 'ribosome skipping', 'stop carry-on' or 'stop-go' translation (Atkins J F, RNA 2007; 13:1-8).

As used herein, a "2A sequence" refers to any nucleic acid sequence encoding a 2A or "2A-like" oligopeptide serving as a linker between two proteins, allowing autonomous intraribosomal self-processing of polyproteins (See e.g., de Felipe. Genetic Vaccines and Ther. 2:13 (2004); deFelipe et al. Traffic 5:616-626 (2004)). These oligopeptides allow co-expression of multiple proteins from a single vector. Many 2A elements are known in the art. For example, viral 2A sequences have been described in U.S. Pat. Nos. 9,175, 311, 8,865,881, 7,939,059, 7,947,493, all of which are incorporated by reference herein. For example, a viral 2A sequence can be a picornaviral, a tetraviral 2A sequence, or a combination thereof. A picornaviral 2A sequence can be selected from any one of the Enteroviral 2A sequences, Rhinoviral 2A sequences, Cardioviral 2A sequences, Aphthoviral 2A sequences, Hepatoviral 2A sequences, Erboviral 2A sequences, Kobuviral 2A sequences, Teschoviral 2A sequences, and the Parechoviral 2A sequences. A tetraviral 2A sequences can be selected from any of the Betatetraviral 2A sequences or Omegatetraviral 2A sequences. Examples of 2A sequences that can be used in the methods and system disclosed herein, without limitation, include 2A sequences from the foot-and-mouth disease virus (F2A), equine rhinitis A virus (E2A), Thosea asigna virus (T2A), and porcine teschovirus-1 (P2A). In some embodiments, a 2A sequence encodes a viral 2A oligopeptide selected from T2A (EGRGSLLTCGDVEENPGP (SEQ ID NO: 52) or GSGEGRGSLLTCGDVEENPGP (SEQ ID NO: 53)), P2A (ATNFSLLKQAGDVEENPGP (SEQ ID NO: 54) or GSGATNFSLLKQAGDVEENPGP (SEQ ID NO: 55)), E2A (QCTNYALLKLAGDVESNPGP (SEQ ID NO: 56) or GSGQCTNYALLKLAGDVESNPGP (SEQ ID NO: 57)), or F2A (VKQTLNFDLLKLAGDVESNPGP (SEQ ID NO: 58) or GSGVKQTLNFDLLKLAGDVESNPGP (SEQ ID NO: 59)).

Non-viral 2A sequence has been described in U.S. Pat. No. 8,945,876, which is incorporated by reference herein. For example, a non-viral 2A sequence can be a sea urchin (*Strongylocentrotus purpuratus*) 2A sequence (DGFCI-LYLLLILLMRSGDVETNPGP) (SEQ ID NO: 60); a sponge (*Amphimedon queenslandica*) 2A sequence (LLCFMLLLLLSGDVELNPGP (SEQ ID NO: 61) or HHFMFLLLLLAGDIELNPGP (SEQ ID NO: 62)); an acorn worm (*Saccoglossus kowalevskii*) 2A sequence (WFLVLLSFILSGDIEVNPGP (SEQ ID NO: 63)); or an amphioxus (*Branchiostoma floridae*) 2A sequence (KNCAMYMLLLSGDVETNPGP (SEQ ID NO: 64) or MVISQLMLKLAGDVEENPGP (SEQ ID NO: 65)). In some embodiments, the 2A sequence is a naturally occurring or synthetic sequence that includes the 2A consensus sequence D-X-E-X-NPGP (SEQ ID NO: 66), in which X is any amino acid residue.

In some embodiments, the expression vector comprises a 2A sequence encoding a 2A oligopeptide selected from any one of SEQ ID NOs: 52-66.

In some embodiments, a nucleic acid encoding a human MINION polypeptide may also include a sequence encoding a secretion signal sequence so that the polypeptide is secreted from the host cell. Such a sequence can be provided by the vector, or as part of the MINION nucleic acid that is present in the vector.

Generation of an expression vector can utilize a vector that includes a multiple cloning site (MCS), which is a nucleic acid region that contains multiple restriction enzyme sites, any of which can be used in conjunction with standard recombinant technology to digest the vector. See Carbonelli et al., 1999, Levenson et al., 1998, and Cocea, 1997, incorporated herein by reference. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation: nucleic acid conjugates, naked DNA, artificial virions, fusion to the herpes virus structural protein VP22, agent-enhanced uptake of DNA, and ex vivo transduction. For long-term, high-yield production of recombinant proteins, stable expression will often be desired. For example, cell lines which stably express polypeptides of the invention can be prepared using expression vectors of the invention which contain viral origins of replication or endogenous expression elements and a selectable marker gene.

Also provided herein are cells that include any of the expression vectors described herein. In some embodiments, such cells comprising an expression vector for expressing a MINION polypeptide (e.g., a human MINION polypeptide). In some embodiments, such cells comprising an expression vector for expressing both a MINION polypeptide (e.g., a human MINION polypeptide) and a Myomaker polypeptide (e.g., a human Myomaker polypeptide). In some embodiments, such cells comprising an expression vector for expressing a MINION polypeptide (e.g., a human MINION polypeptide) and a second expression vector for expressing a Myomaker polypeptide (e.g., a human Myomaker polypeptide). Such cells can be a host cell or a therapeutic cell.

In some embodiments, the disclosure features a host cell that includes a nucleic acid molecule described herein. A host cell can be used to produce or express a human MINION polypeptide described herein. The terms "host cell" and "recombinant host cell" are used interchangeably herein, which refer to not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a protein can be expressed in bacterial cells (such as *E. coli*), insect cells, yeast cells, or mammalian cells (such as Chinese hamster ovary cells (CHO) or COS cells e.g., COS-7 cells, CV-1 origin SV40 cells; Gluzman (1981) Cell 23:175-182). Other suitable host cells are known to those skilled in the art.

A host cell can be used to produce or express a human MINION polypeptide described herein. Accordingly, the disclosure also features methods for producing a human MINION polypeptide using a host cell. In one embodiment, the method includes culturing the host cell (into which a recombinant expression vector encoding a protein has been introduced) in a suitable medium, such that a human MINION polypeptide is produced. In another embodiment, the method further includes isolating a human MINION polypeptide from the medium or the host cell.

In some embodiments, the disclosure features a therapeutic cell that includes a nucleic acid molecule described herein. As used herein, the term "therapeutic cell" refers to a cell that has been genetically engineered to express a polypeptide, e.g., a MINION polypeptide, e.g., a human MINION polypeptide, that is capable of fusing to a dysfunctional cell or tumor cell. Such a therapeutic cell can be a human cell, e.g., a human muscle cell such as a myoblast, a cardiac muscle cell, a skeletal muscle cell, or a smooth muscle cell; or a human non-muscle cell such as a fibroblast, a bone marrow cell, a blood cell, a hepatocyte, a stem cell, an epithelial cell, an endothelial cell, a dendritic cell, or a tumor cell. In some embodiments, the therapeutic cells comprise an expression vector expressing a MINION polypeptide, variant or fragment thereof disclosed herein. In some embodiments, the therapeutic cells comprise an expression vector expressing a Myomaker polypeptide, variant or fragment thereof disclosed herein. In some embodiments, such a therapeutic cell expresses a detectable marker, e.g., a fluorescent molecule (e.g., fluorescein, Texas red, rhodamine, green fluorescent protein, and the like), an enzyme (e.g., horse radish peroxidase, alkaline phosphatase), a luminescent molecule (e.g., luciferase), a radioactive molecule (e.g., $^3H$, $^{125}I$, $^{35}S$, $^{14}C$, or $^{32}P$), or calorimetric labels such as colloidal gold or colored beads. Cells expressing a detectable marker can be traced or visualized by appropriate detection methods such as microscopy, autoradiography, and/or other imaging methods known in the art.

In some embodiments, the therapeutic cells may be able to restore the function of the dysfunctional cell by fusing to the dysfunctional cell. As used herein, a "dysfunctional cell" refers to a cell that has partially or completely lost its normal function, for example, due to a genetic abnormality, e.g., a genetic mutation. Non-limiting examples of dysfunctional cells include: a muscle cell having a mutation in the dystrophin gene resulting in cell death which is the underlying cause for Duchenne muscular dystrophy (DMD) and Becker muscular dystrophy (BMD); a muscle cell having a mutation in the Dysferlin gene resulting in Miyoshi myopathy (MM), Limb-girdle muscular dystrophy type 2B (LGMD2B), and Distal Myopathy (DM), a cell having a mutation in the gene encoding fumaryl acetoacetate hydrolase (Fah), which leads to Hereditary Tyrosinemia type I, etc.

In some embodiments, the therapeutic cells may restore the function of the dysfunctional cell by introducing a gene of interest, e.g., a correct version of the gene that is mutated in the dysfunctional cell, to the dysfunctional cell, and thereby correct the genetic abnormality in the dysfunctional cell. For example, the therapeutic cells may contain a correct version of the dystrophin gene, a correct version of the gene encoding Fah, etc. The therapeutic cells may be autologous or allogeneic. In embodiments where the therapeutic cells are autologous, the genetic abnormality of the therapeutic cells may be corrected by a variety of gene editing systems known in the art. As used herein, the term "gene editing system" refers to a system comprising one or more DNA-binding domains or components and one or more DNA-modifying domains or components, or isolated nucleic acids, e.g., one or more vectors, encoding said DNA-binding and DNA-modifying domains or components. Gene editing systems are used for modifying the nucleic acid of a target gene and/or for modulating the expression of a target gene. In known gene editing systems, for example, the one or more DNA-binding domains or components are associated with the one or more DNA-modifying domains or components, such that the one or more DNA-binding domains target the one or more DNA-modifying domains or components to a specific nucleic acid site.

Gene editing systems are known in the art, and include but are not limited to, zinc finger nucleases, transcription activator-like effector nucleases (TALENs); clustered regularly interspaced short palindromic repeats (CRISPR)/Cas systems, and meganuclease systems. Without wishing to be bound by theory, it is believed that the known gene editing systems may exhibit unwanted DNA-modifying activity which is detrimental to their utility in therapeutic applications. These concerns are particularly apparent in the use of gene editing systems for in vivo modification of genes or gene expression, e.g., where cells are engineered to constitutively express components of a gene editing system, such as through lentiviral or adenoviral vector transfection.

"CRISPR" as used herein refers to a set of clustered regularly interspaced short palindromic repeats, or a system comprising such a set of repeats. "Cas," as used herein, refers to a CRISPR-associated protein. The diverse CRISPR-Cas systems can be divided into two classes according to the configuration of their effector modules: class 1 CRISPR systems utilize several Cas proteins and the crRNA to form an effector complex, whereas class 2 CRISPR systems employ a large single-component Cas protein in conjunction with crRNAs to mediate interference.

One example of class 2 CRISPR-Cas system employs Cpf1 (CRISPR from *Prevotella* and *Francisella* 1). See, e.g., Zetsche et al., Cell 163:759-771 (2015), the content of which is herein incorporated by reference in its entirety. The term "Cpf1" as used herein includes all orthologs, and variants that can be used in a CRISPR system.

It is contemplated that the therapeutic cells may be the same or different cell type from the dysfunctional cell or tumor cell. For example, in embodiments where the dysfunctional cell is a muscle cell, the therapeutic cell may be a muscle cell such as a myoblast, a cardiac muscle cell, a skeletal muscle cell, or a smooth muscle cell; or a non-muscle cell such as a fibroblast, a bone marrow cell, a blood cell, a hepatocyte, a stem cell, an epithelial cell, an endothelial cell, a dendritic cell, etc.

Antibodies that Bind MINION

Provided herein are antibodies or antigen-binding fragments thereof that specifically bind to a MINION protein, e.g., a MINION protein of Table 1. In some embodiments, provided herein are antibodies or antigen-binding fragments thereof that specifically bind to a MINION protein comprising an amino acid sequence selected from any of SEQ ID NO: 1, 3, 5, 7, 9, 11, 13, or 15. In some embodiments, provided herein are antibodies or antigen-binding fragments thereof that specifically bind to a MINION protein consisting of an amino acid sequence selected from any of SEQ ID NO: 1, 3, 5, 7, 9, 11, 13, or 15.

In some embodiments, provided herein are antibodies or antigen-binding fragments thereof that specifically bind to a human MINION protein, e.g., a protein comprising SEQ ID NO: 1 or 3, or a variant thereof. In some embodiments, provided herein are antibodies or antigen-binding fragments thereof that specifically bind to a human MINION protein of SEQ ID NO: 1. In some embodiments, provided herein are antibodies or antigen-binding fragments thereof that specifically bind to a human MINION protein of SEQ ID NO: 3.

An antibody that specifically binds a MINION protein (e.g., a human MINION protein, e.g., the protein of SEQ ID NO: 1 or 3) can be a monoclonal or polyclonal antibody. In some embodiments, an antibody that specifically binds a MINION protein (e.g., a human MINION protein, e.g., the protein of SEQ ID NO: 1 or 3) is a monoclonal antibody. In some embodiments, an antibody that specifically binds a MINION protein (e.g., a human MINION protein, e.g., the protein of SEQ ID NO: 1 or 3) is a human or humanized antibody.

In some embodiments, an antibody of the invention has a full length antibody heavy chain sequence and a full length antibody light chain sequence. A naturally occurring antibody usually comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component of the classical complement system.

An antibody can be a monoclonal antibody, human antibody, humanized antibody, camelised antibody, or chimeric antibody. The antibodies can be of any isotype (e.g., IgG, IgE, IgM, IgD, IgA and IgY), class (e.g., IgG1, IgG2, IgG3, IgG4, IgA1 and IgA2) or subclass.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and CL domains actually comprise the carboxy-terminus of the heavy and light chain, respectively. In particular, the term "antibody" specifically includes an IgG-scFv format.

The term "antigen binding fragment" refers to portions of a binding molecule (e.g., an antibody or antigen-binding fragment or derivative thereof), that specifically interacts with (e.g., by binding, steric hindrance, stabilizing/destabilizing, spatial distribution) a binding site on a target epitope, e.g., a MINION epitope. Examples of antibody fragments include, but are not limited to, an scFv, a Fab fragment, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., (1989) Nature 341:544-546), which consists of a VH domain; and an isolated complementarity determining region (CDR).

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., (1988) Science 242:423-426; and Huston et al., (1988) Proc. Natl. Acad. Sci. 85:5879-5883).

Such single chain antibodies are also intended to be encompassed within the terms "fragment", "epitope-binding fragment" or "antibody fragment." These fragments are obtained using conventional techniques known to those of skill in the art, and the fragments are screened for utility in the same manner as are intact antibodies.

Antibody fragments can be incorporated into single chain molecules comprising a pair of tandem Fv segments (VH-CH1-VH-CH1) which, together with complementary light chain polypeptides, form a pair of antigen binding regions (Zapata et al., (1995) Protein Eng. 8:1057-1062; and U.S. Pat. No. 5,641,870), and also include Fab fragments, F(ab') fragments, and anti-idiotypic (anti-Id) antibodies (including, e.g., anti-Id antibodies to antibodies of the invention), and epitope-binding fragments of any of the above.

Antigen binding fragments also include single domain antibodies, maxibodies, unibodies, minibodies, triabodies, tetrabodies, v-NAR and bis-scFv, as is known in the art (see, e.g., Hollinger and Hudson, (2005) Nature Biotechnology 23: 1126-1136), bispecific single chain diabodies, or single chain diabodies designed to bind two distinct epitopes. Antigen binding fragments also include antibody-like molecules or antibody mimetics, which include, but not limited to minibodies, maxybodies, Fn3 based protein scaffolds, Ankrin repeats (also known as DARpins), VASP polypeptides, Avian pancreatic polypeptide (aPP), Tetranectin, Affililin, Knottins, SH3 domains, PDZ domains, Tendamistat, Neocarzinostatin, Protein A domains, Lipocalins, Transferrin, and Kunitz domains that specifically bind epitopes, which are within the scope of the invention. Antibody fragments can be grafted into scaffolds based on polypeptides such as Fibronectin type III (Fn3) (see U.S. Pat. No. 6,703,199, which describes fibronectin polypeptide monobodies).

An isolated antibody can be a monovalent antibody, bivalent antibody, multivalent antibody, bivalent antibody, biparatopic antibody, bispecific antibody, monoclonal antibody, human antibody, recombinant human antibody, or any other type of antibody or epitope-binding fragment or derivative thereof.

The phrase "isolated antibody," as used herein, refers to antibody that is substantially free of other antibodies having different antigenic specificities (e.g., an isolated antibody that specifically binds a MINION protein (e.g., a human MINION protein, e.g., the protein of SEQ ID NO: 1 or 3) is substantially free of antibodies that specifically bind antigens other than a MINION protein (e.g., a human MINION protein, e.g., the protein of SEQ ID NO: 1 or 3). An isolated antibody that specifically binds a target molecule may, however, have cross-reactivity to the same antigens from other species, e.g., an isolated antibody that specifically binds a MINION protein (e.g., a human MINION protein, e.g., the protein of SEQ ID NO: 1 or 3) may bind MINION molecules from other species. Moreover, an isolated antibody may be substantially free of other cellular material and/or chemicals.

The term "monovalent antibody" as used herein, refers to an antibody that binds to a single epitope on a target molecule.

The term "bivalent antibody" as used herein, refers to an antibody that binds to two epitopes on at least two identical target molecules. The bivalent antibody may also crosslink the target molecules to one another. A "bivalent antibody" also refers to an antibody that binds to two different epitopes on at least two identical target molecules.

The term "multivalent antibody" refers to a single binding molecule with more than one valency, where "valency" is described as the number of antigen-binding moieties present per molecule of an antibody construct. As such, the single binding molecule can bind to more than one binding site on a target molecule. Examples of multivalent antibodies include, but are not limited to bivalent antibodies, trivalent antibodies, tetravalent antibodies, pentavalent antibodies, and the like, as well as bispecific antibodies and biparatopic antibodies. For example, for a MINION protein (e.g., a human MINION protein, e.g., the protein of SEQ ID NO: 1 or 3), the multivalent antibody has a binding moiety for two domains of the MINION protein (e.g., human MINION protein, e.g., the protein of SEQ ID NO: 1 or 3), respectively.

The term "multivalent antibody" also refers to a single binding molecule that has more than one antigen-binding moiety for two separate target molecules. For example, an antibody that binds to a MINION protein (e.g., a human MINION protein, e.g., the protein of SEQ ID NO: 1 or 3) and a second target molecule that is not MINION. In one embodiment, a multivalent antibody is a tetravalent antibody that has four epitope binding domains. A tetravalent molecule may be bispecific and bivalent for each binding site on that target molecule.

The term "biparatopic antibody" as used herein, refers to an antibody that binds to two different epitopes on a single target molecule. The term also includes an antibody, which binds to two domains of at least two target molecules, e.g., a tetravalent biparatopic antibody.

The term "bispecific antibody" as used herein, refers to an antibody that binds to two or more different epitopes on at least two different targets (e.g., MINION and a target that is not MINION).

The phrases "monoclonal antibody" or "monoclonal antibody composition" as used herein refers to polypeptides, including antibodies, bispecific antibodies, etc., that have substantially identical amino acid sequence or are derived from the same genetic source. This term also includes preparations of antibody molecules of single molecular composition. A monoclonal antibody composition displays a single binding specificity and affinity for a particular epitope.

The phrase "human antibody," as used herein, includes antibodies having variable regions in which both the framework and CDR regions are derived from sequences of human origin. Furthermore, if the antibody contains a constant region, the constant region is also derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86). The structures and locations of immunoglobulin variable domains, e.g., CDRs, may be defined using well known numbering schemes, e.g., the Kabat numbering scheme, the Chothia numbering scheme, or a combination of Kabat and Chothia (see, e.g., Sequences of Proteins of Immunological Interest, U.S. Department of Health and Human Services (1991), eds. Kabat et al.; Al Lazikani et al., (1997) J. Mol. Bio. 273:927 948); Kabat et al., (1991) Sequences of Proteins of Immunological Interest, 5th edit., NIH Publication no. 91-3242 U.S. Department of Health and Human Services; Chothia et al., (1987) J. Mol. Biol. 196:901-917; Chothia et al., (1989) Nature 342:877-883; and Al-Lazikani et al., (1997) J. Mal. Biol. 273:927-948.

The human antibodies of the invention may include amino acid residues not encoded by human sequences (e.g., mutations introduced by random or site-specific mutagenesis in vitro or by somatic mutation in vivo, or a conservative substitution to promote stability or manufacturing). However, the term "human antibody" as used herein, is not intended to include antibodies in which CDR sequences derived from the germline of another mammalian species, such as a mouse, have been grafted onto human framework sequences.

The phrase "recombinant human antibody" as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "Fc region" as used herein refers to a polypeptide comprising the CH3, CH2 and at least a portion of the hinge region of a constant domain of an antibody. Optionally, an Fc region may include a CH4 domain, present in some antibody classes. An Fc region, may comprise the entire hinge region of a constant domain of an antibody. In one embodiment, the invention comprises an Fc region and a CH1 region of an antibody. In one embodiment, the invention comprises an Fc region CH3 region of an antibody. In another embodiment, the invention comprises an Fc region, a CH1 region and a Ckappa/lambda region from the constant domain of an antibody. In one embodiment, a binding molecule of the invention comprises a constant region, e.g., a heavy chain constant region. In one embodiment, such a constant region is modified compared to a wild-type constant region. That is, the polypeptides of the invention disclosed herein may comprise alterations or modifications to one or more of the three heavy chain constant domains (CH1, CH2 or CH3) and/or to the light chain constant region domain (CL). Example modifications include additions, deletions or substitutions of one or more amino acids in one or more domains. Such changes may be included to optimize effector function, half-life, etc.

The term "binding site" as used herein comprises an area on a target molecule to which an antibody or antigen binding fragment selectively binds.

The term "epitope" as used herein refers to any determinant capable of binding with high affinity to an immunoglobulin. An epitope is a region of an antigen that is bound by an antibody that specifically targets that antigen, and when the antigen is a protein, includes specific amino acids that directly contact the antibody. Most often, epitopes reside on proteins, but in some instances, may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics.

Generally, antibodies specific for a particular target antigen will bind to an epitope on the target antigen in a complex mixture of proteins and/or macromolecules.

As used herein, the term "affinity" refers to the strength of interaction between antibody and antigen at single antigenic sites. Within each antigenic site, the variable region of the antibody "arm" interacts through weak non-covalent forces with the antigen at numerous sites; the more interactions, the stronger the affinity. As used herein, the term "high affinity" for an IgG antibody or fragment thereof (e.g., a Fab fragment) refers to an antibody having a knock down of $10^{-8}$ M or less, $10^{-9}$ M or less, or $10^{-10}$ M, or $10^{-11}$ M or less, or $10^{-12}$ M or less, or $10^{-13}$ M or less for a target antigen. However, high affinity binding can vary for other antibody isotypes. For example, high affinity binding for an IgM isotype refers to an antibody having a knock down of $10^{-7}$ M or less, or $10^{-8}$ M or less.

As used herein, the term "avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids such as by, e.g., x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots.

Generation of Monoclonal Antibodies

Monoclonal antibodies (mAbs) can be produced by a variety of techniques, including conventional monoclonal antibody methodology, e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

In some embodiments, the antibodies of the invention are humanized monoclonal antibodies. Chimeric or humanized antibodies and antigen-binding fragments thereof of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6,180,370 to Queen et al.

In some embodiments, the antibodies of the invention are human monoclonal antibodies. Such human monoclonal antibodies directed against a MINION protein (e.g., a human MINION protein, e.g., the protein of SEQ ID NO: 1 or 3) can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (mu and gamma) and kappa light chain immunoglobulin sequences, together with targeted mutations that inactivate the endogenous mu and kappa chain loci (see e.g., Lonberg, et al., 1994 Nature 368 (6474): 856-859). Accordingly, the mice exhibit reduced expression of mouse IgM or K, and in response to immunization, the introduced human heavy and light chain transgenes undergo class switching and somatic mutation to generate high affinity human IgG-kappa monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In some embodiments, human antibodies can be raised using a mouse that carries human immunoglobulin sequences on transgenes and transchomosomes such as a mouse that carries a human heavy chain transgene and a human light chain trans chromosome. Such mice, referred to herein as "KM mice," are described in detail in PCT Publication WO 02/43478 to Ishida et al.

Still further, alternative transgenic animal systems expressing human immunoglobulin genes are available in the art and can be used to raise MINION-binding antibodies and antigen-binding fragments thereof. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise MINION-binding antibodies of the invention. For example, mice carrying both a human heavy chain transchromosome and a human light chain transchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise MINION-binding antibodies of the invention.

Human monoclonal antibodies can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al; U.S. Pat. Nos. 5,427,908 and 5,580,717 to Dower et al; U.S. Pat. Nos. 5,969,108 and 6,172,197 to McCafferty et al; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies and antigen-binding fragments thereof of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In one embodiment, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In some embodiments, the MINION-binding molecule contains a human IgG1 constant region. In some embodiments, the human IgG1 constant region includes an Fc region.

In some embodiments, the Fc region of the MINION-binding molecule includes one or more mutations mediating reduced or no antibody-dependent cellular cytotoxicity (ADCC) or complement-dependent cytotoxicity (CDC). In some embodiments, amino acid residues L234 and L235 of the IgG1 constant region are substituted to A234 and A235. In some embodiments, amino acid residue N267 of the IgG1 constant region is substituted to A267. In some embodiments, amino acid residues D265 and P329 of the IgG1 constant region are substituted to A265 and A329. In certain embodiments, the Fc region optionally comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A. In some embodiments, the Fc region comprises a mutation or combination of mutations conferring reduced effector function selected from any of D265A, P329A, P329G, N297A, D265A/P329A, D265A/N297A, L234/L235A, P329A/L234A/L235A, and P329G/L234A/L235A (all positions by EU numbering).

In yet another embodiment, the Fc region is modified to increase the ability of the antibody to mediate antibody dependent cellular cytotoxicity (ADCC) and/or to increase the affinity of the antibody for an Fc-gamma receptor by modifying one or more amino acids. This approach is described further in PCT Publication WO 00/42072 by Presta. Moreover, the binding sites on human IgG1 for Fc-gamma RI, Fc-gamma RII, Fc-gamma RIII and FcRn have been mapped and variants with improved binding have been described (see Shields, R. L. et al., 2001 J. Biol. Chen. 276:6591-6604). For example, the Fc region can comprise a mutation or combination of mutations conferring increased effector function selected from any of S239D, I332E, A330L, S298A, E333A, E333S, K334A, K236A, K236W, F243L, P247I, D280H, K290S, R292P, S298D, S298V, Y300L, V305I, A339D, A339Q, A339T, P396L (all positions by EU numbering).

In still another embodiment, the glycosylation of an antibody is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta (1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

In some embodiments, the MINION-binding molecule is an antibody. In some embodiments, the antibody has an IgG1 isotype with one or more mutations (e.g., relative to a wild-type Fc region of the same isotype). In some embodiments, the one or more mutations are selected from N297A, N297Q (Bolt S et al. (1993) Eur J Immunol 23:403-411), D265A, L234A, L235A (McEarchern et al., (2007) Blood, 109:1185-1192), C226S, C229S (McEarchern et al., (2007) Blood, 109:1185-1192), P238S (Davis et al., (2007) J Rheumatol, 34:2204-2210), E233P, L234V (McEarchern et al., (2007) Blood, 109:1185-1192), P238A, A327Q, A327G, P329A (Shields R L. et al., (2001) J Biol Chem. 276(9): 6591-604), K322A, L234F, L235E (Hezareh, et al., (2001) J Viral 75, 12161-12168; Oganesyan et al., (2008). Acta Crystallographica 64, 700-704), P331S (Oganesyan et al., (2008) Acta Crystallographica 64, 700-704), T394D (Wilkinson et al. (2013) MAbs 5(3): 406-417), A330L, M252Y, S254T, and/or T256E, where the amino acid position is according to the EU or Kabat numbering convention. In certain embodiments, the Fc region further includes an amino acid deletion at a position corresponding to glycine 236 according to the EU or Kabat numbering convention.

In some embodiments, the antibody has an IgG1 isotype with a heavy chain constant region that contains a C220S mutation according to the EU or Kabat numbering convention.

In some embodiments, the Fc region further contains one or more additional mutations selected from A330L, L234F; L235E, and/or P331S according to EU or Kabat numbering convention.

In certain embodiments, the antibody has an IgG2 isotype. In some embodiments, the antibody contains a human IgG2 constant region. In some embodiments, the human IgG2 constant region includes an Fc region. In some embodiments, the Fc region contains one or more modifications. For example, in some embodiments, the Fc region contains one or more mutations (e.g., relative to a wild-type Fc region of the same isotype). In some embodiments, the one or more mutations are selected from V234A, G237A, H268E, V309L, N297A, N297Q, A330S, P331S, C232S, C233S, M252Y, S254T, and/or T256E, where the amino acid position is according to the EU or Kabat numbering convention.

In certain embodiments, the antibody has an IgG4 isotype. In some embodiments, the antibody contains a human IgG4 constant region. In some embodiments, the human IgG4 constant region includes an Fc region. In some embodiments, the Fc region contains one or more modifications. For example, in some embodiments, the Fc region contains one or more mutations (e.g., relative to a wild-type Fc region of the same isotype). In some embodiments, the one or more mutations are selected from E233P, F234V, L235A, G237A, E318A (Hutchins et al. (1995) Proc Nat/ Acad Sci USA, 92:11980-11984), S228P, L236E, S241P, L248E (Reddy et al., (2000) J Immuno/, 164:1925-1933; Angal et al., (1993) Mol Immunol. 30(1):105-8; U.S. Pat. No. 8,614,299 B2), T394D, M252Y, S254T, T256E, N297A, and/or N297Q, where the amino acid position is according to the EU or Kabat numbering convention.

In some embodiments, the Fc region further contains one or more additional mutations selected from a M252Y, S254T, and/or T256E, where the amino acid position is according to the EU or Kabat numbering convention.

In some embodiments, one or more of the IgG1 variants described herein may be combined with an A330L mutation (Lazar et al., (2006) Proc Natl Acad Sci USA, 103:4005-

4010), or one or more of L234F, L235E, and/or P331S mutations (Sazinsky et al., (2008) Proc Natl Acad Sci USA, 105:20167-20172), where the amino acid position is according to the EU or Kabat numbering convention, to eliminate complement activation. In some embodiments, the IgG variants described herein may be combined with one or more mutations to enhance the antibody half-liFc in human serum (e.g. M252Y, S254T, T256E mutations according to the EU or Kabat numbering convention) (Dall'Acqua et al., (2006) J Biol Chern, 281:23514-23524; and Strohl e al., (2009) Current Opinion in Biotechnology, 20:685-691).

In some embodiments, an IgG4 variant of the present disclosure may be combined with an S228P mutation according to the EU or Kabat numbering convention (Angal et al., (1993) Mol Immunol, 30:105-108) and/or with one or more mutations described in Peters et al., (2012) J Biol Chern. 13; 287(29):24525-33) to enhance antibody stabilization.

In some embodiments, the antibody has an Fc region selected from an IgG2 Fc region, an IgG4 Fc region, or an IgG2/IgG4 hybrid Fc region.

Methods of Engineering Altered Antibodies

As discussed above, the MINION-binding antibodies having VH and VL sequences or full length heavy and light chain sequences shown herein can be used to create new MINION-binding antibodies by modifying full length heavy chain and/or light chain sequences, VH and/or VL sequences, or the constant region (s) attached thereto. Thus, in another aspect of the invention, the structural features of MINION-binding antibody of the invention are used to create structurally related MINION-binding antibodies that retain at least one functional property of the antibodies and antigen-binding fragments thereof of the invention, such as binding to MINION.

For example, one or more CDR regions of the antibodies and antigen-binding fragments thereof of the present invention, or mutations thereof, can be combined recombinantly with known framework regions and/or other CDRs to create additional, recombinantly-engineered, MINION-binding antibodies and antigen-binding fragments thereof of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence (s) is used as the starting material to create a "second generation" sequence (s) derived from the original sequence (s) and then the "second generation" sequence (s) is prepared and expressed as a protein.

The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the MINION-binding antibodies described herein, which functional properties include, but are not limited to, specifically binding to MINION protein.

The functional properties of the altered antibodies can be assessed using standard assays available in the art and/or described herein, such as those set forth in the Examples (e.g., ELISAs).

In some embodiments, the methods of engineering antibodies and antigen-binding fragments thereof of the invention, mutations can be introduced randomly or selectively along all or part of a MINION-binding antibody coding sequence and the resulting modified MINION-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Characterization of the Antibodies of the Invention

The antibodies and antigen-binding fragments thereof of the invention can be characterized by various functional assays. For example, they can be characterized by their ability to bind a MINION protein (e.g., a human MINION protein, e.g., the protein of SEQ ID NO: 1 or 3).

The ability of an antibody to bind to MINION can be detected by labelling the antibody of interest directly, or the antibody may be unlabeled and binding detected indirectly using various sandwich assay formats known in the art.

In some embodiments, the MINION-binding antibodies and antigen-binding fragments thereof of the invention block or compete with binding of a reference MINION-binding antibody to MINION protein. These can be fully human or humanized antibodies that bind specifically to MINION described above. They can also be other human, mouse, chimeric or humanized antibodies which bind to the same epitope on MINION as the reference antibody. The capacity to block or compete with the reference antibody binding indicates that MINION-binding antibody under test binds to the same or similar epitope as that defined by the reference antibody, or to an epitope which is sufficiently proximal to the epitope bound by the reference MINION-binding antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as MINION protein. A test antibody competes with the reference antibody for specific binding to the antigen if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of an antibody with a reference antibody for binding to a particular protein, in this case, MINION. These include, e.g., solid phase direct or indirect radioimmunoassay (RIA), solid phase direct or indirect enzyme immunoassay (EIA), sandwich competition assay (see Stahli et al., Methods in Enzymology 9:242-253, 1983); solid phase direct biotin-avidin EIA (see Kirkland et al., J. Immunol. 137:3614-3619, 1986); solid phase direct labeled assay, solid phase direct labeled sandwich assay (see Harlow & Lane, supra); solid phase direct label RIA using I-125 label (see Morel et al., Molec. Immunol. 25:7-15, 1988); solid phase direct biotin-avidin EIA (Cheung et al., Virology 176:546-552, 1990); and direct labeled RIA (Moldenhauer et al., Scand. J. Immunol. 32:77-82, 1990). Typically, such an assay involves the use of purified antigen bound to a solid surface or cells bearing either of these, an unlabeled test MINION-binding antibody and a labelled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected MINION-binding monoclonal antibodies bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using MINION protein coated-ELISA plates. Biotinylated MAb binding can be detected with a strep-avidin-alkaline phosphatase probe. To determine the isotype of a purified MINION-binding antibody, isotype ELISAs can be performed. For example, wells of microtiter plates can be coated with 1 □g/ml of anti-human IgG overnight at 4 degrees C. After blocking with 1% BSA, the plates are reacted with 1 □g/ml or less of the monoclonal MINION-binding antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined.

To demonstrate binding of monoclonal MINION-binding antibodies to live cells expressing MINION protein, flow cytometry can be used. Briefly, cell lines expressing MINION (grown under standard growth conditions) can be mixed with various concentrations of MINION-binding antibody in PBS containing 0.1% BSA and 10% fetal calf serum, and incubated at 37 degrees ° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

MINION-binding antibodies and antigen-binding fragments thereof of the invention can be further tested for reactivity with MINION protein or antigenic fragment by Western blotting. Briefly, purified MINION protein or fusion proteins, or cell extracts from cells expressing MINION can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Liposomes Comprising MINION Polypeptide and Methods of Delivering Therapeutic Agents Provided herein are also liposomes comprising a MINION polypeptide described herein, e.g., a MINION polypeptide of Table 1. Liposomes are closed lipid carriers characterized by lipid bilayers encapsulating an aqueous core. Liposomes can be used as carriers for a therapeutic agent. In some embodiments, the MINION polypeptide expresses on the surface of the liposomes. The fusogenic activity of the MINION polypeptide can induce fusion of the liposome lipids with a cell membrane, thereby delivering the liposomal content directly into the cytoplasm, bypassing the degradative endocytic entry pathway. Liposomes comprising a MINION polypeptide can fuse to a broad range of cell types, making them compatible with many therapeutic agents such as a nucleic acid (e.g., e.g., an antisense oligonucleotide, plasmid, siRNA, shRNA, aptamer), a protein or polypeptide (e.g., an antibody, antigen, enzyme, or therapeutic polypeptide), a peptide nucleic acid (PNA), or a low molecular weight compound.

In some embodiments, the liposomes described herein include a MINION polypeptide comprising an amino acid sequence selected from SEQ ID NO: 1, 3, 5, 7, 9, 11, 13, or 15, or a variant thereof. In some embodiments, the liposomes described herein include a MINION polypeptide consisting of an amino acid sequence selected from SEQ ID NO: 1, 3, 5, 7, 9, 11, 13, or 15, or a variant thereof. In some embodiments, the liposomes described herein include a polypeptide consisting of SEQ ID NO: 1. In some embodiments, the liposomes described herein include a polypeptide consisting of SEQ ID NO: 3. In some embodiments, the liposomes described herein include a polypeptide consisting of SEQ ID NO: 5. In some embodiments, the liposomes described herein include a polypeptide consisting of SEQ ID NO: 7.

In some embodiments, the liposomes described herein also include a Myomaker polypeptide, e.g., a Myomaker polypeptide of Table 2. In some embodiments, the liposomes described herein include a Myomaker polypeptide comprising an amino acid sequence selected from SEQ ID NO: 16, 18, 20, 22, 24, 26, 28, or 30, or a variant thereof. In some embodiments, the liposomes described herein include a Myomaker polypeptide consisting of an amino acid sequence selected from SEQ ID NO: 16, 18, 20, 22, 24, 26, 28, or 30, or a variant thereof. In some embodiments, the liposomes described herein include a Myomaker polypeptide consisting of SEQ ID NO: 16. In some embodiments, the liposomes described herein include a Myomaker polypeptide consisting of SEQ ID NO: 18. In some embodiments, the liposomes described herein include a Myomaker polypeptide consisting of SEQ ID NO: 20.

In some embodiments, liposomes described herein include a MINION polypeptide and a therapeutic agent encapsulated in the liposome. The therapeutic agent can be a nucleic acid (e.g., an antisense oligonucleotide, plasmid, siRNA, shRNA, aptamer), a protein or polypeptide (e.g., an antibody, antigen, enzyme, or therapeutic polypeptide), a peptide nucleic acid (PNA), or a low molecular weight compound. Such liposomes are fusogenic and can be used to deliver the therapeutic agent into a target cell, e.g., a human cell, e.g., a dysfunctional cell or a tumor cell, through the fusion of the liposome lipids into the cell membrane.

Methods of making liposomes comprising a fusogenic protein have been described in US patent application publications, e.g., US 20140314831, US 20140134232, US 20090280163, US 20090142267, each of which is incorporated by reference herein. For example, a MINION polypeptide can be inserted into the liposomal membrane by the detergent depletion method derived from the concepts outlined in publications such as Rigaud et al., 1995, Biochim Biophys Acta 1231(3):223-46; Rigaud and Levy, 2003, Methods Enzymol., 372:65-86; and Top et al., 2005, EMBO J, 24(17):2980-8, the contents of which are incorporated herein by reference. Briefly, the purified MINION polypeptide can be reconstituted into the liposomes by mixing the detergent-suspended MINION polypeptide with liposomes pre-saturated with detergent, followed by removal of the detergent. To assist in the process of inserting the MINION polypeptide into the liposome membrane, n-octyl β-D-glucopyranoside (OG) can be used in the detergent. Based on the size and type of liposomes used, an optimal concentration of OG should be determined by incrementally adding OG to a solution of liposomal lipids across a 0-2.0% final volume concentration spectrum. Absorbance can be detected at $\lambda_{600\ nm}$ and a plot derived of absorbance versus OG %. The optimal concentration is just below the critical OG concentration which causes dissolution of the liposomes.

In some embodiments, a MINION polypeptide can be associated with the liposome through an electrostatic or hydrophobic interaction. For example, electrostatic interactions between the positively charged amino acids (Glu or Asp) of the MINION polypeptide and the negatively charged phospholipid membrane of the liposome can result in an association between them.

Neutral or anionic liposomes, and cationic lipids are known to facilitate delivery of substance(s) to a host cell. These compounds are readily available to one skilled in the art; for example, see Liposomes: A Practical Approach, RCP New Ed, IRL press (1990). The liposomal lipids can include cationic lipids, synthetic lipids, glycolipids, phospholipids, cholesterol or derivatives thereof, and equivalent molecules known to those of skill in the art. Anionic and neutral liposomes are well-known in the art (see, e. g., Liposomes: A Practical Approach, RPC New Ed, IRL press (1990), for a detailed description of methods for making liposomes) and are useful for delivering a large range of therapeutic agents. Phospholipids can comprise preferably phosphatidylcholine, sphingomyelin, phosphatidylethanolamine, phosphatidylserine, phosphatidylglycerol, phosphatidic acid, cardiolipin and phosphatidylinositol with varying fatty acyl compositions.

Cationic lipids are also known in the art and are commonly used for drug or gene delivery. Such lipids include Lipofectin™ also known as DOTMA (N-[1-(2,3-dioleyloxy) propyls-N,N,N-trimethylammonium chloride), DOTAP (1,2-bis(oleyloxy)-3-(trimethylammonio) propane), DDAB (dimethyldioctadecylammonium bromide), DOGS (dioctadecylamidologlycyl spermine) and cholesterol derivatives such as DC-Chol (3 beta-(N—(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for delivery of polynucleotides are preferably used in association with a neutral lipid such as DOPE (dioleyl phosphatidylethanolamine), as described in WO 90/11092 as an example. Formulations containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Unilamellar liposomes can be prepared from multilamellar lipid vesicles. For example, a mixture of DOPC:COPE: cholesterol:DC-cholesterol in a molar ratio of 60:30:4:6 can be used to prepare a multilamellar lipid vesicle suspension. However, lipid vesicles containing PE-PEG2000 and/or DOTAP may be required in certain circumstances. The multilamellar lipid vesicles can be prepared by a number of different methods, which will be known to a person skilled in the art, such as the thin film method described by Fenske and Cullis, 2005, Methods Enzymol. 391:7-40.

Unilamellar liposomes can be extruded from the multilamellar lipid vesicle suspension by manual extrusion through a polycarbonate membrane of defined pore size, using gas-tight, glass syringes, such as the LiposoFast-Basic (Avestin Inc., Ottawa, ON, Canada). In this procedure, the sample is passed through the membrane by pushing the sample back and forth between two syringes. In order to achieve a specific diameter of liposome, the multilamellar lipid vesicle suspension is passed through a filter having a specific diameter of pore size.

Examples of liposomes or liposome compositions include those described in U.S. Pat. Nos. 4,789,633; 4,902,512; 4,925,661; 4,983,397; 5,013,556; 5,292,524; 5,534,241; 5,593,622; 5,648,478; 5,676,971; 5,756,069; 5,834,012; 5,846,458; 5,891,468; 5,945,122; 6,046,225; 6,057,299; 6,056,973; 6,077,834; 6,126,966; 6,153,596; 6,197,333; 6,228,391; 6,316,024; 6,387,397; 6,417,326; 6,476,068; 6,586,559; 6,627,218; 6,723,338; 6,897,196; 6,936,272; 7,384,923; US Pat. App. Publication. Nos. 2001/0033860; 2001/0038851; 2002/0136707; 2002/0034537; 2003/0224037; 2003/0113262; 2003/0072794; 2003/0082228; 2003/0212031; 2003/0203865; 2003/0175205; 2003/0162748; 2003/0130190; 2003/0059461; 2003/0215490; 2003/0166601; 2004/0022842; 2004/0142025; 2004/0071768; 2004/0234588; 2004/0213833; 2004/0029210; 2005/0271588; 2005/0136064; and International Patent Applications WO 99/30686; WO 02/41870; WO 00/74646; WO 96/13250; WO 98/33481; Aliminana et al., Prep. Biochem. Biotech. (2004) 34(1): 77-96; Papahadjopolulos D, Allen T M, Gbizon A, et al. "Sterically stabilized liposomes: Improvements in pharmacokinetics and antitumor therapeutic efficacy" Proc Natl Acad Sci U.S.A. (1991) 88: 11460-11464; Allen T M, Martin F J. "Advantages of liposomal delivery systems for anthracyclines" Semin Oncol (2004) 31: 5-15 (suppl 13); Weissig et al. Pharm. Res. (1998) 15: 1552-1556.

In an effort to prolong the circulatory half-life of liposomes and avoid uptake by the reticuloendothelial system, researchers developed liposomes that were modified by the incorporation of polyethylene glycol or other hydrophilic polymers (e.g., a PEG liposome where one or more of the constituent lipids was modified by attachment of PEG). PEG-modified liposomes were also often referred to as "shielded" liposomes. Doxil™ (doxorubicin HCl liposome injection) is a liposome-enclosed doxorubicin, with adjunct polyethylene glycol (PEG) utilized to avoid the reticuloendothelial system (RES) and prolong drug circulation time. See Vail D M, Amantea M A, Colbern G T, et al., "Pegylated Liposomal Doxorubicin: Proof of Principle Using Preclinical Animal Models and Pharmacokinetic Studies." Semin Oncol. (2004) 31 (Suppl 13): 16-35. However, adverse effects were also caused by prolonged blood retention (e.g., hand-foot syndrome, an adverse effect of Doxil® on the peripheral system, etc.) became recognized as a problem.

In addition to PEG-modified liposomes, researchers developed a variety of other derivatized lipids. These derivatized lipids could also be incorporated into liposomes. See, for example: International Patent Application WO 93/01828; Park Y S, Maruyama K, Huang L. "Some negatively charged phospholipids derivatives prolong the liposome circulation in vivo." Biochimica et Biophysica Acta (1992) 1108: 257-260; Ahl et al., Biochimica Biophys. Acta (1997) 1329: 370-382.

In addition to modification of liposomes with PEG and other hydrophilic polymers, researchers also developed liposomes that aimed to specifically target particular cell types by incorporating targeting factors (also referred to as targeting ligands) for particular cell types. Examples of targeting factors/ligands include asialoglycoprotein, folate, transferrin, antibodies, etc. In some cases one or more of the constituent lipids could be modified by the attachment of a targeting factor.

Examples of lipid compositions including targeting factors include U.S. Pat. Nos. 5,049,390; 5,780,052; 5,786,214; 6,316,024; 6,056,973; 6,245,427; 6,524,613; 6,749,863; 6,177,059; 6,530,944; 7,829,113; 8,758,810; U.S. Pat. App. Publication. Nos. 2004/0022842; 2003/0224037; 2003/143742; 2003/0228285; 2002/0198164; 2003/0220284; 2003/0165934; 2003/0027779; International Patent Application Nos. WO 95/33841; WO 95/19434; WO 2001037807; WO 96/33698; WO 2001/49266; WO 9940789; WO 9925320; WO 9104014; WO 92/07959; EP 1369132; JP 2001002592; Iinuma H, Maruyama K, et al., "Intracellular targeting therapy of cisplatin-encapsulated transferring-polyethylene glycol liposome on peritoneal dissemination of gastric cancer" Int J Cancer (2002) 99 130-137; Ishida O, Maruyama K, Tanahashi H, Iwatsuru M, Sasaki K, et al., "Liposomes bearing polyethylene glycol-coupled transferrin with intracellular targeting property to the solid tumors in vivo." Pharmaceutical Research (2001) 18: 1042-1048; Holmberg et al., Biochem. Biophys. Res. Comm. (1989) 165(3):1272-1278; Nam et al., J. Biochem. Mol. Biol. (1998) 31(1): 95-100; Nag et al., J. Drug Target. (1999) 6(6): 427-438.

Also provided herein are methods of delivering a therapeutic agent to a cell (e.g., a human cell, e.g., a dysfunctional cell or a tumor cell) by contacting a liposome comprising a MINION polypeptide described herein with the cell, wherein the liposome fuses with the cell and thereby delivers the therapeutic agent to the cell. The method can be performed in vitro or in vivo.

Methods of Fusing Cells and Therapeutic Uses

Provided herein are methods of fusing a first cell to a second cell using a MINION polypeptide, e.g., a MINION polypeptide of Table 1. In some embodiments, such methods can include the steps of (a) providing a first cell expressing a MINION polypeptide and a Myomaker polypeptide; and (b) contacting the first cell with a second cell expressing Myomaker, wherein the first cell fuses with the second cell. The step (b) of the method can be performed in vitro or in vivo.

In some embodiments, the MINION polypeptide comprises an amino acid sequence selected from SEQ ID NO: 1, 3, 5, 7, 9, 11, 13, or 15, or a variant thereof. In some embodiments, the MINION polypeptide consists of an amino acid sequence selected from SEQ ID NO: 1, 3, 5, 7, 9, 11, 13, or 15, or a variant thereof. In some embodiments, the MINION polypeptide comprises SEQ ID NO: 1 or a variant thereof. In some embodiments, the MINION polypeptide comprises SEQ ID NO: 3 or a variant thereof. In some embodiments, the MINION polypeptide consists of SEQ ID NO: 1 or a variant thereof. In some embodiments, the MINION polypeptide consists of SEQ ID NO: 3 or a variant thereof.

In some embodiments, the Myomaker polypeptide comprises an amino acid sequence selected from SEQ ID NO: 16, 18, 20, 22, 24, 26, 28, or 30, or a variant thereof. In some embodiments, the Myomaker polypeptide consists of an amino acid sequence selected from SEQ ID NO: 16, 18, 20, 22, 24, 26, 28, or 30, or a variant thereof. In some embodiments, the Myomaker polypeptide comprises SEQ ID NO: 16 or a variant thereof. In some embodiments, the Myomaker polypeptide consists of SEQ ID NO: 16 or a variant thereof.

In some embodiments, methods of fusing a first cell to a second cell can include the steps of (a) providing a first cell expressing a MINION polypeptide and a receptor that mediates homotypic interaction; and (b) contacting the first cell with a second cell expressing the same receptor expressed by the first cell, wherein the first cell fuses with the second cell. The receptor that mediates homotypic interaction includes but not limited to, e.g., a cadherin (e.g., N-Cadherin, P-Cadherin, E-Cadherin, or M-Cadherin), a selectin, a claudin, an occludin, a junctional adhesion molecule, or a tricellulin. The step (b) of the method can be performed in vitro or in vivo. In some embodiments, the MINION polypeptide comprises an amino acid sequence selected from SEQ ID NO: 1, 3, 5, 7, 9, 11, 13, or 15, or a variant thereof. In some embodiments, the MINION polypeptide consists of an amino acid sequence selected from SEQ ID NO: 1, 3, 5, 7, 9, 11, 13, or 15, or a variant thereof. In some embodiments, the MINION polypeptide comprises SEQ ID NO: 1 or a variant thereof. In some embodiments, the MINION polypeptide comprises SEQ ID NO: 3 or a variant thereof. In some embodiments, the MINION polypeptide consists of SEQ ID NO: 1 or a variant thereof. In some embodiments, the MINION polypeptide consists of SEQ ID NO: 3 or a variant thereof.

These methods can be used to fuse any types of muscle cells, e.g., human muscle cells; or non-muscle cells, e.g., human non-muscle cells. Thus, the first and second cells can be selected from a muscle cell, a fibroblast, a bone marrow cell, a blood cell, a hepatocyte, a stem cell, an epithelial cell, an endothelial cell, a dendritic cell, or a tumor cell. In some embodiments, the methods are used to fuse a muscle cell or a non-muscle cell (e.g., a fibroblast, a bone marrow cell, a blood cell, a hepatocyte, a stem cell, an epithelial cell, an endothelial cell, or a dendritic cell) with a tumor cell or a dysfunctional cell.

In some embodiments, the first cell can express a detectable marker, e.g., a fluorescent molecule (e.g., fluorescein, Texas red, rhodamine, green fluorescent protein, and the like), an enzyme (e.g., horse radish peroxidase, alkaline phosphatase), a luminescent molecule (e.g., luciferase), a radioactive molecule (e.g., $^3$H, $^{125}$I, $^{35}$S, $^{14}$C, or $^{32}$P), or calorimetric labels such as colloidal gold or colored beads. Cells expressing a detectable marker can be traced or visualized by appropriate detection methods such as microscopy, autoradiography, and/or other imaging methods.

In some embodiments, the first cell can include a gene of interest, and the fusion of the first and the second cells delivers the gene of interest to the second cell. In some embodiments, the gene of interest corrects a pathologic phenotype of the second cell. In some embodiments, the second cell can include a gene of interest, and the fusion of the first and the second cells delivers the gene of interest to the first cell. In some embodiments, the gene of interest corrects a pathologic phenotype of the first cell.

In some embodiments, the gene of interest is a gene of the mitochondrial DNA, and the methods described herein can be used to treat a mitochondrial disease. For example, the pathologic phenotype can be selected from mitochondrial DNA depletion; mitochondrial myopathy; Myoclonic Epilepsy with Ragged Red Fibers (MERRF); mitochondrial myopathy, encephalomyopathy, lactic acidosis, stroke-like symptoms (MELAS); Kearns-Sayre syndrome (KSS); Leigh syndrome (subacute necrotizing encephalomyopathy) and maternally inherited Leigh syndrome (MILS); Mitochondrial neurogastrointestinal encephalomyopathy (MNGIE); Myoclonus epilepsy with ragged red fibers (MERRF); Neuropathy, ataxia and retinitis pigmentosa (NARP); or Pearson syndrome.

In some embodiments, the gene of interest is a gene encoding fumaryl acetoacetate hydrolase (Fah), and the methods described herein can be used to treat Hereditary Tyrosinemia type I. In some embodiments, the gene of interest is a gene encoding Dystrophin, and the methods described herein can be used to treat Duchenne muscular dystrophy (DMD) or Becker muscular dystrophy (BMD). In some embodiments, the gene of interest is a gene encoding Dysferlin, and the methods described herein can be used to treat Miyoshi myopathy (MM), Limb-girdle muscular dystrophy type 2B (LGMD2B), and Distal Myopathy (DM).

The compositions and methods described herein can be used to treat a cancer, e.g., head and neck cancer, skin cancer, breast cancer, prostate cancer, ovarian cancer, cervical cancer, lung cancer, liver cancer, renal cancer, pancreatic cancer, colorectal cancer, brain cancer, neuroblastoma, glioma, sarcoma, lymphoma, or leukemia. In some embodiments, the compositions and methods described herein can be used to treat a sarcoma selected from angiosarcoma, dermatofibrosarcoma, epithelioid sarcoma, Ewing's sarcoma, fibrosarcoma, gastrointestinal stromal tumors (GISTs), Kaposi sarcoma, Leiomyosarcoma, liposarcoma, malignant fibrous histiocytoma, neurofibrosarcoma, rhabdomyosarcoma, undifferentiated pleomorphic sarcoma, or synovial sarcoma.

Methods of Treating Cancer Using Oncolytic Virus

Provided herein are methods of treating cancer in a subject by administering to the subject a virus, e.g., an oncolytic virus, comprising a nucleic acid encoding a MINION polypeptide. In an alternative embodiment, provided herein is a virus, e.g. an oncolytic virus, comprising a nucleic acid encoding a MINION polypeptide for use in treating cancer. Infection of a cell with a virus encoding a fusogenic protein can cause extensive multinucleated syncytial formation, effectively increasing the area and number of cells transduced by the virus (Wong, PLOS ONE, DOI: 10.1371/journal.pone.0151516, Mar. 17, 2016). Mixing of cytoplasmic contents of fusing cells means that any gene product encoded within the vector is efficiently transferred to all cells fused into the syncytium. Moreover, fusogenic proteins can act as effective single-agent therapeutics, as the process of fusion ultimately compromises cell function and induces cell death. In the context of oncolytic virus, in addition to normal tumor cell lysis resulting in release of virus, an infected cell can spread its infectious payload through direct cell-cell fusion (Wong, PLOS ONE, DOI: 10.1371/journal.pone.0151516, Mar. 17, 2016).

In some embodiments, methods of treating cancer in a subject can include administering to the subject an effective amount of an oncolytic virus comprising a nucleic acid encoding a MINION polypeptide, and a nucleic acid encoding a Myomaker polypeptide. In an alternative embodiment, provided herein is an oncolytic virus comprising a nucleic acid encoding a MINION polypeptide and a nucleic acid encoding a Myomaker polypeptide for use in treating cancer in a subject, wherein an effective amount of the oncolytic virus is administered to the subject.

In some embodiments, the MINION polypeptide comprises an amino acid sequence selected from SEQ ID NO: 1, 3, 5, 7, 9, 11, 13, or 15, or a variant thereof. In some embodiments, the MINION polypeptide consists of an amino acid sequence selected from SEQ ID NO: 1, 3, 5, 7, 9, 11, 13, or 15, or a variant thereof. In some embodiments, the MINION polypeptide comprises SEQ ID NO: 1 or a variant thereof. In some embodiments, the MINION polypeptide comprises SEQ ID NO: 3 or a variant thereof. In some embodiments, the MINION polypeptide consists of SEQ ID NO: 1 or a variant thereof. In some embodiments, the MINION polypeptide consists of SEQ ID NO: 3 or a variant thereof.

In some embodiments, the Myomaker polypeptide comprises an amino acid sequence selected from SEQ ID NO: 16, 18, 20, 22, 24, 26, 28, or 30, or a variant thereof. In some embodiments, the Myomaker polypeptide consists of an amino acid sequence selected from SEQ ID NO: 16, 18, 20, 22, 24, 26, 28, or 30, or a variant thereof. In some embodiments, the Myomaker polypeptide comprises SEQ ID NO: 16 or a variant thereof. In some embodiments, the Myomaker polypeptide consists of SEQ ID NO: 16 or a variant thereof.

In some embodiments, methods of treating cancer in a subject can include administering to the subject an effective amount of an oncolytic virus comprising a nucleic acid encoding a MINION polypeptide, and a nucleic acid encoding a receptor that mediates homotypic interaction. In an alternative embodiment, provided herein is an oncolytic virus comprising a nucleic acid encoding a MINION polypeptide and a nucleic acid encoding a receptor that mediates homotypic interaction for use in treating cancer in a subject, wherein an effective amount of the oncolytic virus is administered to the subject. The receptor that mediates homotypic interaction includes but not limited to, e.g., a cadherin (e.g., N-Cadherin, P-Cadherin, E-Cadherin, or M-Cadherin), a selectin, a claudin, an occludin, a junctional adhesion molecule, or a tricellulin. In some embodiments, the MINION polypeptide comprises an amino acid sequence selected from SEQ ID NO: 1, 3, 5, 7, 9, 11, 13, or 15, or a variant thereof. In some embodiments, the MINION polypeptide consists of an amino acid sequence selected from SEQ ID NO: 1, 3, 5, 7, 9, 11, 13, or 15, or a variant thereof. In some embodiments, the MINION polypeptide comprises SEQ ID NO: 1 or a variant thereof. In some embodiments, the MINION polypeptide comprises SEQ ID NO: 3 or a variant thereof. In some embodiments, the MINION polypeptide consists of SEQ ID NO: 1 or a variant thereof. In some embodiments, the MINION polypeptide consists of SEQ ID NO: 3 or a variant thereof.

Suitable oncolytic viruses are known in the art, e.g., those described in Kaufman, Nat Rev Drug Discov. 2015; 14(9): 642-662, which is incorporated by reference herein in its entirety. In some embodiments, the oncolytic virus specifically targets cancer cells, e.g., the oncolytic virus has no effect or a minimal effect on non-cancer cells. In some embodiments, the oncolytic virus selectively replicates in cancer cells. In embodiments, the oncolytic virus is capable of selectively replicating in and triggering the death of or slowing the growth of a cancer cell. An oncolytic virus includes but is not limited to an oncolytic adenovirus, oncolytic adeno-associated virus, oncolytic Herpes Simplex Virus (HSV), oncolytic parvovirus, oncolytic retrovirus, oncolytic lentivirus, oncolytic vaccinia virus, oncolytic Sinbis virus, oncolytic influenza virus, oncolytic reovirus, oncolytic Newcastle disease virus (NDV), oncolytic measles virus, oncolytic vesicular stomatitis virus (VSV), oncolytic poliovirus, oncolytic poxvirus, oncolytic Seneca Valley virus, oncolytic coxsackievirus, oncolytic enterovirus, oncolytic myxoma virus, or oncolytic maraba virus.

In some embodiments, the oncolytic virus is a recombinant oncolytic virus, such as those described in US2010/0178684, which is incorporated herein by reference in its entirety. In some embodiments, a recombinant oncolytic virus comprises a nucleic acid sequence (e.g., heterologous nucleic acid sequence) encoding an inhibitor of an immune or inflammatory response, e.g., as described in US2010/0178684, which is incorporated herein by reference in its entirety. In embodiments, the recombinant oncolytic virus, e.g., oncolytic NDV, comprises a pro-apoptotic protein (e.g., apoptin), a cytokine (e.g., GM-CSF, CSF, interferon-gamma, interleukin-2 (IL-2), tumor necrosis factor-alpha), an immunoglobulin (e.g., an antibody against ED-B fibronectin), tumor associated antigen, a bispecific adapter protein (e.g., bispecific antibody or antibody fragment directed against NDV HN protein and a T cell co-stimulatory receptor, such as CD3 or CD28; or fusion protein between human IL-2 and single chain antibody directed against NDV HN protein). See, e.g., Zamarin et al. Future Microbiol. 7.3(2012):347-67, incorporated herein by reference in its entirety. In some embodiments, the oncolytic virus is a chimeric oncolytic NDV described in U.S. Pat. No. 8,591,881 B2, US 2012/0122185 A1, or US 2014/0271677 A1, each of which is incorporated herein by reference in their entireties.

In some embodiments, the oncolytic virus comprises a conditionally replicative adenovirus (CRAd), which is designed to replicate exclusively in cancer cells. See, e.g., Alemany et al. Nature Biotechnol. 18(2000):723-27. In some embodiments, an oncolytic adenovirus comprises one described in Table 1 on page 725 of Alemany et al., incorporated herein by reference in its entirety.

Exemplary oncolytic viruses include but are not limited to the following:
Group B Oncolytic Adenovirus (ColoAd1) (PsiOxus Therapeutics Ltd.) (see, e.g., Clinical Trial Identifier: NCT02053220);
ONCOS-102 (previously called CGTG-102), which is an adenovirus comprising granulocyte-macrophage colony stimulating factor (GM-CSF) (Oncos Therapeutics) (see, e.g., Clinical Trial Identifier: NCT01598129);
VCN-01, which is a genetically modified oncolytic human adenovirus encoding human PH20 hyaluronidase (VCN Biosciences, S.L.) (see, e.g., Clinical Trial Identifiers: NCT02045602 and NCT02045589);
Conditionally Replicative Adenovirus ICOVIR-5, which is a virus derived from wild-type human adenovirus serotype 5 (Had5) that has been modified to selectively replicate in cancer cells with a deregulated retinoblastoma/E2F pathway (Institut Català d'Oncologia) (see, e.g., Clinical Trial Identifier: NCT01864759);
Celyvir, which comprises bone marrow-derived autologous mesenchymal stem cells (MSCs) infected with ICOVIR5, an oncolytic adenovirus (Hospital Infantil Universitario Niño Jesús, Madrid, Spain/Ramon Alemany) (see, e.g., Clinical Trial Identifier: NCT01844661);
CG0070, which is a conditionally replicating oncolytic serotype 5 adenovirus (Ad5) in which human E2F-1 promoter drives expression of the essential E1a viral genes, thereby restricting viral replication and cytotoxicity to Rb pathway-defective tumor cells (Cold Genesys, Inc.) (see, e.g., Clinical Trial Identifier: NCT02143804); or
DNX-2401 (formerly named Delta-24-RGD), which is an adenovirus that has been engineered to replicate selectively in retinoblastoma (Rb)-pathway deficient cells and to infect cells that express certain RGD-binding integrins more efficiently (Clinica Universidad de Navarra, Universidad de Navarra/DNAtrix, Inc.) (see, e.g., Clinical Trial Identifier: NCT01956734).

In some embodiments, the oncolytic virus can express a detectable marker, e.g., a fluorescent molecule (e.g., fluorescein, Texas red, rhodamine, green fluorescent protein, and the like), an enzyme (e.g., horse radish peroxidase, alkaline phosphatase), a luminescent molecule (e.g., luciferase), a radioactive molecule (e.g., $^{3}H$, $^{125}I$, $^{35}S$, $^{14}C$, or $^{32}P$), or calorimetric labels such as colloidal gold or colored beads.

In some embodiments, an oncolytic virus described herein is administering by injection, e.g., subcutaneous, intra-arterial, intravenous, intramuscular, intrathecal, or intraperitoneal injection. In some embodiments, an oncolytic virus described herein is administered intratumorally, transdermally, transmucosally, orally, intranasally, subcutaneously, intra-arterially, intravenously, intramuscularly, intrathecally, or intraperitoneally, or via pulmonary administration.

Cancer Vaccines and Therapeutic Uses

Cancer vaccines based on tumor-dendritic cell heterokaryons can potently induce immunity through the enhanced presentation of tumor antigens via both class I and class II MHC (Gong et al., Induction of antitumor activity by immunization with fusions of dendritic and carcinoma cells. Nat Med 1997, 3:558-561, the content of which is hereby incorporated by reference in its entirety), and co-expression of Minion/Myomerger and Myomaker could dramatically improve the efficiency of forming these hybrids.

Accordingly, in some embodiments, provided herein are a cancer vaccine comprising a dendritic-tumor fusion cell comprising a nucleic acid encoding a MINION polypeptide, and a nucleic acid encoding a Myomaker polypeptide. In an alternative embodiment, provided herein is a cancer vaccine comprising a dendritic-tumor fusion cell comprising a nucleic acid encoding a MINION polypeptide and a nucleic acid encoding a Myomaker polypeptide for use in treating cancer in a subject, wherein an effective amount of the cancer vaccine is administered to the subject. In some embodiments, provided herein is a cancer vaccine comprising a dendritic-tumor fusion cell comprising a nucleic acid encoding a MINION polypeptide, and a nucleic acid encoding a receptor that mediates homotypic interaction. In an alternative embodiment, provided herein is a cancer vaccine comprising a dendritic-tumor fusion cell comprising a nucleic acid encoding a MINION polypeptide and a nucleic acid encoding a receptor that mediates homotypic interaction for use in treating cancer in a subject, wherein an effective amount of the cancer vaccine is administered to the subject.

In some embodiments, the MINION polypeptide comprises an amino acid sequence selected from SEQ ID NO: 1, 3, 5, 7, 9, 11, 13, or 15, or a variant thereof. In some embodiments, the MINION polypeptide consists of an amino acid sequence selected from SEQ ID NO: 1, 3, 5, 7, 9, 11, 13, or 15, or a variant thereof. In some embodiments, the MINION polypeptide comprises SEQ ID NO: 1 or a variant thereof. In some embodiments, the MINION polypeptide comprises SEQ ID NO: 3 or a variant thereof. In some embodiments, the MINION polypeptide consists of SEQ ID NO: 1 or a variant thereof. In some embodiments, the MINION polypeptide consists of SEQ ID NO: 3 or a variant thereof.

In some embodiments, the Myomaker polypeptide comprises an amino acid sequence selected from SEQ ID NO: 16, 18, 20, 22, 24, 26, 28, or 30, or a variant thereof. In some embodiments, the Myomaker polypeptide consists of an amino acid sequence selected from SEQ ID NO: 16, 18, 20, 22, 24, 26, 28, or 30, or a variant thereof. In some embodiments, the Myomaker polypeptide comprises SEQ ID NO: 16 or a variant thereof. In some embodiments, the Myomaker polypeptide consists of SEQ ID NO: 16 or a variant thereof.

The receptor that mediates homotypic interaction includes but not limited to, e.g., a cadherin (e.g., N-Cadherin, P-Cadherin, E-Cadherin, or M-Cadherin), a selectin, a claudin, an occludin, a junctional adhesion molecule, or a tricellulin.

Methods of producing a dendritic-tumor fusion cell as a cancer vaccine are known in the art. For example, fusing dendritic cells (DC) and whole tumor cells by chemical, physical, or biological means creates heterokaryons, which include dendritic cell-derived MHC class I, MHC class II, and costimulatory molecules as well as whole tumor-derived tumor-associated antigens. See, e.g., Koido, S.; Ohana, M.; Liu, C.; Nikrui, N.; Durfee, J.; Lerner, A.; Gong, J. Dendritic cells fused with human cancer cells: Morphology, antigen expression, and T cell stimulation. Clin. Immunol. 2004, 113, 261-269; Gong, J.; Koido, S.; Calderwood, S. K. Cell fusion: From hybridoma to dendritic cell-based vaccine. Expert Rev. Vaccines 2008, 7, 1055-1068; Kajihara, M.; Takakura, K.; Ohkusa, T.; Koido, S. The impact of dendritic cell-tumor fusion cells on cancer vaccines—Past progress and future strategies. Immunotherapy 2015, 7, 1111-1122; Takakura, K.; Kajihara, M.; Ito, Z.; Ohkusa, T.; Gong, J.; Koido, S. Dendritic-tumor fusion cells in cancer immunotherapy. Discov. Med. 2015, 19, 169-174, the contents of which are hereby incorporated by reference in their entireties. DC-tumor fusion approach offers the following advantages for inducing antitumor immune responses: (1) DC-tumor FCs present whole tumor-derived antigenic peptides, which avoids the need to identify antigenic peptides for individual patients; (2) a broad array of known and unidentified tumor-associated antigens (TAAs) can be simultaneously presented on the surface of DC-tumor FCs, which increases the frequency of polyclonal antigen-specific CD4+ and CD8+ T cells, resulting in long-term efficient antitumor immunity; (3) numerous TAAs are presented in the context of co-stimulatory molecules, which prevents tolerance induction, resulting in efficient antitumor immune response; and (4) DC-tumor FCs migrate into draining lymph nodes and form clusters with CD4+ and CD8+ T cells in the T cell area of lymph nodes, such that DC-tumor FCs do not have to take up exogenous TAAs in order to activate CD4+ and CD8+ T cells. See Koido S., Dendritic-Tumor Fusion Cell-Based Cancer Vaccines. Int'l J. Mol. Sci. 2016, 17, 828, the content of which is hereby incorporated by reference in its entirety.

In some embodiments, the dendritic-tumor fusion cell is produced by fusing a dendritic cell and a tumor cell, whereas the fusion of the dendritic cell and the tumor cell is facilitated by the expression of a MINION polypeptide and a Myomaker polypeptide. In some embodiments, the dendritic cell comprises a nucleic acid encoding a MINION polypeptide, and a nucleic acid encoding a Myomaker polypeptide. In some embodiments, the tumor cell comprises a nucleic acid encoding a MINION polypeptide, and a nucleic acid encoding a Myomaker polypeptide. In some embodiments, the dendritic cell comprises a nucleic acid encoding a MINION polypeptide, and the tumor cell comprises a nucleic acid encoding a Myomaker polypeptide, or vice versa.

The dendritic cell and/or the tumor cell can be autologous or allogeneic. For example, the use of DCs from healthy donors as a source of allogeneic DCs to generate allogeneic DC-tumor FC vaccines has been investigated. See, e.g., Koido, S.; Hara, E.; Homma, S.; Ohkusa, T.; Gong, J.; Tajiri, H. Cancer immunotherapy by fusions of dendritic cells and tumor cells. Immunotherapy 2009, 1, 49-62, the content of which is hereby incorporated by reference in its entirety. Alternatively, allogeneic tumor cell lines have been used in place of autologous tumor cells to induce autologous tumor-specific antitumor immune responses. See, e.g., Koido, S.; Hara, E.; Homma, S.; Torii, A.; Toyama, Y.; Kawahara, H.; Watanabe, M.; Yanaga, K.; Fujise, K.; Tajiri, H.; et al. Dendritic cells fused with allogeneic colorectal cancer cell line present multiple colorectal cancer-specific antigens and induce antitumor immunity against autologous tumor cells. Clin. Cancer Res. 2005, 11, 7891-7900; Koido, S.; Tanaka, Y.; Tajiri, H.; Gong, J. Generation and functional assessment of antigen-specific T cells stimulated by fusions of dendritic cells and allogeneic breast cancer cells. Vaccine 2007, 25, 2610-2619; Koido, S.; Hara, E.; Homma, S.; Namiki, Y.; Komita, H.; Takahara, A.; Nagasaki, E.; Ito, M.; Sagawa, Y.; Mitsunaga, M.; et al. Dendritic/pancreatic carcinoma fusions for clinical use: Comparative functional analysis of healthy- versus patient-derived fusions. Clin. Immunol. 2010, 135, 384-400, the content of which is hereby incorporated by reference in its entirety. Further, allogeneic DC lines and allogeneic tumor cell lines may be used instead of autologous cells. Cell lines are well characterized and can be well propagated in vitro under GMP standards. DC-tumor FC vaccines with fully allogeneic components have been demonstrated to induce clinical responses. See Märten, A.; Renoth, S.; Heinicke, T.; Albers, P.; Pauli, A.; Mey, U.; Caspari, R.; Flieger, D.; Hanfland, P.; von Ruecker, A.; et al. Allogeneic dendritic cells fused with tumor cells: Preclinical results and outcome of a clinical phase I/II trial in patients with metastatic renal cell carcinoma. Hum. Gene Ther. 2003, 14, 483-494, the content of which is hereby incorporated by reference in its entirety.

In some embodiments, the DCs may be immunomodulated, e.g., treated by an agonist for a Toll-like receptor (TLR), before being fused to tumor cells. In some embodiments, the DCs may be fused to an immunogenic tumor cell, e.g., a tumor cell treated with heat or ethanol. In some embodiments, the fusion of DCs and immunogenic whole tumor cells activates antigen-specific CD4+ and CD8+ T cells that produce high levels of IFN-γ.

In some embodiments, the DCs may be fused to cancer stem cells (CSCs). For example, the DCs may be fused to CSCs expressing one or more stem cell markers, including OCT3/4, ABCG2, nestin, SOX2, Bmi-1, Notch-1, CD44, CD133, and CD177. In some embodiments, the DCs may be fused to CSCs overexpressing survivin, MUC1, hTERT, HER2, CERP55, COA-1, or WT1.

In some embodiments, the dendritic-tumor fusion cell comprises one or more tumor-associated antigens (TAAs). Exemplary tumor-associated antigens include, but are not limited to, Alphafetoprotein (AFP), Carcinoembryonic antigen (CEA), Immature laminin receptor, TAG-72, HPV E6, HPV E7, BING-4, Calcium-activated chloride channel 2, Cyclin-B1, 9D7, Ep-CAM, EphA3, Her2/neu, Telomerase, Mesothelin, SAP-1, Survivin, CT9, CT10, NY-ESO-1/LAGE-1, PRAME, SSX-2, Melan-A/MART-1, Gp100/ pmel17, TRP-1, TRP-2, P.polypeptide, MC1R, Prostate-specific antigen (PSA), β-catenin, BRCA1, BRCA2, CDK4, CML66, Fibronectin, MART-2, TGF-βRII, CA-125, MUC-1, Epithelial tumor antigen (ETA), Tyrosinase, B melanoma antigen (BAGE), CAGE, GAGE-1, GAGE-2, GAGE-3, GAGE-6, Melanoma-associated antigen (MAGE), sarcoma antigen 1 (SAGE-1), XAGE-1, XAGE-2, XAGE-3, Ras, p53, etc.

Further provided are methods of treating cancer in a subject using the a cancer vaccine disclosed herein. In some embodiments, a cancer vaccine described herein is administering by injection, e.g., subcutaneous, intra-arterial, intravenous, intramuscular, intrathecal, or intraperitoneal injection. In some embodiments, a cancer vaccine described herein is administered intratumorally, transdermally, transmucosally, orally, intranasally, subcutaneously, intra-arterially, intravenously, intramuscularly, intrathecally, or intraperitoneally, or via pulmonary administration.

Methods of Treating Muscular Dystrophy

The compositions and methods disclosed herein may be used to treat a muscular dystrophy, such as Duchenne muscular dystrophy (DMD), Becker muscular dystrophy (BMD), Congenital muscular dystrophy (CMD), Distal muscular dystrophy, Emery-Dreifuss muscular dystrophy (EDMD), Facioscapulohumeral muscular dystrophy (FMD), Limb-Girdle muscular dystrophy (LGMD), Myotonic muscular dystrophy (MMD), Oculopharnyngeal muscular dystrophy (OMD), Miyoshi myopathy (MM), Limb-girdle muscular dystrophy type 2B (LGMD2B), Distal Myopathy (DM), etc. Early work in the mdx mouse model of DMD suggested that exogenously delivered cells arising from either the muscle or hematopoietic lineage could contribute to myofiber formation via cell fusion (Gussoni et al., Dystrophin expression in the mdx mouse restored by stem cell transplantation. Nature 1999, 401:390-394; Gibson et al., Dermal fibroblasts convert to a myogenic lineage in mdx mouse muscle. J Cell Sci 1995, 108 (Pt 1):207-214). The identification of Myomaker opened the door to increasing the fusogenic potential of cell-based therapies, thereby increasing their complementation potential. Studies utilizing non-muscle derived cells, such as fibroblasts and mesenchymal stem cells, indeed demonstrated that overexpression of Myomaker could promote the fusion of these cells into muscle in vivo (Mitani et al., In vivo myomaker-mediated heterologous fusion and nuclear reprogramming. FASEB J 2017, 31:400-411).

Accordingly, provided herein are methods of treating muscular dystrophy in a subject using the compositions disclosed herein. In some embodiments, methods of treating muscular dystrophy in a subject can include administering to the subject an effective amount of a therapeutic cell comprising a nucleic acid encoding a MINION polypeptide. In some embodiments, methods of treating muscular dystrophy in a subject can include administering to the subject an effective amount of a therapeutic cell comprising a nucleic acid encoding a MINION polypeptide, and a nucleic acid encoding a Myomaker polypeptide. In an alternative embodiment, provided herein is a therapeutic cell comprising a nucleic acid encoding a MINION polypeptide and/or a nucleic acid encoding a Myomaker polypeptide for use in treating muscular dystrophy in a subject, wherein an effective amount of the therapeutic cell is administered to the subject.

In some embodiments, the MINION polypeptide comprises an amino acid sequence selected from SEQ ID NO: 1, 3, 5, 7, 9, 11, 13, or 15, or a variant thereof. In some embodiments, the MINION polypeptide consists of an amino acid sequence selected from SEQ ID NO: 1, 3, 5, 7, 9, 11, 13, or 15, or a variant thereof. In some embodiments, the MINION polypeptide comprises SEQ ID NO: 1 or a variant thereof. In some embodiments, the MINION polypeptide comprises SEQ ID NO: 3 or a variant thereof. In some embodiments, the MINION polypeptide consists of SEQ ID NO: 1 or a variant thereof. In some embodiments, the MINION polypeptide consists of SEQ ID NO: 3 or a variant thereof.

In some embodiments, the Myomaker polypeptide comprises an amino acid sequence selected from SEQ ID NO: 16, 18, 20, 22, 24, 26, 28, or 30, or a variant thereof. In some embodiments, the Myomaker polypeptide consists of an amino acid sequence selected from SEQ ID NO: 16, 18, 20, 22, 24, 26, 28, or 30, or a variant thereof. In some embodiments, the Myomaker polypeptide comprises SEQ ID NO: 16 or a variant thereof. In some embodiments, the Myomaker polypeptide consists of SEQ ID NO: 16 or a variant thereof.

In some embodiments, methods of treating muscular dystrophy in a subject can include administering to the subject an effective amount of a therapeutic cell comprising a nucleic acid encoding a MINION polypeptide, and a nucleic acid encoding a receptor that mediates homotypic interaction. In an alternative embodiment, provided herein is a therapeutic cell comprising a nucleic acid encoding a MINION polypeptide and a nucleic acid encoding a receptor that mediates homotypic interaction for use in treating muscular dystrophy in a subject, wherein an effective amount of the therapeutic cell is administered to the subject. The receptor that mediates homotypic interaction includes but not limited to, e.g., a cadherin (e.g., N-Cadherin, P-Cadherin, E-Cadherin, or M-Cadherin), a selectin, a claudin, an occludin, a junctional adhesion molecule, or a tricellulin. In some embodiments, the MINION polypeptide comprises an amino acid sequence selected from SEQ ID NO: 1, 3, 5, 7, 9, 11, 13, or 15, or a variant thereof. In some embodiments, the MINION polypeptide consists of an amino acid sequence selected from SEQ ID NO: 1, 3, 5, 7, 9, 11, 13, or 15, or a variant thereof. In some embodiments, the MINION polypeptide comprises SEQ ID NO: 1 or a variant thereof. In some embodiments, the MINION polypeptide comprises SEQ ID NO: 3 or a variant thereof. In some embodiments, the MINION polypeptide consists of SEQ ID NO: 1 or a variant thereof. In some embodiments, the MINION polypeptide consists of SEQ ID NO: 3 or a variant thereof.

In some embodiments, the therapeutic cells may restore the function of the dysfunctional cell by introducing a gene of interest, e.g., a correct version of the gene that is mutated in the dysfunctional cell, to the dysfunctional cell, and thereby correct the genetic abnormality in the dysfunctional cell. For example, the therapeutic cells may contain a correct version of the dystrophin gene. The therapeutic cells may be autologous or allogeneic. In embodiments where the therapeutic cells are autologous, the genetic abnormality of the therapeutic cells may be corrected by a variety of gene editing systems known in the art. As used herein, the term "gene editing system" refers to a system comprising one or more DNA-binding domains or components and one or more DNA-modifying domains or components, or isolated nucleic acids, e.g., one or more vectors, encoding said DNA-binding and DNA-modifying domains or components. Gene editing systems are used for modifying the nucleic acid of a target gene and/or for modulating the expression of a target gene. In known gene editing systems, for example, the one or more DNA-binding domains or components are associated with the one or more DNA-modifying domains or components, such that the one or more DNA-binding domains target the one or more DNA-modifying domains or components to a specific nucleic acid site.

Gene editing systems are known in the art, and include but are not limited to, zinc finger nucleases, transcription activator-like effector nucleases (TALENs); clustered regularly interspaced short palindromic repeats (CRISPR)/Cas systems, and meganuclease systems. Without wishing to be bound by theory, it is believed that the known gene editing systems may exhibit unwanted DNA-modifying activity which is detrimental to their utility in therapeutic applications. These concerns are particularly apparent in the use of gene editing systems for in vivo modification of genes or gene expression, e.g., where cells are engineered to constitutively express components of a gene editing system, such as through lentiviral or adenoviral vector transfection.

"CRISPR" as used herein refers to a set of clustered regularly interspaced short palindromic repeats, or a system comprising such a set of repeats. "Cas," as used herein, refers to a CRISPR-associated protein. The diverse CRISPR-Cas systems can be divided into two classes according to the configuration of their effector modules: class 1 CRISPR systems utilize several Cas proteins and the crRNA to form an effector complex, whereas class 2 CRISPR systems employ a large single-component Cas protein in conjunction with crRNAs to mediate interference. One example of class 2 CRISPR-Cas system employs Cpf1 (CRISPR from *Prevotella* and *Francisella* 1). See, e.g., Zetsche et al., Cell 163:759-771 (2015), the content of which is herein incorporated by reference in its entirety. The term "Cpf1" as used herein includes all orthologs, and variants that can be used in a CRISPR system.

It is contemplated that the therapeutic cells may be the same or different cell type from the dysfunctional cell. For example, the therapeutic cell may be a muscle cell such as a myoblast, a cardiac muscle cell, a skeletal muscle cell, or a smooth muscle cell; or a non-muscle cell such as a fibroblast, a bone marrow cell, a blood cell, a hepatocyte, a stem cell, an epithelial cell, an endothelial cell, a dendritic cell, etc.

Methods of Studying Cell Fate and Reprogramming

The methods and compositions disclosed herein may be further used to study cell fate and reprogramming, e.g., identifying genes that are expressed or inhibited during cell specialization. Early studies on somatic cell nuclear reprogramming relied on chemical methods such as PEG treatment to induce heterokaryon formation (Blau et al., Cytoplasmic activation of human nuclear genes in stable heterocaryons. Cell 1983, 32:1171-1180, the content of which is hereby incorporated by reference in its entirety). It is contemplated that transient expression of Myomaker and MINION via conditional/inducible systems will allow far greater control of fusion, with resulting insights into the temporal dynamics of nuclear reprogramming.

Accordingly, the methods and compositions disclosed herein may be used to fuse a first cell and a second cell to generate a stable heterokaryon, wherein the first cell is reprogrammed by the second cell, e.g., the expression of one or more genes in the first cell are modulated by the second cell. In some embodiments, the first and second cells can be selected from a muscle cell, a fibroblast, a bone marrow cell, a blood cell, a hepatocyte, a stem cell, an epithelial cell, an endothelial cell, a dendritic cell, or a tumor cell. In some embodiments, the first cell and the second cell are from different species, such as human, monkey, mouse, rat, pig, etc. In some embodiments, the methods may comprise identifying the one or more genes that are modulated, for example, by comparing the gene expression profile of the first cell before fusion to that of the stable heterokaryon.

Pharmaceutical Compositions

Also provided herein are compositions, e.g., pharmaceutical compositions, comprising one or more MINION polypeptides (e.g., one or more human MINION polypeptides), one or more nucleic acids encoding a MINION polypeptide (e.g., a human MINION polypeptide), one or more liposomes comprising a MINION polypeptide (e.g., a human MINION polypeptide), one or more therapeutic cells comprising a MINION polypeptide (e.g., a human MINION polypeptide), one or more oncolytic viruses comprising a MINION polypeptide (e.g., a human MINION polypeptide), or one or more cancer vaccines comprising a MINION polypeptide (e.g., a human MINION polypeptide) described herein. Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Pharmaceutical compositions are typically formulated to be compatible with its intended route of administration. Examples of routes of administration include parenteral (e.g., intravenous, intraarterial, intraperitoneal), oral, intracranial, intrathecal, intranasal (e.g., inhalation), intradermal, subcutaneous, or transmucosal administration.

In some embodiments, the pharmaceutical compositions comprise one or more pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Methods of formulating suitable pharmaceutical compositions are known in the art, see, e.g., Remington: The Science and Practice of Pharmacy. 21st ed., 2005; and the books in the series Drugs and the Pharmaceutical Sciences: a Series of Textbooks and Monographs (Dekker, NY). For example, solutions or suspensions used for parenteral, intradermal, intrathecal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders, for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization.

Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Parenteral formulations can be a single bolus dose, an infusion or a loading bolus dose followed with a maintenance dose. These compositions can be administered at specific fixed or variable intervals, e.g., once a day, or on an "as needed" basis.

A suitable pharmaceutical composition for injection can comprise a buffer (e.g., acetate, phosphate or citrate buffer), a surfactant (e.g., polysorbate), optionally a stabilizer agent (e.g., human albumin), etc. Preparations for peripheral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In some embodiments, the pharmaceutical composition comprises 0.01-0.1 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, and inert gases and the like.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798. Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the therapeutic compounds are prepared with carriers that will protect the therapeutic compounds against rapid elimination from the body, such as a controlled release formulation, including implants and microencapsulated delivery systems.

The pharmaceutical compositions can be included in a container, pack, or dispenser together with instructions for administration.

In non-limiting examples, the pharmaceutical composition containing at least one pharmaceutical agent is formulated as a liquid (e.g., a thermosetting liquid), as a component of a solid (e.g., a powder or a biodegradable biocompatible polymer (e.g., a cationic biodegradable biocompatible polymer)), or as a component of a gel (e.g., a biodegradable biocompatible polymer). In some embodiments, the at least composition containing at least one pharmaceutical agent is formulated as a gel selected from the group of an alginate gel (e.g., sodium alginate), a cellulose-based gel (e.g., carboxymethyl cellulose or carboxyethyl cellulose), or a chitosan-based gel (e.g., chitosan glycerophosphate). Additional, non-limiting examples of drug-eluting polymers that can be used to formulate any of the pharmaceutical compositions described herein include, carrageenan, carboxymethylcellulose, hydroxypropylcellulose, dextran in combination with polyvinyl alcohol, dextran in combination with polyacrylic acid, polygalacturonic acid, galacturonic polysaccharide, polysalactic acid, polyglycolic acid, tamarind gum, xanthum gum, cellulose gum, guar gum (carboxymethyl guar), pectin, polyacrylic acid, polymethacrylic acid, N-isopropylpolyacrylomide, polyoxyethylene, polyoxypropylene, pluronic acid, polylactic acid, cyclodextrin, cycloamylose, resilin, polybutadiene, N-(2-Hydroxypropyl)methacrylamide (HP MA) copolymer, maleic anhydrate-alkyl vinyl ether, polydepsipeptide, polyhydroxybutyrate, polycaprolactone, polydioxanone, polyethylene glycol, polyorganophosphazene, polyortho ester, polyvinylpyrrolidone, polylactic-co-glycolic acid (PLGA), polyanhydrides, polysilamine, poly N-vinyl caprolactam, and gellan.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but are not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population), and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Kits

Also provided are kits including one or more MINION polypeptides (e.g., one or more human MINION polypeptides), one or more nucleic acids encoding a MINION polypeptide (e.g., a human MINION polypeptide), one or more liposomes comprising a MINION polypeptide (e.g., a human MINION polypeptide), one or more cells comprising a MINION polypeptide (e.g., a human MINION polypeptide), one or more oncolytic viruses comprising a MINION polypeptide (e.g., a human MINION polypeptide), or one or more cancer vaccines comprising a MINION polypeptide (e.g., a human MINION polypeptide) described herein, and instructions for use. Instructions for use can include instructions for diagnosis or treatment of a disease. Kits as provided herein can be used in accordance with any of the methods described herein. Those skilled in the art will be aware of other suitable uses for kits provided herein, and will be able to employ the kits for such uses. Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

One skilled in the art will recognize many methods and materials similar or equivalent to those described herein, which could be used in the practice of the present invention. Indeed, the present invention is in no way limited to the methods and materials described.

EXAMPLES

The invention is further described in the following examples, which do not limit the scope of the invention described in the claims.

Example 1: Materials and Methods

The following materials and methods are used in Examples 2-6.

Animals

All animal experiments were approved by the GNF IACUC, and carried out in accordance with approved guidelines. C57BL/6J mice were obtained through in-house breeding. Please see the "Generation of MINION-knockout mice by CRISPR/Cas9-mediated gene editing" section below for details regarding genetically engineered mice generated in-house.

Cardiotoxin (CTX) Injury Model

The cardiotoxin (CTX) injury model is a well-established model to study mouse skeletal muscle regeneration. CTX from *Naja mossambica mossambica* (Sigma C9759) was dissolved in normal saline (0.9% w/v of NaCl) to make a 10 µM working solution which was aliquoted and stored at −20° C. After anesthesia of the mouse with isoflurane (1.5%-2% in oxygen), the anterior aspect of the adult mouse hindlimb (8-10-week C57BL/6) was sterilized with 70% ethanol, shaved to expose the skin, and approximately 50 µL of CTX solution was injected into the midbelly of the tibialis anterior (TA) muscle using a 0.3 ml U100 BD insulin syringe. TA muscles were collected and examined at different time points after CTX. Adult mice at a similar age without CTX injection or with equal volume normal saline injection were used as controls.

Mouse Skeletal Muscle RNA Sequencing

Twelve 8-10-week C57BL/6 mice were injected with CTX into the TA muscle as described above, and their TA muscles were collected at 1, 3, 5, 7 days after CTX injection respectively with 3 mice for each time point. TA muscles from three 8-10-week uninjured mice were also collected. Total RNA from each muscle sample was isolated by TRIzol Reagent (Thermo Fisher 15596026) according to manufacturer's instructions and purified by Qiagen RNeasy columns.

The RNA samples (3 replicates for each time point) were submitted to the in-house Sequencing and Expression Analysis Core for quality checking, library preparation, and next-generation single-read sequencing. One microgram of total RNA was used to make Illumina-compatible sequencing libraries, and the libraries were sequenced using 50 bp single reads on an Illumina HiSeq 1000. Reads were aligned to the mouse transcriptome (Refseq mouse transcripts as of March 2013) using BWA (H. Li, et al., Fast and accurate short read alignment with Burrows-Wheeler transform. *Bioinformatics* 25, 1754, 2009). An average of 36 million reads per sample mapped to the mouse transcriptome. To analyze the raw data, reads per kilobase of transcript per million mapped reads (RPKM) were calculated for each gene at each time point, the RPKM of each gene at CTX day 1, 3, 5, 7 was normalized to that of uninjured muscles, and the results were averaged to generate the fold change in expression level. The data were then analyzed in two ways: 1) genes that exhibited more than 100-fold increase in CTX day 3 muscles compared to uninjured muscles were selected; 2) genes predicted to contain an open reading frame (ORF) of less than 100 codons were selected. Genes meeting both criteria were then selected and further examined against in-house RNA-Seq data from undifferentiated and differentiated primary myoblasts and C2C12 immortalized myoblasts. sMINION was the only small ORF that was not only dynamically expressed and but also exhibited greater than 10-fold change between undifferentiated and differentiated myoblast samples.

Generation of MINION-Knockout Mice by CRISPR/Cas9-Mediated Gene Editing

Four week old female C57BL/6J mice were superovulated by intraperitoneal injection of 5 IU pregnant mare's serum gonadotropin (PMSG) followed 47 hours later by 5 IU of human chorionic gonadotropin (HCG). Female mice were mated 1:1 immediately after HCG injection to C57BL/6J male mice. The following morning, the females were checked for copulatory plugs and zygotes collected from the oviducts of plugged females. In vitro transcribed Cas9 mRNA (100 ng/µL) and two gRNAs (50 ng/µL) were coinjected into the pronuclei of fertilized zygotes. Zygotes surviving the injection procedure were transferred into a single oviduct, (50-60 embryos/oviduct) of pseudopregnant ICR recipient females. Mice produced from injected embryos were genotyped and sequenced (see Assay for genome modification below) to determine the presence of mutations within the genomic region of MINION. Mutant founder animals were then bred to C57BL/6J mice and offspring were analyzed for germline transmission.

In order to generate in vitro transcribed Cas9 mRNA, a 10 bp spacer and the T7 promoter were added to the *Streptococcus pyogenes* Cas9 coding region by PCR amplification from a construct (pCR-Blunt II-TOPO-NLS-Cas9-NLS) made in house, and the amplified gel-purified Cas9 PCR product was used as the template for in vitro transcription using mMESSAGE mMACHINE T7 ULTRA kit (Life Technologies). In order to generate in vitro transcribed gRNA, two oligonucleotides were first synthesized (IDT):

Oligonucleotide 1:
(SEQ ID NO: 67 and 95, respectively)
5' TTAATACGACTCACTATAG-(gRNA protospacer)-GTTTTAGA
GCTAGAAATAGCAAGTTAAAATAAGGCTAGTCG;

Oligonucleotide 2:
(SEQ ID NO: 68)
5' AAAAAGCACCGACTCGGTGCCACTTTTTCAAGTTGATAACGGACTAG
CCTTATTTTAACTT.

After oligonucleotide annealing followed by PCR amplification, the T7 promoter with an additional "G" at the 5' end (see oligonucleotide 1) was added to the gRNA. The amplified gel-purified gRNA PCR product was used as the template for in vitro transcription using a MEGAshortscript T7 kit (Life Technologies). Both the Cas9 mRNA and the gRNAs were purified using a MEGAclear kit (Life Technologies) and eluted into RNase-free water. The gRNA protospacer sequences targeting the mouse MINION ORF region were as follows: sgRNA 1: 5' GGACCGGGCCGTCGTGGAGG (SEQ ID NO: 69); sgRNA 2: 5' CCAGAGTGGACCACTCCCAG (SEQ ID NO: 70) for generation of the 135 bp deletion allele; sgRNA3: 5' GGCGGGCAACAGGCAGCAGC (SEQ ID NO: 104); and sgRNA4: 5' CTGGGAGTGGTC-CACTCTGG (SEQ ID NO: 105) for generation of the 155 bp deletion allele.

Assay for Genome Modification and Genotyping

To detect mutations in the mice arising from injected embryos, PCR was performed using primers flanking the targeted region: Seq-F: 5' GAGTGAACTCCT-TAACCAGCTTTC (SEQ ID NO: 71); Seq-R: 5' GCGTTGCTGTTTCCAGGACCCGTG (SEQ ID NO: 72). The PCR products were used in a surveyor assay according to manufacturer's instructions. The PCR products were then analyzed by agarose gel electrophoresis and selected products were cloned into a pCR-blunt-cloning vector and sequenced. Mice containing mutations in the target region were bred to confirm germline transmission. Among the mouse strains with mutations, one with a 135 bp in-frame deletion within the MINION ORF was selected for further analysis.

For genotyping of the subsequent progeny with the 135 bp deletion, a primer set flanking the targeted region: F0: 5'-CAAAGGGAGGGAGGGATTAAAG-3' (SEQ ID NO: 73); R0: 5'-CAGAGAGGAAG GGTCAATCAAC-3' (SEQ ID NO: 74) was used to amplify genomic DNA, generating a ~760 bp product from the unmodified allele and a ~625 bp product from the mutated allele respectively. For genotyping of the progeny carrying the 155 bp deletion allele, a different primer set was used to amplify genomic DNA: Fwd-2: 5' AACACAATCTGTAGCCTGCTAGGAG (SEQ ID NO: 106); and Rev-2: 5' TATAAGCTGAAGGGAGGACTC-CAC (SEQ ID NO: 107), generating a ~555 bp product from the unmodified allele and a ~400 bp product from the mutant allele, respectively. The PCR products were separated by gel electrophoresis using 2% agarose (Sigma A9539). Wild-type mice demonstrate a single band of the larger size, while homozygotes containing the deletion demonstrate a single band of the smaller size, and heterozygous mice demonstrate both bands.

Myoblast Isolation

For mouse embryonic myoblast isolation, pregnant C57BL/6J female mice were humanely euthanized, embryos from were rapidly but gently dissected and placed into dissection buffer containing Ham's F10 nutrient mix (Gibco 11550043) with 1× antibiotic-antimycotic (Gibco 15240062). For each embryo, the tail was kept in a numbered tube for genotyping, while all four limbs were skinned, dissected, and placed into a 2 ml numbered Eppendorf tube containing ~1.5 ml dissection buffer including 4 mg/ml Collagenase type II (Worthington LS004176; freshly made and filtered before use). The samples were rotated on a platform rocker at 80 rpm and 37° C. for 30-45 min, until the muscles were mostly digested and only bones and soft tissues were left. In general, earlier stage embryos required shorter incubation times. Cell suspensions were checked microscopically after each step to avoid over-digestion. After allowing the unwanted tissues to settle at room temperature, the supernatant was transferred to a 50 ml conical tube. Then Dispase II (Gibco 17105041) was added at a final concentration of >=1.2 mg/ml (>0.6 U/ml) to both tubes: (1) For the supernatant in the 50 ml tubes, cells were incubated at 37° C. for 20-30 min with occasional mixing; (2) For the remaining tissues in the 2 ml tubes, 1.5 ml freshly made and filtered dissection buffer with 4 mg/ml Collagenase type II and >=1.2 mg/ml Dispase II, and the tubes were rotated again on the rocker at 80 rpm and 37° C. for 20-30 min to allow further digestion and dissociation.

After dissociation, the suspension in the 2 ml tube was mixed with that in the 50 ml tube. Then after adding ~4-5 times wash medium (Ham's F10 and 10% horse serum, filtered), the digested mixture was passed through a 10 ml 20 gauge needle slowly and gently approximately 4 times, while scrupulously avoiding bubbles. More wash medium was then added to bring the final volume to 30 ml. This suspension was filtered through a prewashed 40 μm Nylon Mesh filter on top of a new 50 ml conical tube, and the filter was rinsed with 10 ml wash medium into the same tube. All of the 50 ml tubes were then centrifuged at 125 g for 5 min at room temperature, and the supernatant was transferred and spun down again at 125 g for 5 min. The pellets from two centrifugations were resuspended and mixed in 2 ml myoblast isolation medium followed by and additional 20 ml of media containing a 1:1 mixture of DMEM low glucose (Gibco 11885084) and Ham's F-10 Nutrient Mix (Gibco 11550043); 20% (v/v) FBS; 1× antibiotic-antimycotic; and freshly added 2.5 ng/ml rhFGF (Promega G5071). Medium lacking DMEM but containing the remaining items above also produced similar results.

The isolated cell mixture from each embryo was first plated into a regular 150 mm TC-treated dish for 30 min at 37° C. (preplate I) and replated into another 150 mm dish for 30 min at 37° C. (preplate II) in order to eliminate fibroblasts, and then the supernatant containing mostly myoblasts was transferred into two 100 mm collagen-coated dishes. Cells were examined the next day to determine necessity for passaging. Occasionally the preplate II dish also contained a some amount of myoblasts, and these were kept and expanded in addition to those in the collagen dishes. 0.05% trypsin was used for dissociating the cells from dishes. After a few passages, 1× antibiotic-antimycotic was replaced by 1× penicillin-streptomycin (Gibco®). As the fibroblast number decreases in culture, the embryonic myoblasts may start to proliferate very slowly and they should be seeded more densely to recover from the slow growth.

Adult mouse myoblasts were isolated similarly but with a few modifications: the muscles were removed from bones and minced with small scissors; 15 ml conical tubes were used instead of 2 ml tubes, with twice the volume of digestion buffer; and longer digestion and dissociation times were used.

In Vitro Myoblast Differentiation Assay

For primary myoblasts derived from both embryos and adult mice, around 3000 cells in 50 μl myoblast growth medium (1:1 mixture of DMEM low glucose and Ham's F-10 Nutrient Mix; 20% (v/v) FBS; freshly added 2.5 ng/ml rhFGF) were seeded into each well of a 384-well Collagen-coated PerkinElmer CellCarrier™ plate (6007550) for imaging purposes. The next day, differentiation medium (DMEM high glucose (Gibco® 11995073) with 3% to 5% horse serum) was added to the cells (DM day 0). Differentiation medium was replaced daily. The cells were fixed at DM day 3 and day 4 for immunofluorescence staining. For C2C12 cells, ~1500-2000 cells were seeded into each well of a 384-well plate (DMEM high glucose with 10% FBS) and around 2×10$^5$ cells were seeded into each well of a 6-well plate, using C2C12 growth medium (DMEM high glucose with 10% FBS). On the next day, differentiation medium (DMEM high glucose with 2% horse serum) was added to the cells (DM day 0), and differentiation medium was likewise replaced daily. The cells were collected or fixed at different time points as described.

Histology

For paraffin sections with embryonic samples, mouse embryos (E14.5 and later) were decapitated and the tails were collected in numbered tubes for genotyping. To enhance fixation in later-stage embryos (E17.5 and later), embryos were skinned in the area to be studied. Embryos were fixed overnight using 4% paraformaldehyde (PFA; Electron Microscopy Sciences #15714) in PBS at 4° C. with gentle rotation. Following two quick rinses with PBS, embryos were placed into 70% ethanol for dehydration and long-term storage. For the tissues/organs to be studied, the appropriate portions were cut and submitted for paraffin embedding and sectioning using routine protocols.

For cryosections of adult mouse tissue, skeletal muscle samples were dissected and partially embedded in gum tragacanth (Sigma G1128; 10% w/v in PBS) on a wooden dowel, and frozen in 2-methylbutane in a glass beaker cooled in liquid nitrogen. The fresh frozen muscle samples were then sectioned at 10 μm thickness using a cryostat cooled to −20° C. These fresh frozen muscle sections were then fixed in 1% PFA diluted in PBS at room temperature for 5 min before subsequent staining procedures. Both cryosections and paraffin sections were stained with Hematoxylin and Eosin (H&E) following routine protocols.

Immunofluorescence Staining on Tissue Sections

For muscle cryosections, after fixation with 1% PFA/PBS as described above, slides were washed with PBS and permeabilized with 0.2% Triton X-100 diluted in PBS at room temperature for 10 min, and were then washed again with PBS. Sections were blocked at room temperature for 1 hour using a freshly-prepared and filtered solution containing 1% heat-inactivated donkey serum, 1% BSA, 0.025% Tween20 in PBS. After blocking, sections were incubated with primary antibody at 4° C. overnight, washed with PBS, and then incubated with secondary antibody for 2 hours at room temperature. After a 5 min wash with PBS, the sections were incubated with the nuclear stain DAPI (Molecular Probes D1306; 5 mg/ml stock) at a 1:20,000 dilution in PBS for 5 min, and slides were mounted and sealed using ImmuMount (Shandon) and glass coverslips. For paraffin sections with embryonic tissues, the deparaffinized and rehydrated slides were permeabilized with 0.2% Triton X-100 in PBS for 10 min and washed again with PBS. The sections were then blocked at room temperature for 1 hour using a freshly-made and filtered solution containing 5% heat inactivated normal goat serum in PBS. After blocking, similar procedures were performed as mentioned above for cryosections.

Primary antibodies used for immunofluorescence were: Mouse anti-MHC (MY32 clone, Sigma M4276, 1:300 dilution on paraffin sections and 1:500 dilution on cryosections);

Mouse anti-Desmin (D33 clone, DAKO M0760, 1:300 dilution); Sheep anti-MINION (R&D systems AF4580; 1:200 dilution). All secondary antibodies (Invitrogen Alexa-Fluor) were used at 1:250 dilution, and the host species was either donkey or goat. Only secondary antibodies from the same host species were used together for co-staining.

Immunofluorescence Staining with Adherent Cells

For immunofluorescence staining of actin filaments in fibroblasts and myoblasts, the high-affinity F-actin probe Alexa Fluor 546-conjugated phalloidin (Invitrogen, A22283) was used according to manufacturer's instructions. Briefly, 384-well PerkinElmer CellCarrier plates were again used. Cells were fixed with 4% PFA in PBS for 8-10 min and quickly washed twice with PBS before permeabilization with 0.2% Triton X-100 in PBS for 10 min. After one wash with PBS, cells were blocked with freshly made and filtered 5% heat inactivated normal goat serum in PBS for 1 hour, and were incubated with primary antibodies overnight at 4° C. The next day, after two quick washes with PBS, cells were incubated with secondary antibodies for 1-2 hours at room temperature. After three quick washes with PBS, the cells were incubated with DAPI (5 mg/ml stock, 1:20,000 dilution in PBS) for 10 min. The 384-well plate was then imaged using either UltraVIEW confocal or ImageXpress Micro (IXM; Molecular Devices) confocal imaging systems (see the Microscopy part below).

Primary antibodies used were: Mouse anti-MHC (MY32 clone, Sigma M4276, 1:400 dilution); Mouse anti-Desmin (D33 clone, DAKO M0760, 1:300 dilution). All secondary antibodies (Invitrogen Alexa-Fluor) were used at 1:250 dilutions, and the host species was either donkey or goat. Only secondary antibodies from the same host species were used together for co-staining.

Microscopy and Imaging

The Invitrogen EVOS FL Auto Imaging System was used for routine examination of immunofluorescence staining, GFP virus infection, and cell labeling. For imaging of the H&E and immunostained tissue sections on glass slides, the Hamamatsu NanoZoomer and Aperio VERSA scanners were used to obtain whole-slide images using a 20× objective. For imaging of the immunofuorescence cell samples in 384-well plates, the IXM confocal high-content imaging system was used with 10× and 20× objectives. In order to acquire higher resolution images for tissue sections and cell samples, the UltraVIEW VoX 3D live cell imaging system (PerkinElmer) spinning disk confocal microscope system was used with 40× and 60× objectives. All pictures of whole mouse embryos were taken using iPhone 5S in combination with Leica KL200 LED dissection microscope.

Cell Culture

For culture of primary myoblasts isolated from later-stage mouse embryos and adult mice, filtered myoblast growth medium (1:1 mixture of DMEM low glucose and Ham's F-10 Nutrient Mix; 20% FBS) with freshly added 2.5 ng/ml rhFGF was used. In general, around $2-4 \times 10^5$ cells were seeded into a 100 mm collagen-coated dish, and the cells were split once every 2 to 3 days at a ratio of 1:2 to 1:4, depending on proliferation speed. 0.05% trypsin was used for dissociating cells from dishes. Myoblasts typically went through a crisis period after the removal of most fibroblasts, and could be seeded more densely at this point. Primary myoblasts in culture were monitored every day with fresh medium replacement as needed. For the culture of immortalized C2C12 myoblast cells (ATCC), filtered C2C12 growth medium (DMEM high glucose with 10% FBS) was used. Approximately $1-1.5 \times 10^5$ cells were seeded into a 100 mm tissue culture-treated dish, and cells were split every 2 days. 0.25% trypsin was used for cell dissociation. For the culture of the immortalized 10T1/2 fibroblast line, filtered fibroblast growth medium (DMEM high glucose with 15% FBS) was used. Approximately $1 \times 10^5$ cells were seeded into a 100 mm tissue culture-treated dish, and the cells were split once every 3 days. 0.25% trypsin was used for cell dissociation. For the culture of immortalized RAW264.7 macrophage line, filtered growth medium containing DMEM high glucose with 10% FBS was used. Around $2-3 \times 10^6$ cells were seeded into a 175 cm² flask. The cells were split once every 2 to 3 days, when they were ~60-75% confluent. To ensure cell lifting and reduce cell death, 0.25% trypsin and a cell scraper were used in combination. To induce the formation of multinuclear osteoclast-like cells, 50 ng/ml sRANKL (Peprotech, 174aa) was incubated with the cells for 3 days. For the culture of CJ7 embryonic stem cells from 129 mice, freshly made and filtered growth medium was used, consisting of ESGRO Complete PLUS medium (Millipore SF001-500P) with 15% FBS and 3 inhibitors: GSK3β inhibitor which comes with the medium; MEK inhibitor PD184352 (0.8 µM final); and FGFR inhibitor PD173074 (0.1 µM final). Normally the cells were co-cultured with mouse embryonic fibroblasts according to standard procedures, but for the purpose of RNA and protein isolation were seeded into gelatin-coated dishes without the fibroblast feeder layer. Approximately $1 \times 10^6$ cells were seeded into each 100 mm dish. The medium was replaced every day. Cells were split once every two days at a ratio of 1:5 to 1:10, depending on experimental need. 0.05% trypsin was used for cell dissociation. All cell culture media contained 100 units/ml of penicillin and 100 µg/ml of streptomycin, unless otherwise specified.

Tissue and Cell Lysates Preparation for Protein Analysis

Both embryonic and adult mouse tissue samples were weighed, snap-frozen in liquid nitrogen, and stored at −80° C. until use. For preparation of protein lysates, eight volumes of ice-cold lysis buffer (50 mM Tris-HCl pH7.5, 150 mM NaCl, 1 mM EDTA, 10% glycerol, with freshly added 2× Halt protease inhibitor cocktail and 1× Roche PhosSTOP phosphatase inhibitor cocktail) and 1-2 3 mm tungsten carbide beads (Qiagen) were added to each sample in a 1.5 ml or 2 ml Eppendorf tube. These were then homogenized at 30 cycles/s for 3-8 min at 4° C. using a TissueLyser II. Detergents were then added to the lysates to a final concentration of 0.1% SDS, 0.1% sodium deoxycholate and 1% Triton X 100, and the samples were rotated at 4° C. for 2-4 hours. Lysates were then transferred to new tubes and spun down at 15000-21000 g for 10 min at 4° C. For organs containing significant amount of lipids, the supernatant was transferred and spun down again at 15000-21000 g for 10 min at 4° C.

For cell samples, buffer from Alfa Aesar (J60423) was generally used (50 mM Tris-HCl pH7.5, 150 mM NaCl, 5% Glycerol, 0.1% SDS, 0.5% sodium deoxycholate and 1% Triton X 100, with the above mentioned protease and phosphatase inhibitor cocktails). Cells were quickly rinsed with DPBS and then ~300 µL ice-cold lysis buffer was added to each well of a 6-well plate. After incubation on ice for 5 min, the cells were pipetted up and down and transferred to 1.5 ml Eppendorf tubes and incubated on ice for 30 min, with 1-second of vortexing every 10 min. The samples were then spun down at 15000-21000 g for 10 min at 4° C. A second buffer without ionic detergents was used for some of experiments (50 mM Tris-HCl pH7.5, 150 mM NaCl, 10% Glycerol, 1 mM EDTA, and 1% Triton X 100, with the above mentioned protease and phosphatase inhibitor cocktails), with similar results. Bio-Rad DC protein assay with BSA standard was performed to measure protein concentration of supernatants. Lysates were mixed with NuPAGE LDS Sample Buffer (NP0007) and dithiothreitol (100 mM final), and boiled at 94 degree for 10 min prior to SDS-PAGE.

Subcellular Fractionation Analysis

C2C12 cells incubated with differentiation medium for 3 days were used for the subcellular fractionation studies using the Qproteome Cell Compartment system (Qiagen, 37502) following the manufacturer's instructions. The cells were dissociated from the dishes first before adding the first buffer in the kit. The cytosolic/membrane/nuclear/cytoskeletal fractions were extracted from the cells, and around 10 μg protein lysates from each fraction was loaded for Western blot.

SDS-PAGE and Western Blots

Figure 20:
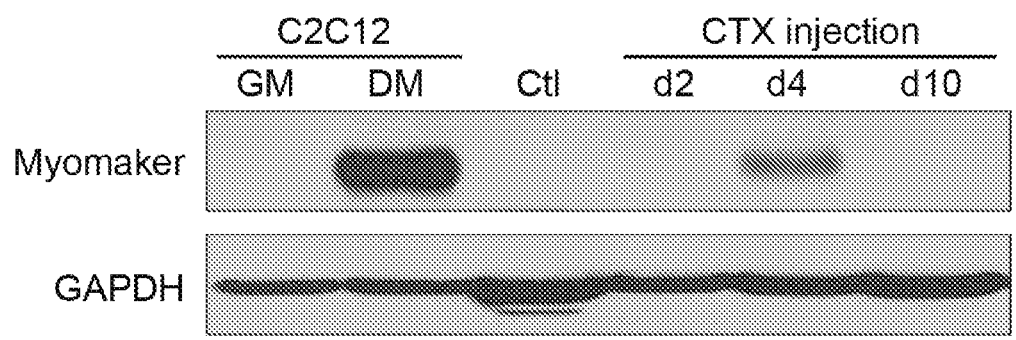
FIG. 20 is representative Western blot showing an anti-human Myomaker antibody recognizes endogenous mouse Myomaker. Myomaker expression in C2C12 myoblasts cultured under either growth conditions (GM), or in differentiation conditions for 3 days (DM); and of uninjured or cardiotoxin injured and regenerating TA muscle (CTX) at different time points (day 2, 4, 10) was examined.

Approximately 10-30 μg cell lysates and 40-60 μg tissue lysates were loaded per well. The NuPAGE Novex gel electrophoresis system was used for the separation of proteins. NuPAGE MES SDS Running Buffer (NP0002) and 4-12% NuPAGE Novex Bis-Tris gels were used. Proteins were transferred to PVDF or nitrocellulose membranes using the iBlot transfer system (Thermo Fisher). Freshly prepared 5% milk in TBST (137 mM NaCl, 20 mM Tris, 0.10% Tween-20, pH7.6) was generally used as the blocking buffer with both PVDF and nitrocellulose membranes. However, for the detection of MINION using primary antibody raised in sheep, freshly made and filtered 10% donkey serum in TBST was used as the blocking buffer with PVDF membrane (Millipore Immobilon-P$^{SQ}$, 0.2 μm pore size). The information of primary and secondary antibodies used in western blots is listed in the table below (Table 3). Two ECL substrates with different sensitivity were used as indicated. We found that the anti-human TMEM8C antibody recognized both endogenous and overexpressed Myomaker protein in both mouse primary muscle and cultured cell lysates (FIGS. 20, 21C-21D), but required extended antibody incubation and exposure times.

TABLE 3

Antibody and ECL substrate information for Western blots

| Primary antibody | Dilution | Primary antibody incubation conditions | HRP conjugated secondary antibody | Dilution | Secondary antibody incubation conditions | ECL substrate used most |
|---|---|---|---|---|---|---|
| Sheep anti-MINION (R&D AF4580) | 1:1000 (1 ug/ml) | 4° C. overnight | Donkey anti-sheep (Thermo Fisher A16047) | 1:5000 | Room temperature (RT) for 1-2 hours | Luminata Forte (EMD Millipore WBLUF0100; increased sensitivity). Diluted with equal volume of water. |
| Mouse anti-GAPDH (EMD Millipore MAB374) | 1:20,000 | RT 30 min-1 hour | Goat anti-mouse (Thermo Fisher A16078) | 1:20,000 | RT 1 hour | SuperSignal West Pico (Thermo Fisher 34080). Diluted with equal volume of water. |
| Mouse anti-alpha-Tubulin (Sigma T9026) | 1:20,000 | RT 1-2 hours | Same as above | 1:20,000 | RT 1-2 hours | SuperSignal West Pico; Diluted with equal volume of water. |
| Mouse anti-MHC MY32 (Sigma M4276) | 1:1000 | 4° C. overnight | Same as above | 1:5000 | RT 1-2 hours | Luminata Forte; Diluted with equal volume of water. |
| Mouse anti-Myogenin (DSHB F5Dc) | 1:200 | 4° C. overnight | Same as above | 1:5000 | RT 1-2 hours | Luminata Forte |
| Mouse anti-Pax7 (sc-81648) | 1:100 | 4° C. overnight | Same as above | 1:5000 | RT 1-2 hours | Luminata Forte |
| Mouse anti-Desmin clone D33 (DAKO M0760) | 1:200 | 4° C. overnight | Same as above | 1:5000 | RT 1-2 hours | Luminata Forte |
| Rabbit anti-MyoD1 (Novus Biologicals NBP1-54153) | 1:5000 | 4° C. overnight | Goat anti-rabbit (Cell Signaling #7074) | 1:2000 | RT 1-2 hours | Luminata Forte |
| Rabbit anti-N-Cadherin(Cell signaling #4061) | 1:1000 | 4° C. overnight | Same as above | 1:2000 | RT 1-2 hours | Luminata Forte |

TABLE 3-continued

Antibody and ECL substrate information for Western blots

| Primary antibody | Dilution | Primary antibody incubation conditions | HRP conjugated secondary antibody | Dilution | Secondary antibody incubation conditions | ECL substrate used most |
|---|---|---|---|---|---|---|
| Rabbit anti-Calnexin (Novus Biologicals NB100-1965SS) | 1:1000 | 4° C. overnight | Same as above | 1:2000 | RT 1-2 hours | SuperSignal West Pico |
| Rabbit anti-H2B (Cell signaling #8135) | 1:1000 | 4° C. overnight | Same as above | 1:2000 | RT 1-2 hours | Luminata Forte |
| Rabbit anti-Vimentin [EPR3776] (Abcam ab92547) | 1:10,000 | 4° C. overnight | Same as above | 1:2000 | RT 1-2 hours | SuperSignal West Pico |
| Rabbit anti-Human TMEM8C (Myomaker) (Abcam ab188300) | 1:200 | 4° C. at least two days | Same as above | 1:500-1:800 | 4° C. overnight plus RT 3 hours; or 4° C. two days | Luminata Forte |
| HRP conjugated mouse anti-FLAG M2 (Sigma A8592) | 1:10,000 | 4° C. overnight | — | — | — | SuperSignal West Pico; Diluted with equal volume of water. |

RNA Preparation and RT-qPCR

Total RNA was isolated from different cell line samples using TRIzol Reagent (Thermo Fisher 15596026) according to manufacturer's instructions. First-strand cDNA synthesis was performed using qScript cDNA SuperMix (Quanta BioSciences) according to manufacturer's instructions. For PCR, cDNA from ~5 ng RNA was used in a 12.5 µl reaction with Power SYBR Green PCR Master Mix (Thermo Fisher 4367659). Reactions with RNA only were prepared as negative controls. An Applied Biosystems 7900HT thermocycler was used with the following primers: MINION (5'-GGACCACTCCCAGAGGAAGGA-3' (SEQ ID NO: 75) and 5'-GGACCGACGCCTGGACTAAC-3' (SEQ ID NO: 76) and GAPDH (5'-AGGTCGGTGTGAACGGATTTG-3' (SEQ ID NO: 77) and 5'-TGTAGACCATGTAGTTGAGGT-3' (SEQ ID NO: 78). Relative quantification was performed using the comparative CT method. The CT value of MINION gene was normalized to that of the reference gene GAPDH in the same sample using the formula: $2^{\Delta\Delta CT}$.

Lung Flotation Assay

Lung flotation assay was adapted from previously described methods (Z. Jakus et al., Lymphatic function is required prenatally for lung inflation at birth. *The Journal of experimental medicine* 211, 815, 2014; and M. Borensztein et al., Myod and H19-Igf2 locus interactions are required for diaphragm formation in the mouse. *Development* 140, 1231, 2013). E18.5 embryos from MINION$^{\Delta/+}$×MINION$^{\Delta/+}$ crosses were quickly isolated by cesarean section from humanely sacrificed pregnant females, and were placed on dry Kimwipes. To maintain body temperature, these newborns were incubated by hand and subsequently in a 37° C. chamber. Pups were exposed to normal room air following delivery, and were monitored for at least 1 hour. MINION$^{\Delta/\Delta}$ newborns were uniformly atonic, apneic, and became cyanotic almost immediately after delivery. The majority of MINION$^{+/+}$ and MINION$^{\Delta/+}$ mice exhibited normal breathing and demonstrated pink body color indicative of adequate perfusion. After at least 1 hour of air breathing, pups were anesthetized, weighed, tailed for genotyping, decapitated, and the lungs were dissected and placed into PBS in 15 ml conical tubes or 2 ml Eppendorf tubes for flotation assay. The lungs were then monitored for more than 15 min, after which they were scored as either floating or sinking. Approximately 50 E18.5 preterm newborns were examined.

Plasmids and Cloning

For the cloning of shRNA constructs, 19-21 nucleotide target sequences were selected using both BLOCK-iT RNAi Designer (Thermo Fisher) and in-house optimized algorithms. For the mouse MINION gene, four shRNA target sequences were chosen initially, two targeting the coding sequence and two targeting the 3' UTR. A control sequence was used targeting the firefly (*Photinus pyralis*) luciferase gene, which exists in the pGL3 luciferase reporter vector but which lacks similar sequence in the mouse transcriptome. For each shRNA, two 55-59 nt oligonucleotides were designed as shown below and synthesized (IDT). The oligonucleotides, each containing sense and antisense target sequences, a 9 nt intervening hairpin loop, and TTTG at the 5'ends with GATC at 3' ends for cohesive-end cloning, were annealed. These were then ligated with BbsI/SpeI-digested pGWL-si2/U6 vector. Subsequently using Gateway LR Clonase II Enzyme Mix, these shRNA cassettes were cloned into the vector pLentiLox3.7-GW (pLL3.7-GW), a 3rd generation lentiviral gateway vector that expresses shRNAs under the mouse U6 promoter. A CMV-EGFP reporter cassette was included in the vector to monitor expression.

TABLE 4 shRNA target sequence and oligonucleotide design information

| shRNA construct name | Target sequence | Oligonucleotide names (S: Sense; A: Antisense) | Oligonucleotide sequence |
|---|---|---|---|
| mMINION-U1 | GCTAAGAGGTGGTATTTAA (SEQ ID NO: 79) | 3'UTR shRNA_1S | TTTGCTAAGAGGTGGTATTTAATTCAAGAGATT AAATACCACCTCTTAGCTTTTT (SEQ ID NO: 84) |
| | | 3'UTR shRNA_1A | CTAGAAAAAGCTAAGAGGTGGTATTTAATCTCT TGAATTAAATACCACCTCTTAG (SEQ ID NO: 85) |
| mMINION-U2 | GCAGCAGGTAGTCAATAAACG (SEQ ID NO: 80) | 3'UTR shRNA_2S | TTTGCAGCAGGTAGTCAATAAACGTTCAAGAGA CGTTTATTGACTACCTGCTGCTTTTT (SEQ ID NO: 86) |
| | | 3'UTR shRNA_2A | CTAGAAAAAGCAGCAGGTAGTCAATAAACGTCT CTTGAACGTTTATTGACTACCTGCTG (SEQ ID NO: 87) |
| mMINION-C1 | GCTGTCTGCTCTTTGTCCT (SEQ ID NO: 81) | CDS shRNA_1S | TTTGCTGTCTGCTCTTTGTCCTTTCAAGAGAAG GACAAAGAGCAGACAGCTTTTT (SEQ ID NO: 88) |
| | | CDS shRNA_1A | CTAGAAAAAGCTGTCTGCTCTTTGTCCTTCTCT TGAAAGGACAAAGAGCAGACAG (SEQ ID NO: 89) |
| mMINION-C2 | GTGGACCACTCCCAGAGGA (SEQ ID NO: 82) | CDS shRNA_2S | TTTGTGGACCACTCCCAGAGGATTCAAGAGATC CTCTGGGAGTGGTCCACTTTTT (SEQ ID NO: 90) |
| | | CDS shRNA_2A | CTAGAAAAAGTGGACCACTCCCAGAGGATCTCT TGAATCCTCTGGGAGTGGTCCA (SEQ ID NO: 91) |
| Control (Ctrl) | GACGAACACTTCTTCATCG (SEQ ID NO: 83) | Ctrl shGL3_S | TTTGACGAACACTTCTTCATCGTTCAAGAGACG ATGAAGAAGTGTTCGTCTTTTT (SEQ ID NO: 92) |
| | | Ctrl shGL3_A | TAGAAAAAGACGAACACTTCTTCATCGTCTCTT GAACGATGAAGAAGTGTTCGT (SEQ ID NO: 93) |

For the cloning of cDNA constructs, the coding sequences (CDS) of mouse MINION (for the 84 aa isoform), human MINION ortholog, mouse tmem8c (myomaker), nanoluc (control A), luciferase (control B), mouse MINION with 1 bp insertion, human MINION with 1 bp deletion, and mouse MINION truncation (39 aa form) were synthesized (IDT) with attB sites at both ends and a consensus Kozak sequence (5' GCCACC (SEQ ID NO: 94)) before the start codon. For mouse and human MINION CDS, both untagged and C-terminally 3×FLAG-1×HA-tagged (3F1H) versions were generated. For the nanoluc CDS, a C-terminal 1×FLAG tag was added. Using Gateway BP Clonase II Enzyme mix (Thermo Fisher 11789020), the synthesized DNA sequences were cloned into the pDONR221 vector and the sequence-confirmed entry vectors were subsequently cloned into the pCIGAR gateway retroviral vector using Gateway LR Clonase II Enzyme mix. The pCIGAR vector is an MSCV-based bicistronic retroviral vector modified to permit Gateway-mediated insertional recombination of transgenes immediately upstream of IRES-eGFP. In addition, the empty pCIGAR vector (MCS version) was used as another control vector (control C). After expression testing of the two 3F1H-tagged mouse and human MINION constructs, it was noticed that two bands were detected by Western blot with anti-FLAG antibody (FIG. 16). This reflects the presence of an extra start codon in-frame with the actual start codon, inherited at the 5' end of the pCIGAR vectors, giving rise to a product with an additional N-terminal 16 aa, indicated by an asterisk. As a 6-nt consensus Kozak sequence was added before the actual start codon, the intensity of the intended product is much stronger. All other cDNA vectors therefore contained an extra T nucleotide immediately prior to the Kozak sequence, in order to avoid upstream translational initiation.

Lentiviral shRNA Knockdown Assay in Primary and Transformed Myoblasts

Lentiviral particles were produced in HEK 293T cells using a $3^{rd}$ generation lentiviral packaging system and FuGENE 6 transfection reagent (Promega). Fresh medium was replaced one day after transfection and the supernatant medium was collected on the following day. The medium was briefly centrifuged to remove dead cells, and neat virus was used for QC infection by reverse infection method on 293T cells with 8 µg/ml polybrene (overnight incubation without spin infection). Analysis of GFP expression by FACS 3 days after infection generally demonstrated a titer of approximately $1 \times 10^6$ vp/mL. Neat virus was further concentrated ~100 fold using a 100 kDa centrifugal filter unit (Amicon), aliquoted, and stored at −80° C.

Figure 24A:
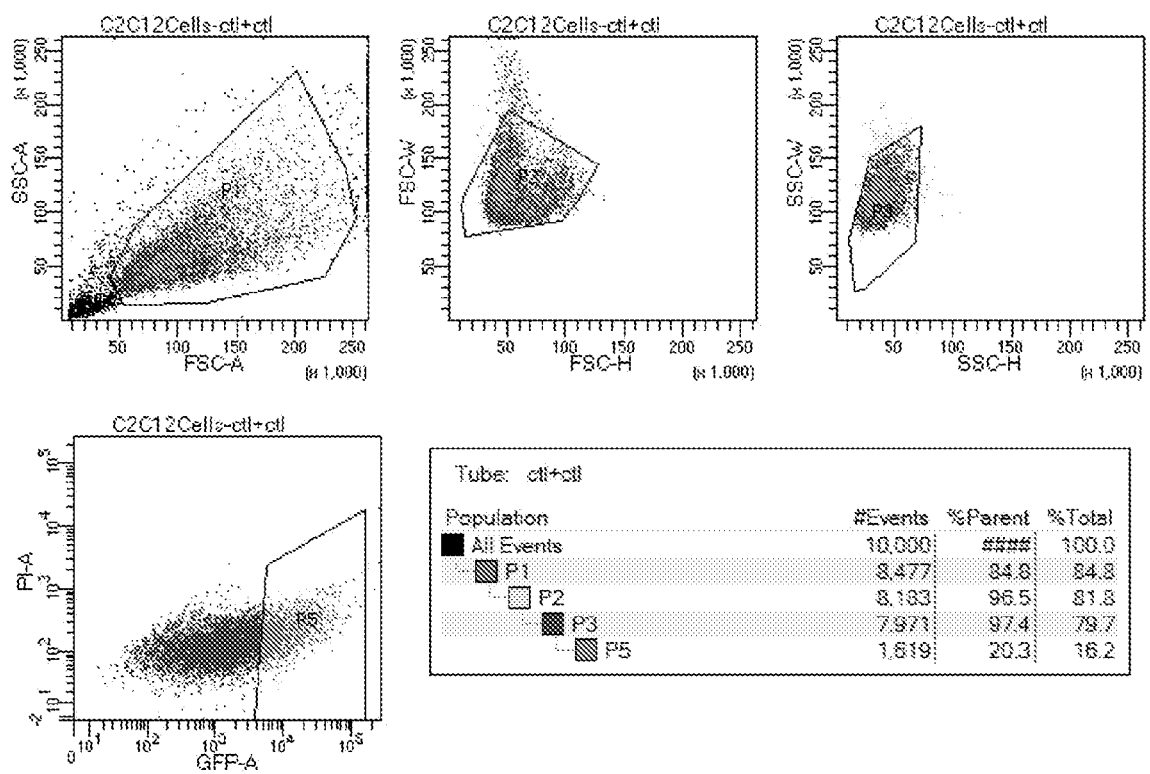
FIGS. 24A-24B show gating strategy for identification and sorting of Ctrl and Minion$^{KD}$ myoblasts.
Figure 24B:
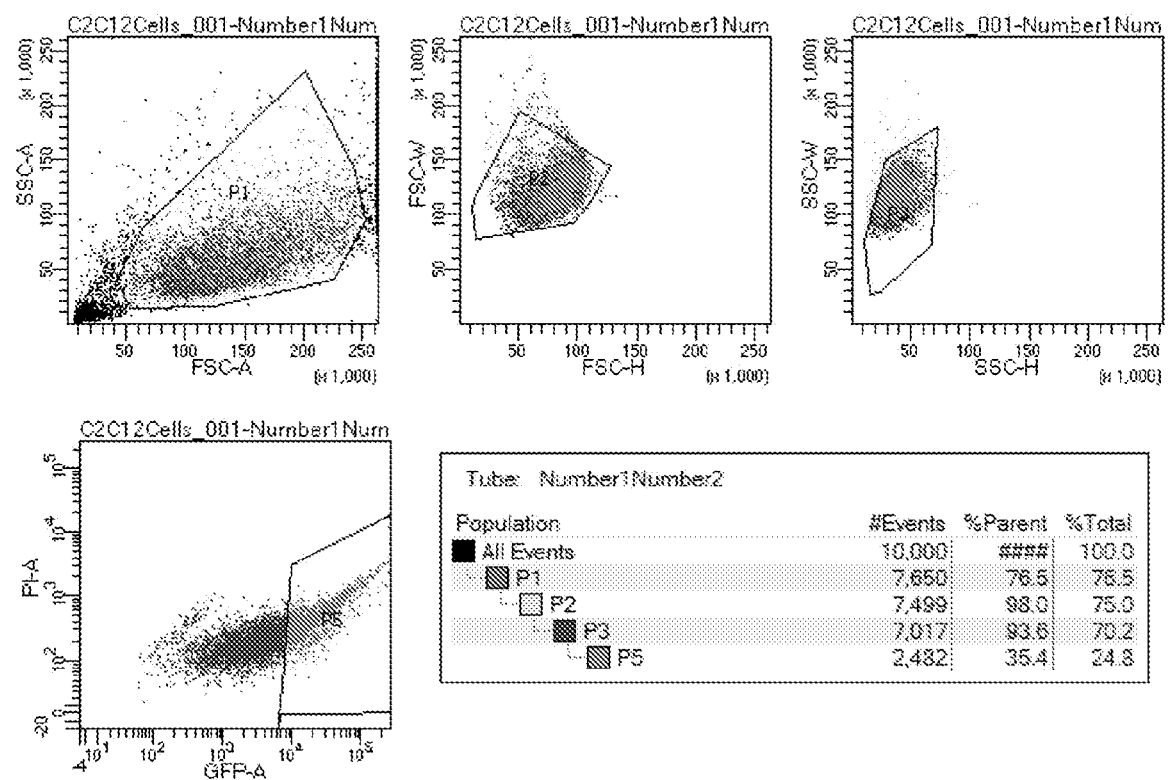

To examine the knockdown efficiency of the mouse MINION transcript, shRNA-encoding lentiviruses were used to infect C2C12 cells. Viruses were diluted in growth medium containing 8 µg/ml polybrene, and after a brief incubation at 37° C. with C2C12 cells, one round of spin infection was performed at 1100 g for 1-1.5 hours and 32° C., using either 24-well or 12-well plates. Based on an estimated viral titer of $1 \times 10^8$ vp/ml (as measured on 293T cells), a virus amount equivalent to MOI30 on 293T cells was used on C2C12 cells. Fresh medium was replaced the next day and GFP+ cells were sorted by FACS two days later (see gating strategy in FIG. 24). Infection efficiency of 70-85% was routinely achieved as judged by FACS analysis, though GFP signal in undifferentiated C2C12 cells was barely discernable by EVOS fluorescence microscopy. Sorted, GFP$^+$ C2C12 cells were recovered, expanded and seeded into 6-well plates for in vitro differentiation assay. At DM day 4-6, cell lysates were collected and the expression of MINION protein was examined by Western blot. The two shRNA constructs targeting the MINION 3'UTR (U1/U2) were found to reduce MINION expression most efficiently (FIG. 14B), and for subsequent experiments in C2C12 and primary myoblasts, cells were infected with U1 and U2 shRNA viruses only. In order to produce the MINION$^{KD}$ C2C12 cells, the U1-infected, GFP$^+$, sorted cells were reinfected with U2 shRNA virus and resorted by GFP signal (top 30-50%). Similarly, wild-type C2C12 cells were infected with the control shGL3 virus (Ctrl) in two rounds and sorted twice to generate the Ctrl$^{KD}$ cells. These MINION$^{KD}$ and Crl$^{KD}$ C2C12 cells were expanded and used for in vitro differentiation assay in 384-well and 6-well plates. The MINION$^{KD}$ cells were also used as the background for in vitro reconstitution assay with cDNA retroviruses.

Similar infection steps were followed in order to knock down MINION in primary myoblasts derived from adult mice, except that 6 µg/ml polybrene was used and fresh medium lacking polybrene was added by the end of the day instead of on the next day, as primary myoblasts appeared more sensitive to polybrene treatment. Due to the difficulty in expanding these infected and sorted primary cells, one round of virus infection was performed using either Ctrl virus or 1:1 ratio mixture of U1 and U2 viruses, and the cells were sorted by GFP signal after 2-3 days. Around one-third or one-half the amount of virus used on C2C12 cells was used on primary myoblasts. The sorted primary myoblasts were recovered for 3 days and then seeded into 384-well plates for in vitro differentiation assay.

Retrovirus Infection of C2C12 and 10T1/2 Cells

The cDNA-encoding retroviruses were made by co-transfecting HEK 293 cells with pCIGAR retroviral vectors and pCL-Eco or pCL-10A1 packaging vectors using FuGENE 6 transfection reagent (Promega). Media was replaced one day after transfection and the supernatant medium was collected on the following day. After a brief centrifugation to eliminate dead cells, the neat virus was used for QC infection in 384-well plate by reverse infection method on NIH-3T3 cells (for pCL-Eco packaged virus) or 293T cells (for pCL-10A1 packaged virus) with 8 µg/ml polybrene (overnight incubation without spin infection). GFP expression was analyzed by FACS 3 days after infection, usually giving a titer of 0.3-1.2×10$^6$ vp/nl.

In order to infect C2C12 cells and 10T1/2 cells, neat virus was incubated with 8 µg/ml polybrene at 37° C. for 10 min and then added to the cells, which were then incubated for 15 min at 37° C. One round of spin infection was performed using 24-well or 12-well plates at 1100 g for 1-1.5 hours and 32° C. After 4-6 hours, fresh neat virus with polybrene was added and a second round of spin infection was performed. Fresh medium was added to the infected cells to dilute the polybrene. Media was replaced the following day, and 2-3 days later, the infected cells usually exhibited very strong GFP fluorescence by microscopy. Infection efficiency of this two-round infection method was generally >95% over a large range of viral concentrations, therefore FACS was not generally necessary. This strong GFP signal was used to mark the boundary of cells, in addition to phase contrast imaging and nuclear markers (FIGS. 22, 23A-23F); moreover, in cells that were fixed with 4% PFA but not permeabilized with detergents, the GFP signal was higher in the nuclear region, allowing unambiguous delineation of both the cell boundary and nuclei.

For each round of infection, a viral amount equivalent to MOI 3-6 on 3T3 or 293T cells was used on MINION$^{KD}$ C2C12 cells, and the infected cells were expanded and used for in vitro reconstitution assay in differentiation medium. For co-expression and cell-mixing experiments on wild type 10T1/2 cells and C2C12 cells, a viral amount equivalent to MOI 2-4 on 3T3 or 293T cells was used. For each comparison, the viruses made with the same packaging plasmid and at similar MOI were used for infection. The experiments were repeated with different types of control viruses (Luciferase, NanoLuc-FLAG, empty vector). For co-expression and mixing experiments, cells were infected with one type of cDNA retrovirus first using the 2-round spin infection protocol described above, expanded for several days, then reinfected with a second cDNA-encoding retrovirus using the same method. On the day following the final infection, the cells were labeled with different dyes, mixed, and seeded into 384-well or 24-well plates as described below.

Cell Labeling and Mixing Experiments

Figure 21A:
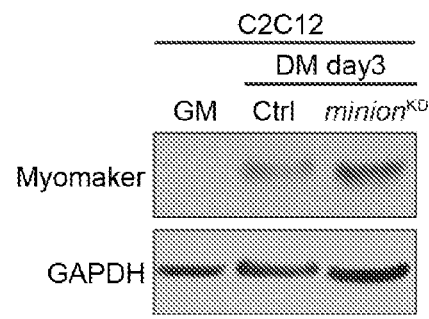
Figure 21B:
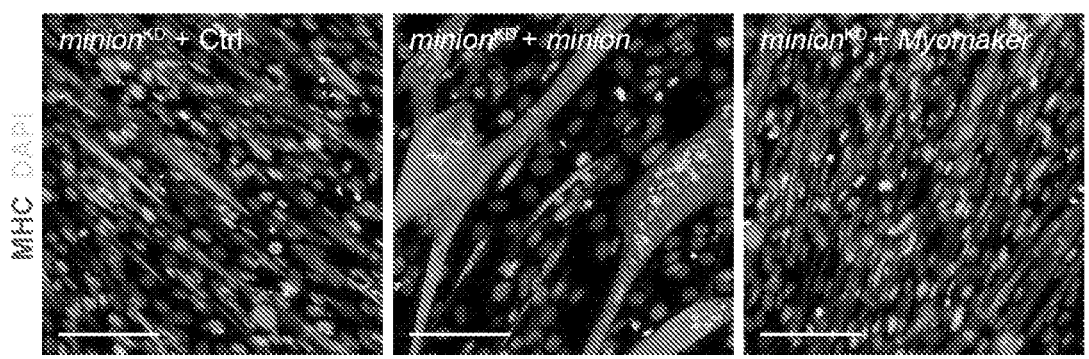
Figure 21B:
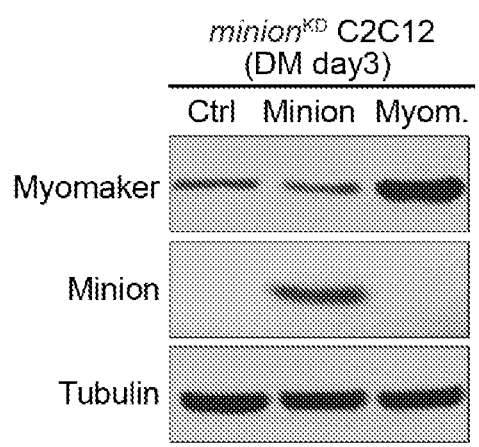
Figure 21B:
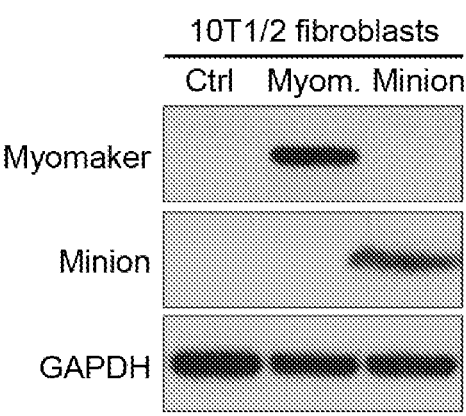
Figure 21E:
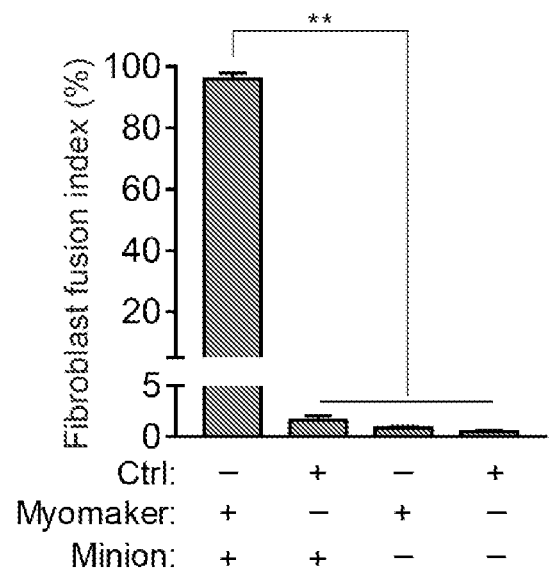
Figure 21F:
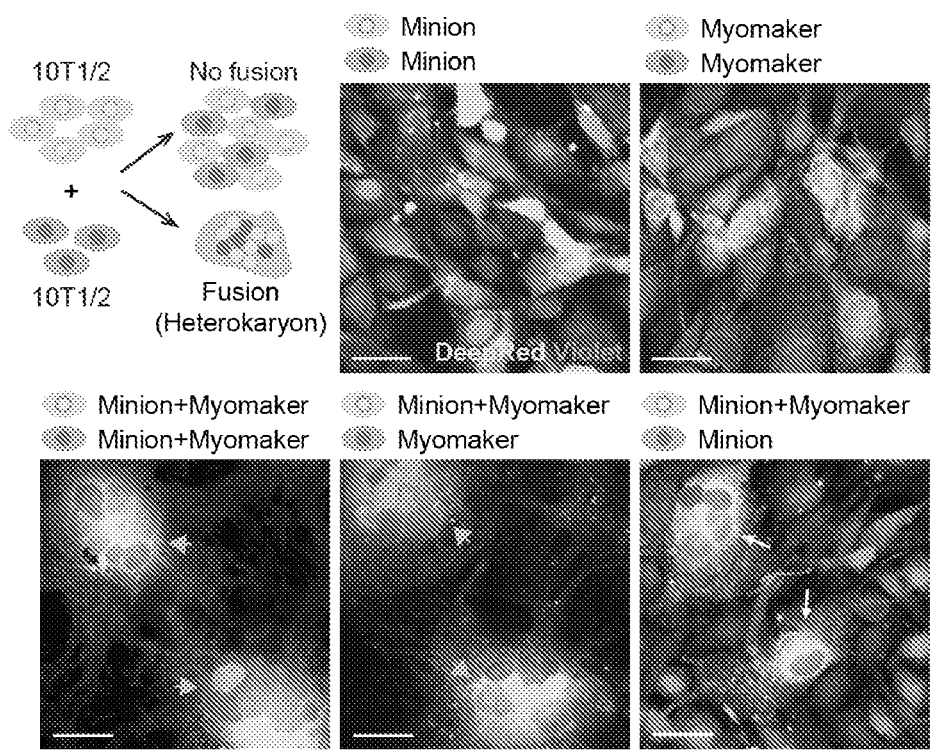
Figure 21G:
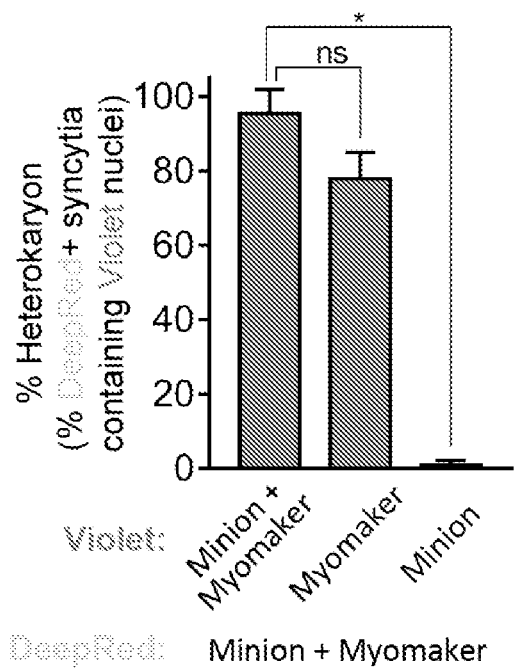

The performance of a series of cell-permeant fluorescent dyes was tested on 10T1/2 fibroblasts and C2C12 myoblasts over multiple dilutions and using different labeling methods, with signal strength and pattern monitored continuously by microscopy for at least four days. CellTracker Deep Red dye (Thermo Fisher C34565, 1:250 final) and CellTrace Violet dye (Thermo Fisher C34571, 1:500 final) were selected for subsequent experiments, and were observed to label the cytoplasmic and nuclear regions of mononuclear cells. However, in fused multinuclear cells (FIGS. 21F, 23A-23F), the CellTrace Violet dye exhibited a strong enrichment in nuclei which had been originally labeled with the dye, and did not diffuse into other non-violet-labeled nuclei, while the CellTracker Deep Red dye demonstrated perinuclear enrichment and was helpful in recognizing the cell boundary. These features allowed facile quantification of fusion efficiency (FIG. 21G).

Cell labeling was performed according to manufacturer's instructions with slight modifications. Cells were trypsinized, centrifuged, washed once with PBS, transferred to a 2 ml Eppendorf tube, centrifuged, and resuspended in PBS at a concentration of 0.8-1×10$^6$ cells/ml. 2× cell labeling solution was prepared separately in PBS with fluorescent dyes (Deep Red dye at 1:125 and Violet dye at 1:250) and was mixed well by brief vortexing. Equal volumes of the 2× labeling solution and the cell suspension (usually 250 µL each) were mixed and incubated at 37° C. for 40-45 min with occasional mixing. The labeled cells were then mixed with 1 ml fresh medium, incubated at 37° C. for 5 min and centrifuged at 150 g. At this point, 3 more washes of the labeled cells was performed using fresh medium, incubation at 37° C. for 10-15 min, and centrifugation at 150×g. After the last wash, the cells were counted and diluted to the concentration needed for the final mixing experiment in a 384-well or 24-well plate, and were incubated at 37° C. for 30 min. These additional washes and incubation steps were used to eliminate remaining unbound dye in the cell suspension and on the cell surface, which was critical for cell mixing experiments performed on the same day. After incubation, cells labeled with Deep Red dye were mixed with those labeled with Violet dye at a 1:1 ratio, and were seeded into 384-well or 24-well plates, with a range of concentrations tested from 800-4000 cells per well. Cells in 384-well plates were fixed at different time points (24-48 hours) with 4% PFA for 10 min at room temperature, and were washed with PBS before imaging. Growth medium containing 10%-15% FBS was used for all experiments in both 10T1/2 and C2C12 cells.

Differentiation and Fusion Indices

Figure 12A:
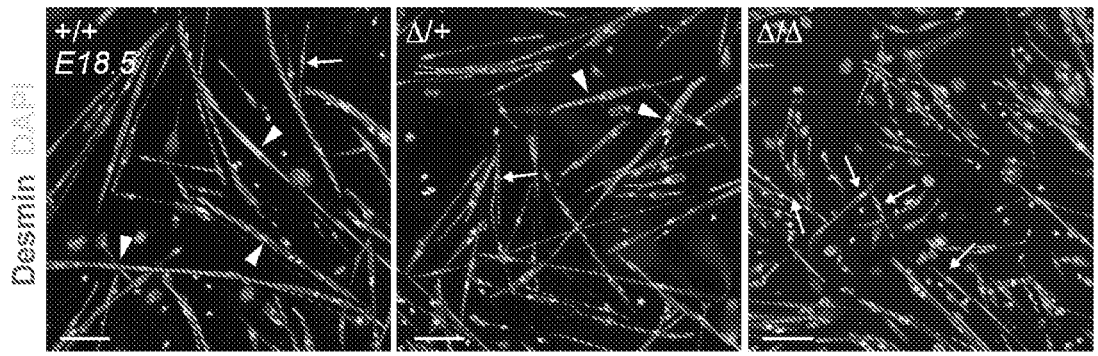
FIGS. 12A-H show MINION is specifically required for fusion of muscle progenitors.
Figure 12B:
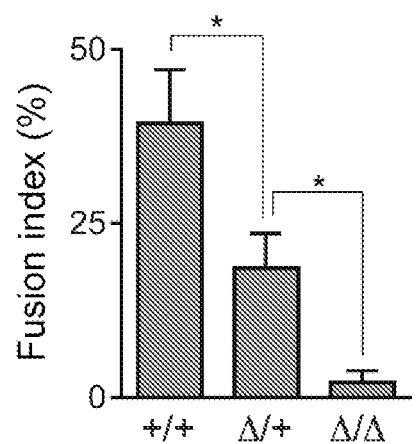
Figure 12C:
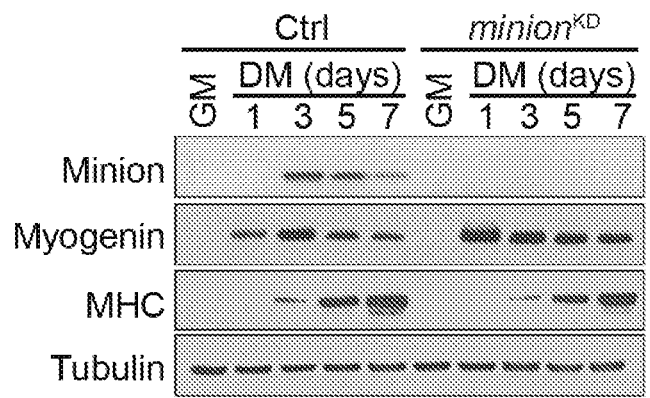
Figure 12D:
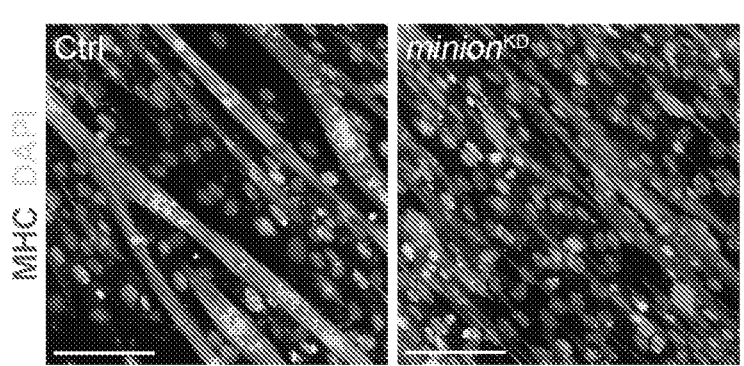
Figure 12E:
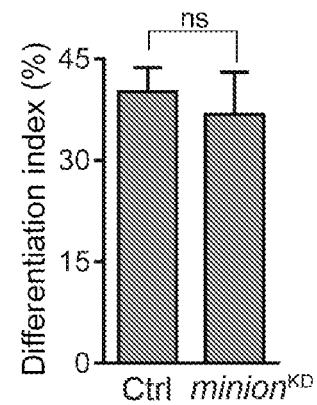
Figure 12F:
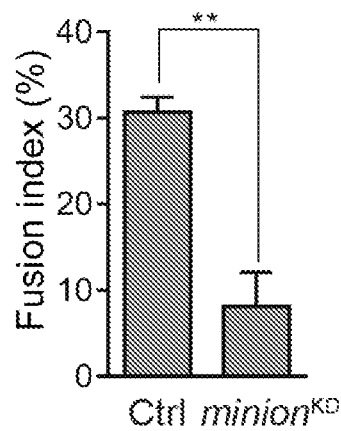
Figure 12G:
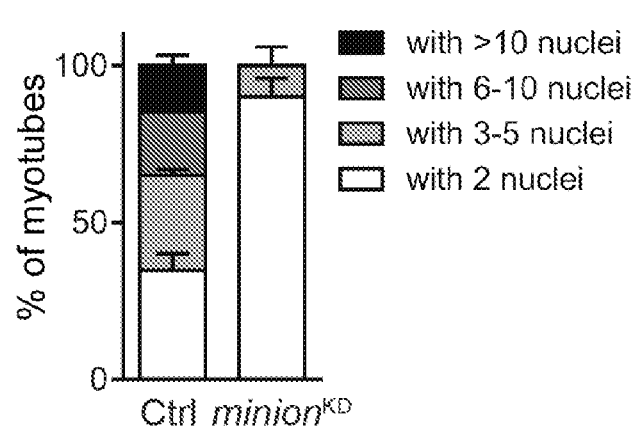
Figure 12H:
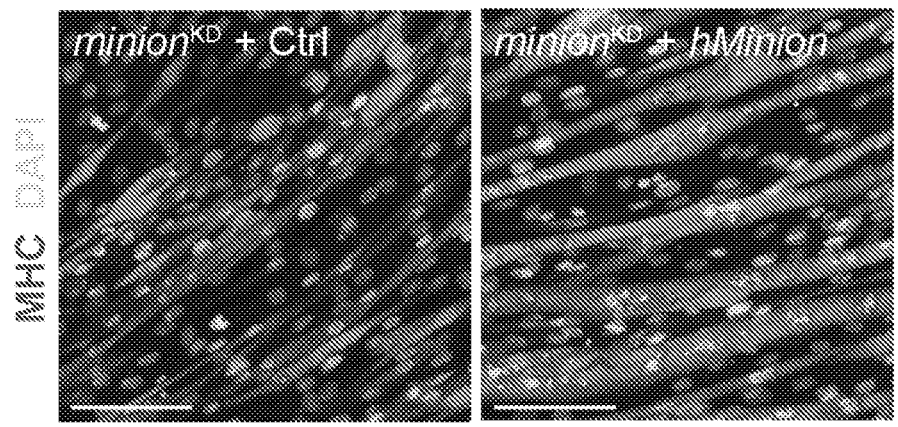
Figure 15A:
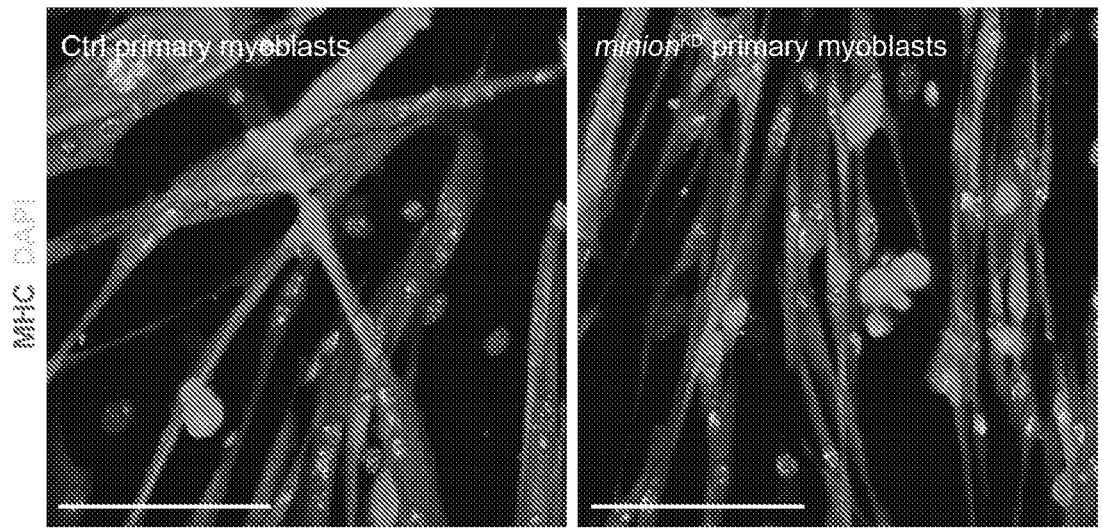
Figure 15A:
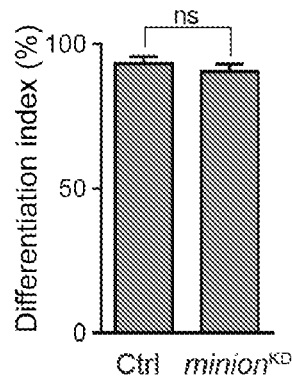
Figure 15A:
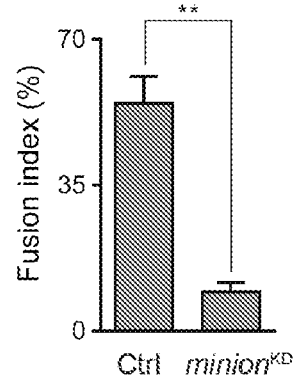
Figure 15A:
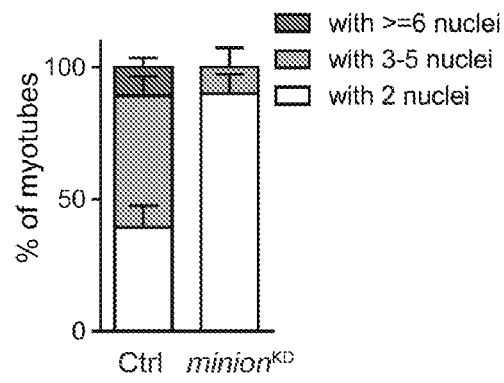

Several indices were used to examine the fusion efficiency in C2C12 cells as well as adult and embryonic primary myoblasts during in vitro differentiation. The differentiation index shown in C2C12 (FIG. 12F) and adult primary myoblasts (FIG. 15B) was calculated as the fraction of nuclei contained within all MHC⁺ cells, including both mononuclear and multinuclear cells, as compared with the number of total nuclei within each 20× image acquired by IXM confocal high-content imaging. At least 6 separate fields from independent replicate wells were quantified for each genotype. The fusion index shown in C2C12 (FIG. 12G) and adult primary myoblasts (FIG. 15C) was calculated as the fraction of nuclei contained within MHC⁺ myotubes which had two or more nuclei, as compared to the number of total nuclei within each 20× image taken by IXM imaging. At least 6 separate fields from independent replicate wells were quantified for each genotype. The fusion index shown for embryonic primary myoblasts (FIG. 12C) was calculated as the fraction of nuclei contained within Desmin⁺ myotubes having three or more nuclei, as compared to the number of nuclei within all Desmin⁺ cells on each 20×IXM image. At least 6 separate fields from independent replicate wells were quantified for each genotype. Since fibroblasts still existed in these early-passage primary cultures, only the total nuclei in Desmin⁺ cells were included for quantification. Another index used to examine the fusion efficiency in C2C12 cells (FIG. 12H) and adult primary myoblasts (FIG. 15D) was focused on myotubes. Myotubes were divided into 3 to 4 subgroups by the number nuclei number contained within each tube: 2 nuclei, 3-5 nuclei, 6-10 nuclei, or more than 10 nuclei (FIG. 12H). The fraction of each subgroup was calculated for each genotype in comparison to total myotube number. At least 6 separate fields from independent replicate wells were quantified for each genotype.

For co-expression experiments in 10T1/2 cells, two indices were used to examine fusion efficiency. The first fusion index (FIG. 21E) was based on the experiment shown in FIG. 22, and was calculated as the percentage of nuclei within GFP⁺ syncytia containing 4 or more nuclei, as compared with the number of total nuclei. At least four separate 10×IXM images from different replicate wells were used for quantification of each genotype. In order to examine the ability of MINION-only or Myomaker-only expressing cells to fuse with MINION and Myomaker co-expressing cells, a second index was used (FIG. 21G) to calculate the fusion efficiency between Deep Red dye-labeled cells and Violet dye-labeled cells in four different combinations (FIGS. 21F, 23A-23F). In these combinations, all of the Deep Red dye-labeled cells had co-expression of Myomaker and MINION, no matter which protein was expressed first by infection, and these cells were able to fuse to themselves, becoming Deep Red⁺ syncytia. The Violet dye-labeled cells expressed either Myomaker and MINION (either Myomaker or MINION was expressed first); Myomaker only (together with empty vector control); or MINION only (together with the Luciferase control). The fraction of Deep Red⁺ syncytia (containing 4 or more nuclei) containing one or more Violet dye-labeled nucleus was compared with the total number of Deep Red⁺ syncytia on each 10×IXM image. At least 12 separate fields from independent replicate wells were quantified for each combination.

Example 2: MINION is a Skeletal Muscle-Specific Microprotein Highly Expressed During Muscle Regeneration, Development, and Differentiation Muscle development requires requires temporally regulated stem cell activation and differentiation, fusion of progenitors to form syncytial myotubes, and maturation of myotubes to generate contractile myofibers. While the early and late stages of this process have been intensively studied (Comai, et al., Molecular and cellular regulation of skeletal myogenesis. *Current Topics In Developmental Biology* 110: 1, 2014; Buckingham, et al., Gene regulatory networks and transcriptional mechanisms that control myogenesis. *Developmental Cell* 28: 225, 2014), our understanding of the mechanisms and regulatory factors controlling cell fusion remains incomplete, particularly in mammals (Hindi, et al., Signaling mechanisms in mammalian myoblast fusion. *Science signaling* 6, re2, 2013; Hochreiter-Hufford et al., Phosphatidylserine receptor BAI1 and apoptotic cells as new promoters of myoblast fusion. *Nature* 497, 263, 2013). Recently, the transmembrane protein Tmem8c/Myomaker was identified and was shown to be necessary for myoblast fusion and sufficient for fusion of non-muscle cells to differentiating myoblasts (Millay et al., Myomaker is a membrane activator of myoblast fusion and muscle formation. *Nature* 499: 301, 2013). Importantly however, Myomaker expression was insufficient to drive fusion of a non-muscle cell to another non-muscle cell.

In addition to canonically defined protein coding genes, recent studies have indicated that existence of a new class of regulatory factors in muscle. These small ORFs (smORFs) are transcribed and translated but are largely bioinformatically silent by virtue of their size, typically encoding microproteins <100 amino acids (aa) in length. Although estimates vary widely, the human and mouse genomes are thought to contain at least several thousand of these "hidden" genes (Saghatelian et al., Discovery and characterization of smORF-encoded bioactive polypeptides. *Nature chemical biology* 11, 909, 2015). Intriguingly, of the small number of mammalian microproteins reported to date, several have been identified in muscle, all of which encode regulatory factors for the sarco/endoplasmic reticulum $Ca^{2+}$-ATPase (SERCA), with structural similarity to known SERCA-regulatory proteins such as sarcolipin and phospholamban (Nelson et al., A peptide encoded by a transcript annotated as long noncoding RNA enhances SERCA activity in muscle. *Science* 351, 271, 2016; Anderson et al., A micropeptide encoded by a putative long noncoding RNA regulates muscle performance. *Cell* 160, 595, 2015; Magny et al., Conserved regulation of cardiac calcium uptake by peptides encoded in small open reading frames. *Science* 341, 1116, 2013).

Figure 1B:
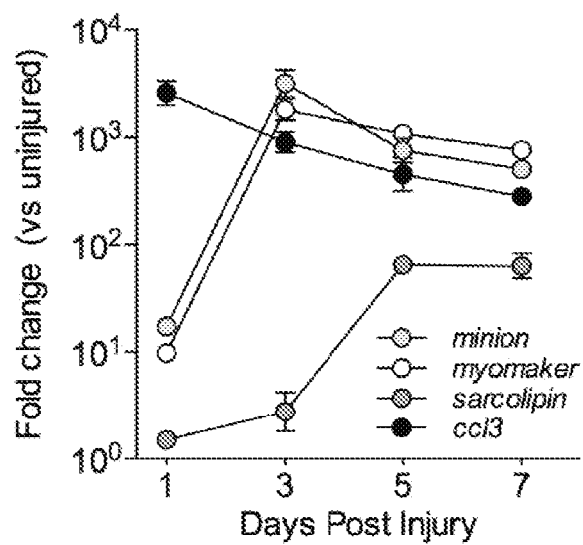

Whole transcriptome RNA-seq analysis of uninjured and regenerating muscle was performed to identify novel microproteins that play an important role in skeletal muscle development and regeneration (Bentzinger, et al., Building muscle: molecular regulation of myogenesis. *Cold Spring Harbor perspectives in biology* 4, 2012). We searched for transcripts demonstrating strong temporal regulation (up-regulation at day 3 following injury), annotated ORF length of less than 100 codons, and a similarly dynamic pattern of regulation during mouse myoblast differentiation in vitro (FIG. 1A). The predicted gene 7325 (Gm7325) was the only gene meeting all criteria, encoding a putative 84 aa microprotein with possible expression in ES cells but no known function (Chen, et al., Molecular cloning and functional analysis of ESGP, an embryonic stem cell and germ cell specific protein. *Acta biochimica et biophysica Sinica* 37: 789, 2005). For reasons described below, we named this gene MINION (microprotein inducer of fusion). The temporal pattern of MINION expression was very similar to that of Myomaker, but distinct from that of two other smORFs, ccl3 or sarcolipin (FIG. 1B).

Figure 1C:
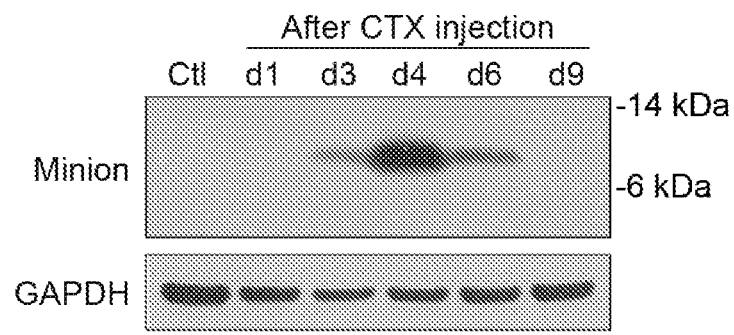
Figure 1D:
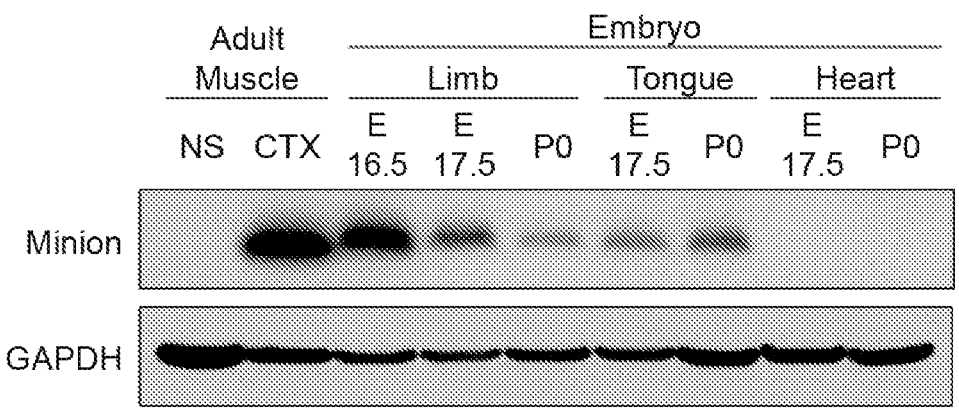
Figure 1E:
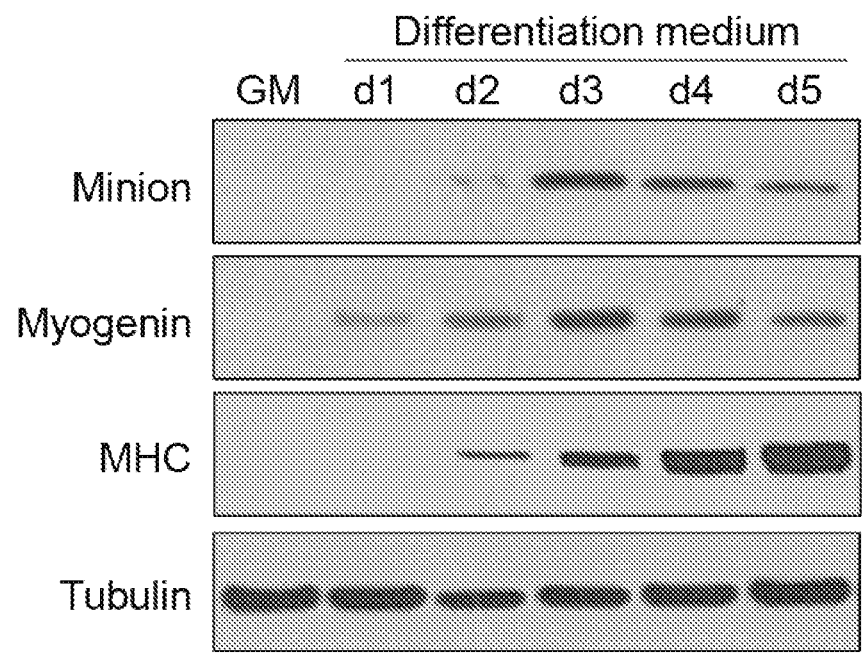
Figure 2A:
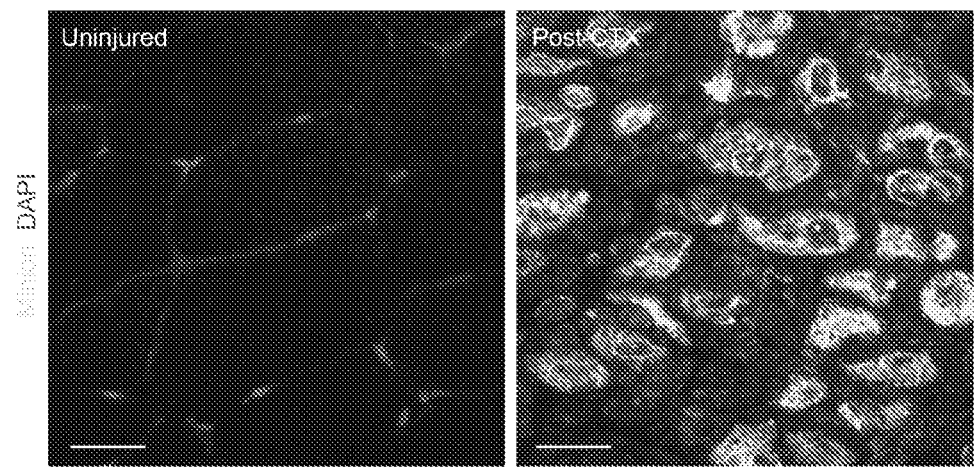
FIGS. 2A-2E show MINION is specifically expressed in regenerating adult skeletal muscle but not cardiac muscle.
Figure 2B:
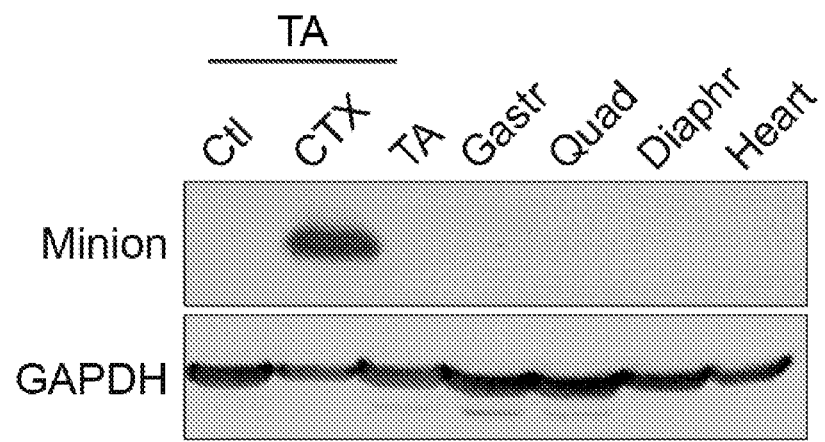
Figures 2C, 2D:
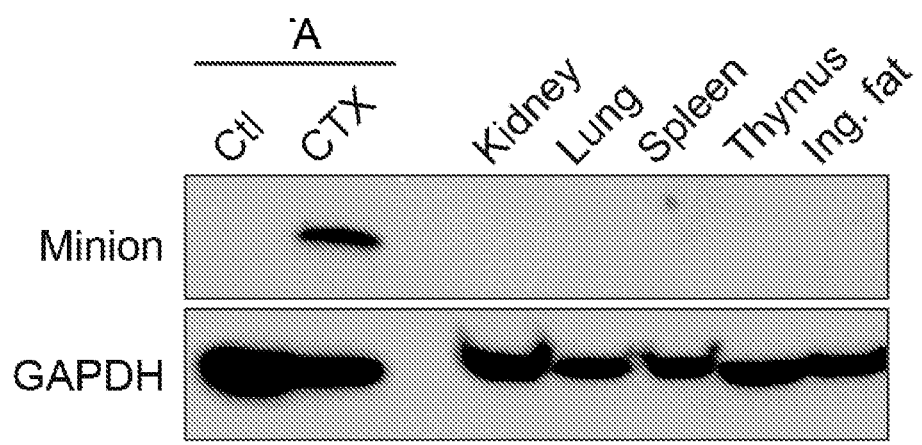
Figure 2E:
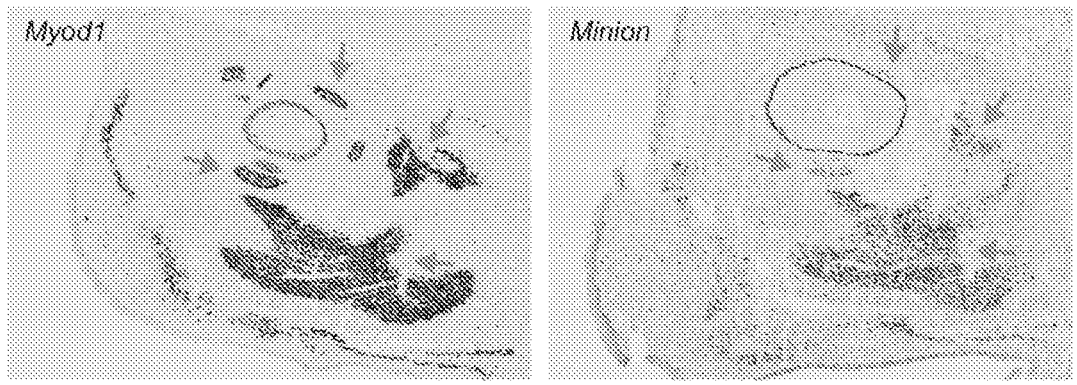
Figure 3A:
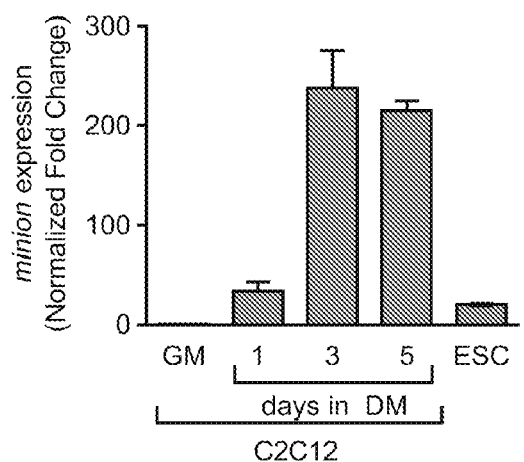
FIGS. 3A-3E show that MINION is highly expressed in differentiating muscle cells and is membrane associated.
Figure 3B:
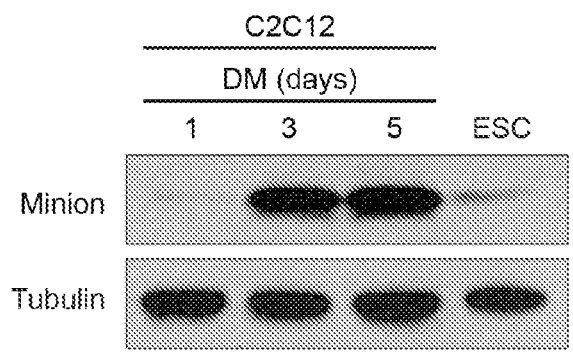
Figure 3C:
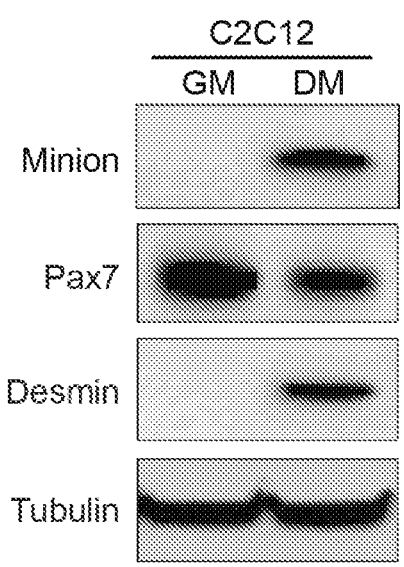
Figure 3D:
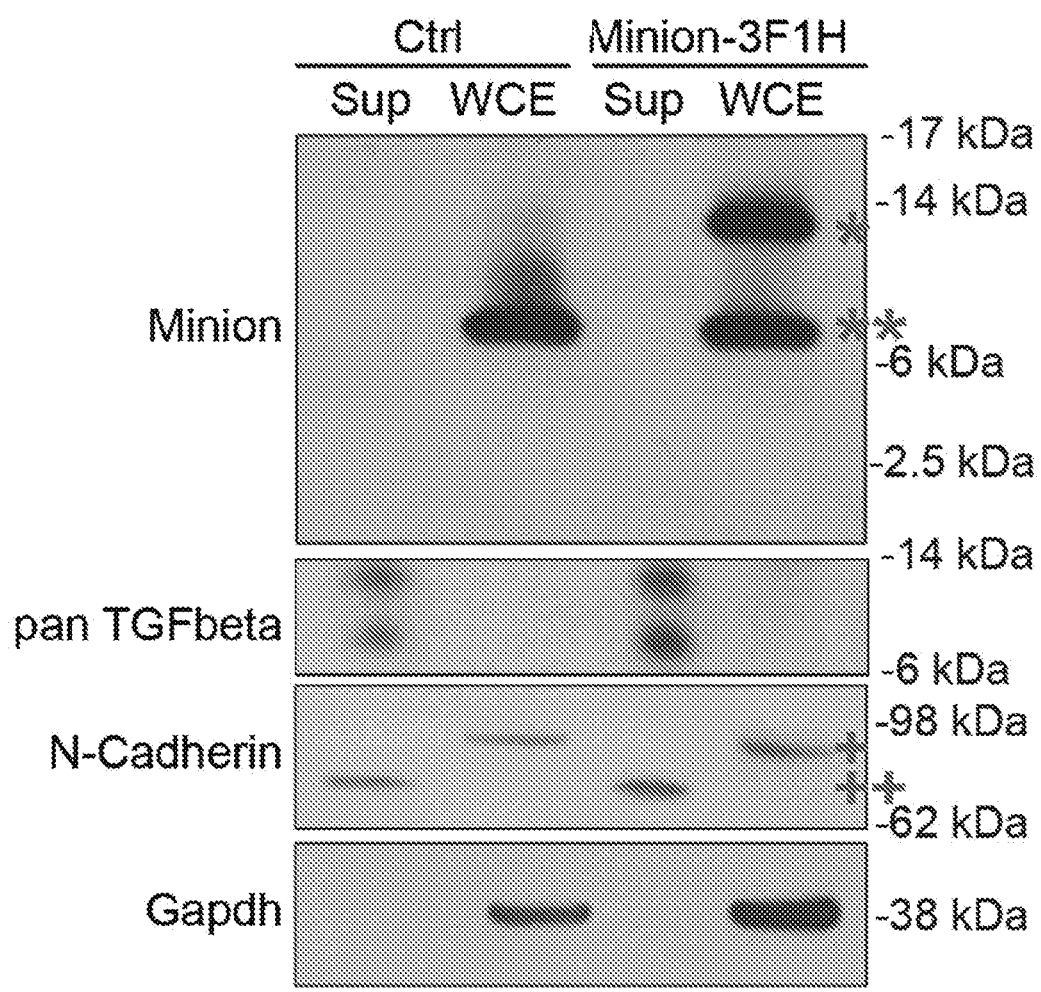
Figure 3E:
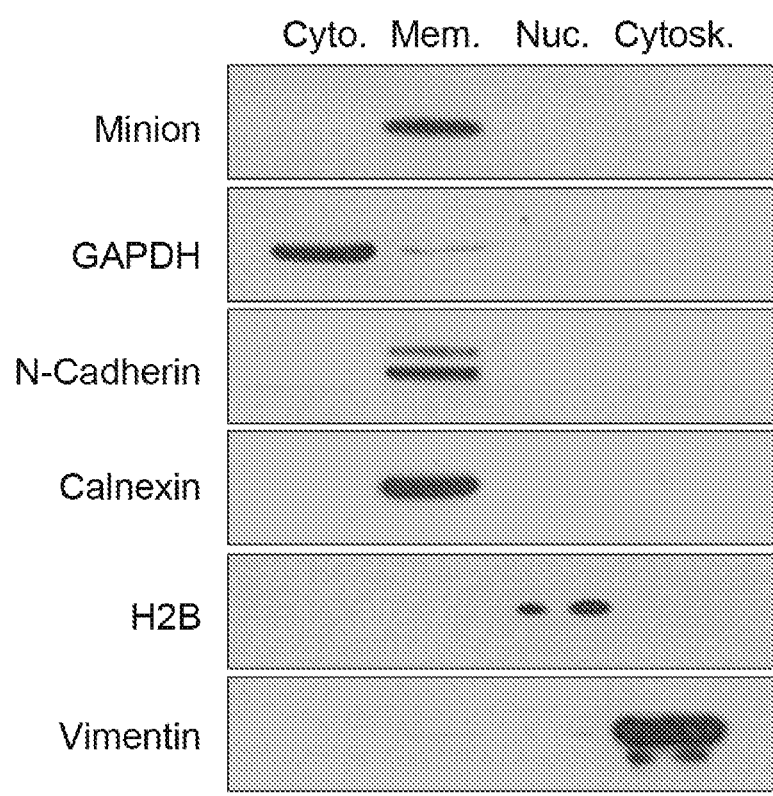

Western blot confirmed that MINION transcript is translated; MINION protein was absent in uninjured tibialis anterior (TA) muscle but strongly induced during regeneration, peaking on day 3-4 following injury (FIG. 1C). Immunofluorescence analysis demonstrated MINION expression within nascent regenerating myofibers (FIG. 2A), whereas MINION protein was not detectable in uninjured adult muscle (FIG. 2B) nor in other non-muscle tissues (FIG. 2C). RNA-seq analysis of early embryonic development revealed Minion expression which was detectable as early as somite stage 15 but greatly increased by somite stage 36, following limb and tail bud formation (FIG. 2D). Developmental expression of MINION was seen in mouse limb and tongue (both containing skeletal muscle), but not in embryonic or neonatal heart muscle (FIG. 1D, FIG. 2E). Both mRNA and protein levels of MINION increased rapidly during in vitro myoblast differentiation (FIG. 1D and FIGS. 3A-3C). Although the full-length protein is predicted to contain an N-terminal signal sequence and predominant alpha-helical secondary structure (FIG. 1E), overexpression and supernatant concentration demonstrated no evidence of protein secretion (data not shown). Subcellular fractionation did however confirm significant enrichment within the membrane-associated fraction (including plasma membrane, ER, and Golgi), suggesting insertion into or association with a membrane compartment (FIG. 3D).

Figure 4A:
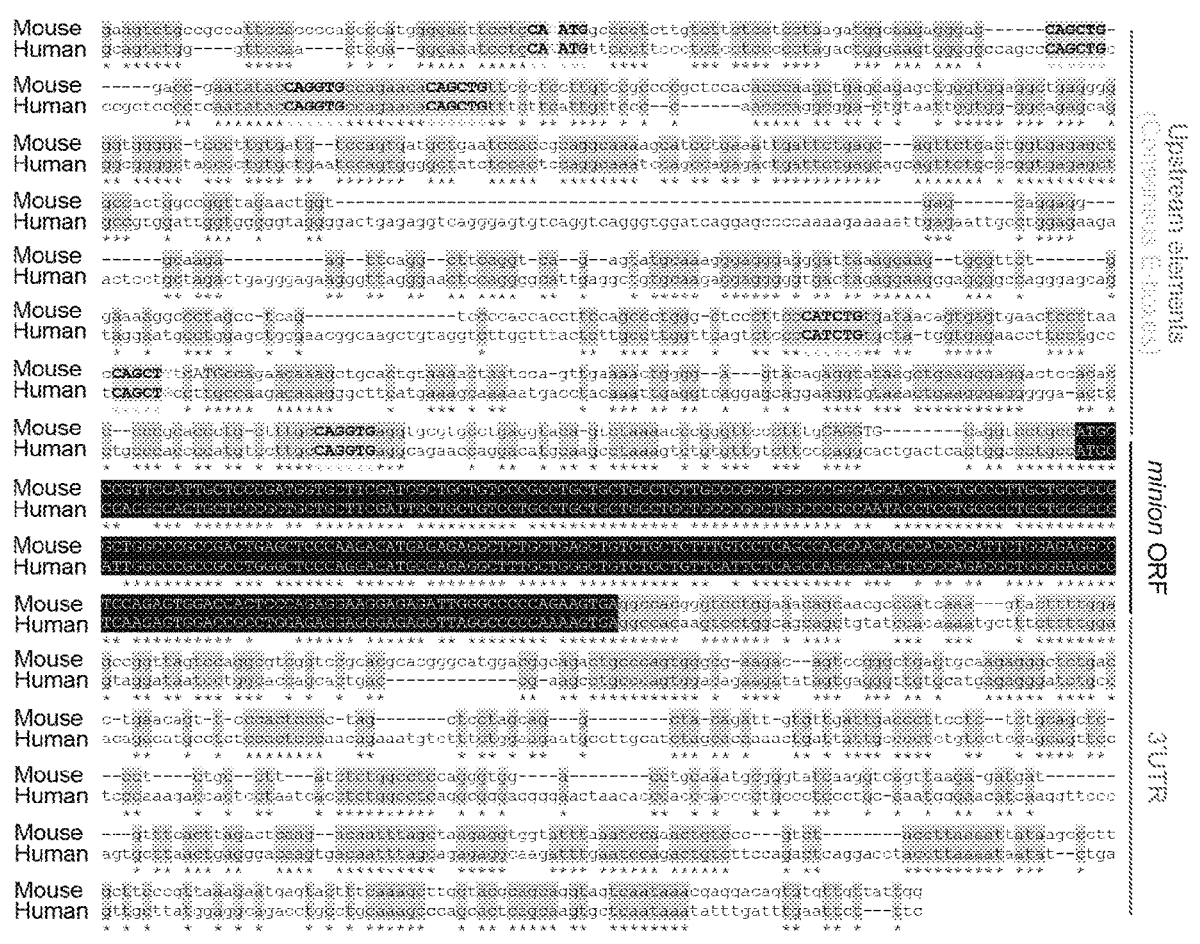
Figure 4B:
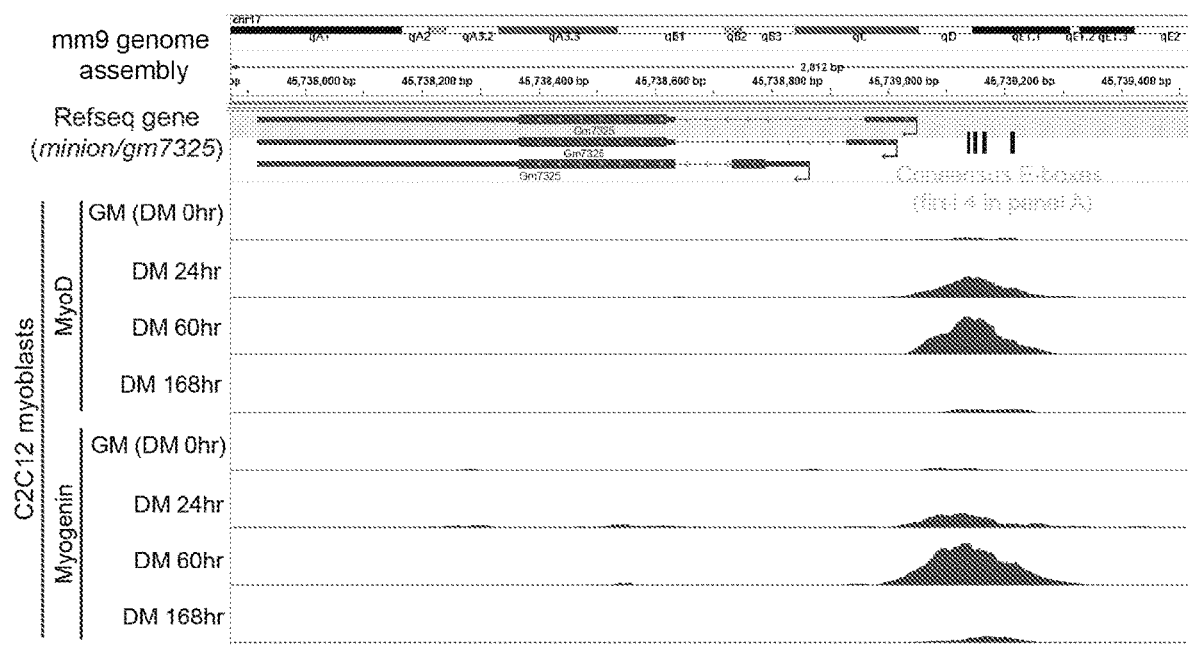

TBLASTN search revealed a putative human MINION homolog with an intact ORF of 84 codons (FIG. 4A), despite prior annotation of the transcript as a long noncoding RNA (RP1-302G2.5; LOC101929726). Evolutionary conservation was seen across mammalian species (FIG. 1F), but no convincing sequence homolog was found in *Drosophila* or other invertebrates. No sequence similarity was seen to sarcolipin, phospholamban, or the recently reported microprotein DWORF (Nelson et al., A peptide encoded by a transcript annotated as long noncoding RNA enhances SERCA activity in muscle. *Science* 351, 271, 2016). Minion expression slightly trailed that of the basic helix-loop-helix transcription factor Myogenin (FIG. 1E), suggesting control by canonical muscle regulatory factors (MRFs, e.g. MyoD and Myogenin). Indeed, analysis of the upstream regulatory regions of human and mouse MINION loci revealed evolutionarily conserved E-box binding sites for MRFs (FIG. 4A). Both MyoD and Myogenin specifically bound these sites in differentiating myoblasts, as shown by ENCODE whole genome ChIP-seq (FIG. 4B) (see also Sloan et al., ENCODE data at the ENCODE portal. *Nucleic acids research* 44, D726, 2016).

In summary, these data show MINION is a membrane associated microprotein specifically expressed in developing and regenerating skeletal muscle, at a time of rapid expansion and fusion of stem cell-derived myoblasts.

Example 3: The MINION Microprotein is Required for Skeletal Muscle Development

Figure 5A:
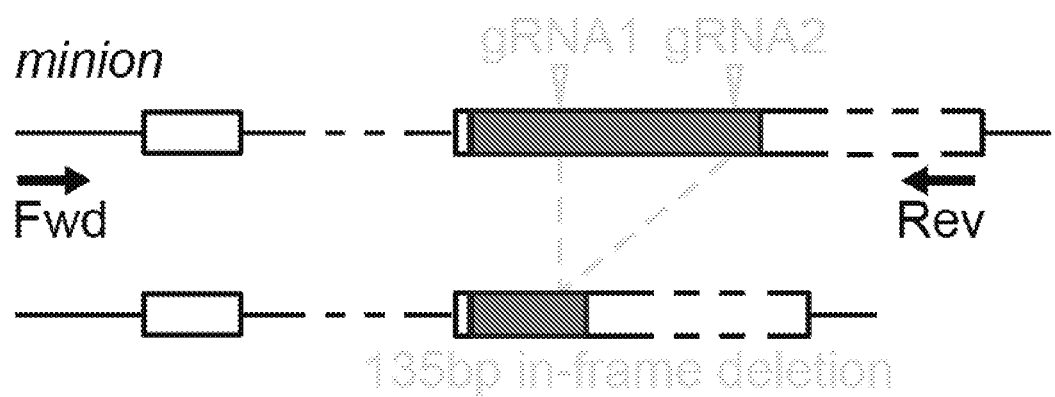
FIGS. 5A-5G show the MINION microprotein is required for skeletal muscle development.
Figure 5B:
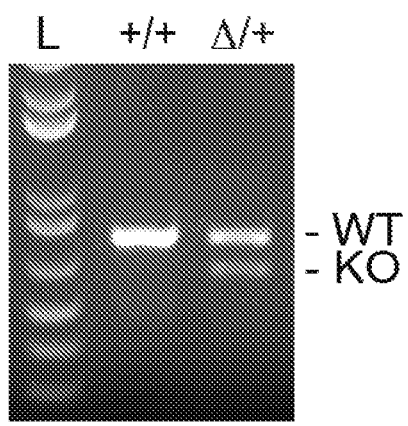
Figure 5C:
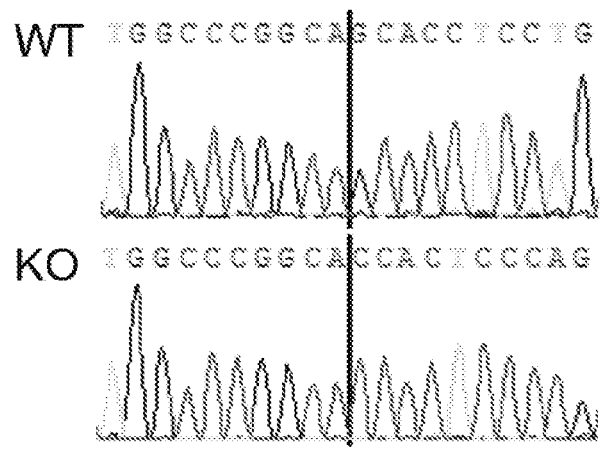
Figures 6A, 6B:
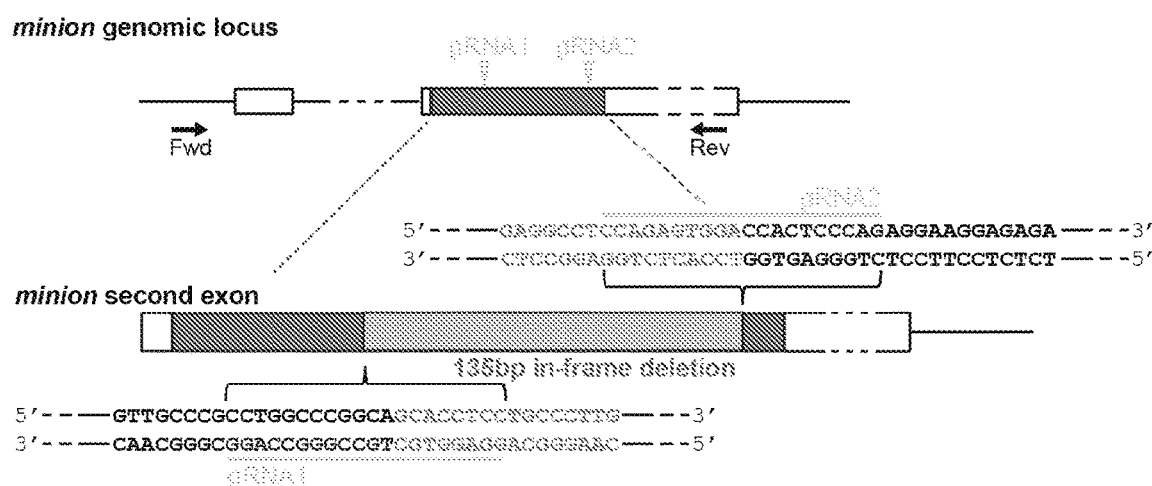
FIGS. 6A-6D show perinatal lethality of MINION-deficient knockout mice.
Figures 6C, 6D:
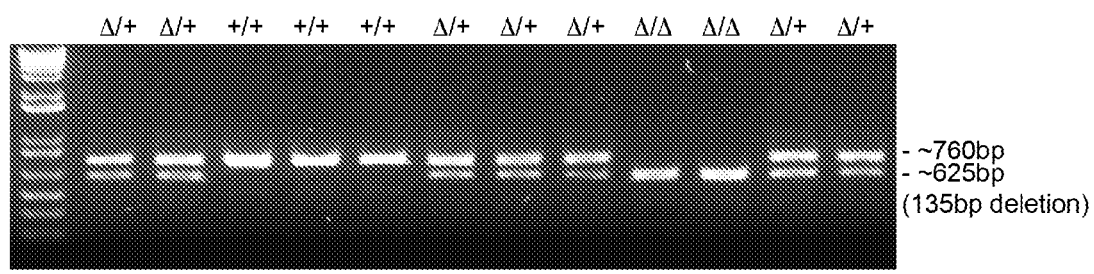
Figure 7A:
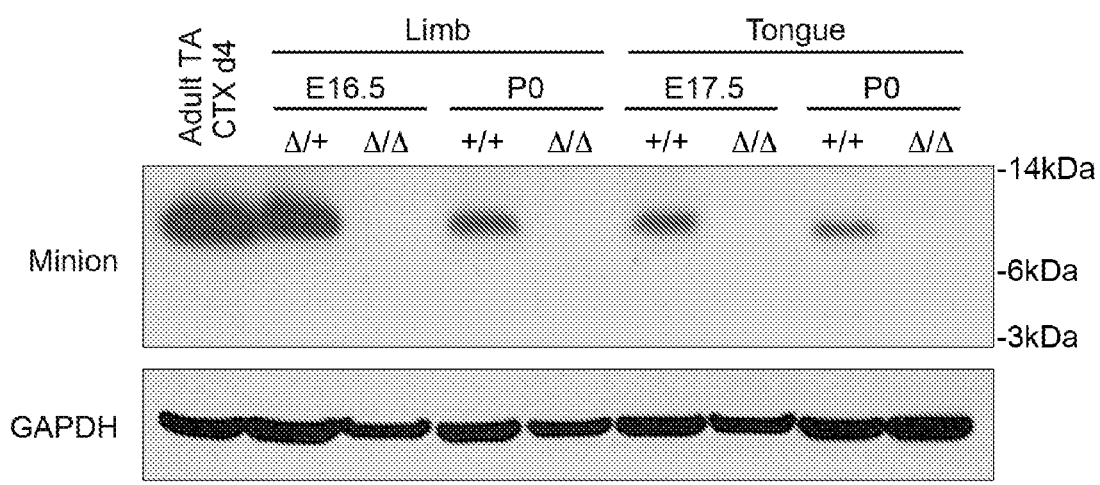
FIGS. 7A-7B show loss of MINION protein expression in MINION-deficient animals.
Figure 7B:
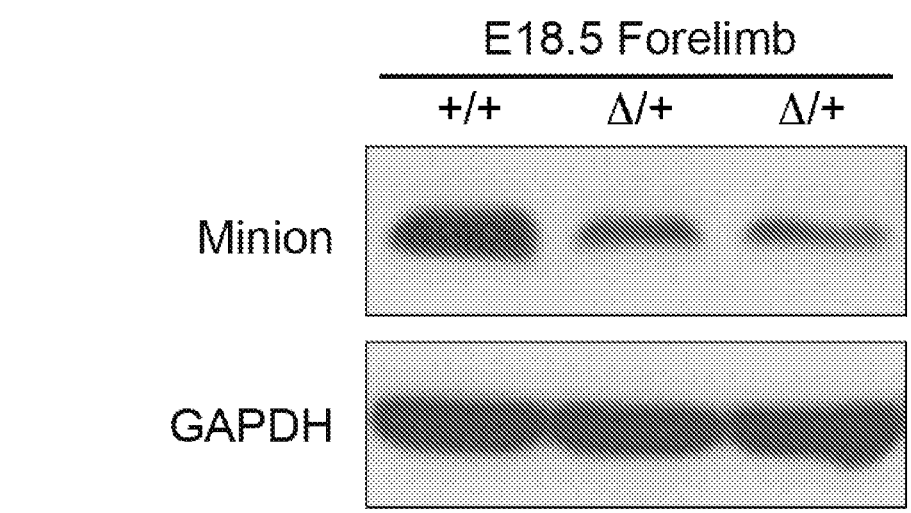
Figure 25A:
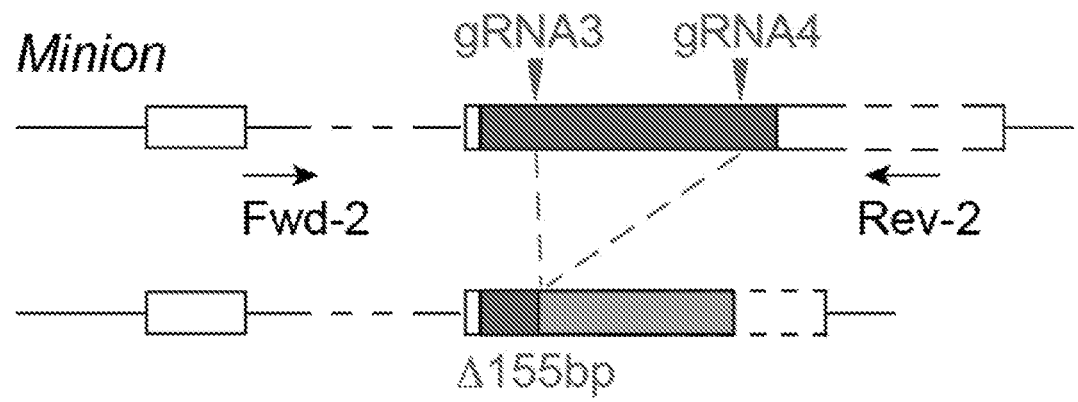
Figure 25B:
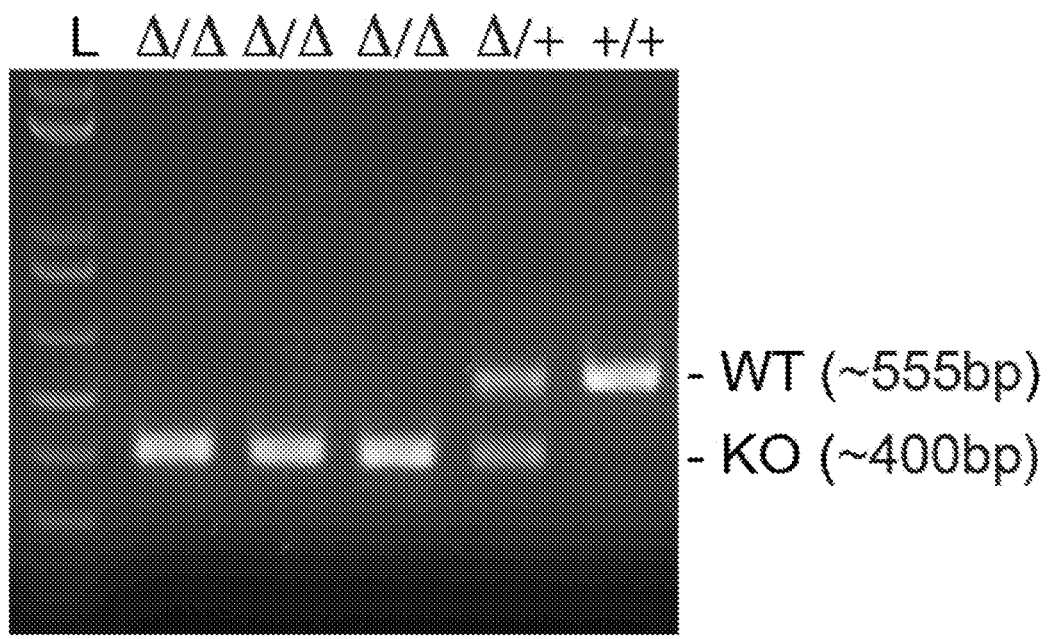
Figure 25C:
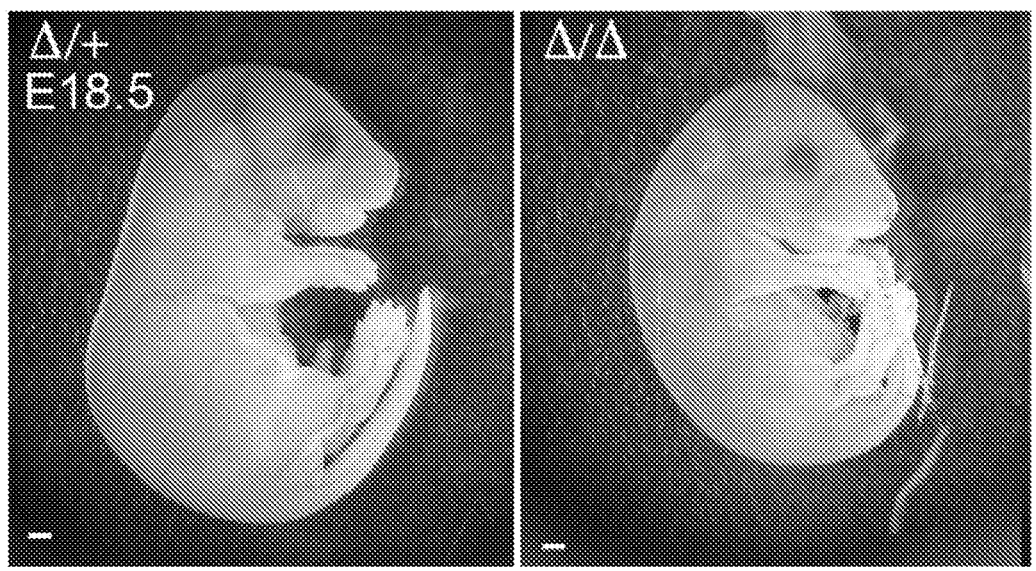
Figure 26A:
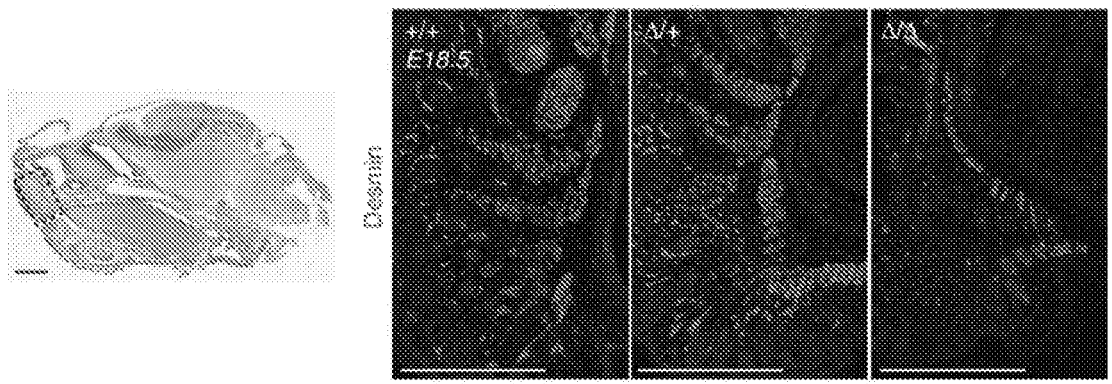
FIGS. 26A-26B show Minion deficiency blocks non-somitic skeletal muscle formation.
Figure 26B:
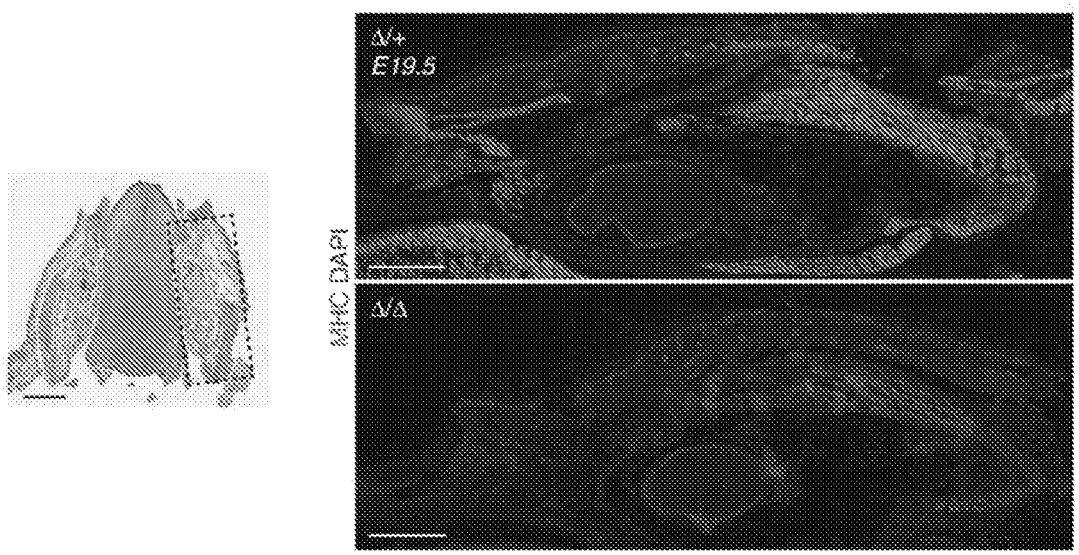

The spatial and temporal expression pattern of MINION and the presence of functional MRF-binding E-boxes in MINION regulatory sequences suggested a role in skeletal muscle development. To test this, CRISPR/Cas9 genome editing was used to generate MINION-deficient mice (FIG. 5A). Two guide RNAs (gRNAs) targeting the single coding exon were coinjected into embryos, and $F_0$ pups were screened for mutations (FIGS. 5A & 6, FIG. 25). Small insertion/deletion mutations as well as larger deletions between gRNA target sites were identified (FIG. 6A), and two founder lines containing either a 135 bp in-frame deletion (MINION$^{\Delta/\Delta}$; FIGS. 5A-5C, FIG. 6B) or a 155 bp frameshift deletion (FIGS. 25A, 25B, 25D) were characterized further. Subsequent experiments are with the 135 bp deletion allele unless otherwise mentioned. Although heterozygous MINION$^{\Delta/+}$ animals were viable and recovered at expected Mendelian ratios, and late-stage homozygous mutant MINION$^{\Delta/\Delta}$ embryos were also obtained, no live homozygous MINION$^{\Delta/\Delta}$ animals were recovered after birth (FIGS. 6C-6D), consistent with perinatal lethality. Loss of MINION protein was confirmed in embryonic and perinatal limb and tongue skeletal muscle from MINION-deficient animals (FIGS. 7A-7B).

Figure 5D:
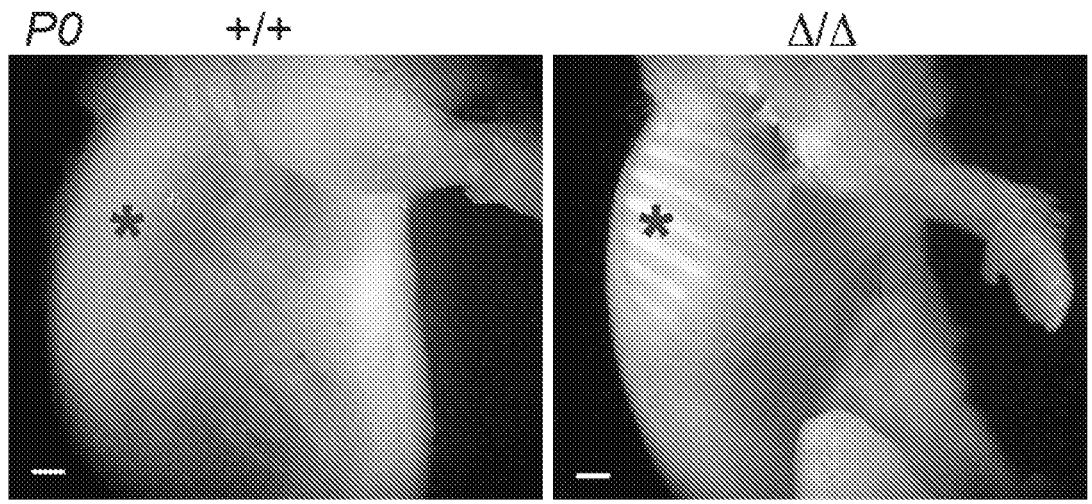
Figure 5E:
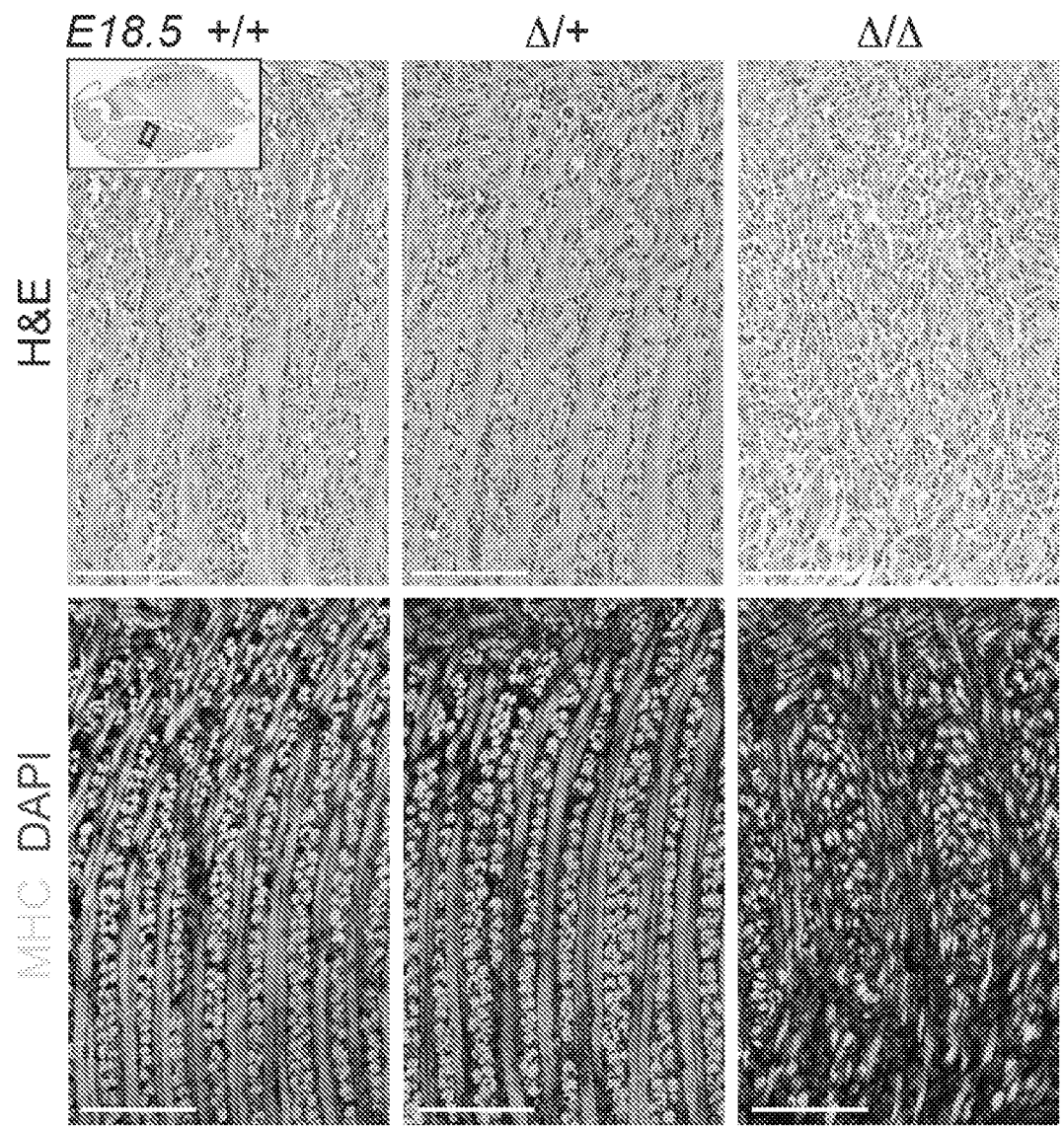
Figure 5F:
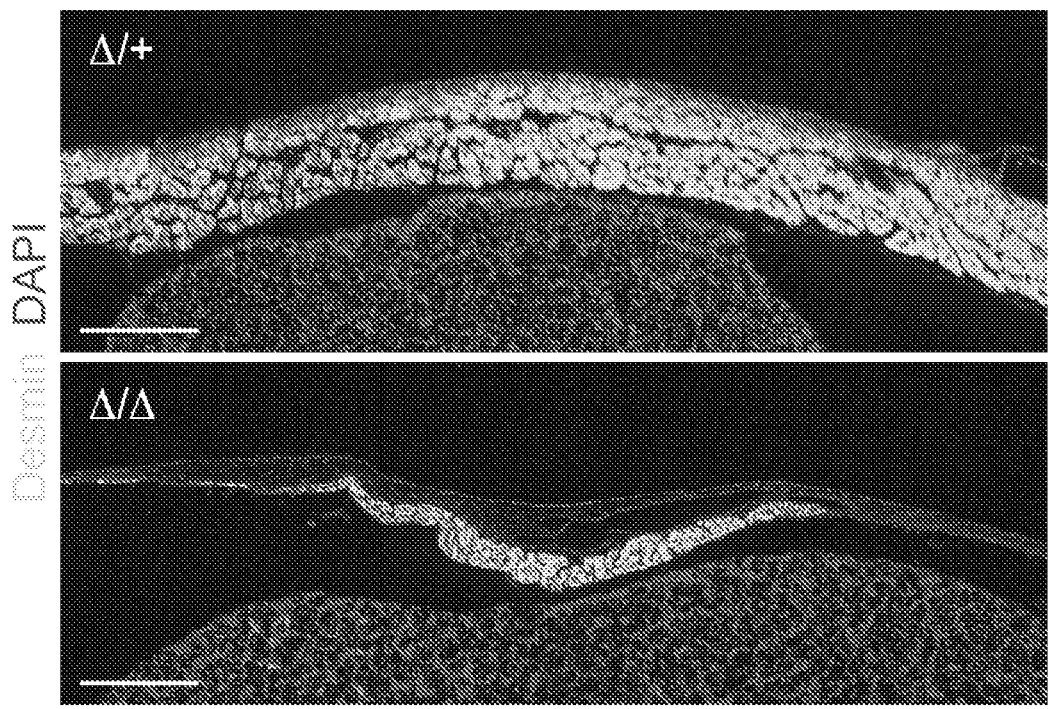
Figure 5G:
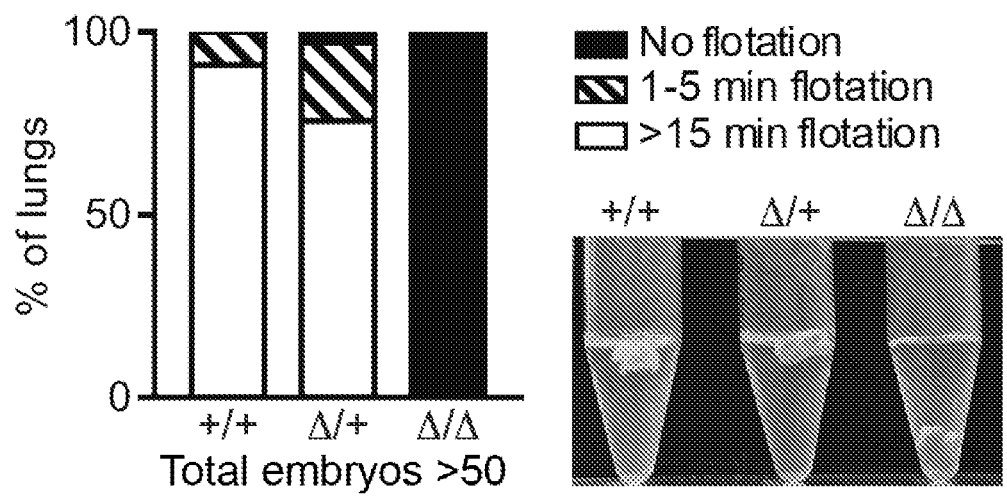
Figure 8A:
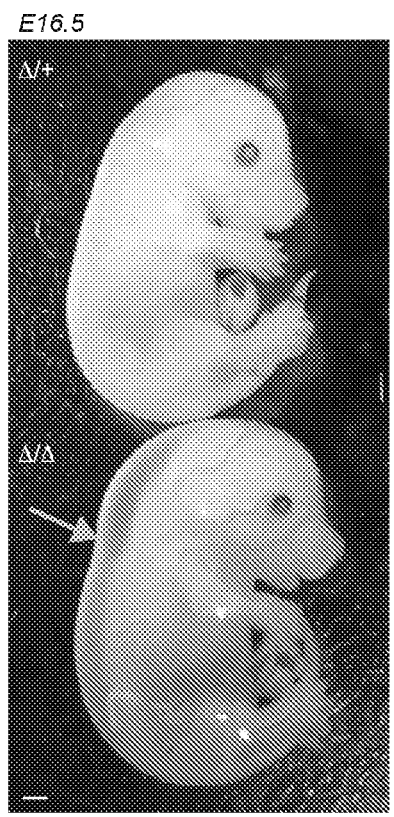
FIGS. 8A-8D show developmental abnormalities in MINION-deficient animals.
Figure 8B:
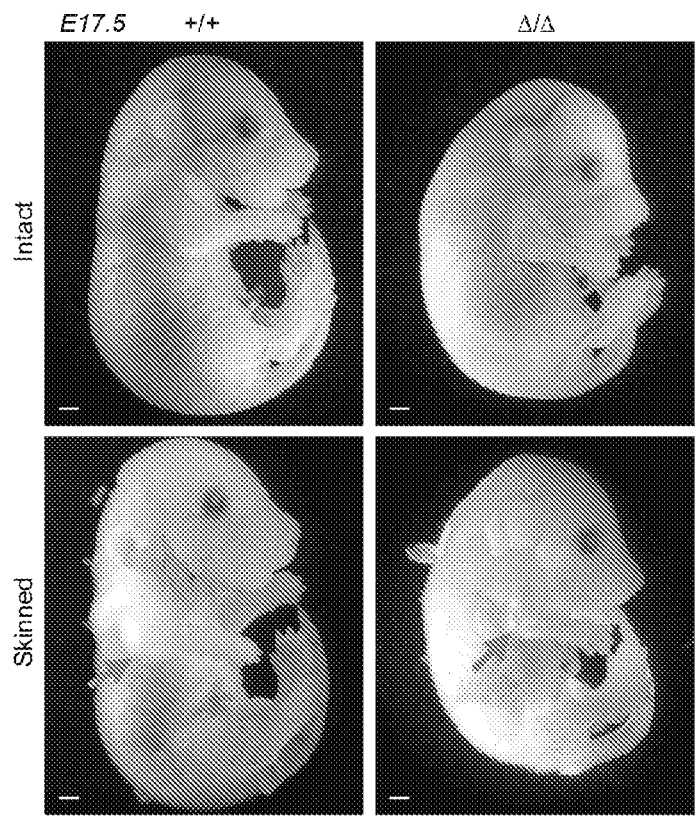
Figure 8C:
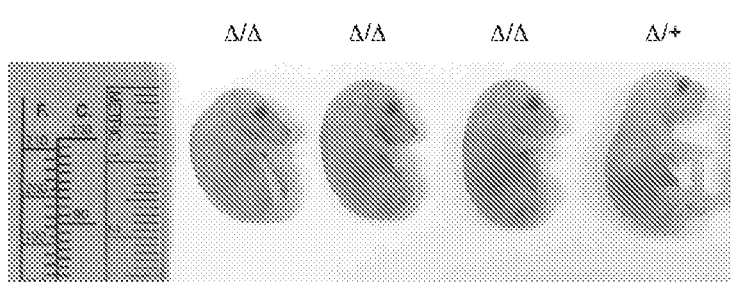
Figure 8D:
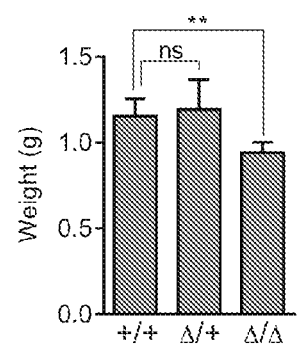
Figure 9A:
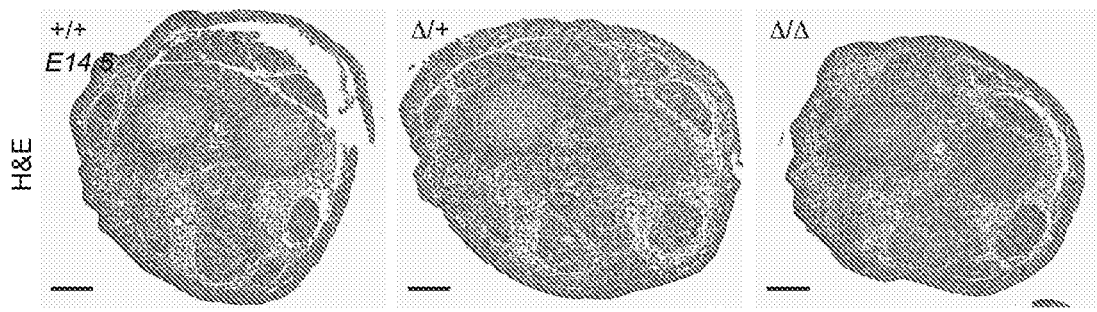
FIGS. 9A-9D show MINION deficiency affects later stages of skeletal muscle formation, causing a reduction of muscle group size.
Figure 9B:
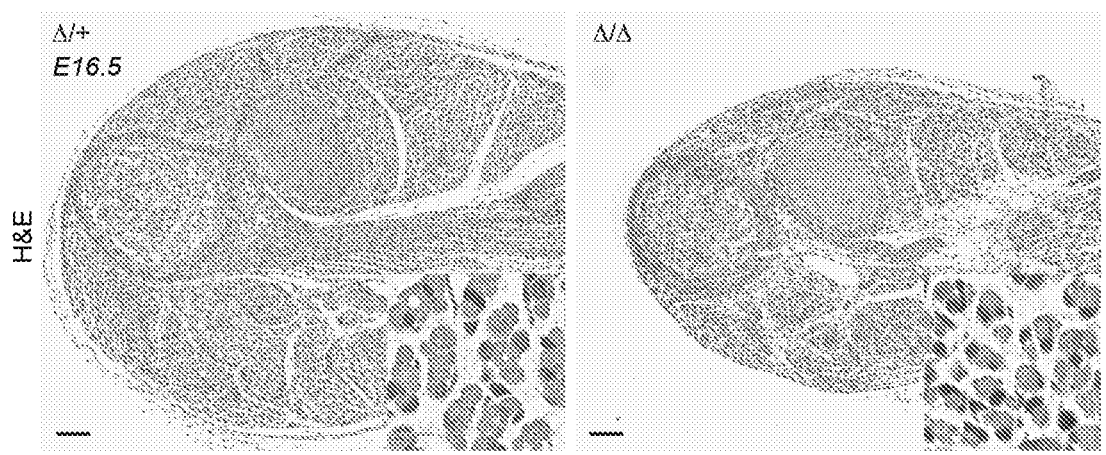
Figure 9C:
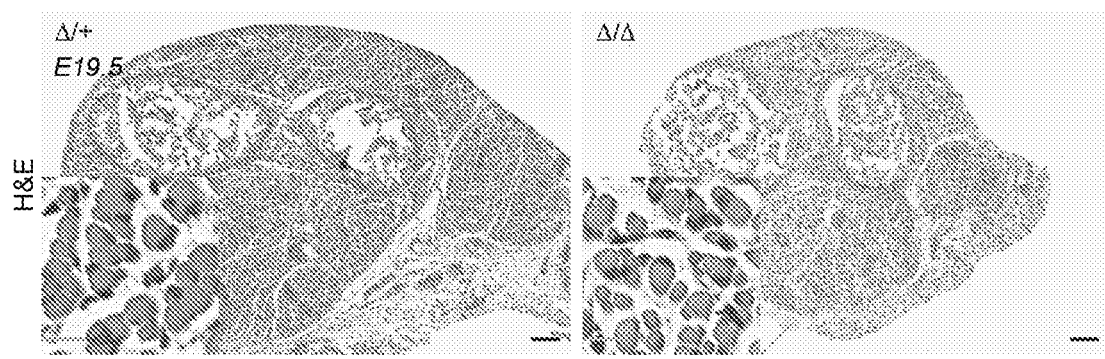
Figure 9D:
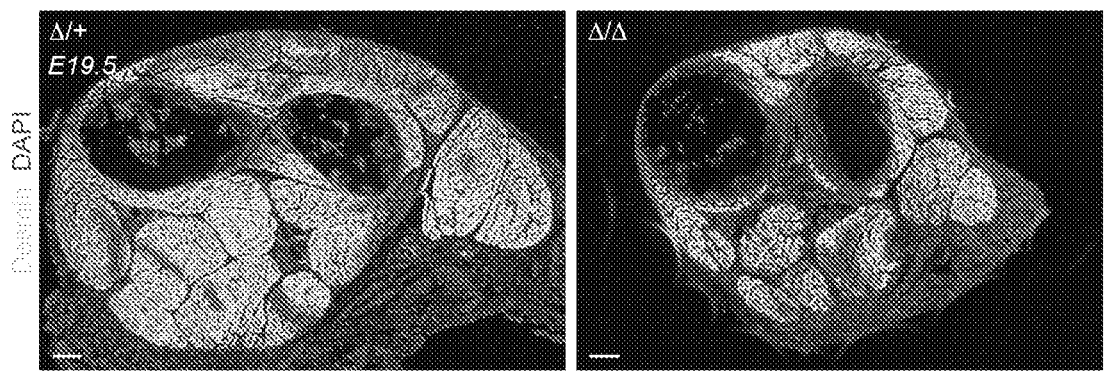
Figure 10A:
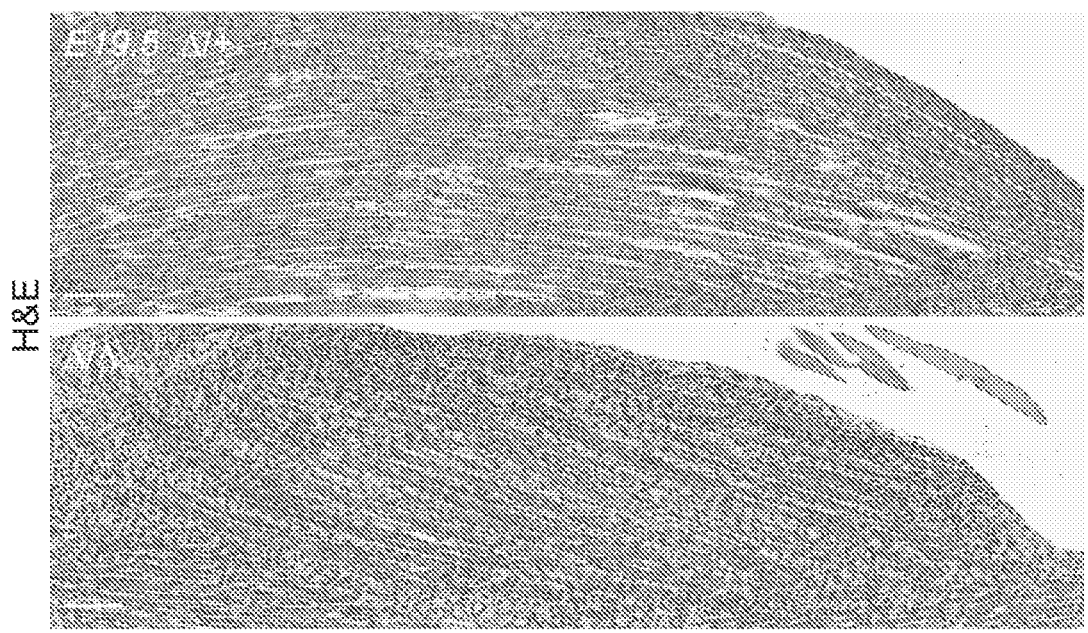
FIGS. 10A-10C show MINION deficiency leads to defects in limb and intercostal skeletal muscle formation.
Figure 10B:
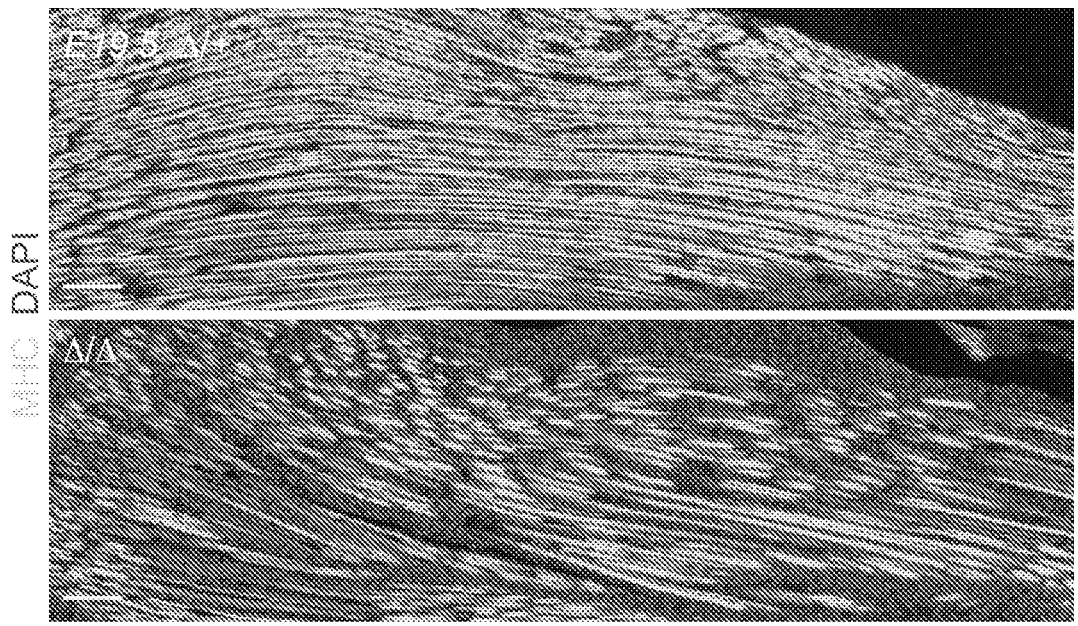
Figure 10C:
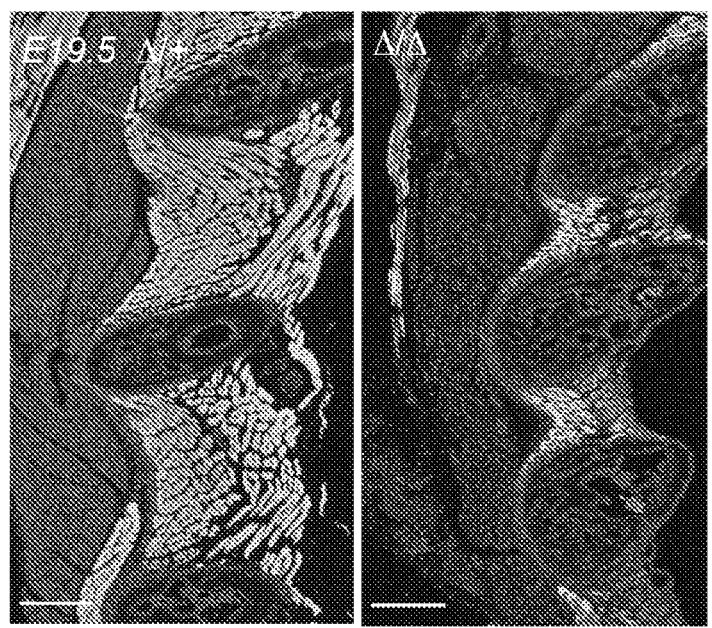
Figure 11A:
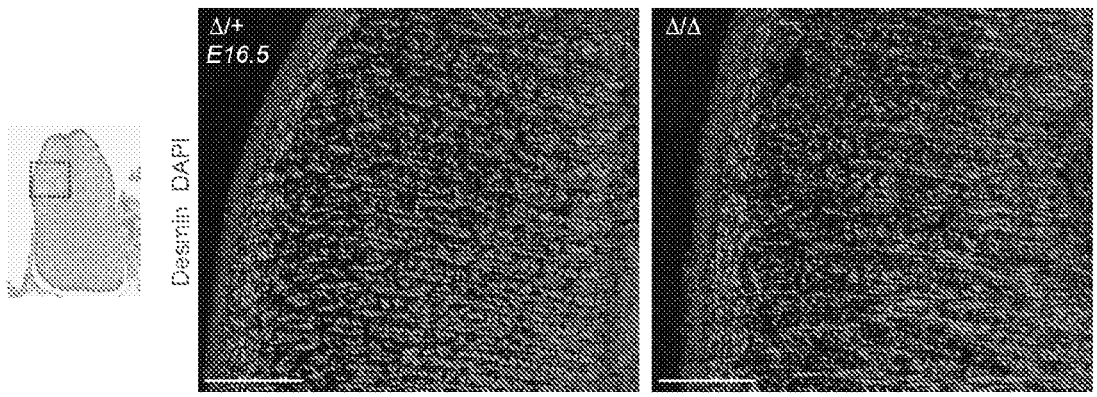
FIGS. 11A-11C show loss of MINION does not affect differentiation of skeletal muscle progenitors in vivo but blocks formation of multinucleated fibers.
Figure 11B:
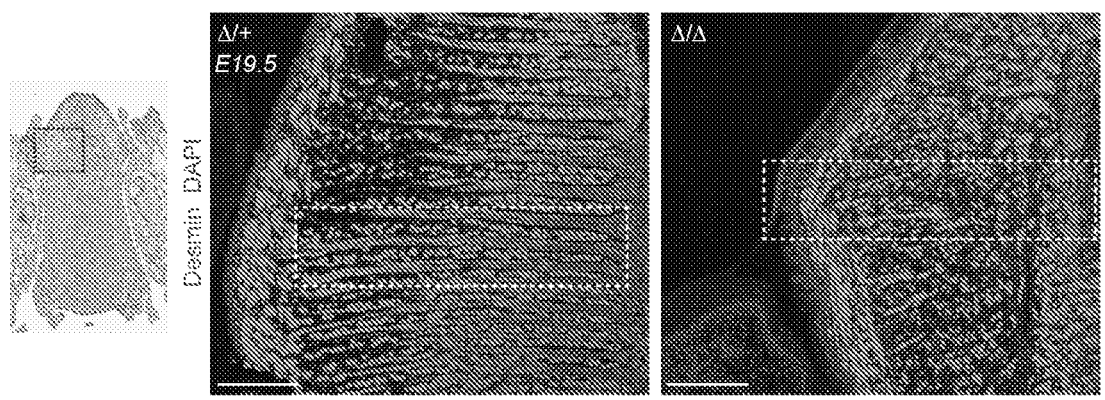
Figure 11C:
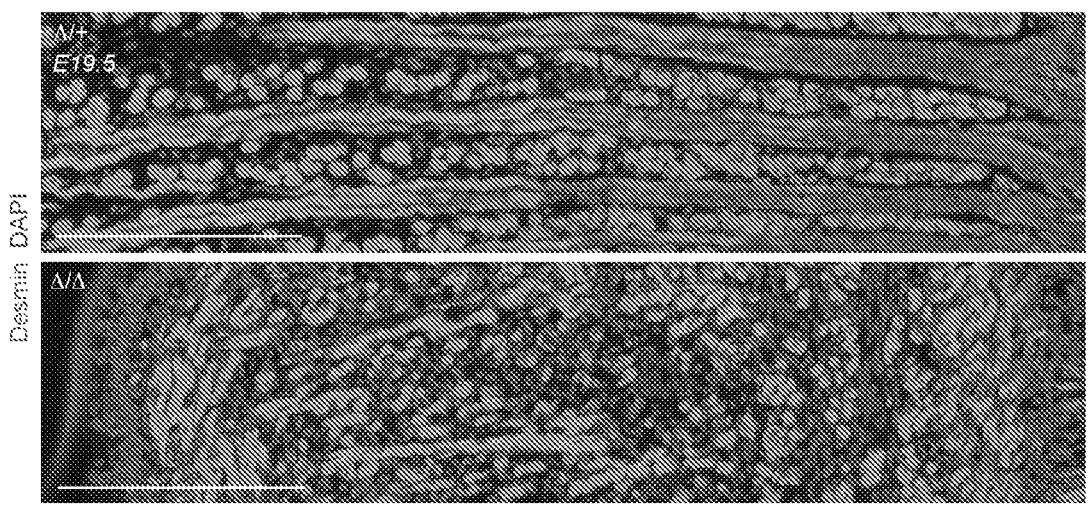

Late stage MINION$^{\Delta/\Delta}$ embryos were distinguishable by their decreased size and weight, reduced limb diameter, spinal curvature, and atony, as well as by characteristic dorsal and nuchal subcutaneous edema at earlier stages (FIGS. 8A-8C). Analysis of MINION$^{\Delta/\Delta}$ E17.5 embryos and P0 neonatal pups demonstrated diminutive appearance of the forelimb musculature (FIGS. 5D, 8B), and decreased total size of muscle groups, despite no obvious impairment at early embryonic stages (FIGS. 9A-9D). Clear abnormality in skeletal muscle formation was seen at E18.5-19.5 by both histology and immunofluorescence staining for muscle cell markers (MHC and Desmin); whereas control tongue skeletal muscle contained abundant elongated multinucleated myotubes, MINION$^{\Delta/\Delta}$ muscle demonstrated marked reduction in fused fibers, with accumulation of both short nascent fibers as well as unfused mononucleated cells (FIG. 2D, FIGS. 9A-9D). Similar defects were present in MINION$^{\Delta/\Delta}$ forelimb, diaphragm, and intercostal musculature (FIGS. 10A and 10B, FIG. 26, FIG. 5F, FIG. 9D, FIG. 10C), with the latter observation suggesting that MINION$^{\Delta/\Delta}$ perinatal lethality could reflect absence of respiratory function. Late stage fetuses were therefore delivered by cesarean section, exposed to room air, and monitored for 1 hour, after which lungs were dissected and subjected to flotation testing. E18.5 MINION$^{\Delta/\Delta}$ embryos demonstrated cardiac contraction and reflex reactions (data not shown), but died soon after exposure to air. In keeping with the dramatic decrease in diaphragm and intercostal muscle formation, lungs from MINION$^{\Delta/\Delta}$ but not control animals failed to float, indicating absence of lung inflation after birth (FIG. 5G) and likely perinatal lethality related to skeletal muscle insufficiency.

Cumulatively, these data suggest that MINION$^{\Delta/\Delta}$ embryos die at perinatal stages due to sequela of skeletal muscle insufficiency.

Example 4: The MINION Microprotein is Required for Fusion of Muscle Progenitors

Figure 13:
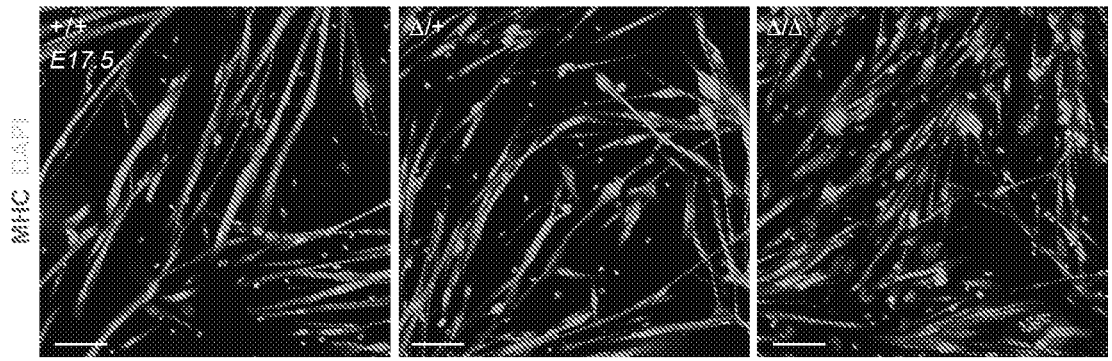
FIG. 13 is a set of MHC immunofluorescence images of E17.5 primary embryonic myoblasts of indicated genotypes following 3 days in differentiation medium, which shows genetic loss of MINION blocks embryonic myoblast fusion in vitro. Nuclei were counterstained with DAPI. Scale bar: 100 µm.
Figure 14A:
FIGS. 14A-14C show generation and validation of lentiviral shRNA constructs targeting mouse MINION.
Figure 14B:
Figure 14C:
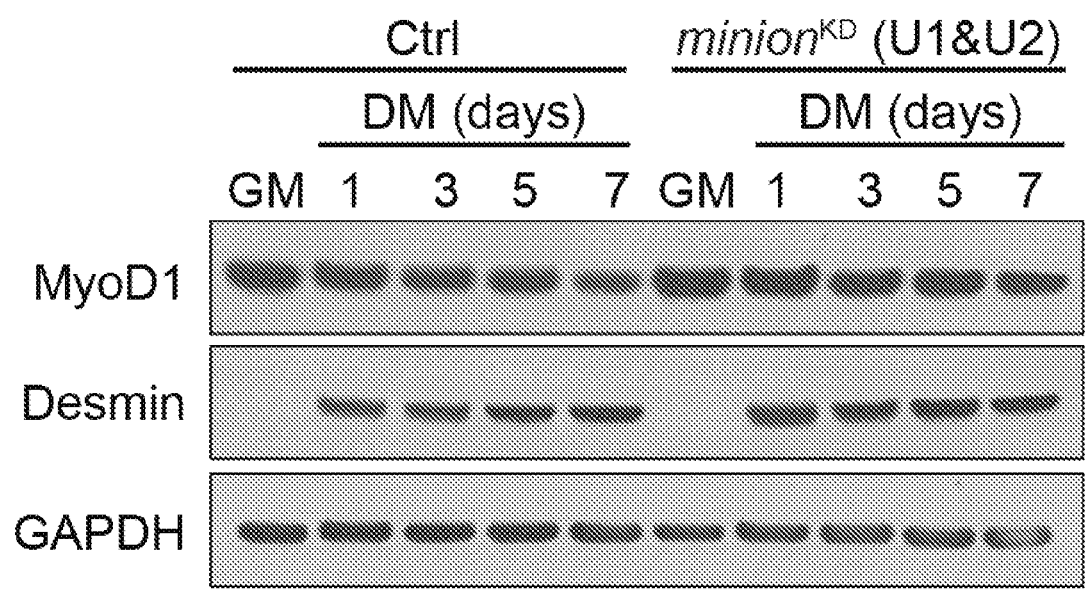
Figure 27A:
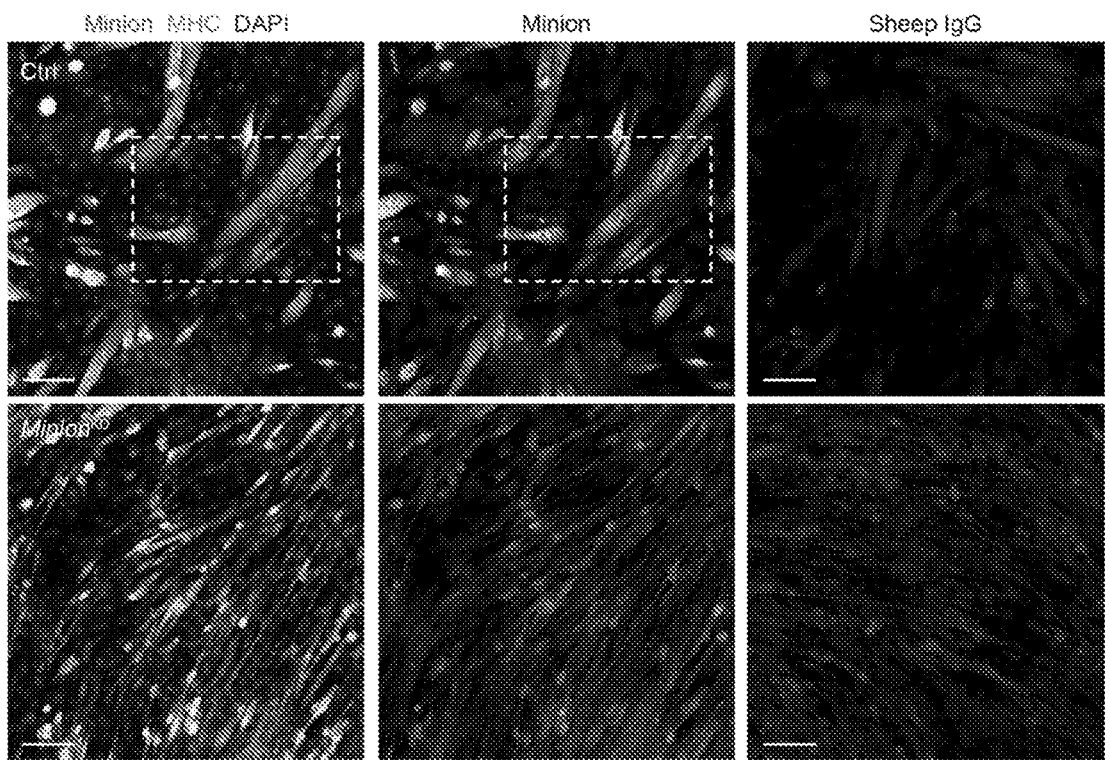
FIGS. 27A-27C show that Minion is expressed in differentiating myoblasts and nascent myotubes.
Figure 27B:
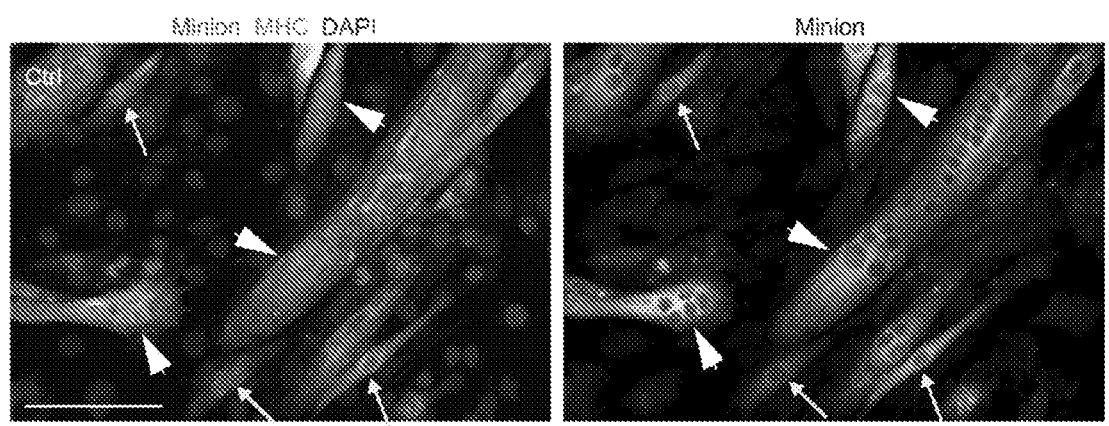
Figure 27C:
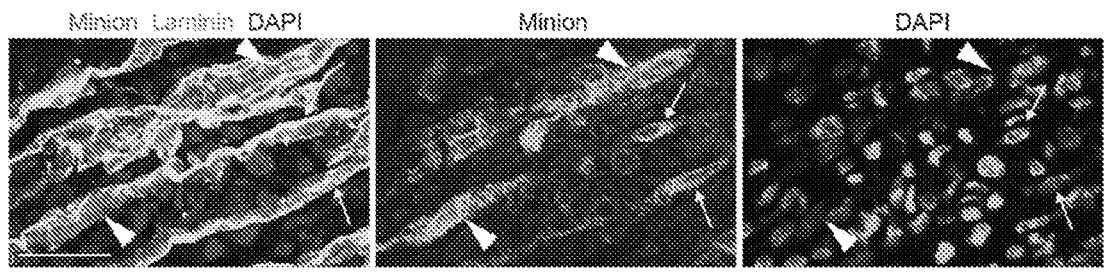

The absence of multinucleated myofibers in MINION$^{\Delta/\Delta}$ muscle suggests that MINION may be specifically required for myoblast fusion. Indeed, induction of differentiation and fusion in primary embryonic myoblasts derived from MINION$^{\Delta/\Delta}$ or control muscle demonstrated near complete failure to form multinucleated myotubes (≥3 nuclei) specifically in MINION-deficient cells (FIGS. 12A-12B, FIG. 13). Importantly, markers of myogenic commitment and terminal differentiation were induced normally in MINION$^{\Delta/\Delta}$ myoblasts both in vivo and in vitro (FIG. 6E, FIGS. 10A-10B, FIGS. 11A-11C, FIG. 13), suggesting that the muscle formation defect did not result from blocked progenitor differentiation per se. We further confirmed this using loss-of-function in immortalized mouse C2C12 myoblasts via stable lentiviral transduction with shRNAs targeting the MINION coding sequence and 3' untranslated region (UTR) (FIG. 14A). Near complete suppression of MINION expression was achieved using individual shRNAs (FIG. 14B), and a combination of the two most active shRNAs resulted in undetectable protein levels in differentiating cells (MINION$^{KD}$; FIG. 12C). Immunofluorescence staining of both wild type and Minion$^{KD}$ myoblasts demonstrated endogenous expression of Minion protein in both differentiating mononuclear myoblasts and nascent multinuclear myotubes (FIGS. 27A-27B). This expression pattern was further confirmed by immunofluorescence staining of longitudinal regenerating limb muscle sections at 3 days post cardiotoxin (CTX) injection (FIG. 27C). Analysis of Myogenin, MyoD, Desmin, and MHC expression confirmed both the absence of any molecular differentiation defect in MINION$^{KD}$ cells (FIGS. 12C, 12E, FIG. 14C), as well as the presence of a severe block to myoblast fusion (FIGS. 12D, 12F and 12G). Interestingly, MINION-deficient myoblasts elongated and aligned normally despite failing to fuse (FIG. 12D), suggesting that myoblast adhesion was not affected. Similar results were obtained using lentiviral shRNA transduction of primary, non-immortalized adult mouse myoblasts (FIGS. 15A-15D).

Figure 16A:
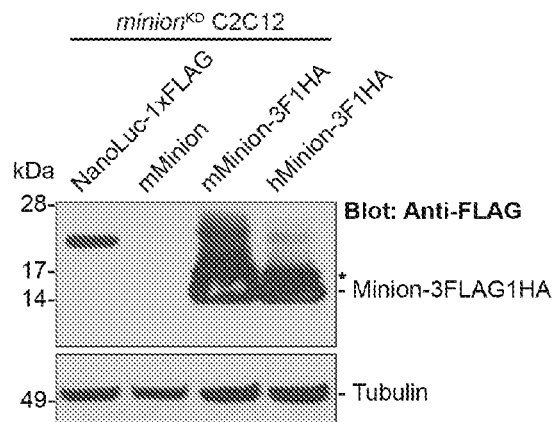
FIGS. 16A-16C show exogenous expression of mouse MINION or its human ortholog rescues the fusion defect of MINION$^{KD}$ myoblasts.
Figure 16B:
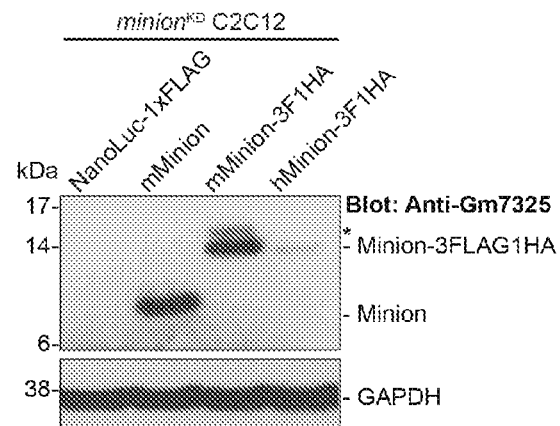
Figure 16C:
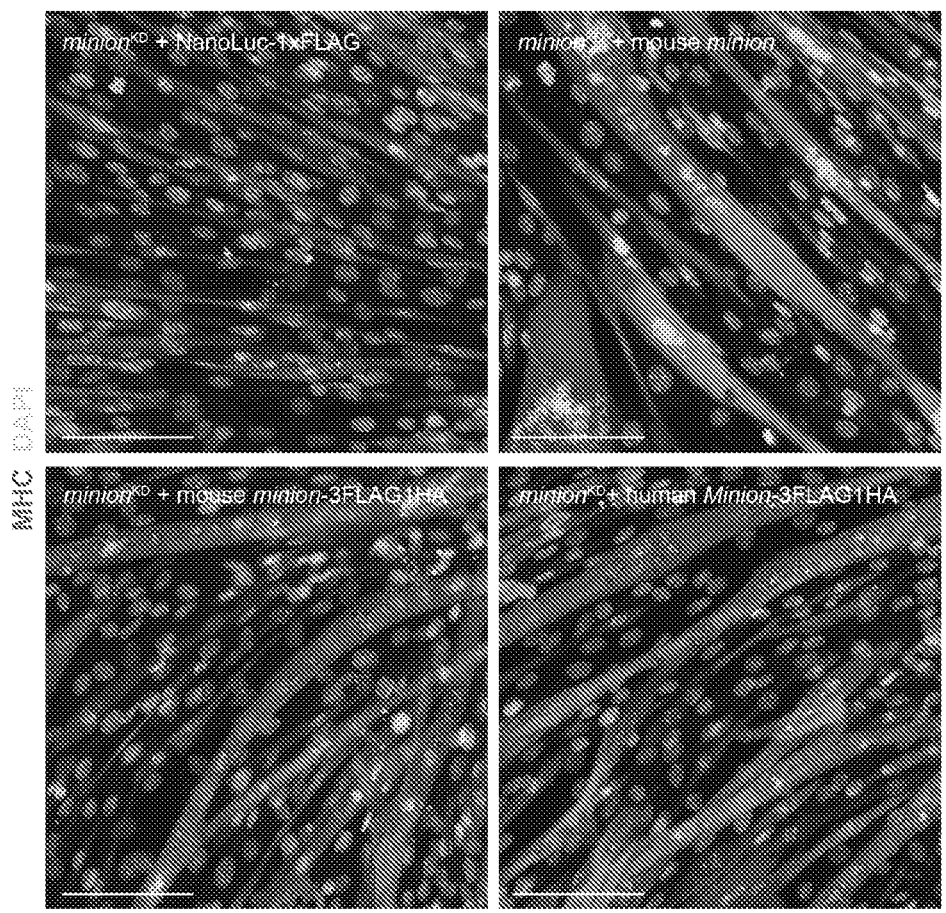
Figure 17A:
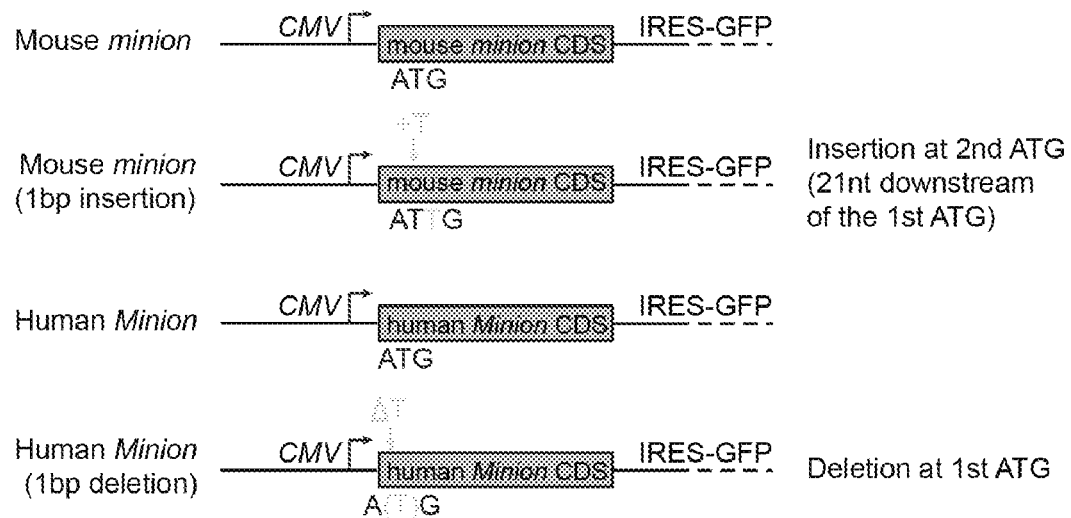
FIGS. 17A-17B show mouse and human MINION transcripts do not function as lncRNAs (long non-coding RNA).
Figure 17B:
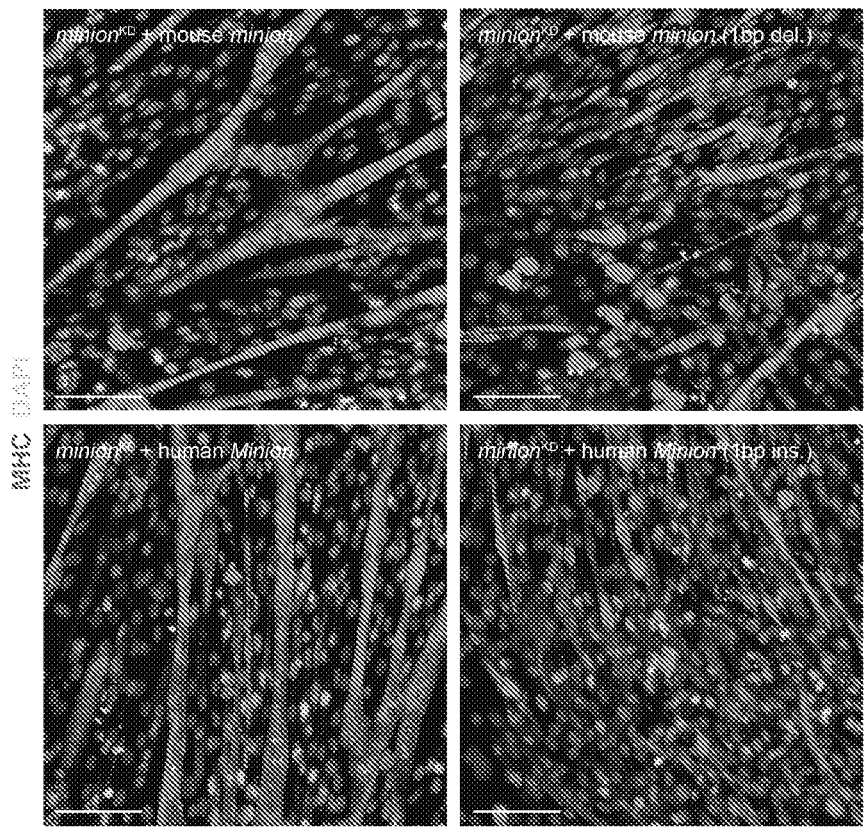
Figure 18:
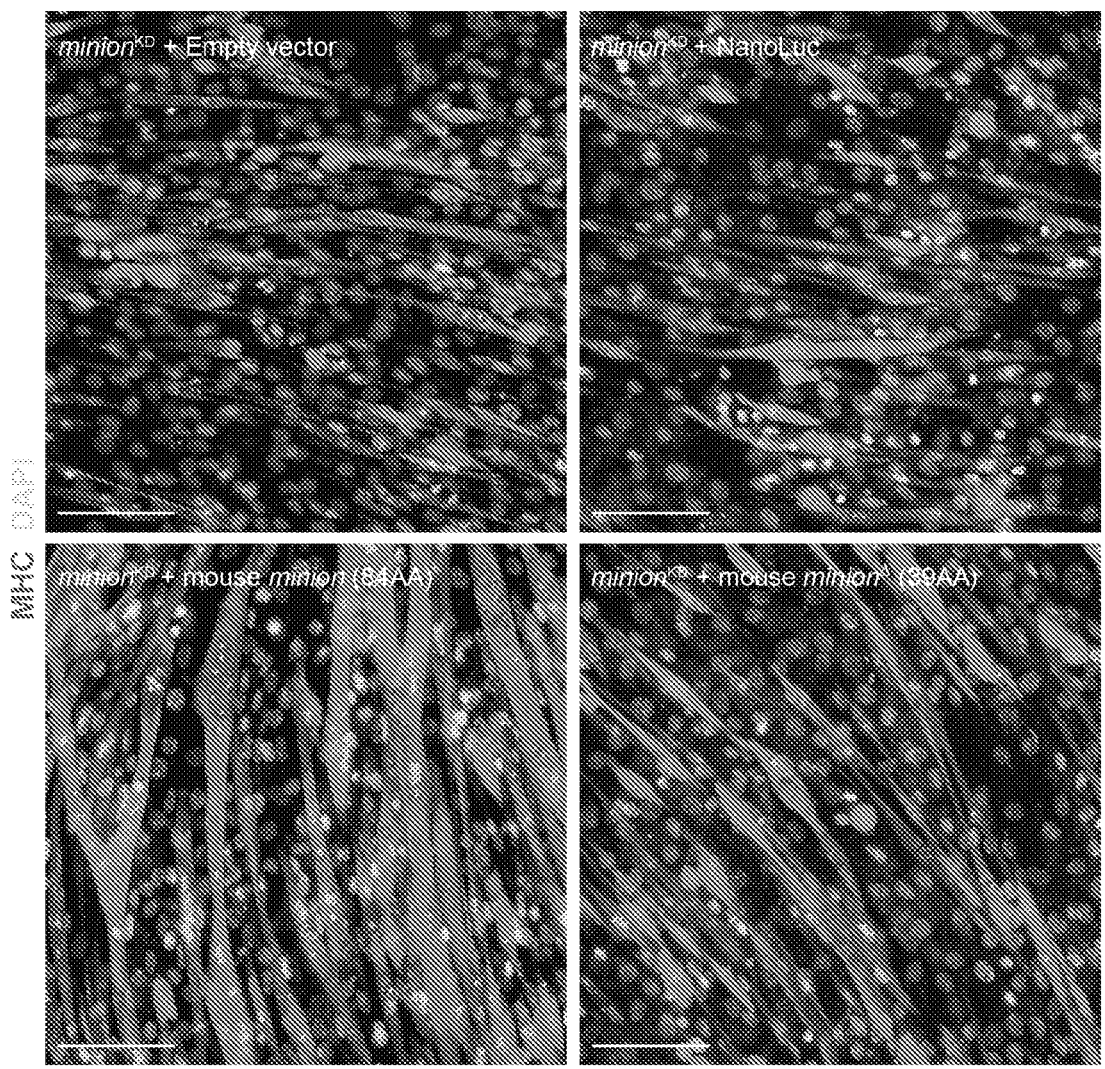
FIG. 18 is a set of MHC immunofluorescence images of MINION$^{KD}$ C2C12 cells transduced with retroviral constructs encoding either empty vector (negative control), NanoLuc (negative control), full-length mouse MINION, or the truncated 39AA MINION mutant (predicted from the MINION$^{\Delta}$ knockout allele containing the 135 bp in-frame deletion), showing the MINION$^{\Delta}$ truncation mutant predicted from the MINION$^{\Delta}$ knockout allele does not rescue the fusion defect observed in MINION$^{KD}$ C2C12 cells. Cells were cultured in differentiation medium for 5 days. Nuclei were counterstained with DAPI. Scale bars: 100 µm.

Since the shRNAs used to target MINION transcript recognize the 3' UTR, we tested the ability of various cDNAs to complement the MINION$^{KD}$ cell fusion defect (FIG. 16A-16B). Both full-length C-terminally tagged and untagged mouse MINION robustly rescued fusion (FIG. 16C), demonstrating that the cell fusion defect observed in MINION$^{KD}$ cells was not the result of off-target effects. The putative human Minion ortholog, previously annotated as a long noncoding RNA (GRCh37 genome assembly), was then tested in a similar complementation assay, demonstrating that both untagged and C-terminally epitope-tagged human Minion ORFs strongly reconstituted cell fusion in MINION$^{KD}$ cells (FIG. 12H, FIG. 16C). To definitively establish that these ORFs function via protein coding, single nucleotide insertion or deletion were introduced into the untagged mouse and human Minion cDNA, respectively. These frameshift point mutants failed to complement the fusion defect (FIGS. 17A and 17B), confirming that the transcripts function as microproteins and not as non-coding RNAs. Reconstitution of MINION$^{KD}$ cells with cDNA mimicking the 135 bp-deletion allele found in the MINION$^{\Delta/\Delta}$ mice likewise failed to rescue the fusion defect (FIG. 18), confirming that this represents a true loss-of-function allele.

Figure 19A:
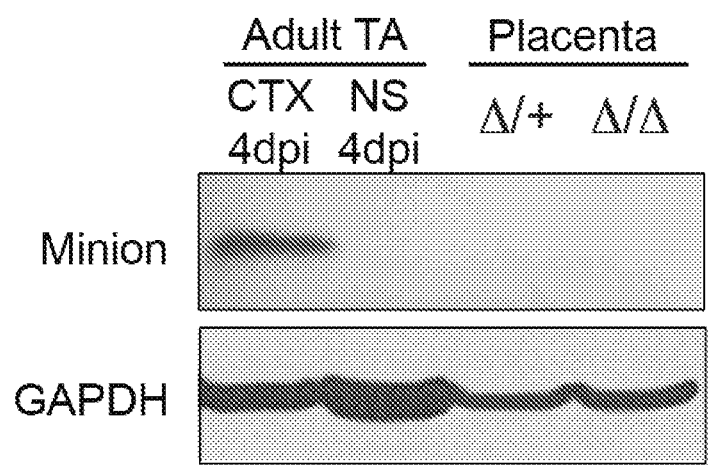
FIGS. 19A-19B show MINION is undetectable in two models of non-myogenic cell-cell fusion.
Figure 19B:
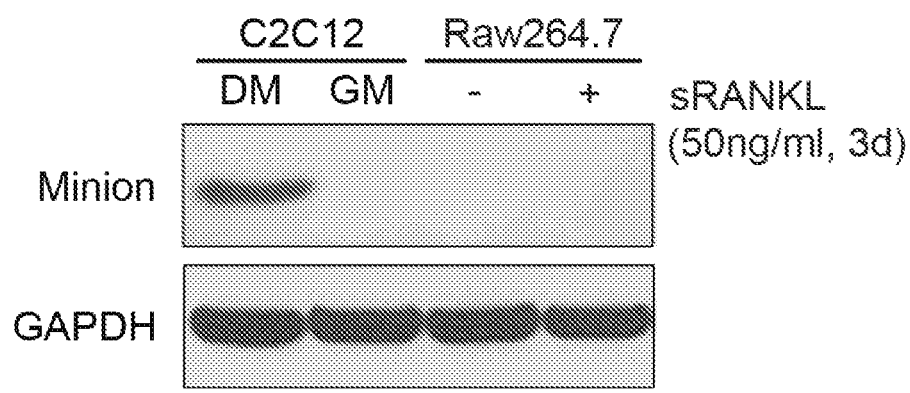

The above results demonstrate that MINION protein is required for cell fusion in developing muscle. Interestingly, this effect appears to be muscle-specific, as MINION expression was not detectable in other settings of physiologic cell fusion, such as the placenta or fusing macrophage lineage cells (FIGS. 19A-19B).

Example 5: Coexpression of MINION and Myomaker is Sufficient to Induce Cell Fusion in a Heterologous System To better understand the mechanism of MINION-associated cell fusion, and the functional relationship between MINION and Myomaker was investigated. Myomaker protein was readily detectable in regenerating muscle and differentiating mouse myoblasts (FIG. 20), when MINION levels are likewise high (FIGS. 1B & 1E).

Figure 28A:
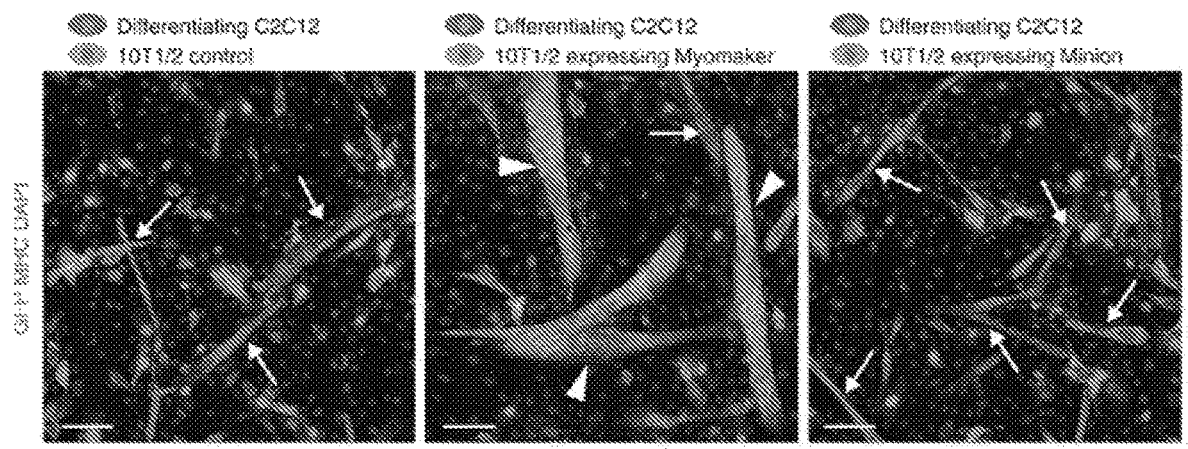
FIGS. 28A-28B show that Minion is required for Myomaker-mediated fusion.
Figure 28B:
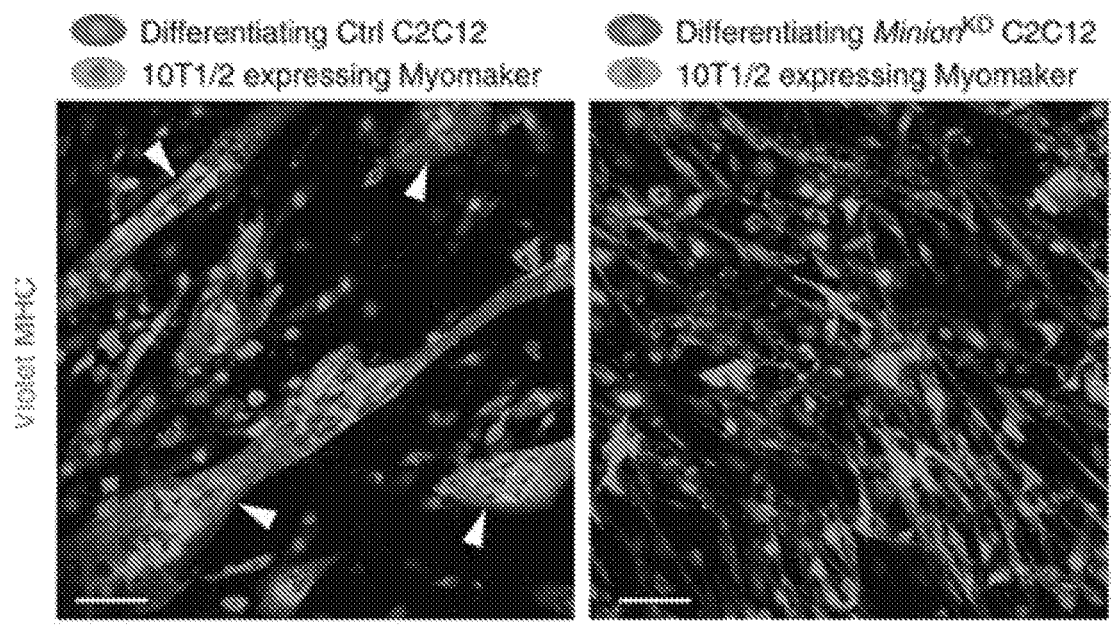

It was previously reported that Myomaker is sufficient to induce the fusion of fibroblasts to differentiating myoblasts (Anderson et al. Widespread control of calcium signaling by a family of SERCA-inhibiting micropeptides. *Sci. Signal.* 9, ra119, 2016), and we therefore examined whether Minion exhibited a similar phenotype when expressed in fibroblasts. C3H 10T1/2 fibroblasts were infected with retroviruses encoding GFP and either control, Myomaker or Minion; GFP-positive fibroblasts were then mixed with wild-type C2C12 myoblasts and kept in differentiation medium for 3-4 days. Differentiating myoblasts and myotubes were marked by MHC expression, and fusion of GFP-positive fibroblasts to myotubes was readily detected when Myomaker, but not Minion or control, was expressed (FIG. 28A). However, Myomaker-expressing fibroblasts failed to fuse to differentiating Minion$^{KD}$ myoblasts (FIG. 28B). Loss of MINION expression did not impair Myomaker expression in differentiating myoblasts (FIG. 21A), and myomaker overexpression was incapable of rescuing the fusion defect in MINION$^{KD}$ cells (FIGS. 21B-21C). Co-immunoprecipitation revealed no detectable physical interaction (data not shown).

Figure 22:
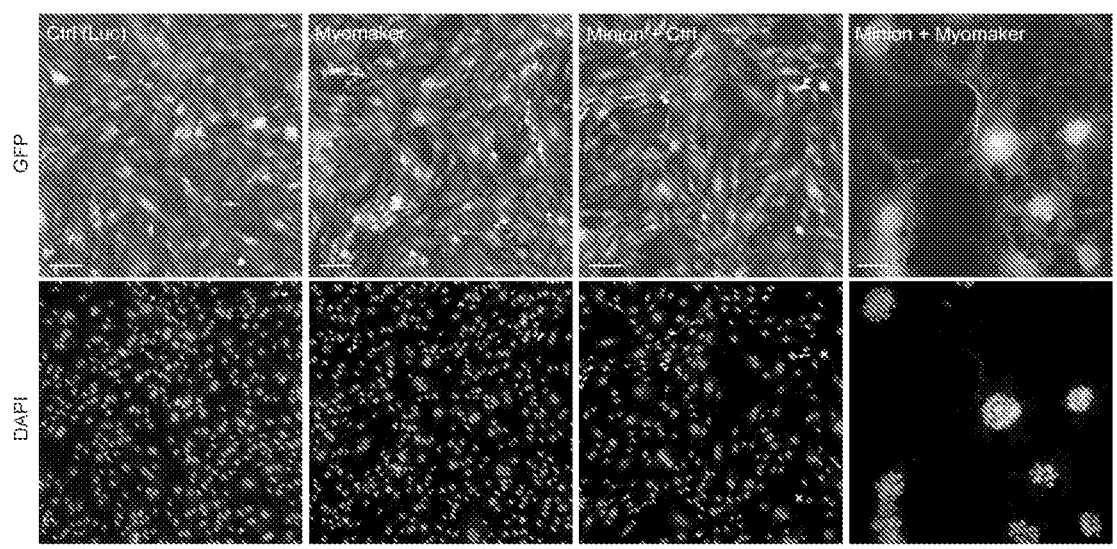
FIG. 22 is a set of immunofluorescent images of 10T1/2 fibroblasts infected with retroviral vectors encoding Luciferase, Myomaker, or MINION as indicated, showing MINION and Myomaker together are sufficient to induce multinuclear syncytia formation in 10T1/2 fibroblasts. All retroviral vectors contain IRES-GFP downstream of the gene of interest, causing infected cells to uniformly express GFP. Split-channel grayscale images for GFP and DNA are included. Quantification of the data was shown in FIG. 21E. Fusion index was calculated as the percentage of nuclei found within GFP-positive syncytia containing 4 or more nuclei. Scale bars: 100 µm.
Figure 23A:
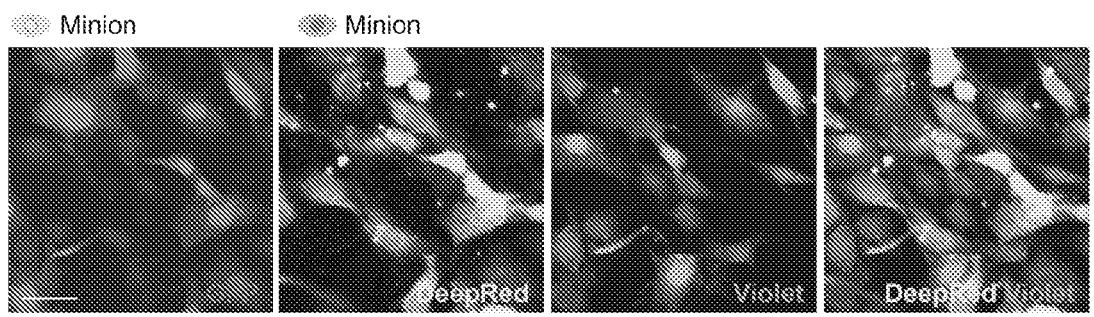
FIGS. 23A-23E are sets of split-channel fluorescence images of the cell mixing experiments described in FIG. 21F, showing MINION and Myomaker are sufficient to induce cell-cell fusion in fibroblasts, with MINION required only on one side of the fusion pair. Fluorescence images are shown from the cell mixing experiments using fibroblasts expressing the indicated combinations of proteins and labeled with either CellTrace Violet and CellTracker Deep Red dyes. 10T1/2 fibroblasts were serially infected with retroviruses encoding either MINION, myomaker or control vectors (omitted in the labeling for simplicity). All vectors contain IRES-GFP downstream of the gene of interest, causing infected cells to express GFP. Relevant cell color and proteins expressed are indicated above each image. The arrowheads indicate syncytia derived from Deep Red$^+$ cells co-expressing MINION and Myomaker that also contain Violet$^+$ nuclei from the second cell type expressing either Myomaker only, or MINION and Myomaker together. The arrows indicate syncytia derived from Deep Red$^+$ cells co-expressing MINION and Myomaker that do not contain Violet$^+$ nuclei from the second cell type expressing MINION only. Scale bars: 50 µm.
Figure 23B:
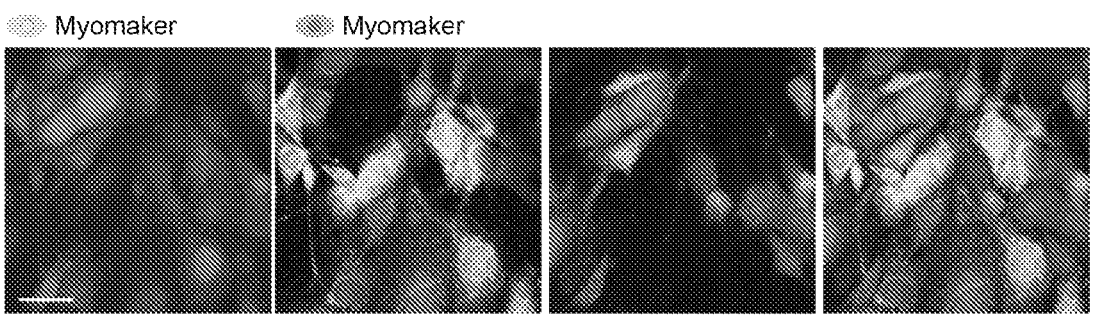
Figure 23C:
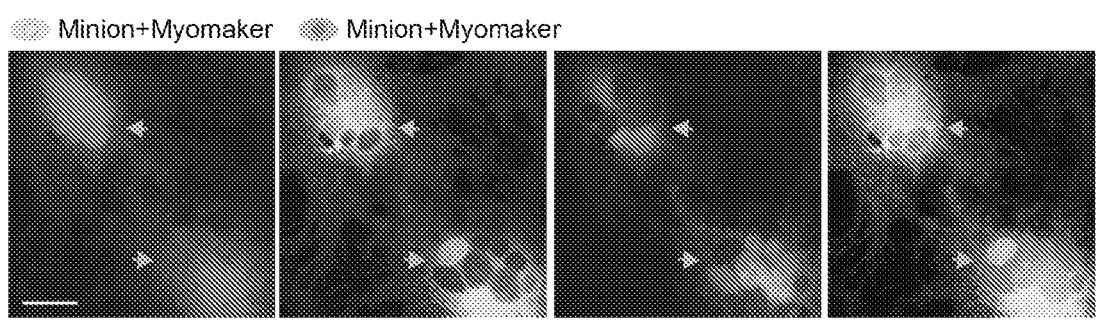
Figure 23D:
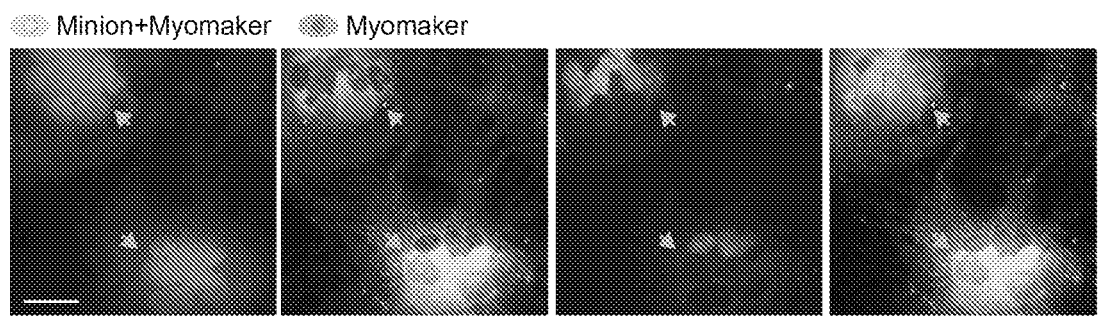
Figure 23E:
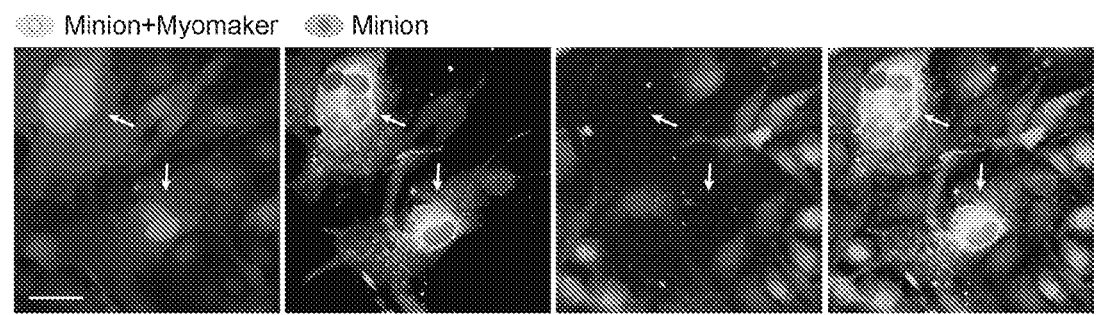

Previous studies have demonstrated that myomaker alone is incapable of inducing fusion between non-myogenic cells (Millay et al., *Nature* 499, 301, 2013). When expressed heterologously in 10T1/2 fibroblasts, neither Myomaker nor Minion alone (FIG. 21D) was sufficient to drive cell fusion between fibroblasts (FIG. 21F, FIG. 22, and data not shown). Remarkably, however, co-expression of MINION and Myomaker drove rapid and uniform fusion of transduced fibroblasts with one another to form large multinuclear syncytia (FIG. 21E and FIG. 22). Similar results were observed in myoblasts cultured under growth conditions (data not shown). Cell mixing experiments using cell populations expressing MINION and/or Myomaker and differentially labeled with fluorescent dyes demonstrated that this represented true cell fusion and not incomplete cytokinesis, and that cell fusion under these conditions requires MINION expression on only one side of the fusion pair, whereas Myomaker expression is required within both fusing cells (FIGS. 21F-21G, FIGS. 23A-23E).

Therefore, MINION is required for Myomaker to mediate cell fusion with differentiating myoblasts, and that MINION and Myomaker together represent a minimal program for induction of fusion in both muscle cells as well as non-fusogenic lineages such as non-muscle cells, e.g., fibroblasts.

Example 6: Minion-Induced Fusion Requires Cytoskeletal Remodelling

Figure 29A:
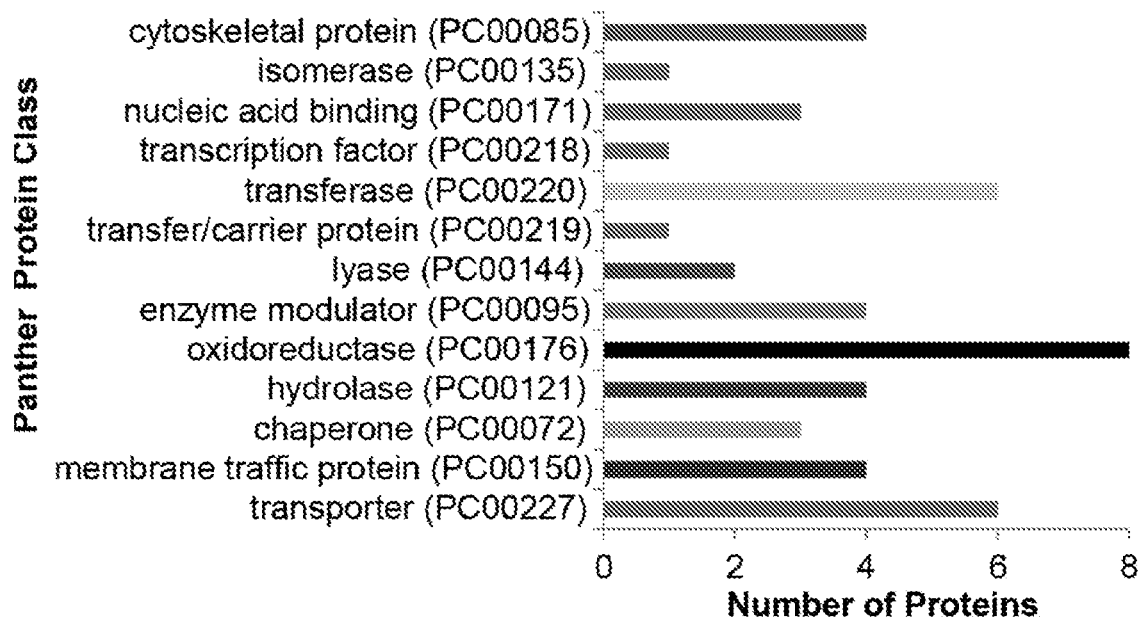
FIGS. 29A-29B show results for identification of Minion-interacting proteins.
Figure 29B:
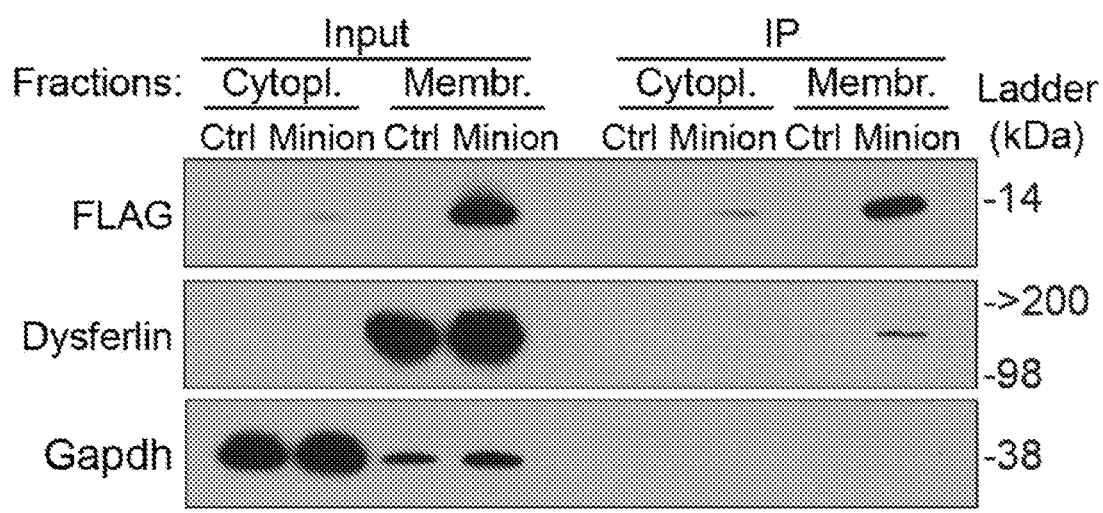
Figure 30A:
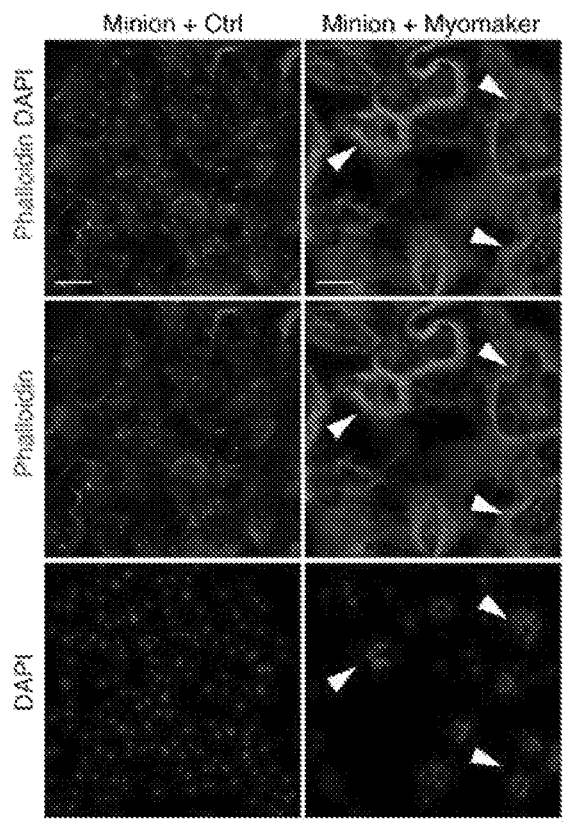
FIGS. 30A-30C show that Minion and Myomaker-induced fusion requires cytoskeleton reorganization.
Figure 30B:
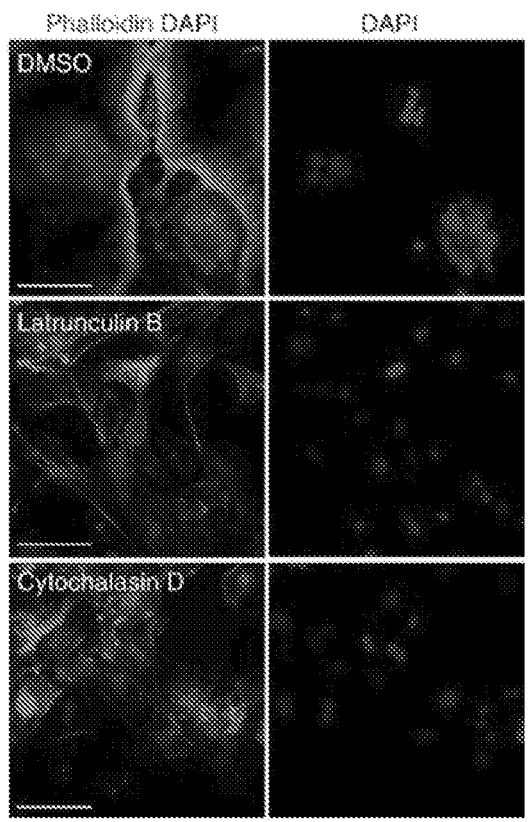
Figure 30C:
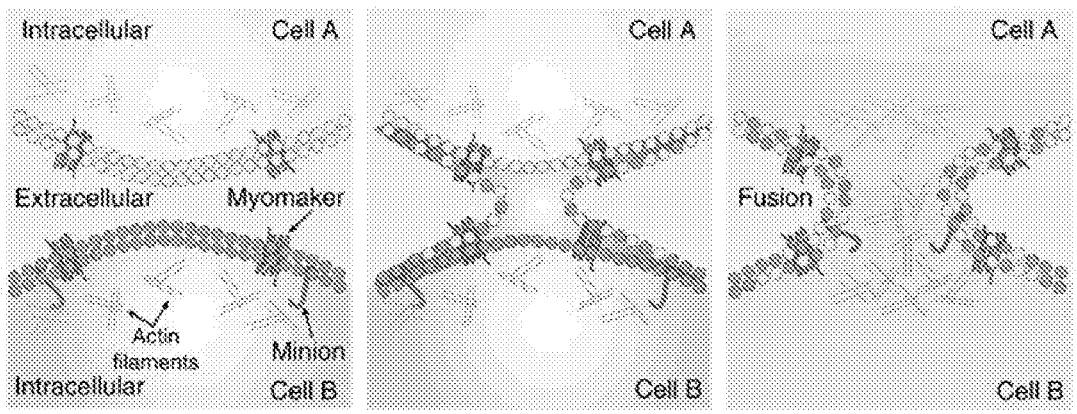

Mechanistically, the small size and lack of functional domains within microproteins has led to the suggestion that they function primarily via protein-protein interactions (Ma J. et al. Improved identification and analysis of small open reading frame encoded polypeptides. *Anal. Chem.* 88, 3967-3975, 2016). While the simplest model for Minion function is physical interaction with Myomaker, such a model would not explain the differences in loss of function phenotype (lack of alignment and presence of alignment, respectively). In fact, extensive attempts at co-immunoprecipitation using both tagged and untagged versions of Minion with endogenous and overexpressed Myomaker revealed no detectable physical interaction between the two proteins in differentiating muscle cells, as determined by western blot (data not shown). We therefore performed affinity purification followed by mass spectrometry (AP-MS) analysis using FLAG-tagged Minion expressed in differentiating myoblasts. Whereas Myomaker was again not recovered as a specific interacting protein, several classes of highly enriched interacting proteins were identified (FIGS. 29A-29B; Table 5), including cytoskeletal proteins. Indeed, we observed that multinuclear fibroblasts induced by co-expression of Minion and Myomaker exhibited dramatic cytoskeletal rearrangement, with formation of an actin wall at the cell periphery (Duan R. & Gallagher P. J. Dependence of myoblast fusion on a cortical actin wall and nonmuscle myosin IIA. Dev. Biol. 325, 374-385 2009) (FIG. 30A). Treatment with two different actin-polymerization inhibitors, which disrupt cytoskeleton remodelling, blocked both actin reorganization and cell fusion in this minimal two-factor system (FIG. 30B). We conclude that Minion is the previously unknown factor required for Myomaker to mediate fusion of cells into differentiating skeletal muscle, and that Minion and Myomaker can together function as a minimal programme for the induction of cytoskeletal rearrangements leading to fusion (FIG. 30C).

TABLE 5

Proteins significantly enriched in complex with Minion following affinity purification-mass spectrometry.

| Description | Accession Number | Molecular Weight | Fisher's Exact Test (p-value) *(p < 0.00414) | Number of Spectra | Unique Peptide | Sequence Coverage (%) |
| --- | --- | --- | --- | --- | --- | --- |
| Embryonic stem cell-and germ cell-specific protein ESGP OS = Mus musculus GN = Gm7325 PE = 2 SV = 1 | Q2Q5T5 | 9.6 kDa | <0.00010 | 33 | 3 | 50 |
| Dysferlin OS = Mus musculus GN = Dysf PE = 1 SV = 3 | DYSF_MOUSE | 238 kDa | <0.00010 | 23 | 17 | 13 |
| Aldehyde dehydrogenase family 3 member B1 OS = Mus musculus GN = Aldh3b1 PE = 2 SV = 1 | AL3B1_MOUSE | 52 kDa | <0.00010 | 58 | 15 | 46 |
| ATPase family AAA domain-containing protein 1 OS = Mus musculus GN = Atad1 PE = 1 SV = 1 | ATAD1_MOUSE | 41 kDa | <0.00010 | 15 | 7 | 30 |
| Signal recognition particle 68 kDa protein OS = Mus musculus GN = Srp68 PE = 2 SV = 2 | SRP68_MOUSE | 71 kDa | <0.00010 | 19 | 11 | 25 |
| Calsequestrin-2 OS = Mus musculus GN = Casq2 PE = 2 SV = 3 | CASQ2_MOUSE | 48 kDa | <0.00010 | 35 | 9 | 24 |
| Calcium uniporter protein, mitochondrial OS = Mus musculus GN = Mcu PE = 2 SV = 2 | MCU_MOUSE | 40 kDa | <0.00010 | 34 | 12 | 38 |
| Inositol 1,4,5-trisphosphate receptor type 3 OS = Mus musculus GN = Itpr3 PE = 1 SV = 3 | ITPR3_MOUSE | 304 kDa | 0.0027 | 14 | 11 | 6 |
| Synaptopodin 2-like protein OS = Mus musculus GN = Synpo2l PE = 2 SV = 1 | SYP2L_MOUSE | 103 kDa | 0.0024 | 9 | 5 | 8 |
| DnaJ homolog subfamily C member 16 OS = Mus musculus GN = Dnajc16 PE = 1 SV = 2 | DJC16_MOUSE | 89 kDa | 0.00032 | 12 | 9 | 19 |

TABLE 5-continued

Proteins significantly enriched in complex with Minion following affinity purification-mass spectrometry.

| Description | Accession Number | Molecular Weight | Fisher's Exact Test (p-value) *(p < 0.00414) | Number of Spectra | Unique Peptide | Sequence Coverage (%) |
|---|---|---|---|---|---|---|
| Syntaxin-8 OS = *Mus musculus* GN = Stx8 PE = 1 SV = 1 | STX8_MOUSE | 27 kDa | 0.00062 | 11 | 4 | 19 |
| NADH-ubiquinone oxidoreductase 75 kDa subunit, mitochondrial OS = *Mus musculus* GN = Ndufs1 PE = 1 SV = 2 | NDUS1_MOUSE | 80 kDa | 0.00010 | 19 | 9 | 20 |
| Adenylate kinase isoenzyme 4, mitochondrial OS = *Mus musculus* GN = Ak4 PE = 2 SV = 1 | KAD4_MOUSE | 25 kDa | 0.00010 | 15 | 6 | 52 |
| Sorbin and SH3 domain-containing protein 2 OS = *Mus musculus* GN = Sorbs2 PE = 1 SV = 2 | SRBS2_MOUSE | 132 kDa | 0.0024 | 9 | 6 | 7 |
| Vacuolar protein sorting-associated protein 45 OS = *Mus musculus* GN = Vps45 PE = 1 SV = 1 | VPS45_MOUSE | 65 kDa | 0.0012 | 10 | 7 | 15 |
| NADH dehydrogenase lubiquinonel flavoprotein 1, mitochondrial OS = *Mus musculus* GN = Ndufv1 PE = 1 SV = 1 | NDUV1_MOUSE | 51 kDa | 0.0022 | 12 | 7 | 24 |
| B-cell receptor-associated protein 31 OS = Mus musculus GN = Bcap31 PE = 1 SV = 3 | BAP31_MOUSE | 28 kDa | 0.00032 | 12 | 7 | 27 |
| NADH dehydrogenase [ubiquinone] 1 alpha subcomplex subunit 10, mitochondrial OS = *Mus musculus* GN = Ndufa10 PE = 1 SV = 1 | NDUAA_MOUSE | 41 kDa | 0.0040 | 12 | 7 | 24 |
| Cluster of Guanine nucleotide-binding [7] protein G(s) subunit alpha isoforms short OS = *Mus musculus* GN = Gnas PE = 1 SV = 1 (GNAS2_MOUSE) | GNAS2_MOUSE | 46 kDa | 0.00012 | 22 | 9 | 34 |
| Acetolactate synthase-like protein OS = *Mus musculus* GN = Ilvbl PE = 2 SV = 1 | ILVBL_MOUSE | 68 kDa | 0.0011 | 22 | 10 | 32 |
| Cytoskeleton-associated protein 5 OS = *Mus musculus* GN = Ckap5 PE = 2 SV = 1 | CKAP5_MOUSE | 226 kDa | 0.0038 | 23 | 13 | 8 |

TABLE 5-continued

Proteins significantly enriched in complex with Minion following affinity purification-mass spectrometry.

| Description | Accession Number | Molecular Weight | Fisher's Exact Test (p-value) *(p < 0.00414) | Number of Spectra | Unique Peptide | Sequence Coverage (%) |
|---|---|---|---|---|---|---|
| Voltage-dependent anion-selective channel protein 1 OS = *Mus musculus* GN = Vdac1 PE = 1 SV = 3 | VDAC1_MOUSE | 32 kDa | 0.00094 | 28 | 10 | 15 |
| Apolipoprotein O-like OS = *Mus musculus* GN = Apool PE = 2 SV = 1 | APOOL_MOUSE | 29 kDa | 0.0039 | 28 | 9 | 49 |
| Junctional sarcoplasmic reticulum protein 1 OS = *Mus musculus* GN = Jsrp1 PE = 1 SV = 2 | JSPR1_MOUSE | 36 kDa | 0.0023 | 31 | 8 | 53 |
| Tripartite motif-containing protein 72 OS = *Mus musculus* GN = Trim72 PE = 1 SV = 1 | TRI72_MOUSE | 53 kDa | 0.00048 | 40 | 16 | 55 |
| Cytochrome b-c1 complex subunit 1, mitochondrial OS = *Mus musculus* GN = Uqcrc1 PE = 1 SV = 2 | QCR1_MOUSE | 53 kDa | 0.0010 | 38 | 13 | 41 |
| Eukaryotic initiation factor 4A-II OS = *Mus musculus* GN = Eif4a2 PE = 2 SV = 2 | IF4A2_MOUSE | 46 kDa | 0.0023 | 45 | 9 | 53 |
| T-complex protein 1 subunit theta OS = *Mus musculus* GN = Cct8 PE = 1 SV = 3 | TCPQ_MOUSE | 60 kDa | <0.00010 | 57 | 22 | 48 |
| Isovaleryl-CoA dehydrogenase, mitochondrial OS = *Mus musculus* GN = Ivd PE = 1 SV = 1 | IVD_MOUSE | 46 kDa | 0.0012 | 50 | 16 | 49 |
| T-complex protein 1 subunit beta OS = *Mus musculus* GN = Cct2 PE = 1 SV = 4 | TCPB_MOUSE | 57 kDa | 0.00076 | 53 | 20 | 55 |
| Nascent polypeptide-associated complex subunit alpha, muscle-specific form OS = *Mus musculus* GN = Naca PE = 1 SV = 2 | NACAM_MOUSE | 220 kDa | 0.0031 | 50 | 23 | 18 |
| Coproporphyrinogen-III oxidase, mitochondrial OS = *Mus musculus* GN = Cpox PE = 1 SV = 2 | HEM6_MOUSE | 50 kDa | 0.0014 | 57 | 19 | 52 |
| T-complex protein 1 subunit alpha OS = *Mus musculus* GN = Tcp1 PE = 1 SV = 3 | TCPA_MOUSE | 60 kDa | 0.0035 | 65 | 20 | 52 |

TABLE 5-continued

Proteins significantly enriched in complex with Minion following affinity purification-mass spectrometry.

| Description | Accession Number | Molecular Weight | Fisher's Exact Test (p-value) *(p < 0.00414) | Number of Spectra | Unique Peptide | Sequence Coverage (%) |
|---|---|---|---|---|---|---|
| Very long-chain specific acyl-CoA dehydrogenase, mitochondrial OS = *Mus musculus* GN = Acadv1 PE = 1 SV = 3 | ACADV_MOUSE | 71 kDa | 0.0017 | 72 | 26 | 57 |
| Trifunctional enzyme subunit beta, mitochondrial OS = *Mus musculus* GN = Hadhb PE = 1 SV = 1 | ECHB_MOUSE | 51 kDa | <0.00010 | 93 | 22 | 68 |
| Trifunctional enzyme subunit alpha, mitochondrial OS = *Mus musculus* GN = Hadha PE = 1 SV = 1 | ECHA_MOUSE | 83 kDa | <0.00010 | 201 | 33 | 66 |
| ATP synthase subunit beta, mitochondrial OS = *Mus musculus* GN = Atp5b PE = 1 SV = 2 | ATPB_MOUSE | 56 kDa | <0.00010 | 231 | 26 | 77 |
| Cytoplasmic dynein 1 heavy chain 1 OS = *Mus musculus* GN = Dync1h1 PE = 1 SV = 2 | DYHC1_MOUSE | 532 kDa | <0.00010 | 444 | 157 | 46 |
| Cluster of Myc box-dependent-interacting protein 1 OS = *Mus musculus* GN = Bin1 PE = 1 SV = 1 (BIN1_MOUSE) | BIN1_MOUSE [3] | 64 kDa | 0.003 | 75 | 16 | 42 |

The data provided herein uncover an evolutionarily conserved pathway for cell fusion mediated by the microprotein MINION and the transmembrane protein Myomaker. Our studies revealed an unanticipated polarity within the fusion pair, in which both cells must express Myomaker but only one cell need express MINION in order to drive cell fusion. This suggests that vertebrate muscle formation has previously unrecognized similarities with invertebrates, in which fusion occurs between distinct populations of founder cells and fusion competent myoblasts (Chen, et al., Unveiling the mechanisms of cell-cell fusion. *Science* 308: 369, 2005). Based on this asymmetry, we propose a model for vertebrate muscle development, in which fusion involves the coordinated action of a transmembrane protein (Myomaker) which may induce apposition or adhesion of cell membranes, and a fusogenic protein, MINION, which may serve as the alpha-helical, hydrophobic fusion peptide to drive pore formation.

Beyond the implications for muscle biology, the current description of a defined two-component system opens the door to programmable and potentially targeted cell fusion, which may find a variety of therapeutic and research applications, including oncolytic fusion of cancer cells (see Nakamura et al., Antibody-targeted cell fusion. *Nature biotechnology* 22, 331, 2004), fusion of dendritic cells to cancer cells in immunotherapy (see Avigan, et al., Dendritic/tumor fusion cells as cancer vaccines. *Seminars in oncology* 39: 287, 2012), uses in regenerative medicine (see Dittmar, et al., Cell fusion in health and disease. Volume II: cell fusion in disease. Introduction. *Advances in experimental medicine and biology* 714: 1, 2011), and for heterokaryon-based studies of nuclear reprogramming (see Blau et al., Plasticity of the differentiated state. *Science* 230: 758, 1985). Finally and importantly, our studies constitute the first report, to our knowledge, of an essential mammalian microprotein-MINION. As such, they represent the strongest evidence to date that this class of small, little studied, and mostly bioinformatically silent proteins has critical and unexplored functions in vertebrate biology.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

The invention claimed is:

1. An expression vector comprising a nucleic acid encoding a polypeptide comprising an amino acid sequence selected from any of SEQ ID NO: 1, 3, 9, 11, 13, and 15, further comprising a second nucleic acid encoding a Myomaker polypeptide.

2. The vector of claim 1, wherein the nucleic acid comprises SEQ ID NO: 2 or SEQ ID NO: 4.

3. The vector of claim 1, wherein the second nucleic acid encodes a Myomaker polypeptide comprising an amino acid sequence selected from SEQ ID NO: 16, 18, 20, 22, 24, 26, 28, and 30.

4. The vector of claim 1, wherein the vector is selected from a plasmid, a cosmid, an RNA, and a viral vector.

5. The vector of claim 4, wherein the viral vector is based on any of the following viruses: adenovirus, adeno-associated virus, Herpes Simplex Virus (HSV), parvovirus, retrovirus, lentivirus, vaccinia virus, Sinbis virus, influenza virus, reovirus, Newcastle disease virus (NDV), measles virus, vesicular stomatitis virus (VSV), poliovirus, poxvirus, Seneca Valley virus, coxsackievirus, enterovirus, myxoma virus, or maraba virus.

6. A liposome comprising a polypeptide comprising an amino acid sequence selected from SEQ ID NO: 1, 3, 5, 7, 9, 11, 13, and 15, further comprising a Myomaker polypeptide.

7. The liposome of claim 6, wherein the Myomaker polypeptide comprises an amino acid sequence selected from SEQ ID NO: 16, 18, 20, 22, 24, 26, 28, and 30.

8. The liposome of claim 6, further comprising a therapeutic agent, wherein the therapeutic agent is encapsulated in the liposome.

9. The liposome of claim 8, wherein the therapeutic agent is selected from a nucleic acid, a protein, a low molecular weight compound, and a peptide nucleic acid.

10. A method of delivering a therapeutic agent to a cell, the method comprising contacting the liposome of claim 8 with the cell, wherein the liposome fuses with the cell and thereby delivers the therapeutic agent to the cell.

11. The method of claim 10, wherein the cell is a human cell.

12. The method of claim 10, wherein the cell is a tumor cell.

13. The method of claim 10, wherein the method is performed in vitro.

14. The method of claim 10, wherein the method is performed in vivo.

* * * * *

SEQUENCE LISTING

```
<160> NUMBER OF SEQ ID NOS: 108

<210> SEQ ID NO 1
<211> LENGTH: 84
<212> TYPE: PRT
<213> ORGANISM: Homo sapiens

<400> SEQUENCE: 1

Met Pro Thr Pro Leu Leu Pro Leu Leu Leu Arg Leu Leu Leu Ser Arg
1               5                   10                  15

Leu Leu Leu Pro Ala Ala Arg Leu Ala Arg Gln Tyr Leu Leu Pro Leu
                20                  25                  30

Leu Arg Arg Leu Ala Arg Arg Leu Gly Ser Gln Asp Met Arg Glu Ala
            35                  40                  45

Leu Leu Gly Cys Leu Leu Phe Ile Leu Ser Gln Arg His Ser Pro Asp
        50                  55                  60

Ala Gly Glu Ala Ser Arg Val Asp Arg Leu Glu Arg Arg Glu Arg Leu
65                  70                  75                  80

Gly Pro Gln Lys

<210> SEQ ID NO 2
<211> LENGTH: 817
<212> TYPE: DNA
<213> ORGANISM: Homo sapiens

<400> SEQUENCE: 2
gagactgatt ctgagcagca gttctgcccg gcactgactc actggccctg ccatgcccac      60
gccactgctc ccgctgctgc ttcgattgct gctgtcccgc ctgctgctgc ctgctgcccg     120
cctggcccgc caatacctcc tgccctgct gcgccgattg gccgccgcc tgggctccca     180 ggacatgcga gaggctttgc tgggctgtct gctgttcatt ctcagccagc gacactcgcc     240
agacgctggg gaggcctcaa gagtggaccg cctggagagg agggagaggt taggccccca     300
aaagtgaggc cacaagtcct ggcagcagct gtatccacaa aatgctttct tttggagtag     360
gataagactg gcaccagcac tgaccgaagc ctgcccagtg gacagaagat atagtgaggg     420
ttgtgcatga gagggatctg ccacagacat gcctctccac tcccaacaga aatgtctttc     480
tggaagaatg ccttgcatct agcacaaaac tgattattgc ccctctgtcc tccagcagtt     540
cctcccaaag accactccta atcacctctg gcctcaggcg ggaggggaac taacacccac     600
ccacccctgc cctccctgca aatgggaaca tcaaggttcc cagtgcttaa ctgagggaca     660
agtgacaatt tagcagagag gcaagatttg aatccagact gtcttccaga ctcaggacct     720
accttaaaat aatatctgag ttgcctatgg aggcagacct gcctgcaaag cccagcactc     780
agcaagtgct caataaatat ttgatttgaa ttctttc                              817
```

<210> SEQ ID NO 3
<211> LENGTH: 84
<212> TYPE: PRT
<213> ORGANISM: Homo sapiens

<400> SEQUENCE: 3

Met Pro Thr Pro Leu Leu Pro Leu Leu Leu Arg Leu Leu Leu Ser Cys
1               5                   10                  15

Leu Leu Leu Pro Ala Ala Arg Leu Ala Arg Gln Tyr Leu Leu Pro Leu
            20                  25                  30

Leu Arg Arg Leu Ala Arg Arg Leu Gly Ser Gln Asp Met Arg Glu Ala
        35                  40                  45

Leu Leu Gly Cys Leu Leu Phe Ile Leu Ser Gln Arg His Ser Pro Asp
    50                  55                  60

Ala Gly Glu Ala Ser Arg Val Asp Arg Leu Glu Arg Arg Glu Arg Leu
65                  70                  75                  80

Gly Pro Gln Lys

<210> SEQ ID NO 4
<211> LENGTH: 817
<212> TYPE: DNA
<213> ORGANISM: Homo sapiens

<400> SEQUENCE: 4
gagactgatt ctgagcagca gttctgcccg gcactgactc actggccctg ccatgcccac      60
gccactgctc ccgctgctgc ttcgattgct gctgtcctgc ctgctgctgc ctgctgcccg     120
cctggcccgc caatacctcc tgcccctgct gcgccgattg gcccgccgcc tgggctccca     180
ggacatgcga gaggctttgc tgggctgtct gctgttcatt ctcagccagc gacactcgcc     240
agacgctggg gaggcctcaa gagtggaccg cctggagagg agggagaggt taggccccca     300
aaagtgaggc cacaagtcct ggcagcagct gtatccacaa aatgctttct tttggagtag     360
gataatcctg gcaccagcac tgaccgaagc ctgcccagtg gacagaagat atagtgaggg     420
ttgtgcatga gagggatctg ccacagacat gcctctccac tcccaacaga aatgtctttc     480
tggaagaatg ccttgcatct agcacaaaac tgattattgc ccctctgtcc tccagcagtt     540
cctcccaaag accactccta atcacctctg gcctcaggcg ggaggggaac taacacccac     600 ccaccctgc cctccctgca atgggaaca tcaaggttcc cagtgcttaa ctgagggaca      660
agtgacaatt tagcagagag gcaagatttg aatccagact gtcttccaga ctcaggacct     720
accttaaaat aatatctgag ttgcttatgg aggcagacct gcctgcaaag cccagcactc     780
agcaagtgct caataaatat ttgatttgaa ttctttc                               817

<210> SEQ ID NO 5
<211> LENGTH: 84
<212> TYPE: PRT
<213> ORGANISM: Mus musculus

<400> SEQUENCE: 5

Met Pro Val Pro Leu Leu Pro Met Val Leu Arg Ser Leu Leu Ser Arg
1               5                   10                  15

Leu Leu Leu Pro Val Ala Arg Leu Ala Arg Gln His Leu Leu Pro Leu
            20                  25                  30

Leu Arg Arg Leu Ala Arg Arg Leu Ser Ser Gln Asp Met Arg Glu Ala
        35                  40                  45

```
Leu Leu Ser Cys Leu Leu Phe Val Leu Ser Gln Gln Gln Pro Pro Asp
     50                  55                  60
Ser Gly Glu Ala Ser Arg Val Asp His Ser Gln Arg Lys Glu Arg Leu
65                  70                  75                  80

Gly Pro Gln Lys

<210> SEQ ID NO 6
<211> LENGTH: 808
<212> TYPE: DNA
<213> ORGANISM: Mus musculus

<400> SEQUENCE: 6
gaaattgatt ctgagcagtt ctgactggtg agagctgcca ctggccggtt agaactggtg      60
agcaggaggg caagaagttc aggcttcagg tgcaggtcct gccatgcccg ttccattgct     120
cccgatggtg cttcgatcgc tgctgtcccg cctgctgctg cctgttgccc gcctggcccg     180
gcagcacctc ctgccttgc tgcgccggct ggcccgccga ctgagctccc aagacatgag     240
agaggctctg ctgagctgtc tgctctttgt cctcagccag caacagccac cggattctgg     300
agaggcctcc agagtggacc actcccagag gaaggagaga ttgggccccc agaagtgagg     360
ccacgggtcc tggaaacagc aacgcccatc aaagtacttt ggagccggt tagtccaggc     420 gtcggtccgc acgcacgggc atggacggca gactgcccag tgggcgaaga cagtccgggc     480
tgagtgcaag agggctctga cctgaacagt tcccactccc ctagtcccta gcaggctaca     540
gattgtgttg attgaccctt cctctctgca gctccctctg ccttatctct ggcctccagg     600
gtggacctgc aaatgcgggt atcaaggtca gttaagagat gatgtttcac ttagactcaa     660
gacaatttag ctaagaggtg gtatttaaat ccaaactgtc ccgtctacct taaaattata     720
agcccttgct tcccgttaaa gaatgagtac tttcaaagct tggtacgcag caggtagtca     780
ataaacgagg acagtgtgtt gttattgg                                        808

<210> SEQ ID NO 7
<211> LENGTH: 108
<212> TYPE: PRT
<213> ORGANISM: Mus musculus

<400> SEQUENCE: 7

Met Pro Glu Glu Ser Cys Thr Val Lys Leu Ile Gln Leu Lys Thr Gly
1               5                  10                  15
Glu Tyr Arg Gly Ala Gly Pro Ala Met Pro Val Pro Leu Leu Pro Met
             20                  25                  30
Val Leu Arg Ser Leu Leu Ser Arg Leu Leu Leu Pro Val Ala Arg Leu
         35                  40                  45
Ala Arg Gln His Leu Leu Pro Leu Leu Arg Arg Leu Ala Arg Arg Leu
     50                  55                  60
Ser Ser Gln Asp Met Arg Glu Ala Leu Leu Ser Cys Leu Leu Phe Val
65                  70                  75                  80
Leu Ser Gln Gln Gln Pro Pro Asp Ser Gly Glu Ala Ser Arg Val Asp
                 85                  90                  95
His Ser Gln Arg Lys Glu Arg Leu Gly Pro Gln Lys
            100                 105

<210> SEQ ID NO 8
<211> LENGTH: 852
<212> TYPE: DNA
<213> ORGANISM: Mus musculus
```

<400> SEQUENCE: 8

```
agtccccacc accttccagc cctgggctcc cttcccatct gtgataacag tgagtgaact    60
ccttaaccag ctttcatgcc agaagaaagc tgcactgtaa aactaatcca gttgaaaact   120
ggggagtaca gaggtgcagg tcctgccatg cccgttccat tgctcccgat ggtgcttcga   180
tcgctgctgt cccgcctgct gctgcctgtt gcccgcctgg cccggcagca cctcctgccc   240
ttgctgcgcc ggctggcccg ccgactgagc tcccaagaca tgagagaggc tctgctgagc   300
tgtctgctct ttgtcctcag ccagcaacag ccaccggatt ctggagaggc ctccagagtg   360
gaccactccc agaggaagga gagattgggc cccagaagt gaggccacgg gtcctggaaa    420
cagcaacgcc catcaaagta cttttggagc cggttagtcc aggcgtcggt ccgcacgcac   480
gggcatggac ggcagactgc ccagtgggcg aagacagtcc gggctgagtg caagagggct   540
ctgacctgaa cagttcccac tcccctagct cctagcaggc tacagattgt gttgattgac   600
ccttcctctc tgcagctccc tctgccttat ctctggcctc cagggtggac ctgcaaatgc   660
gggtatcaag gtcagttaag agatgatgtt tcacttagac tcaagacaat ttagctaaga   720
ggtggtattt aaatccaaac tgtcccgtct accttaaaat tataagccct tgcttcccgt   780
taaagaatga gtactttcaa agcttggtac gcagcaggta gtcaataaac gaggacagtg   840
tgttgttatt gg                                                      852
```

<210> SEQ ID NO 9
<211> LENGTH: 84
<212> TYPE: PRT
<213> ORGANISM: Rattus norvegicus

<400> SEQUENCE: 9

```
Met Pro Val Pro Leu Leu Pro Leu Met Leu Arg Ser Leu Leu Ser Arg
1               5                   10                  15
Leu Leu Leu Pro Val Ala Arg Leu Ala Arg Gln His Leu Leu Pro Leu
            20                  25                  30
Leu Arg Arg Leu Ala Arg Arg Leu Ser Ser Gln Asp Val Arg Glu Ala
        35                  40                  45
Leu Leu Ser Cys Leu Leu Phe Val Leu Ser Gln Gln Gln Pro Pro Asp
    50                  55                  60
Ser Gly Glu Thr Ser Arg Val Asp His Ser Gln Arg Lys Glu Arg Leu
65                  70                  75                  80
Gly Pro Arg Lys
```

<210> SEQ ID NO 10
<211> LENGTH: 270
<212> TYPE: DNA
<213> ORGANISM: Rattus norvegicus

<400> SEQUENCE: 10

```
ggtcctggtc ctgccatgcc cgttccactg ctcccgttga tgcttcgatc gctgctatca    60
cgcctgctgc tgcctgttgc ccgcctggcc cgtcagcacc tctgcccctt gctgcgccgt   120
ctggcccgcc gactgagctc ccaagacgtg agagaggctt tgctgagctg tctgctgttt   180
gtcctcagcc aacaacagcc accggattct ggagagacct agagtggac cactcccag    240
aggaaggaga gattgggtcc ccggaagtga                                   270
```

<210> SEQ ID NO 11
<211> LENGTH: 84
<212> TYPE: PRT

<213> ORGANISM: Felis catus

<400> SEQUENCE: 11

```
Met Pro Ala Pro Leu Leu Pro Leu Leu Leu Arg Thr Leu Met Ser Arg
1               5                   10                  15

Leu Leu Leu Pro Ala Thr Arg Leu Ala Arg Arg His Leu Leu Pro Leu
            20                  25                  30

Leu Arg Arg Leu Ala Arg Arg Leu Gly Ser Gln Asp Val Arg Glu Ala
        35                  40                  45

Leu Leu Gly Cys Leu Leu Phe Ile Leu Ser Gln Ser Arg Pro Pro Asp
    50                  55                  60

Ala Glu Glu Val Ser Arg Val Ala Gly Gln Arg Arg Glu Arg Leu
65                  70                  75                  80

Ala Pro Pro Lys
```

<210> SEQ ID NO 12
<211> LENGTH: 255
<212> TYPE: DNA
<213> ORGANISM: Felis catus

<400> SEQUENCE: 12

```
atgcccgctc cactgctccc actgctgctt cgaaccctga tgtcccgctt gctgctgcct      60
gccacccgcc tggcccgccg gcacctcctg cccctcctgc gccgactggc ccgccgcctg     120
ggctcgcagg atgttcgaga agctttgctg ggctgtctgt tgttcatcct cagccagagc     180
cgcccgcccg acgctgagga ggtctccaga gtggctggcc aggagaggag ggagaggcta     240
gctcccccaa aatga                                                     255
```

<210> SEQ ID NO 13
<211> LENGTH: 88
<212> TYPE: PRT
<213> ORGANISM: Sus scrofa

<400> SEQUENCE: 13

```
Met Pro Ala Pro Leu Leu Pro Leu Leu Leu Arg Thr Leu Leu Ala Arg
1               5                   10                  15

Leu Leu Leu Pro Ala Ala Arg Leu Ala Arg Arg His Leu Leu Pro Leu
            20                  25                  30

Leu Arg Arg Leu Ala Arg Arg Leu Gly Ser Gln Asp Met Arg Glu Ala
        35                  40                  45

Leu Leu Gly Cys Leu Val Phe Leu Leu Ser Gln Arg His Pro Pro Asp
    50                  55                  60

Asp Ala Ala Ala Gly Glu Ala Ser Arg Val Ala Arg Leu Glu Arg
65                  70                  75                  80

Arg Glu Arg Ile Val Ser Gln Lys
                85
```

<210> SEQ ID NO 14
<211> LENGTH: 264
<212> TYPE: DNA
<213> ORGANISM: Sus scrofa

<400> SEQUENCE: 14

```
atgcccgctc cgctgctccc gctgctgctg cgaacgctgc tggcccgcct gctgctgccc      60 gctgccgcc tggcccgtcg gcacctcctg cctctgctgc gccggctggc ccgccgcctg      120
ggctcccagg atatgcgaga ggctttactg ggctgtctgg tgttcctcct cagccagaga     180
```

```
cacccgccag atgatgccgc tgctgccggg gaggcctcca gagtggcccg cctggagagg    240
agggagagga tagtttctca aaaa                                           264
```

<210> SEQ ID NO 15
<211> LENGTH: 84
<212> TYPE: PRT
<213> ORGANISM: Macaca mulatta

<400> SEQUENCE: 15

```
Met Pro Ala Pro Leu Phe Pro Leu Leu Leu Arg Leu Leu Leu Ser Arg
1               5                   10                  15

Leu Leu Leu Pro Val Ala Arg Leu Ala Arg Gln Tyr Leu Leu Pro Leu
                20                  25                  30

Leu Arg Arg Leu Ala Arg Arg Leu Gly Ser Gln Asp Met Arg Glu Ala
            35                  40                  45

Leu Leu Gly Cys Leu Leu Phe Ile Leu Ser Gln His Ser Pro Asp
        50                  55                  60

Ala Gly Glu Ala Ser Arg Val Asp Arg Leu Glu Arg Arg Glu Arg Leu
65                  70                  75                  80

Gly Pro Gln Lys
```

<210> SEQ ID NO 16
<211> LENGTH: 221
<212> TYPE: PRT
<213> ORGANISM: Homo sapiens

<400> SEQUENCE: 16

```
Met Gly Thr Leu Val Ala Lys Leu Leu Pro Thr Leu Ser Ser Leu
1               5                   10                  15

Ala Phe Leu Pro Thr Val Ser Ile Ala Ala Lys Arg Arg Phe His Met
                20                  25                  30

Glu Ala Met Val Tyr Leu Phe Thr Leu Phe Phe Val Ala Leu His His
            35                  40                  45

Ala Cys Asn Gly Pro Gly Leu Ser Val Leu Cys Phe Met Arg His Asp
        50                  55                  60

Ile Leu Glu Tyr Phe Ser Val Tyr Gly Thr Ala Leu Ser Met Trp Val
65                  70                  75                  80

Ser Leu Met Ala Leu Ala Asp Phe Asp Glu Pro Lys Arg Ser Thr Phe
                85                  90                  95

Val Met Phe Gly Val Leu Thr Ile Ala Val Arg Ile Tyr His Asp Arg
            100                 105                 110

Trp Gly Tyr Gly Val Tyr Ser Gly Pro Ile Gly Thr Ala Ile Leu Ile
        115                 120                 125

Ile Ala Ala Lys Trp Leu Gln Lys Met Lys Lys Lys Gly Leu Tyr
130                 135                 140

Pro Asp Lys Ser Val Tyr Thr Gln Gln Ile Gly Pro Gly Leu Cys Phe
145                 150                 155                 160

Gly Ala Leu Ala Leu Met Leu Arg Phe Phe Glu Asp Trp Asp Tyr
                165                 170                 175

Thr Tyr Val His Ser Phe Tyr His Cys Ala Leu Ala Met Ser Phe Val
            180                 185                 190

Leu Leu Leu Pro Lys Val Asn Lys Lys Ala Gly Ser Pro Gly Thr Pro
        195                 200                 205

Ala Lys Leu Asp Cys Ser Thr Leu Cys Cys Ala Cys Val
210                 215                 220
```

<210> SEQ ID NO 17
<211> LENGTH: 818
<212> TYPE: DNA
<213> ORGANISM: Homo sapiens

<400> SEQUENCE: 17

```
gccctgccca aagggagctg gccttcccac ttcgtgctcc tgtgctgggg acctgggaca      60
ccagcaccct ccccacccca gccagtgctt tcctcctggc ccatggggac gctggtggcc     120
aagctgctcc tgcccaccct cagcagcctg gccttcctcc ccactgtcag catcgcggcc     180
aagaggcggt tccacatgga ggccatggtc tacctcttca ccctgttctt cgtggcgctc     240
caccatgcct gcaatggacc cggcttgtct gtgctgtgct tcatgcgtca cgacatcctg     300
gagtatttca gtgtctacgg gacagccctg agcatgtggg tctcgctgat ggcactggcc     360
gacttcgacg aacccaagag gtcaacattt gtgatgttcg gcgtcctgac cattgctgtg     420
cggatctacc atgaccgatg gggctacggg gtgtactcgg gccccatcgg cacagccatc     480
ctcatcatcg cggcaaagtg gctacagaag atgaaggaga agaagggcct gtacccagac     540
aagagcgtct acacccagca gataggcccc ggcctctgct cggggcgct ggccctgatg     600
ctacgcttct tctttgagga ctgggactac acttatgtcc acagcttcta ccactgtgcc     660
ctggctatgt cctttgttct gctgctgccc aaggtcaaca agaaggctgg atccccgggg     720
accccggcca agctggactg ctccacccct gctgtgctt tgtctgatg ctgcgcccag      780
cccggctctg agcccctgcc ctccccagct cacacttg                            818
```

<210> SEQ ID NO 18
<211> LENGTH: 221
<212> TYPE: PRT
<213> ORGANISM: Mus musculus

<400> SEQUENCE: 18

```
Met Gly Thr Val Val Ala Lys Leu Leu Pro Thr Leu Ser Ser Leu
1               5                   10                  15

Ala Phe Leu Pro Thr Val Ser Ile Ala Thr Lys Arg Arg Phe Tyr Met
            20                  25                  30

Glu Ala Met Val Tyr Leu Phe Thr Met Phe Val Ala Phe Ser His
            35                  40                  45

Ala Cys Asp Gly Pro Gly Leu Ser Val Leu Cys Phe Met Arg Arg Asp
        50                  55                  60

Ile Leu Glu Tyr Phe Ser Ile Tyr Gly Thr Ala Leu Ser Met Trp Val
65                  70                  75                  80

Ser Leu Met Ala Leu Ala Asp Phe Asp Glu Pro Gln Arg Ser Thr Phe
                85                  90                  95

Thr Met Leu Gly Val Leu Thr Ile Ala Val Arg Thr Phe His Asp Arg
            100                 105                 110

Trp Gly Tyr Gly Val Tyr Ser Gly Pro Ile Gly Thr Ala Thr Leu Ile
        115                 120                 125

Ile Ala Val Lys Trp Leu Lys Lys Met Lys Glu Lys Lys Gly Leu Tyr
    130                 135                 140

Pro Asp Lys Ser Ile Tyr Thr Gln Gln Ile Gly Pro Gly Leu Cys Phe
145                 150                 155                 160

Gly Ala Leu Ala Leu Met Leu Arg Phe Phe Glu Glu Trp Asp Tyr
                165                 170                 175

Thr Tyr Val His Ser Phe Tyr His Cys Ala Leu Ala Met Ser Phe Val
            180                 185                 190
```

Leu Leu Leu Pro Lys Val Asn Lys Lys Ala Gly Asn Ala Gly Ala Pro
        195                 200                 205

Ala Lys Leu Thr Phe Ser Thr Leu Cys Cys Thr Cys Val
    210                 215                 220

<210> SEQ ID NO 19
<211> LENGTH: 1401
<212> TYPE: DNA
<213> ORGANISM: Mus musculus

<400> SEQUENCE: 19

| | | | | | |
|---|---|---|---|---|---|
| gagcacttaa | gccctccttg | tgggtgctgc | cacagctgcg | gtcagggctg | ctggagaagc | 60 |
| aaagaagtgg | gctcttttc | ttcctgccct | ggagaccagg | ggggccttta | ccaccttctc | 120 |
| cccagtcagt | gccttcctcc | tggtccatgg | ggacagttgt | agccaaactg | ctcctgccta | 180 |
| ccctcagcag | cctggccttc | ctcccgacag | tgagcatcgc | taccaagagg | cgtttctaca | 240 |
| tggaggccat | ggtctacctc | ttcaccatgt | tctttgtggc | gttctcccat | gcctgtgatg | 300 |
| ggcctggttt | gtctgtgctg | tgcttcatgc | gccgtgacat | tctggagtac | ttcagcatct | 360 |
| atggaacagc | cctgagcatg | tgggtctccc | tgatggcact | ggccgacttt | gatgaacccc | 420 |
| agagatcgac | cttcacaatg | cttggcgtcc | ttaccatcgc | tgtgcggact | tttcatgacc | 480 |
| gctgggggtta | cggggtatac | tccggtccca | taggcacggc | caccctcatc | attgctgtaa | 540 |
| agtggctgaa | gaagatgaaa | gagaagaagg | gcctgtaccc | cgacaagagc | atctacaccc | 600 |
| agcagatagg | ccccggcctg | tgctttgggg | ccctggccct | gatgcttcga | ttcttctttg | 660 |
| aggaatggga | ttacacctac | gtccacagct | tctaccactg | tgccctggcc | atgtcctttg | 720 |
| tcctgctgct | gcccaaggtc | aacaagaagg | ctgggaacgc | aggggccccc | gccaagctga | 780 |
| ccttctccac | cctctgctgc | acttgtgtct | gactataccc | ccccacacac | acacacacac | 840 |
| caggcccctg | ccttcctgcc | tggcagtcct | gctgtctctc | ccaaggtact | tcctatactt | 900 |
| tgttatgcgg | cctgtacatg | agaaatggtc | ttctctacac | cccaagagac | cagcaggcct | 960 |
| gctgcattct | gctgagtgct | gcttagggac | ccactggttc | tgtgttcacc | agttgcttca | 1020 |
| ctctgttcag | gaaaaaaaag | aactttatcc | cccaaggcct | cacaaccata | ggtgtgcctg | 1080 |
| gcagagaacc | ctagaccagt | aaatacccag | cagcatgcag | ggttatctat | ttcccaggtc | 1140 |
| ctgcctgtca | gaatcgtctg | cttccctag | gaaactggga | ttgcccttt | aaccctgcc | 1200 |
| caggctctga | aagctctcca | cttaggaagc | tggagccagc | gaaccttgca | taccctgcc | 1260 |
| tgagtcccat | cccttctgca | ggttttcgat | caagccattc | acagtaaact | cttgatcagc | 1320 |
| cactagtcat | tagcttcgcc | taacatacat | tctagttcct | ggaaaaaaaa | aaaaaaaaa | 1380 |
| aaaaaaaaa | aaaaaaaaa | a | | | | 1401 |

<210> SEQ ID NO 20
<211> LENGTH: 180
<212> TYPE: PRT
<213> ORGANISM: Mus musculus

<400> SEQUENCE: 20

Met Gly Lys Gly Phe Ser His Ala Cys Asp Gly Pro Gly Leu Ser Val
1               5                   10                  15

Leu Cys Phe Met Arg Arg Asp Ile Leu Glu Tyr Phe Ser Ile Tyr Gly
            20                  25                  30

Thr Ala Leu Ser Met Trp Val Ser Leu Met Ala Leu Ala Asp Phe Asp
        35                  40                  45

```
Glu Pro Gln Arg Ser Thr Phe Thr Met Leu Gly Val Leu Thr Ile Ala
     50                  55                  60

Val Arg Thr Phe His Asp Arg Trp Gly Tyr Gly Val Tyr Ser Gly Pro
 65                  70                  75                  80

Ile Gly Thr Ala Thr Leu Ile Ile Ala Val Lys Trp Leu Lys Lys Met
                 85                  90                  95

Lys Glu Lys Lys Gly Leu Tyr Pro Asp Lys Ser Ile Tyr Thr Gln Gln
                100                 105                 110

Ile Gly Pro Gly Leu Cys Phe Gly Ala Leu Ala Leu Met Leu Arg Phe
                115                 120                 125

Phe Phe Glu Glu Trp Asp Tyr Thr Tyr Val His Ser Phe Tyr His Cys
    130                 135                 140

Ala Leu Ala Met Ser Phe Val Leu Leu Pro Lys Val Asn Lys Lys
145                 150                 155                 160

Ala Gly Asn Ala Gly Ala Pro Ala Lys Leu Thr Phe Ser Thr Leu Cys
                165                 170                 175

Cys Thr Cys Val
            180

<210> SEQ ID NO 21
<211> LENGTH: 1249
<212> TYPE: DNA
<213> ORGANISM: Mus musculus

<400> SEQUENCE: 21
atcagcactt gcttgggggg aatctaaggg cttcctcttt tatggagaga caggggtcca      60
ggataaaagg ctcctatgca aagactggca taggaatgtg tacactttca gtcagtcatg     120
ggcaaaggtt tctcccatgc ctgtgatggg cctggtttgt ctgtgctgtg cttcatgcgc     180
cgtgacattc tggagtactt cagcatctat ggaacagccc tgagcatgtg ggtctccctg     240
atggcactgg ccgactttga tgaacccag agatcgacct tcacaatgct ggcgtccttt     300
accatcgctg tgcggacttt tcatgaccgc tggggttacg gggtatactc cggtcccata     360
ggcacggcca ccctcatcat tgctgtaaag tggctgaaga agatgaaaga gaagaagggc     420
ctgtaccccg acaagagcat ctacacccag cagataggcc ccggcctgtg ctttggggcc     480
ctggccctga tgcttcgatt cttctttgag aatgggatt acacctacgt ccacagcttc     540
taccactgtg ccctggccat gtcctttgtc ctgctgctgc caaggtcaa caagaaggct     600
gggaacgcag ggcccccgc caagctgacc ttctccaccc tctgctgcac ttgtgtctga     660
ctataccccc ccacacacac acacacacca ggcccctgcc ttcctgcctg gcagtcctgc     720
tgtctctccc aaggtacttc ctatactttg ttatgcggcc tgtacatgag aaatggtctt     780
ctctacaccc caagagacca gcaggcctgc tgcattctgc tgagtgctgc ttagggaccc     840
actggttctg tgttcaccag ttgcttcact ctgttcagga aaaaaagaa ctttatcccc      900
caaggcctca caaccatagg tgtgcctggc agagaaccct agaccagtaa atacccagca     960
gcatgcaggg ttatctattt cccaggtcct gcctgtcaga atcgtctgct ttccctagga    1020
aactgggatt gcccttttaa cccctgccca ggctctgaaa gctctccact taggaagctg    1080
gagccagcga accttgcata cccctgcctg agtcccatcc cttctgcagg ttttcgatca    1140
agccattcac agtaaactct tgatcagcca ctagtcatta gcttcgccta acatacattc    1200
tagttcctgg aaaaaaaaaa aaaaaaaaaa aaaaaaaaaa aaaaaaaaa                1249
```

<210> SEQ ID NO 22
<211> LENGTH: 228
<212> TYPE: PRT
<213> ORGANISM: Rattus norvegicus

<400> SEQUENCE: 22

| Met | Gly | Leu | His | Leu | Arg | Ser | Gln | Leu | Leu | Pro | Leu | Arg | Pro | Gly | His |
|---|---|---|---|---|---|---|---|---|---|---|---|---|---|---|---|
| 1 | | | | 5 | | | | | 10 | | | | | 15 | |

| Val | Leu | Arg | Pro | Ala | Ala | Ala | Gln | Gly | Gln | Gln | Glu | Gly | Trp | Glu | Arg |
| | | | 20 | | | | | 25 | | | | | 30 | | |

| Arg | Gly | Pro | Arg | Gln | Ala | Asp | Leu | Leu | His | Ser | Leu | Leu | His | Leu | Cys |
| | | 35 | | | | | 40 | | | | | 45 | | | |

| Leu | Thr | Val | Ala | Pro | Leu | Leu | Gln | Ala | Pro | Ala | Phe | Leu | Ser | Gly | Ser |
| 50 | | | | | 55 | | | | | 60 | | | | | |

| Pro | Ala | Val | Ser | Pro | Gly | Ile | Leu | Pro | Thr | Leu | Ser | Gln | Trp | Asn | Val |
| 65 | | | | | 70 | | | | | 75 | | | | | 80 |

| His | Glu | Glu | Trp | Pro | Pro | Leu | His | Pro | Glu | Arg | Pro | Ala | Gly | Leu | Leu |
| | | | | 85 | | | | | 90 | | | | | 95 | |

| Gln | Ser | Ala | Lys | Cys | Cys | Leu | Gly | Thr | His | Glu | Phe | Cys | Val | His | Gln |
| | | | 100 | | | | | 105 | | | | | 110 | | |

| Leu | Leu | His | Ser | Ile | Gln | Glu | Lys | Lys | Glu | Arg | Glu | Leu | Tyr | Pro | Pro |
| | | 115 | | | | | 120 | | | | | 125 | | | |

| Arg | Leu | His | Asn | His | Arg | Cys | Ala | Leu | Gln | Ser | Pro | Arg | Pro | Val | Ser |
| 130 | | | | | 135 | | | | | 140 | | | | | |

| Ile | Gly | Pro | Lys | Ser | Gln | Pro | Ser | Ser | Val | His | Asn | Ser | Ser | Ile | Arg |
| 145 | | | | | 150 | | | | | 155 | | | | | 160 |

| Val | Ile | Tyr | Phe | Pro | Gly | Pro | Ala | Cys | Gln | Asp | Cys | Leu | Pro | Phe | Leu |
| | | | | 165 | | | | | 170 | | | | | 175 | |

| Gly | Asn | Trp | Asp | Cys | Pro | Phe | Tyr | Pro | Cys | Pro | Gly | Pro | Glu | Ser | Ser |
| | | | 180 | | | | | 185 | | | | | 190 | | |

| Gln | Phe | Arg | Glu | Leu | Asp | Pro | Val | Ser | Pro | Val | Pro | Val | Trp | Thr | Gln |
| | | 195 | | | | | 200 | | | | | 205 | | | |

| Ala | Trp | Cys | Pro | Cys | Leu | Ser | Pro | Ile | Pro | Ser | Ala | Val | Phe | Arg | Ser |
| 210 | | | | | 215 | | | | | 220 | | | | | |

| Ser | His | Ser | Gln |
| 225 | | | |

<210> SEQ ID NO 23
<211> LENGTH: 1418
<212> TYPE: DNA
<213> ORGANISM: Rattus norvegicus

<400> SEQUENCE: 23

```
gcatcagctg ttggaccttc tccatgtgtc actgggcaca tgctgcctca gagcacttaa      60
gccctcctcg tgggcgctgc cacagctgcg gcaagggttg ctgaagaaga gaagtgggct     120
ctattttttcc ctgccctgga gaccaaggag gccttcacta ccttctcccc tgccagtgcc    180
ttcttcctgg cccatgggga cagttgtagc caaactgctc ctgcctaccc tcagcagcct    240
ggccttcctc cccacagtga gcattgctac aagcggcgt ttttacatgg aggccatgat     300
ctatctcttc accatgttct tgtggcgtt ctcccatgcc tgcgacgggc tggcttgtc      360
cgtgctatgc ttcatgcgcc gtgatattct ggagtacttc agcatctatg gacagccct    420
gagcatgtgg gtctccctga tggcactggc cgactttgat gaaccccaga gatcaacctt    480
cacgatgttt ggtgtcctta ccattgccgt gcggacttac catgaccact ggggctacgg   540
ggtgtactct ggtcccatag gcaccgccac cctcatcatt gcagtaaagt ggctgaagaa    600
```

```
gatgaaagag aagaagggtc tgtaccctga caagagcatc tacacccagc agataggtcc      660
cggcctctgc tttggggccc tggccctgat gcttcgcttc ttctttgagg aatgggatta      720
cacctacgtt cacagcttct accactgcgc cctggccatg tccttcgtcc tgctgctgcc      780
caaggtcaac aagaaggctg ggaacgcagg gacccccgcc aagctgacct tctccactct      840
ctgctgcact tgtgtctgac agtagccccc tgctccaggg ccctgccttc ctgtctggc       900 agccctgctg tctctcccgg gatacttcct acactttccc agtggaatgt ccatgaggaa      960
tggcctcctc tgcaccccga gaccagca gggctgctgc agtcggcgaa gtgctgctta       1020
gggacccacg aattctgtgt tcaccagttg cttcactcta ttcaggaaaa aaaagagaga     1080
gaactttatc ccccaaggct gcataaccat aggtgtgcct tgcagagccc taggccagtc    1140
agtattggcc ccaagtcaca acccagcagt gtacacaaca gcagcatacg ggttatctat    1200
ttcccaggcc ctgcctgcca ggattgtctg cctttcctag gaaactggga ttgcccttc     1260 taccctgcc caggccctga aagctcccag tttcgggagc tggacccagt gagcccagtt    1320
ccagtctgga cccaggcttg gtgcccctgc ctgagtccca tcccttcagc agttttttcgg  1380 tcgagccact cacagtaaac tcttgatcag tcactagt                            1418
```

<210> SEQ ID NO 24
<211> LENGTH: 221
<212> TYPE: PRT
<213> ORGANISM: Felis catus

<400> SEQUENCE: 24

```
Met Gly Thr Leu Val Ala Lys Leu Leu Leu Pro Thr Leu Ser Ser Leu
1               5                   10                  15

Ala Phe Leu Pro Thr Val Ser Ile Ala Ala Lys Arg Arg Phe His Met
            20                  25                  30

Glu Ala Met Val Tyr Leu Phe Thr Met Phe Phe Val Ala Phe His His
        35                  40                  45

Ala Cys Asn Gly Pro Gly Leu Ser Val Leu Cys Phe Met Arg His Asp
    50                  55                  60

Val Leu Glu Tyr Phe Ser Val Tyr Gly Thr Ala Leu Ser Met Trp Val
65                  70                  75                  80

Ser Leu Met Ala Leu Ala Asp Phe Asp Glu Pro Lys Arg Ser Thr Phe
                85                  90                  95

Val Met Phe Gly Val Leu Thr Ile Ala Val Arg Ile Tyr His Asp Arg
            100                 105                 110

Trp Gly Tyr Gly Val Tyr Ser Gly Pro Ile Gly Val Ala Val Leu Val
        115                 120                 125

Ile Ala Thr Lys Trp Leu Gln Leu Met Lys Glu Lys Lys Gly Leu Tyr
    130                 135                 140

Pro Asp Lys Ser Val Tyr Thr Gln Gln Ile Gly Pro Gly Leu Cys Phe
145                 150                 155                 160

Gly Ala Leu Ala Leu Met Leu Arg Phe Phe Glu Asp Trp Asp Tyr
                165                 170                 175

Thr Tyr Val His Ser Phe Tyr His Cys Ala Leu Ala Met Ser Phe Val
            180                 185                 190

Leu Leu Leu Pro Lys Val Asn Lys Lys Ala Gly Ser Ala Gly Pro Pro
        195                 200                 205

Ala Lys Leu Asn Cys Pro Ala Leu Cys Cys Ala Cys Val
    210                 215                 220
```

<210> SEQ ID NO 25
<211> LENGTH: 3395
<212> TYPE: DNA
<213> ORGANISM: Felis catus

<400> SEQUENCE: 25

| | | | | | |
|---|---|---|---|---|---|
| tcggagcccc | caccgaacgg | agcaggcctc | gtcccttccg | tgttctctgc | cctggggacc | 60 |
| cgggcggccc | gcaccctccc | ctcctcccca | accggcgccc | tcctccctgg | cccatgggga | 120 |
| cgctcgtggc | aaagctgctc | ctccccaccc | tcagcagcct | ggctttcctc | cccacggtca | 180 |
| gcatcgctgc | caagcgccgc | ttccacatgg | aggccatggt | ctacctgttc | accatgttct | 240 |
| tcgtggcgtt | ccaccacgcc | tgcaacgggc | ccggcctgtc | agtcctctgc | ttcatgcgcc | 300 |
| acgacgtcct | ggagtacttc | agcgtctacg | ggacagcgct | gagcatgtgg | gtctcactga | 360 |
| tggcgctggc | cgacttcgac | gaacccaaga | ggtcgacctt | tgtgatgttt | ggcgtcctga | 420 |
| ccatcgcggt | ccggatctac | cacgaccgct | ggggctatgg | cgtgtactcg | ggccccattg | 480 |
| gcgtggctgt | ccttgtcatc | gccaccaagt | ggctgcagct | catgaaggag | aagaagggtc | 540 |
| tgtaccccga | caagagcgtc | tacacccagc | agataggccc | cggcctctgt | ttcggggcgc | 600 |
| tggccctcat | gttacgattc | ttctttgagg | attgggatta | cacctacgtg | cacagtttct | 660 |
| accactgcgc | gctggccatg | tcctttgtcc | tcctgctgcc | caaggtcaac | aagaaggccg | 720 |
| gaagcgcggg | gccccccgcc | aagctgaact | gccccgccct | ctgctgtgct | tgcgtctgac | 780 |
| cgcgcgccgc | gcccgccccc | tgccccctgc | cagcccctgc | cctgccgcat | ctcccgcctg | 840 |
| cggagagacc | cccatggccc | cccccccggg | ctctgagcac | ccaggagaaa | tgtctcccct | 900 |
| cagagggatt | tggggagcat | cctgccaagg | gctgctggga | gcccacttac | taggtttcta | 960 |
| cggagcacaa | accaccgtgc | tggaaggaaa | aggacttcct | gccccgctcc | tgctccccca | 1020 |
| cagtcatggc | cagtctgcgt | ccgcaggacc | ccacagccaa | catgggtccc | ccaccccgt | 1080 |
| cccccttttcc | tcctcaccca | gccacaaagg | gactctgccc | atgcccccct | cacaacaccc | 1140 |
| gtctcctcct | ggaccctggt | tgtcaccgct | tctgtcctgt | gccctcgggc | tctgagcaga | 1200 |
| cccgtgtagg | aagccaaggc | cagtggggac | cggctctgtc | caggcctgct | ggccgtccct | 1260 |
| ccagccgggt | ccctgaatca | agccctgtca | gttacggcag | cccacaggaa | gctcctcagc | 1320 |
| ccttgacctt | cccgtgtgcc | agaggccgta | tgatcatcgc | ttcatctaat | tcgtgaaaca | 1380 |
| agtctgcatt | aaaggatgat | cactcccttc | tacagacaga | agcccgaggc | gcagggtcca | 1440 |
| tggggtgccc | gaggcctcga | gcaggcgagt | gcagacccgg | gccaggcccg | ccgccaccaa | 1500 |
| gcccgccccc | tcgctgtgca | gccgcccacg | ggctgggcgc | gagcacctgt | gttggccctt | 1560 |
| cgagcggctc | caccctgggc | taacggccag | cgtgggaagg | gggtctgggc | cagggacac | 1620 |
| ccgcgcggag | gccagcgggc | ccggagccgg | gcgcacgggg | caggcttgcg | gcagcgctga | 1680 |
| gggagggcgg | ccggctcccg | cctacagccc | gtctgtgctg | gccccgcga | gggtgggggc | 1740 |
| cggcctccca | gacatcacct | cacaaacctg | agcctcccca | gcagcccag | cccacccag | 1800 |
| cttcccgaac | gatgtgggca | catctgtcag | gcaggaagtt | acctacacct | gtctggggcc | 1860 |
| cgttttgtgt | ttccagacgg | tgcaccccca | ccccaccgc | acgggcggc | cccttatttg | 1920 |
| tcctgaagtc | acctcttgct | ccctcaggg | ggccgggaga | gagctgggga | caaggctggc | 1980 |
| ccctcggcga | ggcaccccg | gtctgtcggc | ctccctgact | gtccagaggt | cccacgcgtg | 2040 |
| gggcccggac | gcccacagtc | tcactctggc | tcagccctt | cctgagccta | cagactggat | 2100 |
| gacagagcag | cctctgggca | gctcgcacgg | gctcggagtc | ctggccgggc | cccggggagc | 2160 |

| | | | | |
|---|---|---|---|---|
| aggcctcagc ctcgctctgc ttcccagttg aggaagctga gcccacagct tcggggtcgt | 2220 |
| cctcccagac ggacatgtcc ccgcatcccc cgcccggcgc agggacgggc agaagccgct | 2280 |
| tccgttggct tctggtccgg ttgaggggtg tgcacacaca ggtgcccgct cacaccgtga | 2340 |
| agagataggg cccctggaa acagcatcgt cctgtccggc ctgtctccca gctccgcgag | 2400 |
| gggagacacc gggcaggaag gaaagcgaag gctgtggggg ccacgcgggg ggcccgcggg | 2460 |
| catcactctg gaagcaggcc tctgccagtc gcctccctcc ccgtcacctc cctcccatcc | 2520 |
| cctcccccgt gccccccca cacacacacc cgacgagcac atcccagctc ccagctccgc | 2580 |
| ggcagcagat ggaaagttgg aggccgcggg atgctcctga gcaggaggga ggtgaggggc | 2640 |
| cggccaagag cgttaaggac catactaaca ggctactcac tgcggccacg ctgatttatg | 2700 |
| aggccgtctg ggagcccagc caagtctgta agtcatggac aattaggagg ctcgctccag | 2760 |
| ccctcagccc cgtccgcctc tggggctcta ggcccaccgc gcccctcctc agcagggtca | 2820 |
| gcaccgtgga gaccccacgg tgcagatagg gacacggagg gccgggaggc cggcggccgg | 2880 |
| ccccggtgac ttggacactg ggtgctgagc ggtggctgtg cccagggtct gactcctaac | 2940 |
| cctagcggca tcttcctctg cttccaaggc ccactttgac atcttggggg ctccagccaa | 3000 |
| gggccggtgg ggggagtgcc cgggaggggg acagaaagag aagaggacac ttggaacctc | 3060 |
| cagccctaca cctagagact aacaaggaag aaaagaagtc tcatggcctt cagaccaaac | 3120 |
| acctctgagt cccagtgtcc tcgagcccgg ggccttcgtg ccctacaatc cagcagtcat | 3180 |
| ggcatccggt gccaggaggg acctccgagg cccccccag accccctgg ggctctggac | 3240 |
| gggactcacc tccagccaga tctgatgagg gaagcctggg tcccgactcc agcgtgcgcc | 3300 |
| tggaagccga gcccgagatg atggcagccc cagagcagcc tgtgcagtag aacttgcttt | 3360 |
| aatgatggag gcgaggcggg ggcgcccggg gggct | 3395 |

<210> SEQ ID NO 26
<211> LENGTH: 182
<212> TYPE: PRT
<213> ORGANISM: Felis catus

<400> SEQUENCE: 26

Met Gly Thr Leu Val Ala Lys Leu Leu Leu Pro Thr Leu Ser Ser Leu
1               5                   10                  15

Ala Phe Leu Pro Thr Val Ser Ile Ala Ala Lys Arg Arg Phe His Met
            20                  25                  30

Glu Ala Met Val Tyr Leu Phe Thr Met Phe Phe Val Ala Phe His His
        35                  40                  45

Ala Cys Asn Gly Pro Gly Leu Ser Val Leu Cys Phe Met Arg His Asp
    50                  55                  60

Val Leu Glu Tyr Phe Ser Val Tyr Gly Thr Ala Leu Ser Met Trp Val
65                  70                  75                  80

Ser Leu Met Ala Leu Ala Asp Phe Asp Glu Pro Lys Arg Ser Thr Phe
                85                  90                  95

Val Met Phe Gly Val Leu Thr Ile Ala Val Arg Ile Tyr His Asp Arg
            100                 105                 110

Trp Gly Tyr Gly Val Tyr Ser Gly Pro Ile Gly Val Ala Val Leu Val
        115                 120                 125

Ile Ala Thr Lys Trp Asp Trp Asp Tyr Thr Tyr Val His Ser Phe Tyr
    130                 135                 140

His Cys Ala Leu Ala Met Ser Phe Val Leu Leu Leu Pro Lys Val Asn

| | | | | |
|---|---|---|---|---|
| 145 | | 150 | 155 | 160 |

Lys Lys Ala Gly Ser Ala Gly Pro Pro Ala Lys Leu Asn Cys Pro Ala
                 165                       170                       175

Leu Cys Cys Ala Cys Val
           180

<210> SEQ ID NO 27
<211> LENGTH: 3278
<212> TYPE: DNA
<213> ORGANISM: Felis catus

<400> SEQUENCE: 27

| | |
|---|---|
| tcggagcccc caccgaacgg agcaggcctc gtcccttccg tgttctctgc cctggggacc | 60 |
| cgggcggccc gcaccctccc ctcctcccca accggcgccc tcctccctgg cccatgggga | 120 |
| cgctcgtggc aaagctgctc ctccccaccc tcagcagcct ggctttcctc cccacggtca | 180 |
| gcatcgctgc caagcgccgc ttccacatgg aggccatggt ctacctgttc accatgttct | 240 |
| tcgtggcgtt ccaccacgcc tgcaacgggc cggcctgtc agtcctctgc ttcatgcgcc | 300 |
| acgacgtcct ggagtacttc agcgtctacg gacagcgct gagcatgtgg gtctcactga | 360 |
| tggcgctggc cgacttcgac gaacccaaga ggtcgacctt tgtgatgttt ggcgtcctga | 420 |
| ccatcgcggt ccggatctac cacgaccgct ggggctatgg cgtgtactcg gccccattg | 480 |
| gcgtggctgt ccttgtcatc gccaccaagt gggattggga ttacacctac gtgcacagtt | 540 |
| tctaccactg cgcgctggcc atgtcctttg tcctcctgct gcccaaggtc aacaagaagg | 600 |
| ccggaagcgc ggggccccc gccaagctga actgccccgc cctctgctgt gcttgcgtct | 660 |
| gaccgcgcgc cgcgcccgcc ccctgccccc tgccagcccc tgcctgccg catctcccgc | 720 |
| ctgcggagag accccatgg ccccccccc cggctctgag cacccaggag aaatgtctcc | 780 |
| cctcagaggg atttggggag catcctgcca agggctgctg ggagcccact tactaggttt | 840 |
| ctacggagca caaccaccg tgctggaagg aaaaggactt cctgccccgc tcctgctccc | 900 |
| ccacagtcat ggccagtctg cgtccgcagg accccacagc caacatgggt cccccaccc | 960 |
| cgtccccctt tcctcctcac ccagccacaa agggactctg cccatgcccc cctcacaaca | 1020 |
| cccgtctcct cctggacccct ggttgtcacc gcttctgtcc tgtgccctcg ggctctgagc | 1080 |
| agacccgtgt aggaagccaa ggccagtggg gaccggctct gtccaggcct gctggccgtc | 1140 |
| cctccagccg ggtccctgaa tcaagccctg tcagttacgg cagcccacag gaagctcctc | 1200 |
| agcccttgac cttcccgtgt gccagaggcc gtatgatcat cgcttcatct aattcgtgaa | 1260 |
| acaagtctgc attaaaggat gatcactccc ttctacagac agaagcccga ggcgcagggt | 1320 |
| ccatggggtg cccgaggcct cgagcaggcg agtgcagacc cgggccaggc ccgccgccac | 1380 |
| caagcccgcc ccctcgctgt gcagccgccc acgggctggg cgcgagcacc tgtgttggcc | 1440 |
| cttcgagcgg ctccaccctg gctaacggc cagcgtggga aggggtctg gcccaggga | 1500 |
| cacccgcgcg gaggccagcg ggcccggagc cgggcgcacg ggcaggctt gcggcagcgc | 1560 |
| tgagggaggg cggccggctc ccgcctacag cccgtctgtg ctgggccccg cgagggtggg | 1620 |
| ggccggcctc ccagacatca cctcacaaac ctgagcctcc ccagcagccc cagcccaccc | 1680 |
| cagcttcccg aacgatgtgg gcacatctgt caggcaggaa gttacctaca cctgtctggg | 1740 |
| gcccgttttg tgtttccaga cggtgcaccc ccacccccac cgcacggggc ggccccttat | 1800 |
| ttgtcctgaa gtcacctctt gctcccctca ggggccggg agagagctgg ggacaaggct | 1860 |
| ggccccctcgg cgaggcaccc ccggtctgtc ggcctccctg actgtccaga ggtcccacgc | 1920 |

```
gtggggcccg gacgcccaca gtctcactct ggctcagccc cttcctgagc ctacagactg   1980
gatgacagag cagcctctgg gcagctcgca cgggctcgga gtcctggccg ggccccgggg   2040
agcaggcctc agcctcgctc tgcttcccag ttgaggaagc tgagcccaca gcttcggggt   2100
cgtcctccca gacggacatg tccccgcatc ccccgcccgg cgcagggacg ggcagaagcc   2160
gcttccgttg gcttctggtc cggttgaggg gtgtgcacac acaggtgccc gctcacaccg   2220
tgaagagata gggccccctg gaaacagcat cgtcctgtcc ggcctgtctc ccagctccgc   2280
gaggggagac accgggcagg aaggaaagcg aaggctgtgg gggccacgcg ggggggcccgc  2340 gggcatcact ctggaagcag gcctctgcca gtcgcctccc tccccgtcac ctccctccca   2400 tccctcccc cgtgccccc ccacacacac acccgacgag cacatcccag ctcccagctc     2460
cgcggcagca gatggaaagt tggaggccgc gggatgctcc tgagcaggga ggaggtgagg   2520
ggccggccaa gagcgttaag gaccatacta acaggctact cactgcggcc acgctgattt   2580
atgaggccgt ctgggagccc agccaagtct gtaagtcatg gacaattagg aggctcgctc   2640
cagccctcag ccccgtccgc ctctggggct ctaggcccac cgcgcccctc ctcagcaggg   2700
tcagcaccgt ggagacccca cggtgcagat agggacacgg agggccggga ggccggcggc   2760
cggccccggt gacttggaca ctgggtgctg agcggtggct gtgcccaggg tctgactcct   2820
aaccctagcg gcatcttcct ctgcttccaa ggcccacttt gacatcttgg gggctccagc   2880
caagggccgg tgggggagt gcccgggagg gggacagaaa gagaagagga cacttggaac    2940
ctccagccct acacctagag actaacaagg aagaaaagaa gtctcatggc cttcagacca   3000
aacacctctg agtcccagtg tcctcgagcc cggggccttc gtgccctaca atccagcagt   3060
catggcatcc ggtgccagga gggacctccg aggccccccc cagaccccccc tggggctctg  3120 gacgggactc acctccagcc agatctgatg agggaagcct gggtcccgac tccagcgtgc   3180
gcctggaagc cgagcccgag atgatggcag ccccagagca gcctgtgcag tagaacttgc   3240
tttaatgatg gaggcgaggc gggggcgccc gggggggct                          3278
```

<210> SEQ ID NO 28
<211> LENGTH: 221
<212> TYPE: PRT
<213> ORGANISM: Sus scrofa

<400> SEQUENCE: 28

```
Met Gly Thr Val Met Ala Lys Leu Leu Pro Thr Leu Ser Ser Leu
1               5                   10                  15

Ala Phe Leu Pro Thr Val Ser Ile Ala Ala Lys Arg Arg Phe His Met
                20                  25                  30

Glu Ala Met Val Tyr Leu Phe Thr Thr Phe Val Ala Phe Tyr His
            35                  40                  45

Ala Cys His Gly Pro Gly Leu Ala Met Ile Cys Phe Leu Arg Leu Asp
        50                  55                  60

Ile Leu Glu Tyr Phe Ser Val Tyr Gly Thr Ala Leu Ser Met Trp Val
65                  70                  75                  80

Ser Leu Met Ala Leu Ala Asp Phe Asp Glu Pro Lys Arg Ser Thr Phe
                85                  90                  95

Val Met Phe Gly Val Leu Thr Ile Ala Val Arg Ile Tyr His Asp Arg
                100                 105                 110

Trp Gly Tyr Gly Val Tyr Ser Gly Pro Ile Gly Thr Ala Ala Leu Ile
            115                 120                 125
```

```
Ile Ala Ala Lys Trp Leu Gln Gln Met Lys Asp Gln Arg Arg Leu Tyr
    130                 135                 140
Pro Asp Lys Ser Val Tyr Thr Gln Gln Ile Gly Pro Gly Leu Cys Phe
145                 150                 155                 160
Gly Ala Leu Ala Leu Met Leu Arg Phe Phe Phe Glu Glu Trp Asp Tyr
                165                 170                 175
Thr Tyr Val His Ser Phe Tyr His Cys Ala Leu Ala Met Ser Phe Val
            180                 185                 190
Leu Leu Leu Pro Lys Ala Asn Lys Lys Ala Gly Ser Ala Gly Pro Pro
        195                 200                 205
Ala Lys Leu Asp Cys Ser Thr Leu Cys Cys Ala Cys Ile
    210                 215                 220

<210> SEQ ID NO 29
<211> LENGTH: 2112
<212> TYPE: DNA
<213> ORGANISM: Sus scrofa

<400> SEQUENCE: 29
gatgagacaa gacaagaaaa aagaaaagga agagctcctc ccaccgtacg ttttaaatcc      60
gtgccttta tcgtgggcgg catcattcga tcacgatgaa aaacacaacg ggagaaatgc     120
tgttctttta ctgacaacaa tcaaggatg aactcatgaa gccagcatga ttccgtcagt     180
gcctgtaggg agagagggtc gcctgcgcag ctcacacgcc cggatcgtct cttggcagag    240
ggatgatggg gggggggagc atcctgccag gctgctccct cgagacctgt ttagcaagag    300
aaggaatgtc tccagggcca aggaaggccg agagccctag catccgcctt gccttgggga    360
cactgataga ggtggtcctg gcttgtgtcc ttcaggttca aagctatgtg accgcagaga    420
aaagacagtg agtttcgtgt gttcaggcac caaggaagcc tgcttggagc aggagcaggt    480
gagcaagaag ggcatgggcg ctggtaggtt ggcttcttct ggtgaccgga acgggctcag    540
ccttggcctc tctctcgccc caccccccgg gccctgtgca cacgtgactc cagcagcagg    600
gtctgctttc ctctcgtgtt ctgggctcct gagcgccctg gagaggggcg aggatggaga    660
gtggctgaac atcgggggtg cggatgggga ctccgctcca tcgaagctgt ggcctccaaa    720
aacaagggggg gactccttga atcaactgct ctgatccctc caaaacaaag agagagagag    780
gggtgaggca agggccgacc agcgggatca gctgttggct ctcctccccg gcggtggac     840
atgtgcgcgc cctcccccgc ctcgcagggt atttaaaccg cagctgccat cggagccccc    900
gctggcagga gcgaccccttc tccctgcctc ttccctgccc tggggacccg ggaggcccgc    960
accctcccttt cctcccccggc ccatggggac cgtcatggcc aaactgctgc tacccacgct   1020
gagcagcctg gccttcctcc ccacggtcag catcgctgcc aagcggcggt tccacatgga   1080
ggccatggtc tatctcttca ccacgttctt cgtggcgttc taccacgcct gccacgggcc   1140
gggcctggct atgatctgct ttctgcgcct tgacatcctg gagtatttca gcgtctacgg   1200
aaccgccctg agcatgtggg tctcgctgat ggcgctggct gacttcgacg agcccaagag   1260
gtcgactttc gtgatgtttg gcgtcctgac catcgccgtg cggatctacc acgaccgctg   1320
gggctacggc gtgtactcgg gccccatcgg cacggccgcc ctcatcatcg gcgccaagtg   1380
gctgcagcag atgaaggacc aacggcgcct gtatccagac aagagcgtgt acacacagca   1440
gataggcccc ggcctctgct cggggcgct ggccctcatg ctgcgctttt tcttcgagga    1500
gtgggattat acctacgtcc acagcttcta ccactgcgcc ctggccatgt ccttcgtcct   1560
gctgctgccc aaggccaaca gaaggctgg aagcgcaggg ccaccgcca agctggactg    1620
```

-continued

```
ctccaccctc tgctgtgctt gtatctgacc gcgtggccca aagctcccag ccccccccc       1680 gccctgcctg gtccttccgg actgcagaaa cgcccttct cagagcctgc gggctctctg       1740
gggtctgggg agcatcccgc caagtgcttt ttgagaaccc acttcttctg tgtccccgg       1800 gtgccaagga gggtgctgga agaaacaaa catcctgatg gacaggtgtg tctgcagaag       1860
cccggagcca gacactgccc ccctccacg tcccctcccc gcttccccgg acagccccat       1920
cccagccacc aagggccct gcctgccacc ctggtcccac acgctcccca caccctctgt       1980
ttcctgctct tgacccatgc cctcaggttc ggcgagccag ggccagcagg gccacttggt       2040
ccctgcccca ggcctggctg ccccttggct gtccccccag ccaggtcgct aaatcaaacc       2100
atttccactc ac                                                           2112
```

<210> SEQ ID NO 30
<211> LENGTH: 221
<212> TYPE: PRT
<213> ORGANISM: Macaca mulatta

<400> SEQUENCE: 30

```
Met Gly Thr Leu Val Ala Lys Leu Leu Leu Pro Thr Leu Ser Ser Leu
1               5                   10                  15

Ala Phe Leu Pro Thr Val Ser Ile Ala Ala Lys Arg Arg Phe His Met
            20                  25                  30

Glu Ala Met Val Tyr Leu Phe Thr Leu Phe Phe Val Ala Leu His His
        35                  40                  45

Ala Cys Asn Gly Pro Gly Leu Ser Val Leu Cys Phe Met Arg His Asp
    50                  55                  60

Ile Leu Glu Tyr Phe Ser Val Tyr Gly Thr Ala Leu Ser Met Trp Val
65                  70                  75                  80

Ser Leu Met Ala Leu Ala Asp Phe Asp Glu Pro Lys Arg Ser Thr Phe
                85                  90                  95

Val Met Phe Gly Val Leu Thr Ile Ala Val Arg Ile Tyr His Asp Arg
            100                 105                 110

Trp Gly Tyr Gly Val Tyr Ser Gly Pro Ile Gly Thr Ala Ile Leu Ile
        115                 120                 125

Ile Ala Ala Lys Trp Leu Gln Lys Met Lys Glu Lys Lys Gly Leu Tyr
    130                 135                 140

Pro Asp Lys Ser Val Tyr Thr Gln Gln Ile Gly Pro Gly Leu Cys Phe
145                 150                 155                 160

Gly Ala Leu Ala Leu Met Leu Arg Phe Phe Glu Asp Trp Asp Tyr
                165                 170                 175

Thr Tyr Val His Ser Phe Tyr His Cys Ala Leu Ala Met Ser Phe Val
            180                 185                 190

Leu Leu Leu Pro Lys Val Asn Lys Lys Ala Gly Ala Pro Gly Ala Pro
        195                 200                 205

Ala Lys Leu Asp Cys Ser Thr Leu Cys Cys Ala Cys Val
    210                 215                 220
```

<210> SEQ ID NO 31
<211> LENGTH: 1531
<212> TYPE: DNA
<213> ORGANISM: Macaca mulatta

<400> SEQUENCE: 31

```
tccgtctcaa aaaagaaaa gagaaaatca gagacaagtg ctggtcacgt ggcgcgtcag       60
```

-continued

| | |
|---|---|
| ctgtcggccc tccccatgtg ttgcttgaca tgtgcatgta catccccgcc tccgtccagg | 120 |
| gcatttaaac cctctcgtgg gcgctccccg cagctgccat cagagccctg ctcaaaggga | 180 |
| gctggccttc cccttcgtg ctcctgtgct ggggacccag ggcgccagca cccaccccgc | 240 |
| cccagccagt gcttccctcc aggcctatgg ggacgctggt ggccaagcta ctcctgccca | 300 |
| ccctcagcag cctggccttc ctccccactg tcagcatcgc ggccaagagg cggttccaca | 360 |
| tggaggccat ggtctacctc ttcaccctgt tcttcgtggc gctccaccat gcctgcaacg | 420 |
| gacccggctt gtctgtgctg tgcttcatgc gacacgacat cctggaatac ttcagcgtct | 480 |
| acggaacagc cctgagcatg tgggtctcgc tgatggcact ggccgacttc gatgagccca | 540 |
| agaggtcaac atttgtgatg ttcggcgtcc tgaccattgc tgtgaggatc taccacgacc | 600 |
| gctgggctta cggggtgtac tcaggcccca tcggcacagc catcctcatc attgcggcaa | 660 |
| agtggctgca gaagatgaag gagaagaagg gcctgtaccc agacaagagc gtctacaccc | 720 |
| agcagatagg ccccgcctc tgcttcgggg cgctggccct gatgctacgc ttcttcttcg | 780 |
| aggactggga ctacacctat gtccacagct tctaccactg tgccctggcc atgtcctttg | 840 |
| ttctgctgct gcccaaggtc aacaagaagg ctggagcccc ggggccccg gccaagctgg | 900 |
| actgctccac cctgtgctgt gcttgtgtct gatgctgcgc ccagcccggc tctgagcccc | 960 |
| tgccctcccc agctcacgct tggccagagt cccagacagt ttctcctcct gcagctcctg | 1020 |
| ctgtccttcc ctgccccaga gcatgcagga gaaacatctc ttgcataccc taagaggccc | 1080 |
| ccggggggtct gtgaagggcc catcacactg cactaaatgc ttcttaagaa cccgcttatt | 1140 |
| ccgttgtgac ggggtgcaca gcagcaggac caagctggaa agataagaat gttctcctcc | 1200 |
| caggccttgt cacgacccat tggcgtgtct ggtggagccc taggtctggc gtctgcccac | 1260 |
| cccactgctg gccagcggcc caggagtccc agccgtgtgc cagccatgac gggggggctc | 1320 |
| ccatgtcttc agttttctcc tgggaactgc tatcaccatc tctgtcctgt gtcctcaggc | 1380 |
| tccgagcaac cccatttagg aagctgaggc cagcggggcc agctggatcc ctggcccagg | 1440 |
| ccagtctggc cccacccctt ccgctgggtc cctgaatcaa gccgttttca taattataac | 1500 |
| caataagaag tgcctcaatg tatcaacctc a | 1531 |

<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 32

Tyr Pro Tyr Asp Val Pro Asp Tyr Ala
1               5

<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 33

Glu Gln Lys Leu Ile Ser Glu Glu Asp Leu
1               5                   10

```
<210> SEQ ID NO 34
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Asp Tyr Lys Asp Asp Asp Asp Lys
1               5

<210> SEQ ID NO 35
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

His His His His His His
1               5

<210> SEQ ID NO 36
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gly Ala Pro Val Pro Tyr Pro Asp Pro Leu Glu Pro Arg
1               5                   10

<210> SEQ ID NO 37
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Lys Pro Ile Pro Asn Pro Leu Leu Gly Leu Asp Ser Thr
1               5                   10

<210> SEQ ID NO 38
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Tyr Thr Asp Ile Glu Met Asn Arg Leu Gly Lys
1               5                   10

<210> SEQ ID NO 39
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Glu Glu Glu Glu Glu Glu
1               5

<210> SEQ ID NO 40
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gly Leu Asn Asp Ile Phe Glu Ala Gln Lys Ile Glu Trp His Glu
1               5                   10                  15

<210> SEQ ID NO 41
<211> LENGTH: 38
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Trp Ser His Pro Gln Phe Glu Lys
1               5

<210> SEQ ID NO 43
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Asp Leu Tyr Asp Asp Asp Asp Lys
1               5
```

-continued

```
<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Lys Glu Thr Ala Ala Ala Lys Phe Glu Arg Gln His Met Asp Ser
1               5                   10                  15

<210> SEQ ID NO 45
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Ser Leu Ala Glu Leu Leu Asn Ala Gly Leu Gly Gly Ser
1               5                   10

<210> SEQ ID NO 46
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Thr Gln Asp Pro Ser Arg Val Gly
1               5

<210> SEQ ID NO 47
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 48
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Cys Cys Pro Gly Cys Cys
1               5

<210> SEQ ID NO 49
```

```
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Thr Asp Lys Asp Met Thr Ile Thr Phe Thr Asn Lys Lys Asp Ala Glu
1               5                   10                  15

<210> SEQ ID NO 50
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ala His Ile Val Met Val Asp Ala Tyr Lys Pro Thr Lys
1               5                   10

<210> SEQ ID NO 51
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Lys Leu Gly Asp Ile Glu Phe Ile Lys Val Asn Lys
1               5                   10

<210> SEQ ID NO 52
<211> LENGTH: 18
<212> TYPE: PRT
<213> ORGANISM: Thosea asigna virus

<400> SEQUENCE: 52

Glu Gly Arg Gly Ser Leu Leu Thr Cys Gly Asp Val Glu Glu Asn Pro
1               5                   10                  15

Gly Pro

<210> SEQ ID NO 53
<211> LENGTH: 21
<212> TYPE: PRT
<213> ORGANISM: Thosea asigna virus

<400> SEQUENCE: 53

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 54
<211> LENGTH: 19
<212> TYPE: PRT
<213> ORGANISM: Porcine teschovirus-1

<400> SEQUENCE: 54

Ala Thr Asn Phe Ser Leu Leu Lys Gln Ala Gly Asp Val Glu Glu Asn
```

Pro Gly Pro

<210> SEQ ID NO 55
<211> LENGTH: 22
<212> TYPE: PRT
<213> ORGANISM: Porcine teschovirus-1

<400> SEQUENCE: 55

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 56
<211> LENGTH: 20
<212> TYPE: PRT
<213> ORGANISM: Equine rhinitis A virus

<400> SEQUENCE: 56

Gln Cys Thr Asn Tyr Ala Leu Leu Lys Leu Ala Gly Asp Val Glu Ser
1               5                   10                  15

Asn Pro Gly Pro
            20

<210> SEQ ID NO 57
<211> LENGTH: 23
<212> TYPE: PRT
<213> ORGANISM: Equine rhinitis A virus

<400> SEQUENCE: 57

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 58
<211> LENGTH: 22
<212> TYPE: PRT
<213> ORGANISM: Foot-and-mouth disease virus

<400> SEQUENCE: 58

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 59
<211> LENGTH: 25
<212> TYPE: PRT
<213> ORGANISM: Foot-and-mouth disease virus

<400> SEQUENCE: 59

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 60
<211> LENGTH: 25
<212> TYPE: PRT
<213> ORGANISM: Strongylocentrotus purpuratus

```
<400> SEQUENCE: 60

Asp Gly Phe Cys Ile Leu Tyr Leu Leu Ile Leu Leu Met Arg Ser
1               5                   10                  15

Gly Asp Val Glu Thr Asn Pro Gly Pro
            20                  25

<210> SEQ ID NO 61
<211> LENGTH: 20
<212> TYPE: PRT
<213> ORGANISM: Amphimedon queenslandica

<400> SEQUENCE: 61

Leu Leu Cys Phe Met Leu Leu Leu Leu Ser Gly Asp Val Glu Leu
1               5                   10                  15

Asn Pro Gly Pro
            20

<210> SEQ ID NO 62
<211> LENGTH: 20
<212> TYPE: PRT
<213> ORGANISM: Amphimedon queenslandica

<400> SEQUENCE: 62

His His Phe Met Phe Leu Leu Leu Leu Ala Gly Asp Ile Glu Leu
1               5                   10                  15

Asn Pro Gly Pro
            20

<210> SEQ ID NO 63
<211> LENGTH: 20
<212> TYPE: PRT
<213> ORGANISM: Saccoglossus kowalevskii

<400> SEQUENCE: 63

Trp Phe Leu Val Leu Leu Ser Phe Ile Leu Ser Gly Asp Ile Glu Val
1               5                   10                  15

Asn Pro Gly Pro
            20

<210> SEQ ID NO 64
<211> LENGTH: 20
<212> TYPE: PRT
<213> ORGANISM: Branchiostoma floridae

<400> SEQUENCE: 64

Lys Asn Cys Ala Met Tyr Met Leu Leu Leu Ser Gly Asp Val Glu Thr
1               5                   10                  15

Asn Pro Gly Pro
            20

<210> SEQ ID NO 65
<211> LENGTH: 20
<212> TYPE: PRT
<213> ORGANISM: Branchiostoma floridae

<400> SEQUENCE: 65

Met Val Ile Ser Gln Leu Met Leu Lys Leu Ala Gly Asp Val Glu Glu
1               5                   10                  15

Asn Pro Gly Pro
            20
```

```
<210> SEQ ID NO 66
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 66

Asp Xaa Glu Xaa Asn Pro Gly Pro
1               5

<210> SEQ ID NO 67
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
ttaatacgac tcactatag                                              19

<210> SEQ ID NO 68
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
aaaaagcacc gactcggtgc cacttttttca agttgataac ggactagcct tattttaact     60
t                                                                      61

<210> SEQ ID NO 69
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
ggaccgggcc gtcgtggagg                                             20

<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
```

-continued

```
ccagagtgga ccactcccag                                        20

<210> SEQ ID NO 71
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 71
gagtgaactc cttaaccagc tttc                                   24

<210> SEQ ID NO 72
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 72
gcgttgctgt ttccaggacc cgtg                                   24

<210> SEQ ID NO 73
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73
caaagggagg gagggattaa ag                                     22

<210> SEQ ID NO 74
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74
cagagaggaa gggtcaatca ac                                     22

<210> SEQ ID NO 75
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75
ggaccactcc cagaggaagg a                                      21

<210> SEQ ID NO 76
<211> LENGTH: 20
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic primer"

<400> SEQUENCE: 76
ggaccgacgc ctggactaac                                                 20

<210> SEQ ID NO 77
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77
aggtcggtgt gaacggattt g                                               21

<210> SEQ ID NO 78
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
tgtagaccat gtagttgagg t                                               21

<210> SEQ ID NO 79
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
gctaagaggt ggtatttaa                                                  19

<210> SEQ ID NO 80
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
gcagcaggta gtcaataaac g                                               21

<210> SEQ ID NO 81
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
gctgtctgct ctttgtcct                                                  19

<210> SEQ ID NO 82
```

```
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
gtggaccact cccagagga                                             19

<210> SEQ ID NO 83
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
gacgaacact tcttcatcg                                             19

<210> SEQ ID NO 84
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
tttgctaaga ggtggtattt aattcaagag attaaatacc acctcttagc ttttt      55

<210> SEQ ID NO 85
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
ctagaaaaag ctaagaggtg gtatttaatc tcttgaatta ataccacct cttag        55

<210> SEQ ID NO 86
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
tttgcagcag gtagtcaata aacgttcaag agacgtttat tgactacctg ctgcttttt  59

<210> SEQ ID NO 87
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87
```
ctagaaaaag cagcaggtag tcaataaacg tctcttgaac gtttattgac tacctgctg    59

<210> SEQ ID NO 88
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
tttgctgtct gctctttgtc ctttcaagag aaggacaaag agcagacagc ttttt    55

<210> SEQ ID NO 89
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
ctagaaaaag ctgtctgctc tttgtccttc tcttgaaagg acaaagagca gacag    55

<210> SEQ ID NO 90
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
tttgtggacc actcccagag gattcaagag atcctctggg agtggtccac ttttt    55

<210> SEQ ID NO 91
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
ctagaaaaag tggaccactc ccagaggatc tcttgaatcc tctgggagtg gtcca    55

<210> SEQ ID NO 92
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 92
tttgacgaac acttcttcat cgttcaagag acgatgaaga agtgttcgtc ttttt    55

<210> SEQ ID NO 93
<211> LENGTH: 54
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 93
tagaaaaaga cgaacacttc ttcatcgtct cttgaacgat gaagaagtgt tcgt        54

<210> SEQ ID NO 94
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94 gccacc                                                              6

<210> SEQ ID NO 95
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
gttttagagc tagaaatagc aagttaaaat aaggctagtc g                      41

<210> SEQ ID NO 96
<211> LENGTH: 1346
<212> TYPE: DNA
<213> ORGANISM: Mus musculus

<400> SEQUENCE: 96
gaagtctgcc gccattccac cccacccat ggggaattcc tgcacatggc ccctcttgtc    60
ttctcctcct aagatggcaa gagggagcag ctggaccgaa taccaggt gccagaacac   120 agctgttccc tccttgtccg ccccgctcca cacccaagct gagcagagct gggtggaggc   180 tgagggggt ggggctccct tgtgatgtcc agtgatgctg aatccaccgc aggcaaaagc    240
atcctgaaat tgattctgag cagttctgac tggtgagagc tgccactggc cggttagaac   300
tggtgagcag gagggcaaga agttcaggct tcaggtcaga gtatgcaaag ggagggaggg   360
attaaaggaa gtgggttctg gaaaaggccc tagcctcagt ccccaccacc ttccagccct   420
gggctccctt cccatctgtg ataacagtga gtgaactcct taaccagctt tcatgccaga   480
agaaagctgc actgtaaaac taatccagtt gaaaactggg gagtacagag gtataagctg   540
aagggaggac tccacacccc cgcaccctgc tttgccaggt gaggtgcgtg cctgaggtac   600
agtctaaaac ccgggttccc tttgcaggtg caggtcctgc catgcccgtt ccattgctcc   660
cgatggtgct tcgatcgctg ctgtcccgcc tgctgctgcc tgttgcccgc ctggcccggc   720
agcacctcct gcccttgctg cgccggctgg cccgccgact gagctcccaa gacatgagag   780
aggctctgct gagctgtctg ctctttgtcc tcagccagca acagccaccg gattctggag   840
aggcctccag agtggaccac tcccagagga aggagagatt gggcccccag aagtgaggcc   900
acgggtcctg gaaacagcaa cgcccatcaa agtactttg gagccggtta gtccaggcgt   960
cggtccgcac gcacgggcat ggacggcaga ctgcccagtg ggcgaagaca gtccgggctg  1020
agtgcaagag ggctctgacc tgaacagttc ccactccct agctcctagc aggctacaga  1080

```
ttgtgttgat tgacccttcc tctctgcagc tccctctgcc ttatctctgg cctccagggt    1140
ggacctgcaa atgcgggtat caaggtcagt taagagatga tgtttcactt agactcaaga    1200
caatttagct aagaggtggt atttaaatcc aaactgtccc gtctacctta aaattataag    1260
cccttgcttc ccgttaaaga atgagtactt tcaaagcttg gtacgcagca ggtagtcaat    1320
aaacgaggac agtgtgttgt tattgg                                         1346
```

<210> SEQ ID NO 97
<211> LENGTH: 1539
<212> TYPE: DNA
<213> ORGANISM: Homo sapiens

<400> SEQUENCE: 97

```
gcagtctggg ttccaactcg agggaaatcc tgcatatgtt cccttccctc tcctccccct      60
agactgggaa gtgggggcca gcccagctgc ccgctcccct caatatacca ggtgccagaa     120
cacagctgtt tcttcattgt tccccaaccc aggcggactg taattggtgg ggcagagcag     180 ggcgggcta cccctgtgct gaatccagtg gggctatctc cactccaggc aaatccagcc      240
agagactgat tctgagcagc agttctgccc ggtgagagct gccgtggatt ggtgggggta     300
ggggactgag aggtcaggga gtgtcaggtc agggtggatc aggagcccca aaagaaaaat    360
tgagaattgc ctggagaaga actcctgcta gactgaggga gaagggttag ggaactccag    420
gggcattgag gctgtgcaag aggaggggt gactagagga agggaggggc cagggagcag     480
taggaatgcc tggagctggg aacggcaagc tgtaggtctt ggtttactct tgccttggtt    540
cagtctcccc atctgtgcta tggtgagaac cttcctgcct cagctgcctt gccaagagaa    600
agggcttcat gaaagcaaaa atgacctaca aattgaggtc aggagcagga aggtgtaaac    660
tgaagggagg gggaactcct gcccacccca tgtccttgcc aggtgaggca gaaccaggac    720
atgcaagcct aaagtctgtg ttgtcttccc aggcactgac tcactggccc tgccatgccc    780
acgccactgc tcccgctgct gcttcgattg ctgctgtcct gcctgctgct gcctgctgcc    840
cgcctggccc gccaatacct cctgcccctg ctgcgccgat tggcccgccg cctgggctcc    900
caggacatgc gagaggcttt gctgggctgt ctgctgttca ttctcagcca gcgacactcg    960
ccagacgctg ggaggcctc aagagtggac cgcctggaga ggagggagag gttaggcccc    1020
caaaagtgag gccacaagtc ctggcagcag ctgtatccac aaaatgcttt cttttggagt    1080
aggataatcc tggcaccagc actgaccgaa gcctgcccag tggacagaag atatagtgag    1140
ggttgtgcat gagagggatc tgccacagac atgcctctcc actcccaaca gaaatgtctt    1200
tctggaagaa tgccttgcat ctagcacaaa actgattatt gcccctctgt cctccagcag    1260
ttcctcccaa agaccactcc taatcacctc tggcctcagg cggaggggga actaacaccc    1320 acccaccct gccctccctg caaatgggaa catcaaggtt cccagtgctt aactgaggga    1380
caagtgacaa tttagcagag aggcaagatt tgaatccaga ctgtcttcca gactcaggac    1440
ctaccttaaa ataatatctg agttgcttat ggaggcagac ctgcctgcaa agcccagcac    1500
tcagcaagtg ctcaataaat atttgatttg aattctttc                          1539
```

<210> SEQ ID NO 98
<211> LENGTH: 20
<212> TYPE: DNA
<213> ORGANISM: Mus musculus

<400> SEQUENCE: 98

-continued tggcccggca gcacctcctg                                           20

<210> SEQ ID NO 99
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
tggcccggca ccactcccag                                           20

<210> SEQ ID NO 100
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
gaggcctcca gagtggacca ctcccagagg aaggagaga                      39

<210> SEQ ID NO 101
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
gttgcccgcc tggcccggca gcacctcctg cccttg                         36

<210> SEQ ID NO 102
<211> LENGTH: 84
<212> TYPE: PRT
<213> ORGANISM: Mus musculus

<400> SEQUENCE: 102

Met Pro Val Pro Leu Leu Pro Met Val Leu Arg Ser Leu Leu Ser Arg
1               5                   10                  15

Leu Leu Leu Pro Val Ala Arg Leu Ala Arg Gln His Leu Leu Pro Leu
            20                  25                  30

Leu Arg Arg Leu Ala Arg Arg Leu Ser Ser Gln Asp Met Arg Glu Ala
        35                  40                  45

Leu Leu Ser Cys Leu Leu Phe Val Leu Ser Gln Gln Pro Pro Asp
    50                  55                  60

Ser Gly Glu Ala Ser Arg Val Asp His Ser Gln Arg Lys Glu Arg Leu
65                  70                  75                  80

Gly Pro Gln Lys

<210> SEQ ID NO 103
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

-continued

```
<400> SEQUENCE: 103

Met Pro Val Pro Leu Leu Pro Met Val Leu Arg Ser Leu Leu Ser Arg
1               5                   10                  15

Leu Leu Leu Pro Val Ala Arg Leu Ala Arg His His Ser Gln Arg Lys
                20                  25                  30

Glu Arg Leu Gly Pro Gln Lys
            35

<210> SEQ ID NO 104
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
ggcgggcaac aggcagcagc                                              20

<210> SEQ ID NO 105
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
ctgggagtgg tccactctgg                                              20

<210> SEQ ID NO 106
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 106
aacacaatct gtagcctgct aggag                                        25

<210> SEQ ID NO 107
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
tataagctga agggaggact ccac                                         24

<210> SEQ ID NO 108
<211> LENGTH: 74
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 108
```

-continued

```
Met Pro Val Pro Leu Leu Pro Met Val Leu Arg Ser Leu Leu Ser Arg
1               5               10                  15

Leu Leu Ser Gly Pro Leu Pro Glu Glu Gly Glu Ile Gly Pro Pro Glu
            20              25                  30

Val Arg Pro Arg Val Leu Glu Thr Ala Thr Pro Ile Lys Val Leu Leu
        35              40                  45

Glu Pro Val Ser Pro Gly Val Gly Pro His Ala Arg Ala Trp Thr Ala
    50              55                  60

Asp Cys Pro Val Gly Glu Asp Ser Pro Gly
65              70
```